US009404098B2

(12) United States Patent
Terns et al.

(10) Patent No.: US 9,404,098 B2
(45) Date of Patent: Aug. 2, 2016

(54) METHOD FOR CLEAVING A TARGET RNA USING A CAS6 POLYPEPTIDE

(75) Inventors: Rebecca M. Terns, Athens, GA (US); Michael P. Terns, Athens, GA (US); Jason Carte, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 13/127,764

(22) PCT Filed: Nov. 5, 2009

(86) PCT No.: PCT/US2009/063432
§ 371 (c)(1),
(2), (4) Date: May 5, 2011

(87) PCT Pub. No.: WO2010/054108
PCT Pub. Date: May 14, 2010

(65) Prior Publication Data
US 2011/0217739 A1    Sep. 8, 2011

Related U.S. Application Data

(60) Provisional application No. 61/112,040, filed on Nov. 6, 2008.

(51) Int. Cl.
*C12P 19/34* (2006.01)
*C12N 9/22* (2006.01)
*C12Q 1/68* (2006.01)

(52) U.S. Cl.
CPC .............. *C12N 9/22* (2013.01); *C12Q 1/6806* (2013.01)

(58) Field of Classification Search
None
See application file for complete search history.

(56) References Cited

U.S. PATENT DOCUMENTS

| 4,703,004 | A  | 10/1987 | Hopp et al. |
| 4,782,137 | A  | 11/1988 | Hopp et al. |
| 5,594,115 | A  | 1/1997  | Sharma |
| 5,935,824 | A  | 8/1999  | Sgarlato |
| 2008/0124725 | A1 | 5/2008 | Barrangou et al. |
| 2011/0189776 | A1* | 8/2011 | Terns et al. ................... 435/471 |

FOREIGN PATENT DOCUMENTS

| WO | 2007/025097 A2 | 3/2007 |
| WO | 2008/108989 A2 | 9/2008 |

OTHER PUBLICATIONS

UnitProt Accession No. Q8U1S4, Oct. 2007, 1 page.*
UnitProt Accession No. B1L7L1, Apr. 2008, 1 page.*
Schut et al., J. Bacteriol. 183:7027-7036, 2001.*
Carte et al., Genes Dev. 22:3489-3496, Dec. 2008.*
Hale et al., RNA 14:2572-2579, Oct. 2008.*
Beloglazova et al., J. Biol. Chem. 283:20361-20371, Jul. 2008.*
Weinberg et al., J. Bacteriol. 187:336-348, 2005.*
Ehretsmann et al., Genes Dev. 6:149-159, 1992.*
Wang et al., Prot. Sci. 21:405-417, 2012.*
Scholz et al., "CRISPR—Cas Systems in the *Cyanobacterium synechocystis* sp. PCC6803 Exhibit Distinct Processing Pathways Involving at Least Two Cas6 and a Cmr2 Protein", PLoS ONE 8:E56470, 2013, 15 pages.*
Richter et al., "Characterization of CRISPR RNA processing in Clostridium thermocellum and Methanococcus maripaludis", Nucleic Acids Res. 40:9887-9896, 2012.*
Makarova et al., "Evolution and classification of the CRISPR—Cas systems", Nat. Rev. Microbiol. 9:467-477, 2011.*
Dictionary definition of "in vitro", obtained from medical-dictionary. thefreedictionary.com/In-vitro, last viewed on Oct. 14, 2014, 1 page.*
Niewoehner et al., Nucleic Acids Res. 42:1341-1353, 2014.*
National Center for Biotechnology Information, National Library of Medicine, National Institutes of Health, GenBank Locus AEO10223, Accession No. AEO10223, "acetamidase, partial (Aspergillus parasiticus)," Retrieved on Mar. 27, 2013. Retrieved from the Internet: <URL:http://www.ncbi.nlm.nih.gov/protein/AEO10223. 1?report=genpept 1 page.
National Center for Biotechnology Information, National Library of Medicine, National Institutes of Health, GenBank Locus AAL81255, Accession No. AAL81255, "hypothetical protein PF1131 (Pyrococcus furiosus DSM 3638)," Retrieved on Mar. 27, 2013. Retrieved from the Internet: <URL: http://www.ncbi.nlm.nih.gov/protein/AAL82155 . 1 page.
National Center for Biotechnology Information, National Library of Medicine, National Institutes of Health, GenBank Locus NC_003413, Accession No. NC_003413, "Pyrococcus furiosus DSM 3638, complete genome," Retrieved on Sep. 30, 2008. Retrieved from the Internet: <URL: http://www.ncbi.nlm.nih.gov/entrez/viewer.fcgi?val=18976372&from=1081470&to=1082 .... 2 pages.
National Center for Biotechnology Information, National Library of Medicine, National Institutes of Health, GenBank Locus NP_578860, Accession No. NP_578860, "hypothetical protein PF1131 (Pyrococcus furiosus DSM 3638)," Retrieved on Sep. 30, 2008. Retrieved from the Internet: <URL: http://www.ncbi.nlm.nih.gov/entrez/viewer.fcgi?db=protein&id=18977503 . 2 pages.

(Continued)

*Primary Examiner* — David J Steadman
(74) *Attorney, Agent, or Firm* — Mueting, Raasch & Gebhardt, P.A.

(57) ABSTRACT

Provided herein are methods for cleaving a target RNA polynucleotide. The target RNA polynucleotide includes a Cas6 recognition domain and a cleavage site, and may be based on a repeat from a CRISPR locus. The methods may be practiced in vivo or in vitro. Also provided are polypeptides that have Cas6 endoribonuclease activity in the presence of a target RNA polynucleotide, and methods for using the polypeptides.

11 Claims, 56 Drawing Sheets

(56) References Cited

OTHER PUBLICATIONS

Andersson et al. "Virus population dynamics and acquired virus resistance in natural microbial communities". 2008. *Science.* 320(5879):1047-1050.

Baker et al. "RNA-guided RNA modification: functional organization of the archael H/ACA RNP" 2005. *Genes & Dev.* 19(10):1238-1248.

Barrangou et al. "CRISPR provides acquired resistance against viruses in prokaryotes" 2007. *Science.* 315(5819):1709-1712.

Bateman et al. "HMM-based databases in InterPro" 2002. *Briefings Bioinformatics.* 3(3):236-245.

Bolotin et al. "Clustered regularly interspaced short palindrome repeats (CRISPRs) have spacers of extrachromosomal origin" 2005. *Microbiology* 151(Pt 8):2551-2561.

Bowie et al. "Deciphering the Message in Protein Sequences: Tolerance to Amino Acid Substitutions" 1990. *Science.* 247:1306-1310.

Brouns et al. "Small CRISPR RNAs guide antiviral defense in prokaryotes" 2008. *Science.* 321(5891):960-964.

Brunger et al. "Crystallography & NMR system: A new software suite for macromolecular structure determination" 1998. *Acta Crystallogr. D. Biol. Crystallogr.* 54(Pt 5):905-921.

Calvin et al. "RNA-splicing endonuclease structure and function" 2008. *Cell. Mol. Life. Sci.* 65(7-8):1176-1185.

Calvin et al. "Probing the Catalytic Triad on an Archael RNA Splicing Endonuclease" 2008. *Biochemistry.* 47:13659-13665.

Deveau et al. "Phage response to CRISPR-encoded resistance in *Streptococcus thermophilus*" 2008. *J. Bacteriol.* 190(4):1390-1440.

Ding et al. "Antiviral immunity directed by small RNAs" 2007. *Cell.* 130(3):413-426.

Ebihara et al. "Crystal structure of hypothetical protein TTHB192 from *Thermus thermophilus* HB8 reveals a new protein family with an RNA recognition motif-like domain" 2006. *Protein Sci.* 15:1494-1499.

Emsley et al. "Coot: model-building tools for molecular graphics" 2004. *Acta Crystallogr. D. Biol. Crystallogr.* 60(Pt 12 Pt 1):2126-2132.

Farazi et al. "The growing catalog of small RNAs and their association with distinct Argonaute/Piwi family members" 2008. *Development* 135(7):1201-1214.

Girard et al. "Conserved themes in small-RNA-mediated transposon control" 2008. *Trends Cell Biol.* 18(3):136-148.

Godde et al. "The repetitive DNA elements called CRISPRs and their associated genes: evidence of horizontal transfer among prokaryotes" 2006. *J. Mol. Evol.* 62(6):718-729.

Grissa et al. CRISPRFinder: a web tool to identify clustered regularly interspaced short palindromic repeats 2007. *Nucleic Acids Research.* 35:W52-W57.

Haft et al. "The TIGRFAMs database of protein families" 2003. *Nucleic Acids Research.* 31(1):371-373.

Haft et al. "A guild of 45 CRISPR-associated (Cas) protein families and multiple CRISPR/Cas subtypes exist in prokaryotic genomes" 2005. *PLoS Comput. Biol.* 1(6):e60. pp. 0474-0483.

Hammond et al. "Dicing and slicing: the core machinery of the RNA interference pathway" 2005. *FEBS Lett.* 579(26):5822-5829.

Horwath et al. "Diversity, activity, and evolution of CRISPR loci in *Streptococcus thermophilus*" 2008. *J. Bacteriol.* 190(4):1401-1412.

Jansen et al. "Identification of genes that are associated with DNAs repeats in prokaryotes" 2002. *Mol. Microbiol.* 43(6):1565-1575.

Jaskiewicz et al. "Role of Dicer in posttranscriptional RNA silencing" 2008. *Curr. Top. Microbiol. Immunol.* 320:77-79.

Kim et al. "Structural and Mutational Analysis of tRNA Intron-Splicing Endonuclease from *Thermoplasma acidophilum* DSM 1728: Catalytic Mechanism of tRNA Intron-Splicing Endonucleases" 2007. *J. Bacteriol.* 189(22):8339-8346.

Kunin et al. "Evolutionary conservation of sequence and secondary structures in CRISPR repeats" 2007. *Genome Biol.* 8(4):R61.1-R61.7.

Lillestol et al. "A putative viral defense mechanism in archael cells" 2006. *Archaea* 2(1):59-72.

Laskowski et al. "PROCHECK: a program to check the sterochemical quality of protein structures" 1993. *J. Appl. Crystallogr.* 26(2):283-291.

Makarova et al. "A DNA repair system specific for thermophilic Archaea and bacteria predicted by genomic contest analysis" 2002. *Nucleic Acids Res.* 30(2):482-496.

Makarova et al. "A putative RNA-interference-based immune system in prokaryotes: computational analysis of the predicted enzymatic machinery, functional analogies with eukaryotic RNAi, and hypothetical mechanisms of action" Published Mar. 16, 2006. *Biol. Direct.* 1:7. 26 pages.

Maris et al. "The RNA recognition motif, a plastic RNA-binding platform to regulate post-transcriptional gene expression" 2005. *FEBS J.*, 272(9):2118-2131.

Matsumi et al. "Disruption of a Sugar Transporter Gene Cluster in a Hyperthermophilic Archaeon Using a Host-Marker System Based on Antibiotic Resistance" 2007. *J. Bacteriol.* 189(7):2683-2691.

Mojica et al. "Intervening sequences of regularly spaced prokaryotic repeats derive from foreign genetic elements" 2005. *J. Mol. Evol.* 60(2):174-182.

Murshudov et al. "Refinement of macromolecular structures by the maximum-likelihood method" 1997. *Acta Crystallogr. D Biol. Crystallogr.* 53(Pt 3):240-255.

Petrey et al. "GRASP2: visualization, surface properties, and electrostatics of macromolecular structures and sequences" 2003. *Methods Enzymol.* 374:492-509.

Polson et al. "Isolation of Viral IgY Antibodies from Yolks of Immunized hens" 1980. *Immunol. Commun.* 9(5):475-493.

Pourcel et al. "CRISPR elements in Yersinia pestis acquire new repeats by preferential uptake of bacteriophage DNA, and provide additional tools for evolutionary studies" 2005. *Microbiology.* 151(Pt 3):653-663.

Sambrook et al. Molecular Cloning: A Laboratory Manual., Cold Spring Harbor Laboratory Press (1989). 30 pages.

Sorek et al. "CRISPR—a widespread system that provides acquired resistance against phages in bacteria and archaea" 2008. *Nat. Rev. Microbiol.* 6(3):181-186.

Tang et al. "Identification of 86 candidates for small non-messenger RNAs from the archaeon Archaeoglobus fulgidus" 2002. *Proc. Natl. Acad. Sci.* 99(11):7536-7541.

Tang et al. "Identification of novel non-coding RNAs as potential antisense regulators in the archaeon Sulfolobus solfataricus" 2005. *Mol. Microbiol.* 55(2):469-481.

Tatusova et al. "A Genomic Perspective on Protein Families" 1997. *Science.* 278:631-637.

Tatusova et al. "BLAST 2 Sequences, a new tool for comparing protein and nucleotide sequences" *FEMS Microbiol. Lett.* 1999. 174:247-250.

Tatusov et al. "The COG database: an updated version includes eukaryotes" 2003. *BMC Bioinformatics.* 4(1):41. 14 pages.

Terwilliger et al. "Automated MAD and MIR structure solution" 1999. *Acta Crystallogr. D. Biol. Crystallogr.* 55(2):849-861.

Tyson et al. "Rapidly evolving CRISPRs implicated in acquired resistance of microorganisms to viruses" 2008. *Microbiol.* 10(1):200-207.

Youssef et al. "Dynamic interactions within sub-complexes of the H/ACA pseudouridylation guide RNP" 2007. *Nucleic Acids. Res.* 35(18):6196-6206.

Edgar. "PILER-CR: Fast and accurate identification of CRISPR repeats". 2007. BMC Bioinformatics. 8:18. 6 pages.

Edgar. Supplementary Material for Edgar, R.C., PILER-CR: Fast and Accurate Identification of CRISPR repeats. Supplementary Table 1 and Supplementary Table 2. 7 pages total, 2007.

\* cited by examiner

＊Site of
                    Cleavage

RNase A:  ▨  ▨  ▨                   ∨
  5' G-U-U-A-C-A-A-U-A-A-G-A-C-U-A-A-A-A-U-A-G-A-A-U-U-G-A-A-A-G 3'
Pb(II):  ▬▬▬▬▬

UniProtKB/TrEMBL Accession No. B1L7L1 (B1L7L1_KORCO)
*Korarchaeum cryptofilum* (strain OPF8)
SEQ ID NO:3
MISIIEVEATSQGDGVIPFTGPFFRAAVLRSISSQDPLLAKALELSSKKIFVEALRKERKQMPCG
SLEEPVYMGSEYRGSIIIFNDNVISDAIKSWVFKKPTITIKDIPFKVTSYSQQEINILDFIQESP
CRNFRLRFLTPTCFKRTTSQYCYLYPNPRLIVSSLASAWNALSPKKGPETRLVATWADLSVVETG
YELCTTKPVEMSGEKTFVGFMGWVNYKVIDHPEWHRSSHEEMATWLATYLMFGELIGVGYMRNMG
FGRIKFEVKRK UniProtKB/TrEMBL Accession No. A4YFX9 (A4YFX9_METS5)
*Metallosphaera sedula* (strain ATCC 51363 / DSM 5348)
SEQ ID NO:4
MSFLVRGTVPVHYNYLIQSAIYHRLPTRLSRALHNKGVVEGPRRFKMFTFSRLYGDFTRSDEGLV
YRDRAYLCFSSPLERVVMEVYRSFLRDPVLRLGGSELNLEVMNVVEPPELGSKTVVYTLSPIAVY
RKSEVGTRYYSPYEKEWELLISLNSLRKYHALRRRYLKTGLVVRPLKAGLSRVKYKDNVVFAWRG
GIRDEGTKVPADGGL UniProtKB/TrEMBL Accession No. Q96X64 (Q96X64_SULTO)
*Sulfolobus tokodaii*
SEQ ID NO:5
MVEFFSEKIVKVEFSAVPESDVILPPLSSKVVKNLILSSKLLPSLSSLVQSGMKNKPLFISNLGK
NGFRLFSTGKPVSVKAGEILNFFISFPYYDGFFTELSSGSFETGYGKFFIELEQLEVIELSSIKG
VSEGNFYVKFVTPALLSSKVLLPPSLKEKYKNVNPGYSLIPSVGLVVSYAYRVYRALYGNTSNME
LDSKSFRLGVLSNSLSRVIGYKLKPLTVVIGNDNKGRLRTSRGFVGWMEFDIPYKKLKKAISKYL
IIASYLGIGKSRGIGLGEVVVKIKS UniProtKB/TrEMBL Accession No. Q96ZT3 (Q96ZT3_SULTO)
*Sulfolobus tokodaii*
SEQ ID NO:6
MQPFTSKVSRIVMNNYPSYVKISESSEPLKPVRVTVIKDEEGRSIFKGMDKNVLRLKPQINYFFD
LTSLDINLFEEIVSNPYFNTKVYSTEASVEVGETKVFEEVEIEDSKAYKIEFKTPTLIQPPRPNF
KRKKNRYLLFPFSPYFLVSIQRHWNKYQEKKIIISYSRALYYFKEVDYNLKPVTVIYDKSKVRGF
VGWTLFTLEARKNSSLREGIRKLLAYSNYIGVGKSRAIGFGEVMVKGVRK UniProtKB/TrEMBL Accession No. Q977A9 (Q977A9_SULTO)
*Sulfolobus tokodaii*
SEQ ID NO:7
MIYLAIFKVSADRDTIIPPFSSKLSRSILAHISSSYAKVMESRQPFKPIRVTVLKDSKGFPLIAF
NGRKTILRANEIYSFSFSTTSNDIANDLIRRDMIDIKIWNSTFTIELTSLKIVEEIEYIDSDFYR
VNFITPTLLQPPKFGKMNRFLLFPYAHFFLLSIARHWNANMKTKIKLSSLKTLYYFKEIDHRIWP
VTTIYDGHPIRGFWGWVLYKIEGERENIIRLLNYANYFGAGKSRSIGFGEIEALPTGFLA

*Figure 15a*

UniProtKB/TrEMBL Accession No. Q97WV8 (Q97WV8_SULSO)
*Sulfolobus solfataricus*
SEQ ID NO:8
MPLIFKIGYNVIPLQDVILPTPSSKVLKYLIQSGKLIPSLKDLITSRDKYKPIFISHLGFNQRRI
FQTNGNLKTITKGSRLSSIIAFSTQANVLSEVADEGIFETVYGKFHIMIESIEIVEVEKLKEEVE
KHMNDNIRVRFVSPTLLSSKVLLPPSLSERYKKIHAGYSTLPSVGLIVAYAYNVYCNLIGKKEVE
VRAFKFGILSNALSRIIGYDLHPVTVAIGEDSKGNLRKARGVMGWIEFDIPDERLKRRALNYLLT
SSYLGIGRSRGIGFGEIRLEFRKIEEKEG UniProtKB/TrEMBL Accession No. Q97Y96 (Q97Y96_SULSO)
*Sulfolobus solfataricus*
SEQ ID NO:9
MPLIFKIGYNVIPLQDVILPTPSSKVLKYLIQSGKLLPSLNNLITSRDKYKPIFISHLGLNQRRI
FQTNGNLKTISRGSKLSSTIAFSTQVNVLPELDEGVFETIYGKFHITIESVEIVEVEKLKEEVEK
HMNDNIRVRFISPTLLSSKVLLPPSLSERYKRVNAGYSTLPSVGLIVAYAYNVYCNLIGKKEVEV
RAFKFGVISNALSRIIGYDLHPVTIVIGEDSKGNLRKARGVMGWIEFDIPDEKLKRRALRYLLAS
SYLGIGRSRGIGFGEIKLEFIKREENH UniProtKB/TrEMBL Accession No. Q97YB0 (Q97YB0_SULSO)
*Sulfolobus solfataricus*
SEQ ID NO:10
MQNTKCVISDITQHSYTFSGRFDMIVAEIFVKPESDAIIPFSSKVGKSLLLDPKNVSISPLKYKG
KYLIKYGSVLTFLEVIGGNVYSFEVGGDERNVYSALINLGDKSLLFNTYWKVVDVEVHEVEVSSI
PKNFGVDILTPALIVSPYVKEKRKVFTNKSEYVFFNNIIDATGFNRGDVKLSEVISRFAQLLWEE
PSIIGYANVRYGDKLVIGMIGKLRYSVKGEDEVLIKVLEDAIVRGIGSSRRNGFGVVRIKGVEAS
WLR UniProtKB/TrEMBL Accession No. Q97YC0 (Q97YC0_SULSO)
*Sulfolobus solfataricus*
SEQ ID NO:11
MIYTLTFRLKPSNDVIIPPFSSKLSRTLFLSFSPTYSKIIESKEPNKPLRITVVKDQGKPLYSNG
KSKVVLKAENTYTFIVNTLLEDVVKEVIRVESVNREIYNTSFHVELVNVSVKENVMAEDARFYRV
HFKTPTLLQPPRPRMKRKENRYVLFPYVPLLFYSIASHWNRYMDKKIVGVTGSKTLYYFREVNYR
IRPMTAYYGNIPNKGFVGWVVFELSARKGSKIRENIRRLLDYVNYFGVGKSRNIGFGEVEVKSLN
G UniProtKB/TrEMBL Accession No. Q97YE5 (Q97YE5_SULSO)
*Sulfolobus solfataricus*
SEQ ID NO:12
MFLSFSPTYSKITESKEPHKPLRITVIKDHGKPLYSTGKNKIVLKTENTYTFTVNTLLEDVVKEV
VKTESVNKEIYNTKFHVELENIIVKEEFKINDARFYKIHFKTPTLLQPPRPSIKRKGNRYVLFPY
VPLLFYSIASHWNRYMNNKIVGVTGSKTLYYFREVNYKIRPLTAYYGNIPNKGFVGWVLFELKAR
KGSNLRENIRRLLDYANYFGIGKSRNIGFGEVDVRPLE

*Figure 15b*

UniProtKB/TrEMBL Accession No. Q4J7D4 (Q4J7D4_SULAC)
*Sulfolobus acidocaldarius*
SEQ ID NO:13
MSYTIIVIFYTSFEITTDHDIILPPFTSKLSRLILVKLSDTYSKLQYQNTSYKPLRVTVIKDPEG
RPVYARGRGKSIINGNQSYSFTFSFQDENIFREIMEKVQTTVEAWNTKFQVNLKDIKVVDQTESL
RSESKLYRMEFLTPTLLQPIRPNLKRKDNRFVLFPYVPILLFSIVKHWNQNMDQKIHGVTGLKTL
YYMREVDYRLRPVTTYYDGKPVRGFTGWTVFELRSKRNSKITRNVQKLLEYANYFGVGKSRAIGF
GEVNVKVIDE UniProtKB/TrEMBL Accession No. Q9YCN0 (Q9YCN0_AERPE)
*Aeropyrum pernix*
SEQ ID NO:14
MVIGLYKVSLILESTRPLPLLSWSGVVAARIVKECIGGREGLVSVEPLQKEGQPLNASPSKPSTI
EEPNILLGATLNTTGFYRLRSSLPGCLDRWGFRVISFEVERWVPRLPRRVTTSRDAIEFTVEYWP
TIYMFRSRPILYPSPQRLVYSVFSALARHTGLSLKGYANTLASNVELLGWNGRVGLYSIGRDRKV
RAFYGRATYAATARYVELLQLVMEAAQVLHVGKSRGIGFGAVKTGSIM UniProtKB/TrEMBL Accession No. A4WJZ4 (A4WJZ4_PYRAR)
*Pyrobaculum arsenaticum*
SEQ ID NO:15
MEPRFERRPILMASSGGVAYLRVRPLWAVSVVLVRGRPTEAVAMGFTGTVAQSLVVSLLGGELH
DARPKSFSVTPFFVNGRPAVDKAVAGPGDILELRAAFAQRELAERFIAEVAKGYTLFGRRVVVEE
LEFYDVFSQPLPEAQCFKLEFLTPLRFAVKPLYRRSRAVFDFLPRPLSVFKSAVRHGRALGLLKL
GAPFLRWVHTYVALTDFGCRGRCVVTVKLPNGGVARGFVGWALYRSFGKRRIADLWRALRVAEAF
NLGTGRGMGLGVVRVTPLDCPGNGPAAQRGDA UniProtKB/TrEMBL Accession No. A3MVN5 (A3MVN5_PYRCJ)
*Pyrobaculum calidifontis* (strain JCM 11548 / VA1)
SEQ ID NO:16
MAYVVRVVLAAREGFSLGGFTGTVVESLVLRLTDPSLHGAGPKPFSVTPLFVGGRPVVDLAVVGP
GDLLEFRVGFAGEGLARGFVERLLGGGVELFGRRVEVAEVEMRDVWLDPLPEARCFKLEFLTPTR
FAVPPLYKRRRALFDFLPRPLTLFKSAVRHGRELGLLKLGAPFLRWVYTYVALTDVGCWCRRRGS
CVRTVKLPNGGVARGFVGWALYRIYGKRRLADVWKTIRLMEAFNVGTGRGMGLGVVRATPLPCPG
ETAKDGGQR UniProtKB/TrEMBL Accession No. Q8ZZK8 (Q8ZZK8_PYRAE)
*Pyrobaculum aerophilum*
SEQ ID NO:17
MSVVVVRGRSPEAIPLLGFTGTVVESLVVSLLGRELHDVKPKPFSVTPFFVGGRPAVDKAMVAPG
DLLEFRVSFAGRELAEKFIAKIMQGYTLFGRRVVVEELEFYDVFSQPTPQTGCFKLEFLTPLRFA
VKPLYKRKRAIFDFLPRPLSVFKSAVKHGRELGLLRLGAPFLRWVHTYVALTDFGCPGRCIITVR
LPNGGIARGFVGWALYRAFGKRRLADMWKTLRFAEAFNIGSGRGMGLGVVRATPLECPS

*Figure 15c*

UniProtKB/TrEMBL Accession No. Q8ZZM1 (Q8ZZM1_PYRAE)
*Pyrobaculum aerophilum*
SEQ ID NO:18
MRAVWRVRVLGRLAGGVVLTGFSGTLVESLVVSRLGGWLHDAKPKPFAVSPLFAGGRPVLDGAAL
GQGTEVEFRVGFADELLALRFVDSLSGGVTLFGKPLELAELEFRDVSSEPLPSTPCFKVEFLSPT
RFAVKPLYKRRRALFDFTPRPLNLFKSAVRQGRALGLLRLGGPFLRWVYTYVALTDFGCWGKCVR
TVKLLGGGVARGFVGWALYRAFGRRRLADVWRALRVAEVFNVGTGRGMGLGAVRVTPLECPGATD
RG UniProtKB/TrEMBL Accession No. Q8ZZU6 (Q8ZZU6_PYRAE)
*Pyrobaculum aerophilum*
SEQ ID NO:19
MWREVEIELVTSAPCPLTGWSGSVAYKTLLELIRREAEPKGKIFAHPLYRGDRPILSGVEGRAVV
LEPMTQVKIRAVLTEQDLFYLLSAVSKAEPTSSTCPMSPAALRFSPLELKLGEGHGFAVVKLRFY
PTAFMFHGRDVLYPSPQRMAYSLAKAYKELFGVDIKPIADRAPTALEIVGMRTKAVRVNIGDSRL
VPAFLGRAQLAVFGNVDAWLSLLKLGESVGVGISRAIGFGKYKIEEVVLHA UniProtKB/TrEMBL Accession No. A1RQV9 (A1RQV9_PYRIL)
*Pyrobaculum islandicum* (strain DSM 4184 / JCM 9189)
SEQ ID NO:20
MYNFFLTALRRVAEPKGRVFAHPLYHGGAPVLSGLNGSQKAFEPGAAFELRALLLEHDARLLLDS
LAAEPRVEVGCVLEVSGIDIVPADGKLEERHGMAVVELVFYPTVFMFHGRDVLYPSPQRLAYSLA
KTYYQLYGVSLKELADRAPTALELVGMRIKTGWLNIGEARKVPVFYGRARLAIYGDVGMWLSLLK
LGELTGVGISRAIGLGKYRIEKVEILI UniProtKB/TrEMBL Accession No. B1YE45 (B1YE45_THENV)
*Thermoproteus neutrophilus* (strain DSM 2338 / JCM 9278 / V24Sta)
SEQ ID NO:21
MRIVAVRARAGSAFAVSGFSGTVVESLVLKTLGRPDLHDARVKPFSVWPLLHRGRPVLWGAAVAP
GDPVEVRVGFADDDMASQFAAAAAGGGLQLFGARLDPEAVEMRDAHHDLPQEQCFKLEFLSPLRF
ATPPLYRRSKPIYEFFPRPLSLFKSAVKHGRALGVTKLGAPFLRWVYTYVALTDFGCHSRCVATV
KLPGGGIARGFLGWALYRAYGKRRITDLWKTIRLMETLNVGTGRSMGLGAVKATPLKCPNQQPTE
KPTYPI UniProtKB/TrEMBL Accession No. A5UJJ7 (A5UJJ7_METS3)
*Methanobrevibacter smithii* (strain PS / ATCC 35061 / DSM 861)
SEQ ID NO:22
MRLEIILKGKNNFKVPFNYNHILSAIIYNKIADLNFANELHSSKSFKFFTFSQIYIPKRRIVKDG
IIAKDGVISFYISSPNDFLIKSLVDGFLEDLEISFQNQKLTIQKIEALKTPEFSSKSEFKTLAPI
IVRTKKEINGELKIWDLAPSDKFFKSLENNLIKKYIKFNNLTKTDKKINIYSDMNFVKRKRISIN
KGNATTHHRAYMMDLILEGDLDLIEFAYDVGIGEKNSMGFGMIKLLE

*Figure 15d*

UniProtKB/TrEMBL Accession No. Q2NFS1 (Q2NFS1_METST)
NCBI GI No. gi:84489743
*Methanosphaera stadtmanae* (strain DSM 3091)
SEQ ID NO:23
MRIEIYLESKDKKNTLIKYNYNYMLSSAIYSKFVDLEFFRNLHESESFKFFNFSKLYIKHINNSN
SEGLIANKGKVKFILSSPNQYIITNFLSGCLENPELRIGKNIYKITQIKEIKDPKIHKKEEINTL
SPIITRTKEEIEGKLKIRDLAPSPHFFRNLEKNLIRKYILFNNIENTNLKVNISSEMRYVKEKRI
LIEKYGYKTYNRCYLMNLSIEGDAELIKFAYDTGIGEKNSMGFGMIKIKENK UniProtKB/TrEMBL Accession No. Q2NH84 (Q2NH84_METST)
*Methanosphaera stadtmanae* (strain DSM 3091)
SEQ ID NO:24
MRLIIKFNPLSDCKYDAIGKYDIQGFIYSLLKDTEFKNYHDIKGFKFFTFSNIFPVCDFKQDNLK
TIIISSPSSAFIKVLYYQLSNLEIFRLNKYYMEKYKVKLIKNNKCSNSIITGTPIVLFENNYENR
YYSFNQKLDFNFFFNRLKENALKKYTAYTQDEINLESDLFDSFEFNREVSMRIIMKNQTFIIIGS
LWKVLEKNIAREDRKFYNFLFDCGLGEKNSLGMGFINNRR UniProtKB/TrEMBL Accession No. O27163 (O27163_METTH)
*Methanobacterium thermoautotrophicum*
SEQ ID NO:25
MEGFIDRPEIDFLRRSVNVEYVEFLEPPEFRRNMKFRTLSPIIIKTVREEDGVLKQWDVNPNDLK
FYENLQNNLVRKYREFYGDYDGDEYLRLVPYQRSIKRKRIMIPKEGAETYHRAYHMKFRVEGDPR
LIEFGYDCGFGEKNSMGFGMVVTS UniProtKB/Swiss-Prot Accession No. Q57820 (Y375_METJA)
NCBI GI No. gi:15668551
*Methanocaldococcus jannaschii (Methanococcus jannaschii)*
SEQ ID NO:26
MRESMRIELELQTDNFTVIPYNHQYYLASAIYNKIHSANPAYAKRLHNYQKFKFFTFSLLQIRKR
VIRKEGIETIDGKAYLYISSPNNEFIENFVAGLLEDGKLRVGNVEFFVRKAKILPIPKKFNILKT
ISPIYLKTMIETEDGLKTYDLLPNNSKFYENLKNNLKKKYEAFYNEKCDMNFEFEVLKFRPKRMR
IKNDIYCRCSEMVFKVWGDYDLIKFGYECGFGEKNSMGFGMVVNVEDKNQKNKKLKTKI UniProtKB/Swiss-Prot Accession No. Q58631 (Y1234_METJA)
*Methanocaldococcus jannaschii (Methanococcus jannaschii)*
SEQ ID NO:27
MRLKLSLTPKQDFSFDKINKHTIQGFIYSLLKDTEFGEMHNQPRFKFWCFSDIFPPNDFVKGEDK
YLLISSPREEFINVLYERLDNLEEVNLNNFKFEVSELKKFDLKVKNKFITGSPIVLYKDKDRGEY
IKFYDDDFDLMFFVQRLQDNAVKKYKAFYNEEPVLNGFIFDRISPRVRNGRVDVYVRIAKKGREF
LVVGTTWKLLEKIKIRKEERKFYKFIMDCGLGEKNSLGFGFINPIK

*Figure 15e*

UniProtKB/TrEMBL Accession No. A8TI44 (A8TI44_METVO)
NCBI GI No. gi:163800065
*Methanococcus voltae A3*
SEQ ID NO:28
MRISINLKCEKNTTIPFNYQYQLSTALYNCMYDNNKEFAENLHKSKDFKFFTHSWLFMPNSKVGK
NGIICKDGNAFFKVSSPNDELMTHLLQGLFKVGYMQINNTKLDVVGVLNEKGYNSNIKKMKTISP
VLLRTKKERNGIDNTEGLKIYDILPQENSEKFHENLKNNLKRKYSLFYDKDYENCDLDFDINISE
AKSKRVKIKDSFQRCSNLKFEISGDEDLIKFAYECGLGELNSMGFGMIDKYSYKC UniProtKB/TrEMBL Accession No. Q5V7W8 (Q5V7W8_HALMA)
*Haloarcula marismortui (Halobacterium marismortui)*
SEQ ID NO:29
MRILARLSARTDAAYDNTYHNKLQGRIWQALEDSKYDALHDKNQPKPFVYSNPFPPQDMDEGDER
TLLVASPEESLLAHIAEDLTHDRELNIGEMPFHVDKVSPLAPDVGEPGTSGTIETGTGLLVRIPP
WRFDDYGMDVNHDQAEFWRPEHTLEPFRTQLEANLDKKHRLYMPDYLAGPSDVDGDLFDSYELIK
TFAIPVTPTTGRTEEWVLSKWRFDYTVRDDDHRRHLNLALDVGLGERNSLGFGFINITDQTRPDE
TELEGENAFP UniProtKB/TrEMBL Accession No. A7D837 (A7D837_9EURY)
*Halorubrum lacusprofundi* ATCC 49239
SEQ ID NO:30
MAHLSARADTAYQDDYHHKLRGRLWNALDGTEYGERHDSGEPPGFAYSNPFPPHDMQEGDERKLI
VSSVEDGLLAHVAADLLEEPEFNIGEMPFHVDDVTSFTPDVGEPGTQGIIESGTGLLIRIPPWRC
EEYGIDHPGGDTAVFWQPEHTTEPLITQLRANLDKKHGLFCPDYLPGPSERDTELFDSYELIKTF
SIPVTVTEGTQMTYVLSKWRFGYTVQDDHHRRHLNLALDTGLGERNSLGLGFINITDKTAPWEVS
S UniProtKB/TrEMBL Accession No. Q6L114 (Q6L114_PICTO)
*Picrophilus torridus*
SEQ ID NO:31
MKLVIELTQNQKTISYSDIYSIFENIIFEIGRSKPLIKSAMIDDFPYYCGSHPLPYKGRISNNTI
SYGKYRIYISSGYYKIIDDIMDAIKSGNVKHRLMRINSVKMENNNCFFDTVNMISRSPVIIKYNG
EYIDANNRNFVDAIKNDIIKKYSFTGLNGYIDFIKIIHFKTLNLRINNED
IKASMIKFTIMSDNKIINNILNTGIGELTKSGFGFIDEERIPLDFGIMY UniProtKB/TrEMBL Accession No. Q6L312 (Q6L312_PICTO)
*Picrophilus torridus*
SEQ ID NO:32
MRIKIKFYTEEEPIPNYNFNKYDFQGMIYSSLLDAGVTDIHDGNSIRFFSFSDVFPYNYVKKDLI
YNFMISSPVDRIINSIYDVLNKNKYFYLSGYKFNIAEIKKFDVNISKSFITGSPI
VLYLDNRKNRYFSIRNGDSIAFFIKRLKENAIKKFNIFYNDEISMNHLLFDKMKFHKEVSVLLNK
GTKNFNIIGTMWYKLDLLRLRRSEVKFYKFIMDAGLGEKNSLGFGFINPVVNNGQ

*Figure 15f*

UniProtKB/TrEMBL Accession No. Q6L357 (Q6L357_PICTO)
*Picrophilus torridus*
SEQ ID NO:33
MKSAILKFRSENKQQIPFEHNYYLGIAIQKKYNQLMYSEKIEMHSGLQNNYTISSIITKDAEIRD
DGIYTKNFFIVLRSLEDEFINRLKVSFSSYPEIRIGNSVFSIVEIKDTKRVDFSS
DIYFKSLSPILIRYSKKLDNFVTQKNEIEPNLKAWMINAYYKNTGRKPETNFSIDIDKVKVKSVI
VSKNRIKLRAPLIYGRFRSADPEMLEMFYYKGMGSKTGLGLGCWEAYQ UniProtKB/TrEMBL Accession No. Q97CI9 (Q97CI9_THEVO)
*Thermoplasma volcanium*
SEQ ID NO:34
MRLKVTFYTKDDENYEFNKYDIQGMIYSALLDAGMTEIHAGNKIRFFCFSDIFPSNILKKDFLFN
FIISSPDSNIIKNIYNILDKNKIFYLSGYKFHIAEIKEFDINISKDFITGSPVVLYLDNKKNKYF
SIKDDSIAFFLRRLKENAIKKFNLYYHENININHLIFDKLKFHREVALLLRKGKTSFNIIGTTWY
NLHLNKLNRDEIKFYNFIMDAGIGEKNSLGFGFLNPVRNYGQ UniProtKB/TrEMBL Accession No. Q5JD42 (Q5JD42_PYRKO)
*Pyrococcus kodakaraensis*
SEQ ID NO:35
MRIKLLLRFKPPFLIPYNYPRYLYSFLLRAIELADKEVAGRIHNNKRDIKFVASKFMPIGSTKRL
EQGLLVESGTVELYVGSTEDIILESLVRGLGQGVGMLHVRGQRLLSYEAELEEIPKHLSGKRFKT
LSPVSVYHNNPPNGFRQWDLSPVGPPNSPFENEPKVWKELLFENLKSKYMMVYGEPYEGSFDIRV
LTKKPKSRRLLVKIDERTGKPIYARVWEFDFKMWGEEELLRVAYELGIGMRNPHGFGMVEVI UniProtKB/TrEMBL Accession No. Q5JGA0 (Q5JGA0_PYRKO)
NCBI GI No. gi:57640399
*Pyrococcus kodakaraensis*
SEQ ID NO:36
MVRFLIRLHPENEPFRIPFSHQHYLQGLIYRRIQRVNPDLSLRLHNPKVPKLFTYSLFMGERREL
AEDKSSLLGRGKGFFYFSTVVPEIAEAFIGGLLQNPEVELWREKFTVEEVKALAEPERLSGKKFV
TLSPIAVTTKRIQFGKPRSYDLSPREPEFYELVRENLREKYVLIYGSKPPEDFEMRVLNAKPKRF
EVKPGIFQIAWHLVFRAYGDEGLLRTGYLAGFGEKNSIGFGMVKVDARKERVKKKWKGGADHQKG
KEA UniProtKB/TrEMBL Accession No. Q5JHS4 (Q5JHS4_PYRKO)
*Pyrococcus kodakaraensis*
SEQ ID NO:37
MRIEIKLRPAEVGTILPFNYNYEVYSQLLEKVYLVSPELGKEVESSGVDYFTFSRIMVRKRELIP
EAGIRVLSDDVSLYVSSHSADVIHAIAEGFLDDPLLKIKDATFIADDVKVLKEPELKGPVLFSTL
SPILVRTVKFVNGRMKVWDLYPDDEMFFDKLRKIMLRYSSIYGRMPENKEFKIEVLKFKPVRIL
VRDTYYRSSLMVFKYSGSPELAWLGYETGFGEKTRYGFGMVKVIDSEQGQEGQE

*Figure 15g*

UniProtKB/TrEMBL Accession No. Q9UY91 (Q9UY91_PYRAB)
*Pyrococcus abyssi*
SEQ ID NO:38
MRIEIKLLPLTETPILPFNYNYDVYTQIVNKVNSIEPKVAGLLSSPHGFWTFSRIIIRKR
KIIPEKGIEILSDDVSLYVSSSNEEIIRAIAEAVEKSPEFKIGNVSFLVGDVKAIKIKEI
GKENVFSTLSPIVVRTIKFEGDKLRHWDLYPHDEMFMDKLRKVMLLRFNEIMGYSPEDKEFQIEV
LKFKPTRLIVGNSYIRGSLMVFKYTGSEEIARFGYENGFGEKTNLGFGMVKLIE UniProtKB/TrEMBL Accession No. Q9UZK6 (Q9UZK6_PYRAB)
NCBI GI No. gi:14521345
*Pyrococcus abyssi*
SEQ ID NO:39
MRFLIRVRPEERKFKVPYNHQYYLQGLIYNRIKMVNPRLSTFLHETRGPKMFTYSLFMTEKRKHP
KGLPYFLGFKRGFFYFSTCIPEIAEAFITGLFREPEIVLWGERFYLEEVKTLREPTKFSGSTFIT
LSPVAVTMVKEGKRYDVSPLEEEFYTLIKENLKDKYVMIKGEKPPDDFEMEVIVAKPKRFEVKPG
IYQMAWHLVFKAYGDDELIKVGYVVGFGEKNSLGFGMVKVENNREEKGMGVQERMLFKNEDGLKT
GP UniProtKB/TrEMBL Accession No. O57900 (O57900_PYRHO)
*Pyrococcus horikoshii*
SEQ ID NO:40
MIYMRLKLSFIYDGDKFQPNKHAVQGFIYNMLRGTEYEDRHNRRGFKFFTFSDVFRDSKGYYSLL
IASPDSGFINALYLSLKDRDHVYIGKDEIKLVEVKKFKLKLKRAFQTGSPVVIYKDSRKNEYFKL
HEHRDLLFFLQRLKENAEKKFNSFYGDEFHLEGLIFDRVIPKVRKNGKVDVYVKVVKNGVPFPVI
GTNWELLEKERIKPEERRFYRFIMDCGLGEKNSLGFGFLNPIKGVKN UniProtKB/TrEMBL Accession No. O58088 (O58088_PYRHO)
*Pyrococcus horikoshii*
SEQ ID NO:41
MRIEVKLLPLKDNPILPFNYNYEVYSQILEKVNSIEPTIAKLLSSPHGFWTFSRIIVRKR
KILPDKGIEILSDDVSLYISSSNEDIIRAIAEAVEKSPEFKIGELSFLVGDIKAIKVKELGKENV
FSTLSPIVVRTVKFEGNKLRHWDLYPHDELFMDRLRKVMILRYSEVMGETPKDRDFTIEVLKFKP
TRLMVGSSYIRGSLMVFRYAGSEEIARFGYENGFGEKTGLGFGMVKLIE UniProtKB/TrEMBL Accession No. O58931 (O58931_PYRHO)
NCBI GI No. gi:14591070
*Pyrococcus horikoshii*
SEQ ID NO:42
MIIMRFLIKVKPEERKFRVPYNHQYFLQGLIYNRIKLTNPRLSTFLHETKGPKLFTYSLFMTERR
EHPKGLPYFLGYRRGFFYFSTCIPEIAEAFITGLFREPEITLWGEKFYLEEVKTLKEPKKFSGST
FITLSPIAVTMEKGGKRYDVSPLEEEFYALIRENLKDKYVMIKGEKPPDDFEMEIIAAKPKRFEV
KPGIYQMAWHLVFRAYGDDELIRVGYVVGFGEKNSLGFGMVKVDEQRKRRKNIGSFQESMSFNEN
RELETGT

*Figure 15h*

UniProtKB/TrEMBL Accession No. Q8U1S4 (Q8U1S4_PYRFU)
NCBI GI No. gi:18977503
*Pyrococcus furiosus*
SEQ ID NO:2
MRFLIRLVPEDKDRAFKVPYNHQYYLQGLIYNAIKSSNPKLATYLHEVKGPKLFTYSLFMAEKR
EHPKGLPYFLGYKKGFFYFSTCVPEIAEALVNGLLMNPEVRLWDERFYLHEIKVLREPKKFNGS
TFVTLSPIAVTVVRKGKSYDVPPMEKEFYSIIKDDLQDKYVMAYGDKPPSEFEMEVLIAKPKRF
RIKPGIYQTAWHLVFRAYGNDDLLKVGYEVGFGEKNSLGFGMVKVEGNKTTKEAEEQEKITFNS
REELKTGV UniProtKB/TrEMBL Accession No. Q8U3R3 (Q8U3R3_PYRFU)
*Pyrococcus furiosus*
SEQ ID NO:44
MRIEIKLLPLQDNPVIPFNYNYELYSQIVEKAGAIEPRIVKLLESPHGYWTFSRIIIRKR
EIIPEKGIKILSDDISLYISSSNKEIIKGIVEGIEKSPEFKIGDVGFLVADIKALKSKEIKNVN
IFSTLSPIVVRTVKFEGDKLKHWDLYPHDELFLDRLRKVMLLRYHEVMGDLPEDKDFRIELIKF
KPTRLIVKDSYIRGSLMVFRYYGSKEIAKFGYENGFGEKTNLGFGMVKIIEEQ UniProtKB/SwissProt Accession No. O28420 (Y1859_ARCFU)
*Archaeoglobus fulgidus*
SEQ ID NO:45
MSFSLQLTRLKARLYFPQYHLPPFLGNKFRGGFGSVLLKAVCSYLKPSCNICKSVDDCLYHALY
TRDRQKRGRSQPVRPIVFIPPFFGRSVSGRGELTLYINVFGDYVKYLPHIIYGLRYLGKMGLNA
TSKYEIVSISDAISGKEVYDGETVFVENLSSIELGKIKPREVEKEIEVDYLTPMEAKTPINLPF
LIHIVRRRLILFVNEYGSGEVPEFYCEAETLESSWEKHELHHRSKRQGLRSFFGVTGRARYSIS
EIDDNALTLLSIGELIGGGAKASFGMGFFRIRS UniProtKB/TrEMBL Accession No. O30164 (O30164_ARCFU)
NCBI GI No. gi:11497692
*Archaeoglobus fulgidus*
SEQ ID NO:46
MRLKISLLSPADSFEIDLNHSYHLASAIYRAIERADPSLSIELHKPDVPKFFTFSKLFIPKRKF
RIEGEKMVSDCEEAYFFFSTLRNEVAASLVEGLLSKPEIRICGVDFIVSEVSVLPEREVKGREK
FVTLSPIYASTSVGENGRRRIFDLYPKDSKFYEVILQNLVKKYVLYYKSAPENLDFHMKPLNVK
AKRIRLKDTFHRCVEMVFKAEGSPELLDVGYKAGFGSKNSMGFGMVKVV UniProtKB/TrEMBL Accession No. Q8TJV5 (Q8TJV5_METAC)
NCBI GI No. gi:20092472
*Methanosarcina acetivorans*
SEQ ID NO:47
MRCRVSIRKISPYPLHYDYQYGLASMLYSKLATSNVELAAKTHSKQGFKFYTFSNLVLDDRIPE
KNGLNFKTAHFFLSSPDPEFIRSFAEGLLLEPEFFLGNNENKVSFIIERIEVLPAVHFSDMCTF
RTLSPIYLKTLRKQNDKLVEFDLYPKDSKFHENLHKNLVARYEEFYGSKIEKDFFEILNIPNFK
PKRVKIENNYRRCSLMDFSISANPELLKFAYDAGLGEKNAMGFGCLDLLQVNTK

*Figure 15i*

UniProtKB/TrEMBL Accession No. Q46FQ7 (Q46FQ7_METBF)
NCBI GI No. gi:73667850
*Methanosarcina barkeri* (strain Fusaro / DSM 804)
SEQ ID NO:48
MRCRVSVRKISPEPLHYDYQYGLASMLYSKLATSNIELANKIHSKKGFKFYTFSNLILEDKIPEK
NGLNFKKAHFFLSSPDPEFIRSFAEGLLIEPEFFLGNNGNKSNFVIERIEVLPLIHFSDTCTFRT
LSPIYLKTQRKQDDRLVEFDLYPKDSKFHENLHKNLVARYEEFYGSKIDKDFFEVIKIPSFKPKR
VKIENNYRRCSLMNLYLSANPELLQFAYDAGLGEKNAMGFCVNVLEVKQK UniProtKB/TrEMBL Accession No. Q12WX9 (Q12WX9_METBU)
NCBI GI No. gi:91773105
*Methanococcoides burtonii* (strain DSM 6242)
SEQ ID NO:49
MRCKVTILKTTNSHIHYDYQYGLASMLYARLANANITLANEIHSHQGFKFYTFSNLIIEDWIPNK
RGLDFNKAHFFISSPDLEFIRSFTEGLLLEPEFFLGRDKKANFIIERIEIMPNLEISESCKFTTL
SPIYVKTMRKKNDKLVEIDLYPKDSKFYENIHTNLTARYEEYYGHKVEHDYFDVLEVKDFKPKRV
SIGNSFRRCSLMKLELEASPELIKFAYDAGLGEKNAMGFCLELVK

*Figure 15j*

UniProtKB/TrEMBL Accession No. Q8REC5 (Q8REC5_FUSNN)
*Fusobacterium nucleatum* subsp. nucleatum
SEQ ID NO:50
MRFILNFELDTVIIPVEIKRTIISFFKKSLTEAHNSKYYPEFFTGTQIKDYSFSVIFPLDKYFGE
EIYLKRPEMKVLVSCSEKNNIGFLLVNVFLSQRNKKFPLPKDTHMILKDVRIIEEKIIKEEEAVF
QTTIGGGVVVREHNKEENKDIYYSVGNERFEEVLNWLMKERFKRLRYPEDIFKDFSCELLEGRKI
VVKHFDLKFPVTTGRFKVKAPKILLEEIYRTGMGSRLSQGFGLLEYLGGEIKDEV UniProtKB/TrEMBL Accession No. A5TU40 (A5TU40_FUSNP)
*Fusobacterium nucleatum* subsp. polymorphum ATCC 10953
SEQ ID NO:51
MRFILSFELDTVKLPIEIRRTVISFFKKSLTEAHNSKYYPDFFTGTQIKDYSFSVIFPLDKYFRE
EIYLKKPEMKVVVSCSEKNNIGFLLVNVFLSQRNKKFPLPKDTCMILKDVRIIEEKIIRGEEAVF
QTTIGGGVVVREHNKEENKDIYYSVGNERFEEVLNWLMKERFKRLGYPEDIFKDFSCELLDGRKI
VVKHFDLKFPVTTGKFKVKAPKILLEEIYRTGMGSRLSQGFGLLEYLGGEIKDEV UniProtKB/TrEMBL Accession No. A1ZPF3 (A1ZPF3_9SPHI)
*Microscilla marina* ATCC 23134
SEQ ID NO:52
MRYKITLKTTDAYTVIPINYQYELSSCILGICKDANTKYQRFLKQHKLPARRKNFQWFSF
SNLYVPRREIFADRLQVISPKISFIISFYLDPSAERFIKDLFLDRQMYLGDKFSQARFIVENVEP
LPLRMPSTTVSFKTLSPLLISKLNNRGNVDYLPPEHPEYENLFLQALLGKYVKVLQETNQTPESS
THQRIEFEVNHYKKIKSRLITVKAHTTNEARIRGFMYEFRLTAPKEIIELGLLTGFGEKNRLGFG
ACETVY UniProtKB/TrEMBL Accession No. A1ZVQ2 (A1ZVQ2_9SPHI)
NCBI GI No, gi:124008802
*Microscilla marina* ATCC 23134
SEQ ID NO:53
MRFRLTLRRLSTPCNIPINYQSYISANIYRLLELADAQYAAFLHDKGYEGEGKRFKYFTF
GQLKIPRGKWQMRESRMLINAPVVHLETSFLVDKTVEKFVAGVFQDQHLYINDAFAHNDFLIEQI
EMLPTVAFGEMMRFSCQSPLIITRKNKHNKHCTYLAPGDALYHEIFIENLRSKHQTYLSQQLPHN
GSNTQIPPQLEVLNNGKMSSKLITLKPWLKQGIKVKGCLFDFELTAPPEMLKVGFYGGFGSNCAQ
GFGMVEVI UniProtKB/TrEMBL Accession No. A3I0J5 (A3I0J5_9SPHI)
*Algoriphagus* sp. PR1
SEQ ID NO:54
MPFHHQYILAQFLKGLIVKGGREEFYNYNFFNFSGLKGQTKVSRSGLHYYSSLVTLVLSSQSEDF
MDYLLEQVFATPKVELGNLILVPEYTEIEIEPVLETSNKFVCISPLVLITPAFNEEAGKRFISPD
SDEFSDLLYESTLTRMEKSGWYTPEQMESFFKFQVVPDMVYVNKLKEQQKKFARIYAVYDMDVKY
EVRGYTLPFTLYAAPEVQDFVFKCGLGAFTHKGFGMLDLATHPPGSRTKTYKFKREGFVPYKPNE
RVRQNVAPPAEGEEKESDSGSEEKSES

*Figure 16a*

UniProtKB/TrEMBL Accession No. Q64T80 (Q64T80_BACFR)
*Bacteroides fragilis*
SEQ ID NO:55
MRIRIKTTSNEKILPFDYQGKLIGVIHKWLGNNELHDKISLYSFSWLLGGVMVDKKGYVFPNGAE
LLISFHEDQHLKKIIDSILLDPEIFYGLCVKDITIVGSPVFTEEPQRFFLASPIFIKRRIEEIMG
YKYYFYDDQESNQLMTETLKHKMREAGLPEDDTLRVEFDISYSKKKKKMV
TIHGIKSIANMCPVIIHGTQTSKRFAWVVGLGNGTGSGYGALI UniProtKB/TrEMBL Accession No. Q5LC91 (Q5LC91_BACFN)
*Bacteroides fragilis* (strain ATCC 25285 / NCTC 9343)
SEQ ID NO:56
MRIRIKTTSNEKILPFDYQGKLIGVIHKWLGNNELHDKISLYSFSWLLGGVMVDKKGYVFPNGAE
LLISFHEDQHLKKIIDSILLDSEIFYGLCVKDITIVGSPVFTEEPQRFFLASPIFIKRRIEEIMG
YKYYFYDDQESNQLMTETLKHKMREAGLPEDDTLRVEFDISYSKKKKKMVTIHGIKSIANMCPVI
IHGTQTSKRFAWVVGLGNGTGSGYGALI UniProtKB/TrEMBL Accession No. Q7MTE6 (Q7MTE6_PORGI)
*Porphyromonas gingivalis (Bacteroides gingivalis)*
SEQ ID NO:57
MRIELSIKADDSLVSFSHQHLLVGTLQKWLGENDMHGKSISYSFSRLNGGKLVSELNSILFADWA
NMFVSAHDPELIRRMLAGIRQDPEMFKSLCVREVTVIEDPDMTDREIFFPASPILLKRWREDNGF
DHIVYTDEAANALLTENLRKKLQAVGIDDPTATASFVPDQGKAKVMLIDYRGVKNKASWCPIRII
GNAETKLFAWNAGIGNSTGIGFGAIK UniProtKB/TrEMBL Accession No. B2RM89 (B2RM89_PORG3)
*Porphyromonas gingivalis* (strain ATCC 33277 / DSM 20709 / JCM 12257)
SEQ ID NO:58
MRIELSIKADDSLVSFSHQHLLVGTLQKWLGENDMHGKSISYSFSRLNGGKFVSELNSILFTDWA
NMFVSAHDPELIRRMLAGIRQDPEMFKSLCVREVTVIEDPDMTDREIFFPAGPILLKRWREDNGF
DHIVYTDEAANALLTENLRKKLQAVGIDDPTATASFVPDQGKAKVMLIDYRGVKNKASWCPIRII
GNAETKLFAWNAGIGNSTGIGFGAIK UniProtKB/TrEMBL Accession No. Q3VVR7 (Q3VVR7_PROAE)
*Prosthecochloris aestuarii* DSM 271
SEQ ID NO:59
MRITLQLSHRSRHLTLPVNINHLVSSLIYNIVSNSSSEFAEKLHEQGYRLEKRTFKLFTFSPLIP
AGHRRWRMNGDGTMTTDAQSVSLLISSGKAEFVEHLVVGLLHQPLVQIGAQRFRVETVKKLDPPQ
LSDDMACIMMSPLVCSAKRDGDKYPRFLLQDDEEFERVLLENLLGKYEAMHGKPYEGRAELHFDV
AKEYIERRNGAITKLITLKEGSPDETKVRGTLAPFRLRVARPLMEVGYDCGFGGLNAQGFGMVKM
SNLTS

*Figure 16b*

UniProtKB/TrEMBL Accession No. B3QT90 (B3QT90_CHLT3)
*Chloroherpeton thalassium* (strain ATCC 35110 / GB-78)
SEQ ID NO:60
MRLYLKLSKNTDPVPFEHNSVLAGIFHKWVNDAEIHDSLSLYSFSWLRGGGVNNNNLDFPKGGYW
FISIYDSETLMKIIKQIQINPNIAYGMTVKEVVIFETPEFSSEQRFMLATPIFIKRTMDKKSIHY
LYFDNESDKLMTETLKTKLKKAGINDESLKISFDRSYDKAKVKLISYKGIKNKANLCPVIITGKP
ETLAFAWNVGIGNSTGIGFGALL UniProtKB/TrEMBL Accession No. B3QWN9 (B3QWN9_CHLT3)
*Chloroherpeton thalassium* (strain ATCC 35110 / GB-78)
SEQ ID NO:61
MRIKIVLKQRRKVEELPINTGYLIASSIYHTLSLASESYATDLHEIGYGKQGERRHFKHF
TFSNIQFPKKEIHKEKIISYSNYIFFMISSPKEEFLQNLVMGLFQDGLFRIAQSYFEKELIETLP
EPIFENKMSFSMMSPLTLSISENVENGVRRKHYLRAHDERFPILIRQNLMAKYESLTGENFGFDE
ADFQFEFDQAYIQKQEKKGRSIEKLITIAAGSEKQTRIKALECPFTITAHPELIKIGYECGFGDS
NSMGFGMVKEMK UniProtKB/TrEMBL Accession No. B3QRJ1 (B3QRJ1_CHLP8)
*Chlorobaculum parvum* (strain NCIB 8327) (*Chlorobium vibrioforme*
subsp. thiosulfatophilum (strain DSM 263 / NCIB 8327))
SEQ ID NO:62
MRITLELSHRRSFVTVPINHSSLISSLIYNVIDRSSSEYAERLHEQGYRLENRAFKLFTFSPLNP
GHHRKWVMHENGTMSTGEKRLYLTISSPKEEFIEHLILGLLHEPFVSVGKERFRVETVRKLDAPL
FSGDMRFVMLSPLVCATKSEADQYPQYLFPGDPDFKRVLVANLCRKYEVLHGKPIACDENDVMFE
LDRDYVAKVHGKVQKLITLKEGRSDESKVKGTLAPFRLVAPTELIEVGYECGFGEKNAQGFGMVK
AIN UniProtKB/TrEMBL Accession No. A1BI29 (A1BI29_CHLPD)
NCBI GI No. gi:119357836
*Chlorobium phaeobacteroides* (strain DSM 266)
SEQ ID NO:63
MRITLELSHRNSSITLPINNSYLLSSLIYNIVDKSSSEYAGRLHAQGYRLQNKAFKLFAFSPLCP
ANRRKWEMQDDGTMSTRERVLHFTISSPKSEFIEHLVVGLLHEPYVFVGRERFRVECVRRLDCPE
ISGDMRFIALSPVVCATKHAGDLYAQYLFPGDDDFERVLFDNLCRKFEALHGRRFDGDNGNFHFT
LDQDYVVRKNGKVQKLITIKEGKPDETRVKGLLAPFRLVAPAELMEVGYECGFGERNSQGFGLVK
VDDCVRC UniProtKB/TrEMBL Accession No. B3EFZ8 (B3EFZ8_CHLL2)
*Chlorobium limicola* (strain DSM 245 / NBRC 103803)
SEQ ID NO:64
MRLKLTLRQQRPVERIPLNHSHHLAAVIYSTLSKSSSEFATVLHDKGYAPEGSRQKFKYFTFSSL
QIPIRTIDSGEIVSRSRQITFYLSSPKEEFLQHLILGLFAEGSLRIHNAVFSKECIEKLPEPEWT
ENMTFSMLSPLAVSVYRDPSAGMNTKEYLRYDDSRLSDMLLHNLQAKYRGLFGCEPPENDIPFSV
RFEEAYLKRVREKGRSVEKLITIKDYSGKETRVKAIQCPFTVTGDPELIKVGYECGFGENNPMGF
GMVKVS

*Figure 16c*

UniProtKB/TrEMBL Accession No. Q3VQH0 (Q3VQH0_9CHLB)
*Pelodictyon phaeoclathratiforme* BU-1
SEQ ID NO:65
MRITLELSHRKRTVTLPINNSHLISSLIYNIVDKSSSEYAERLHDQGYRLQNRAFKLFTF
SPLYPGNRHKWVMHENGTMSTADALLHVTISSPKEEFVEHLVIGLLQEPYVWVGNERFRVETVRK
LDQPELSDDMEFVMLSPLVCTTKGEADHYPQYLYPGDPEFERVLLENLCRKYQVLHGRSFVCESG
QFGFAIDEAYVERMQGKVQKLITLKEGRSDETKIKGTLAPFRLRAPRELMEVGYACGFGEKNSMG
FGMVKVDEA UniProtKB/TrEMBL Accession No. Q72GC1 (Q72GC1_THET2)
*Thermus thermophilus* (strain HB27 / ATCC BAA-163 / DSM 7039)
SEQ ID NO:66
MVLAALVLVLEGEGLPEPLGLRGFFYGLLREVAPEVHDQGENPFALGFGGREGASWARVSLLVEE
LYARLAPRLYALEGEEVRLGPPFRVRAVLQEGHPWAGVSTYPRLFQGPPSRDLALRFASPTFFRR
KGVHYPVPEPRLVLESLLRRLEAFGPLKAPEGVREALLERTTVRSLEGRTLPARTEVDTAGFVGR
VVYHLPRATEEEALWLSALGRFAFYSGVGAKTSLGYGRARAESA UniProtKB/TrEMBL Accession No. Q745V3 (Q745V3_THET2)
*Thermus thermophilus* (strain HB27 / ATCC BAA-163 / DSM 7039)
SEQ ID NO:67
MPQAVVLELVGEKPPLYPARYAHGLFFALLSRVSPELAQKLHEAPRKPFTLAPLPRAGPEGATLK
GTLRLRLTTLDDGLFAPFLRALLEAAPDGLPLGDSSYRLARVLATREGHPLAGATSWEELKEAPK
REKVTFRFLTPTVFATSKPGGRTRYTPLPDPRLIAGSLLDKWQAHSPFPYNPKEEAALRGLFELD
LEVAGFRNLRFHRVQAGKGFFPGFTGEMTLRLWSQSLEAREALGRLHALAFFSGVGAKTPYGMGL
AVPL UniProtKB/TrEMBL Accession No. Q53VU8 (Q53VU8_THET8)
*Thermus thermophilus* (strain HB8 / ATCC 27634 / DSM 579)
SEQ ID NO:68
MPQAVVLELVGEKPPLYPARYAHGLFFALLSRVSPELAQKLHEAPRKPFTLAPLPRAGPEGATLK
GTLRLRLTTLDDGLFAPFLRALLEAAPDGLPLGDSSYRLARVLATREGHPLAGATSWEELKEAPK
REKATFRFLTPTVFATSKPGGRTRYTPLPDPRLIAGSLLDKWQAHSPFPYNPKEEAALRELFELD
LEVAGFRNLRFHRVQAGKGFFPGFTGEATLRLWSQSLEAQEALGRLHALAFFSGVGAKTPYGMGL
AVPL UniProtKB/TrEMBL Accession No. Q5SM65 (Q5SM65_THET8)
*Thermus thermophilus* (strain HB8 / ATCC 27634 / DSM 579)
SEQ ID NO:69
MVLAALVLVLEGEGLPEPLGLRGFFYGLLREVAPEVHDQGENPFALGFGGREGAAWARVSLLVEG
LYARLAPRLYALEGEEVRLGPPFRVRAVLQEGHPWAGVSTYPRLFQGPPSRDLALRFASPTFFRR
KGVHYPVPEPRLVLESLLRRLEAFGPLKAPEGVREALLERTTVRSLEGRTLPARTEVDTAGFVGR
VVYHLPRATEEEALWLSALGRFAFYSGVGAKTSLGYGRARAESA

*Figure 16d*

UniProtKB/TrEMBL Accession No. O66560 (O66560_AQUAE)
*Aquifex aeolicus*
SEQ ID NO:70
MRVKAYLEVPKEISIFYRRSFLSLIKKALEKEDENYAKDLFQKKNFKPFTFCVFFENIRINGEIL
ENNGKAIMTVSSGSPDFFHRFYNGLKKLREYNGRYTNGNIKVKKVLMCEEEQITK
PRQTFRTLSPIVVINRDKKPVLPSKLGNRNDDFILYDDGAFTQELRYSLKCIFNGLPELKFEHQE
GKKSVVKHVVGNRENEKVIKIVAYQGVFTLEGDPYVLNEVYKYGLGFRRYQGFGCLELVKES UniProtKB/TrEMBL Accession No. O66704 (O66704_AQUAE)
*Aquifex aeolicus*
SEQ ID NO:71
MRFLIKMENLKEEPAKVRLDYRSRFISLLKSVLGEEYYSNHKIKPFTFAVFFGKEAKISN
GYIENVRTINFRFSSGDFLTIAKFYNGILQLKKNQYIHPIGTGKFKIIDFRPEKEREIIGFFKTL
SPIVIERIGSKPKDSPEERYITPDEESFEESLVENIYRRYIAIMGSEPQFSKFKFIPVKVKKEYV
RHYGGIVKTFIGKFKIETDSKDLLEFIYKYGLGVRTGQGFGYLEVEDEKRTSKNINI UniProtKB/TrEMBL Accession No. A8UTR0 (A8UTR0_9AQUI)
*Hydrogenivirga* sp. 128-5-R1-1
SEQ ID NO:72
MRFLLKLKSVSDAPVRVGIDYRRRFISLLKRILEDEYDKVKTRPYTFAVYFGKEAKITKDFIEGI
RHINFRFSTGDSILAVKFYNGALALKKQKADHAIGEGRFAVEWIRQEEEKDPTGVYRTLSPVVVE
RMGFSSPKPTERYIIPSEEGFEESLLENILRRYRDIRGTDLKVNRFSFEGLKTKEEFIKHYGGYL
RGFIGKFKIVSDSQELLRFIYQYGLGLRTGQGFGYLEVEDGKA UniProtKB/TrEMBL Accession No. A8UUS5 (A8UUS5_9AQUI)
NCBI GI No. gi:163782737
*Hydrogenivirga* sp. 128-5-R1-1
SEQ ID NO:73
MIVKINLIGEEAIALPKSYNHILQAFFYSNMDPVLSKFLHDIGFTHGKRRFKLFTFSKVIGKITR
RDKRRGFVFFSPDVTLYFASPLIDIVSSSVKTFLKRGNLFLGRNTVSLSSIELVKPEVDGEMTVR
CLSPITVYRTPKGEKRFQYLSPWQDEFYELLRKNLVKKYELVYSKSYKGELEIEPVKVIEGYRKK
VLYRGTLVEAWEGYYKLKGNEDMLRLALEAGLGAKNSQGFGMVERVL UniProtKB/TrEMBL Accession No. A8UXX4 (A8UXX4_9AQUI)
*Hydrogenivirga* sp. 128-5-R1-1
SEQ ID NO:74
MPIRCSVCFVPEKPISPEVLKPKYVHGIFFSLLEEGLAERMHRGRVKPFALRFQRLMRAE
EELDRFFLEVSFLQEELFPSFLSSLILRESQPTINGLSLRYLKKPYIKEENVKSYSRIYEEAQPR
DTIVLDFLTPTSFKRGSFDYPLPEPRLIFRGLIRKWQIFSDLKIDLDLREVVDNHIHIAGAWIRT
RKMELSDRAKFTGFTGRVVLYADVRKEAVLKWLNALAAFGEFAGVGRKTTMGFGAVRVGEPEPDE
VSE

*Figure 16e*

UniProtKB/TrEMBL Accession No. A8UZ56 (A8UZ56_9AQUI)
*Hydrogenivirga* sp. 128-5-R1-1
SEQ ID NO:75
MRMKIYIKTNKTPILYKHKVMSLLKEALKKSDKDYKDFLYKGKITKPFSFNLVLPPKRKPIKAKI
QIDENFTIEDTVFEIEEGYLSLFVSALDYRFLISLFNGLKRLHTFNFSSDTNMLVDGEKITWEIK
KVSPINEKPIKSRHIVFKTNSPIVVENGNDKPVLFSDKNFEYHLNEITDRILKSPHIKGKGLEEP
LKFKPIKMNKQVIKHTLKAFREKTGKPIMYLTGNSGIFKLSGHPKDLEILYKIGIGNRTGQGFGM
VEVLG UniProtKB/TrEMBL Accession No. B2V8M9 (B2V8M9_SULSY)
*Sulfurihydrogenibium* sp. (strain YO3AOP1)
SEQ ID NO:76
MRVKIPITTEKVPIIFRQRVLAFIKEALAQADKDYKESMYSVRMPKAYTFNLVFDRTNPKEEEIS
LDEKFKIKDKVFYQDRPVFLYISSNDYQFLINLFNGMKKIKIFDFNKFDNIYWQVGKPVILREKI
IFNDEIIFKTNAPFIIETKDDRPVVFSDENFQTELNNVMERIFRKLDNRG
LKQPLEFYPIKMKKEVIKHTLRGFREKTGKPIMYITGNSGIFRLKGHPEDLQTIYQIGLG
NRTGQGFGMVST UniProtKB/TrEMBL Accession No. A0H269 (A0H269_9CHLR)
*Chloroflexus aggregans* DSM 9485
SEQ ID NO:77
MPQAIVFTLRPAGAGRAPGNLSRAAHAAVLRLIQRADPQLAARIHDDDGRKPLTVSNVWGLGGGP
SVLVDPERDYHLRVTLLSTELEQIAVEWTPERIGALELDGLPWRVIARADTVAEHPWANRADYQE
LAAPLLRRPDRLPNTWTLEFAAPVTFRQRGMTMPLPLPDLVFGSLLEQWNASAELALPDEVRRYA
TECLAISRFDLRSVAVPTSGGAIQIGALGRCTYRAMTGDRYWRACIDVLAAFAFYSGVGAGTARG
FGQTRLVPAPHPEPNRSTTNGDTLRD UniProtKB/TrEMBL Accession No. A9WEP3 (A9WEP3_CHLAA)
*Chloroflexus aurantiacus* (strain ATCC 29366 / DSM 635 / J-10-fl)
SEQ ID NO:78
MPQAIVFTLRPLTTAQVAGNLSRAAHAAILRLIQQADPALAARIHDDNGRKPLTVSNIWGLAGEP
KVIVDPARDYHLRVTLLSAELEQIATDWTPAALAPLDLDGLAWRITARADNSAEHSWAGRATYQE
LAQPLLSRPNQLPSVWTFQLASPTTFRQRGLNVPLPLPDLVFGSLLEQWNASSELALPDEVRRFA
AECLAINRYDLRSVASPTSGGVIQIGAVGRCSFRAINPDRYWRACIDVLARFAFFSGIGAGTTRG
FGQARLLTKTDQPRQREAVDNGDTLSD UniProtKB/TrEMBL Accession No. B2QTP1 (B2QTP1_9CHLR)
*Chloroflexus* sp. Y-400-fl
SEQ ID NO:79
MPQAIVFTLRPLTTAQVAGNLSRAAHAAILRLIQQADPALAARIHDDNGRKPLTVSNIWGLAGEP
KVIVDPARDYHLRVTLLSAELEQIATDWTPAALAPLDLDGLAWRITARADNSAEHSWAGRATYQE
LAQPLLSRPNQLPSVWTFQLASPTTFRQRGLNVPLPLPDLVFGSLLEQWNASSELALPDEVRRFA
AECLAINRYDLRSVASPTSGGVIQIGAVGRCSFRAINPDRYWRACIDVLARFAFFSGIGAGTTRG
FGQARLLTKTDQPRQREAVDNGDTLSD

*Figure 16f*

UniProtKB/TrEMBL Accession No. A9AX64 (A9AX64_HERA2)
*Herpetosiphon aurantiacus* (strain ATCC 23779 / DSM 785)
SEQ ID NO:80
MLAQPELIACVLELTATHGTQLERTQGHRAHALFLHLMQESDPVLAEQLHAASQTKPWTVTPLPQ
QARRLHNGETYPLRIAFLQASLYWPFAQTFLQRPNRQLRLGSSNFNLQAIHTTKQHSPWAGVSSW
QSLIDQAQPTDEISLWFATPTCFKLGRDRQGKQRVGLIPDGQSVFQSLLRRWNAFAPTPLASPEQ
IEQLDIQIKRYQLRTEMLHAQDKQLGFMGKVSYKLDGDAHERRILATLADAALYLGIGAKTTQGM
GLVQRISTQQPEQA UniProtKB/TrEMBL Accession No. A8F3P6 (A8F3P6_THELT)
*Thermotoga lettingae* (strain ATCC BAA-301 / DSM 14385 / TMO)
SEQ ID NO:81
MRLEIVFKTANSFIPINYQYMLCSFVYKRLKYTDENFASFLHEEGFNGFRMFTFSQLFFE
NSHVKNGSIIISEGKGKWYISSLSEDFIRNFFSSIIENPFIELEGVLFNILQVRVLDEPKITDQM
KFILISPLVVSIPVENQGKLSHKYLTPEDDFFQNAINANLIKKYSAFFGKEISSKVYIQPDWNYI
QRKGRITKLIQIKNTFVRGTVFPFLITGDPGLIKVGYEAGFGEKNSLGFGMVKVCRNDNNLNF UniProtKB/TrEMBL Accession No. A5ILM9 (A5ILM9_THEP1)
*Thermotoga petrophila* (strain RKU-1 / ATCC BAA-488 / DSM 13995)
SEQ ID NO:82
MRIFFRIFFKDNSQEVFPVDYRRIFMSVLKRVYEGTPFEEIVLSHDRIPKPYVFSVGFRR
IKEISGDSIMFESPVFFNFSSSIPQMIGYLYNHIDRIKSFFKGTEILVDLPIPKMITSEKVNFKI
LGSAVLTRSEKDRYYLNPEDDDFEEALNHSLKVRLDLLKDIFEKFGVKAPGFKPVNIVSKDLKKV
PVKHYGGVLEAFSGTITLSGNLNILNFLYENGLGVRTGQGFGMLKVVKEWR UniProtKB/TrEMBL Accession No. A5ILP0 (A5ILP0_THEP1)
NCBI GI No. gi:148270229
*Thermotoga petrophila* (strain RKU-1 / ATCC BAA-488 / DSM 13995)
SEQ ID NO:83
MRLKVSFQAMESTIPLNYNYFLSSFIYKRLASQNENFARFLHEKGYGKRFKFFTFSQLFF
ENSRVSGEKILIFPGKGWWYISSPVIEFVRYMFSSLSEDPVIRVEKTEFIVKSIDIENSLPDQSE
YHFVMLSPLVVSVPEENNGKLYHRYLHPEEEEFYEVFRKNLVKKYRAFYGKEPEG
TVEVIPDWDYIKSRQRITKRIKLKNAFVRAVVFPFKIRGEKKLVEIGYEAGFGEKNSMGF
GMVALKKYER UniProtKB/TrEMBL Accession No. Q9X2D4 (Q9X2D4_THEMA)
NCBI GI No. gi:15644558
*Thermotoga maritima*
SEQ ID NO:84
MRLKVSFQAMESTVPLNYNYFLSSFIYKRLASQNENFARFLHEKGYGKRFKFFTFSQLFFENSRV
SGERIFIFPGKGWWYISSPVVEFVRYMFSSLSEDPVIRVGKTEFIVKSIDIENSLPDQSEYHFVM
LSPLVVSVPEENNGKLYHRYLHPGEEEFYEVFRKNLMKKYRAFYGKDPEGTVEVIPDWDYIKSRH
RITKRIKLKNAFVRAVVFPFKIRGEKKLVEIGYEAGFGEKNSMGFGMVALKKYER

*Figure 16g*

UniProtKB/TrEMBL Accession No. B1LAK9 (B1LAK9_THESQ)
NCBI GI No. gi:170288802
*Thermotoga sp.* (strain RQ2)
SEQ ID NO:85
MRLKVSFQAMESTVPLNYNYFLSSFIYKRLASQNENFARFLHEKGYGKRFKFFTFSQLFFENSRV
SGERIFIFPGKGWWYISSPVVEFVRYMFSSLSEDPVIRVGKTEFIVKSIDIENSLPDQSEYHFIM
LSPLVVSVPEENNGKLYHRYLHPEEEEFYEVFRKNLMKKYRAFYGKDPEGTVEVIPDWDYIKSRH
RITKRIKLKNAFVRAVVFPFKIRGEKKLVEIGYEAGFGEKNSMGFGMVALKKYER UniProtKB/TrEMBL Accession No. A6LJX4 (A6LJX4_THEM4)
*Thermosipho melanesiensis* (strain BI429 / DSM 12029)
SEQ ID NO:86
MRIKVGFISIEDIILPVGFNKYIQALIYNLFSNSLRRFVHEEGFRSKRKFSLFCFSSILEKGQYF
KRMKVFNFGKNISFYISSPVTKLMENLVLNLLNGDKYFLGENDIYLSSVEVVYKEIAKDILKVNA
LTPIEVHQTYKENGRNKTKYFAPFEREFSKLINLNLKSKWEAFYKENLDRDIEIISLGNMNKSVV
YYGFGDKKYVVEGWKGKFLLKGEPSVLAFAYDAGLGSKNSQGFGFIE UniProtKB/TrEMBL Accession No. A6LNL8 (A6LNL8_THEM4)
*Thermosipho melanesiensis* (strain BI429 / DSM 12029)
SEQ ID NO:87
MRLRVKFNFDRLNLPIHYNHILHATILNMINNEEFRKFIHDRGYKFEKRVFKLYTFSRLI
GRFEIDTEIKEINFFDNVYLYISSYDDNFCYYIMEKLLTFENIRMGKNILKVEKIETINFMPTDT
LKVVTRSPVTVYSTYIDETGKKKTLFYHPDDFKFKEIVEKNIIKKYRALHNREPQGRIEVKHVGK
SPKFVLVFYKGFKIKGWMTAFDLIGDPELVKIAYETGLGSKNSQGFGFIE
QIK UniProtKB/TrEMBL Accession No. A7HLK3 (A7HLK3_FERNB)
*Fervidobacterium nodosum* (strain ATCC 35602 / DSM 5306 / Rt17-B1)
SEQ ID NO:88
MRGILTLKLDKPLTLPIHYNHILQAAILNLLSDENYSKFIHDTGFQFGKRRFKMFTFSRLEGKFS
IDIERKTITYFERAYLHISTIEDKFIEYVVNNLLLEGLDIKGERIHVDKIELKSNTTNFGKIITK
SPIVAYSTFELNGRKKTYYYNPKEKEFQEILANNLIKKYIAYFEKEPKNRYFEITPVSNLKESIV
IYKGTVIRGWNGIFQINGSDELINIAYYTGLGAKNSQGFGCFEFI UniProtKB/TrEMBL Accession No. A7HMV7 (A7HMV7_FERNB)
NCBI GI No. gi:154250072
*Fervidobacterium nodosum* (strain ATCC 35602 / DSM 5306 / Rt17-B1)
SEQ ID NO:89
MRLYIKFSFEQLELPTEYNNILQGFVYNIISEEKYRKFLHDKGYQLGKRTYKLFSFSRLL
GKFELNKENKTIKFLNEAKLIISSYDTLLAEFIIEKVGTFDSLRIGRNIVRPEKIEIFEFPQTQK
IVVSTKSPITVYSTIEKDDGKKFTKFHSPNEDDFIRILKENLLRKYQTIHETPFKGELHIENIAE
KPKKVILQYKNRKLDGWITVLKLEGDYEILKIAYDTGLGSKNSAGFGCIELVDKVLT

*Figure 16h*

UniProtKB/TrEMBL Accession No. A9BGZ0 (A9BGZ0_PETMO)
*Petrotoga mobilis* (strain DSM 10674 / SJ95)
SEQ ID NO:90
MRLNVQFSLNSLILPLNYNHIIQAFILDLIDNAEYRNFIHNEGFSYNKRKYKLFSFSRLSGKFSL
NQKDKTIEFSDNVSLKISSHDKNLIQYCADSLLFKDDFELLGQKIHVEKLEYDDLEIKSDKIKVK
TLSPITIYSTIVQNSSKKTIYFSPSEDQFSKLIKENLIKKYLAYYDSYLSKKISNDEFVIKEADQ
KGSKMIITKYKNFIIKGWHGVFEIQGNPSLLKIGYDSGFGAKNSQGFGLVEVI UniProtKB/TrEMBL Accession No. A9BIX0 (A9BIX0_PETMO)
NCBI GI No. gi:160903200
*Petrotoga mobilis* (strain DSM 10674 / SJ95)
SEQ ID NO:91
MVIKLVFGALEGDKIDLPVHYNRPLQGLFYYLMSDTVPKYHDLGTRSEDKKLKLFTFSRIYPYSS
FKVENRRMIFKGLFNIYFASPIDKLVEAVLHSLNEQKVVRIEKNYFTLRKYEVIQNEVDEEMLVK
TLSPITAYSTIVLPNGNRYTHYFSPYSSDFKKLIEENLKRKASALGIVIKNNNFYIEPYGITEKN
EKLLFYKDIIIKGWTGYFILKGETQLLKLALNSGLGAKNAQGFGMILSVEKNSIRERSFLELAEE
G UniProtKB/TrEMBL Accession No. Q1AZD0 (Q1AZD0_RUBXD)
NCBI GI No. gi:108803123
*Rubrobacter xylanophilus* (strain DSM 9941 / NBRC 16129)
SEQ ID NO:92
MRLKIVLSGERGHLHLPLQYNSAVQGFIYANLSRTLADRLHNRGHTYGQRRFKLFTFSRLFGRRE
AGEGGISFRGPVRLYLGSAEAEVLGSLAEHLLRRPETRLGKTRCLVEEVGVEPEPEVEDGRPLLV
RALSPITAYTTLATPEGRKKTYYYSPQEEEWGVAILENIKRKVAALGWAADAEEDLREAYVRPRR
VRSSDQKVLRFKGTVVKGWMGLYELKMPEPYFRLAYDTGLGSKNSQGFGMIALPHPTEGRKR UniProtKB/TrEMBL Accession No. Q7TXS3 (Q7TXS3_MYCBO)
*Mycobacterium bovis*
SEQ ID NO:93
MAARRGGIRRTDLLRRSGQPRGRHRASAAESGLTWISPTLILVGFSHRGDRRMTEPLSRLTLTLE
VDAPLERARVATLGPHLHGVLMESIPADYVQTLHTVPVNPYSQYALARSTTSLEWKISTLTNEAR
QQIVGPINDAAFAGFRLRASGIATQVTSRSLEQNPLSQFARIFYARPETRKFRVEFLTPTAFKQS
GEYVFWPDPRLVFQSLAQKYGAIVDGEEPDPGLIAEFGQSVRLSAFRVASAPFAVGAARVPGFTG
SATFTVRGVDTFASYIAALLWFGEFSGCGIKASMGMGAIRVQPLAPREKCVPKP UniProtKB/TrEMBL Accession No. A1KMG6 (A1KMG6_MYCBP)
*Mycobacterium bovis* (strain BCG / Pasteur 1173P2)
SEQ ID NO:94
MAARRGGIRRTDLLRRSGQPRGRHRASAAESGLTWISPTLILVGFSHRGDRRMTEHLSRLTLTLE
VDAPLERARVATLGPHLHGVLMESIPADYVQTLHTVPVNPYSQYALARSTTSLEWKISTLTNEAR
QQIVGPINDAAFAGFRLRASGIATQVTSRSLEQNPLSQFARIFYARPETRKFRVEFLTPTAFKQS
GEYVFWPDPRLVFQSLAQKYGAIVDGEEPDPGLIAEFGQSVRLSAFRVASAPFAVGAARVPGFTG
SATFTVRGVDTFASYIAALLWFGEFSGCGIKASMGMGAIRVQPLAPREKCVPKP

*Figure 16i*

UniProtKB/TrEMBL Accession No. P71628 (P71628_MYCTU)
*Mycobacterium tuberculosis*
SEQ ID NO:95
MAARRGGIRRTDLLRRSGQPRGRHRASAAESGLTWISPTLILVGFSHRGDRRMTEHLSRLTLTLE
VDAPLERARVATLGPHLHGVLMESIPADYVQTLHTVPVNPYSQYALARSTTSLEWKISTLTNEAR
QQIVGPINDAAFAGFRLRASGIATQVTSRSLEQNPLSQFARIFYARPETRKFRVEFLTPTAFKQS
GEYVFWPDPRLVFQSLAQKYGAIVDGEEPDPGLIAEFGQSVRLSAFRVASAPFAVGAARVPGFTG
SATFTVRGVDTFASYIAALLWFGEFSGCGIKASMGMGAIRVQPLAPREKCVPKP UniProtKB/TrEMBL Accession No. A2VLF6 (A2VLF6_MYCTU)
*Mycobacterium tuberculosis C*
SEQ ID NO:96
MAARRGGIRRTDLLRRSGQPRGRHRASAAESGLTWISPTLILVGFSHRGDRRMTEHLSRLTLTLE
VDAPLERARVATLGPHLHGVLMESIPADYVQTLHTVPVNPYSQYALARSTTSLEWKISTLTNEAR
QQIVGPINDAAFAGFRLRASGIATQVTSRSLEQNPLSQFARIFYARPETRKFRVEFLTPTAFKQS
GEYVFWPDPRLVFQSLAQKYGAIVDGEEPDPGLIAEFGQSVRLSAFRVASAPFAVGAARVPGFTG
SATFTVRGVDTFASYIAALLWFGEFSGCGIKASMGMGAIRVQPLAPREKCVPKP UniProtKB/TrEMBL Accession No. A1QV97 (A1QV97_MYCTF)
*Mycobacterium tuberculosis* (strain F11)
SEQ ID NO:97
MAARRGGIRRTDLLRRSGQPRGRHRASAAESGLTWISPTLILVGFSHRGDRRMTEHLSRLTLTLE
VDAPLERARVATLGPHLHGVLMESIPADYVQTLHTVPVNPYSQYALARSTTSLEWKISTLTNEAR
QQIVGPINDAAFAGFRLRASGIATQVTSRSLEQNPLSQFARIFYARPETRKFRVEFLTPTAFKQS
GEYVFWPDPRLVFQSLAQKYGAIVDGEEPDPGLIAEFGQSVRLSAFRVASAPFAVGAARVPGFTG
SATFTVRGVDTFASYIAALLWFGEFSGCGIKASMGMGAIRVQPLAPREKCVPKP UniProtKB/TrEMBL Accession No. A4KK96 (A4KK96_MYCTU)
*Mycobacterium tuberculosis* str. Haarlem
SEQ ID NO:98
MAARRGGIRRTDLLRRSGQPRGRHRASAAESGLTWISPTLILVGFSHRGDRRMTEHLSRLTLTLE
VDAPLERARVATLGPHLHGVLMESIPADYVQTLHTVPVNPYSQYALARSTTSLEWKISTLTNEAR
QQIVGPINDAAFAGFRLRASGIATQVTSRSLEQNPLSQFARIFYARPETRKFRVEFLTPTAFKQS
GEYVFWPDPRLVFQSLAQKYGAIVDGEEPDPGLIAEFGQSVRLSAFRVASAPFAVGAARVPGFTG
SATFTVRGVDTFASYIAALLWFGEFSGCGIKASMGMGAIRVQPLAPREKCVPKP UniProtKB/TrEMBL Accession No. A5U6H7 (A5U6H7_MYCTA)
*Mycobacterium tuberculosis* (strain ATCC 25177 / H37Ra)
SEQ ID NO:99
MAARRGGIRRTDLLRRSGQPRGRHRASAAESGLTWISPTLILVGFSHRGDRRMTEHLSRLTLTLE
VDAPLERARVATLGPHLHGVLMESIPADYVQTLHTVPVNPYSQYALARSTTSLEWKISTLTNEAR
QQIVGPINDAAFAGFRLRASGIATQVTSRSLEQNPLSQFARIFYARPETRKFRVEFLTPTAFKQS
GEYVFWPDPRLVFQSLAQKYGAIVDGEEPDPGLIAEFGQSVRLSAFRVASAPFAVGAARVPGFTG
SATFTVRGVDTFASYIAALLWFGEFSGCGIKASMGMGAIRVQPLAPREKCVPKP

*Figure 16j*

UniProtKB/TrEMBL Accession No. A4X3N0 (A4X3N0_SALTO)
*Salinispora tropica* (strain ATCC BAA-916 / DSM 44818 / CNB-440)
SEQ ID NO:100
MRFYVDVAGPDAALPWRYVHGVAHAVVYSVIAEQSPALATQLHEGTWAPANSPRPVGISPPVFVG
ARAKPRAYMMSGKGRIWFGSPIPVLAAALLAGITSRRELRWGPVTLTIKGTQLEPTVDAESSTVL
ETRSPVLVKASGNRYLLPDDDGFVGALLANIRHKADLLGLPGDAEVQVVAAGPRRRFDVSGGIRI
GATATVRLDADPRLIAALREWGLGLSTIQGFGWVR UniProtKB/TrEMBL Accession No. Q0REA0 (Q0REA0_FRAAA)
*Frankia alni* (strain ACN14a)
SEQ ID NO:101
MNGGGVRFRVDLAADRSSLQWGDVFTPARALAYDLIRGQDPELAEELHERGYAGSPLRPLGISAP
QFRGAPKSRGVYATSADGSLWLGSPVPRVASALLAGIAGRQTLRWASLRLTLRGVQLEPTPDHQA
GEAVFSTRTPVLLKWEDRYIHPDHPHFAERLSHNLRHKADLLGLPADNDVDVLSAGPPRKFLVQR
APRHGSTAEVHIRANPALLDAVYDWGLGLGTNQGFWIR UniProtKB/TrEMBL Accession No. A8L910 (A8L910_FRASN)
*Frankia sp.* (strain EAN1pec)
SEQ ID NO:102
MRFRVDVGADKATIPWRDVFGPARAVAYELIRGQDADLAEELHGRGYAGSSLRPLGLSSPYFRGP
ARGHDVYRASKDGTVWFGSPVPRIAGALLAGLAGRRQLRWGSVELDVHGVQLESTPDHSSGETVF
STVTPVLARYEDRYIFPDHPAFVATLVHNLSHKADVLGLPNEVEFEVLSAGPPRKFFVQHTPRHG
CVVRARVHAAPALLDALYDWGLGLGTNQGFWIR UniProtKB/TrEMBL Accession No. Q1Q113 (Q1Q113_9BACT)
NCBI GI No. gi:91200631
*Candidatus Kuenenia stuttgartiensis*
SEQ ID NO:103
MPLDFCILKTQPNLKCVQYRLPLLSWCFMRLKISLLSDKEIILPKEFNAITQALIYRLIDRVPAQ
WLHEGGFKVENRSFKLFTFSSIIEKGRYQSSKELFIFPHMVSFYVSSPVFWILEQVAKNTVFSEK
LLFGKNLMNISSVEVIKDEDIKTNKIRVNALTPIETHSTLLKGDGTKKTYYYSPTESEYSTLINE
NLRKKWCAYHRKECPYSIKTEPVQMKYCRERIRSFKDTVIKGWTGHFWLEGEPEFLQFALAAGLG
SRNSGGFGFIEKVRERKDI UniProtKB/TrEMBL Accession No. Q5HK95 (Q5HK95_STAEQ)
*Staphylococcus epidermidis* (strain ATCC 35984 / RP62A)
SEQ ID NO:104
MINKITVELDLPESIRFQYLGSVLHGVLMDYLSDDIADQLHHEFAYSPLKQRIYHKNKKI
IWEIVCMSDNLFKEVVKLFSSKNSLLLKYYQTNIDIQSFQIEKINVQNMMNQLLQVEDLSRYVRL
NIQTPMSFKYQNSYMIFPDVKRFFRSIMIQFDAFFEEYRMYDKETLNFLEKNVNIVDYKLKSTRF
NLEKVKIPSFTGEIVFKIKGPLPFLQLTHFLLKFGEFSGSGIKTSLGMGKYSII

*Figure 16k*

UniProtKB/TrEMBL Accession No. A4IK09 (A4IK09_GEOTN)
NCBI GI No. gi:138893955
*Geobacillus thermodenitrificans* (strain NG80-2)
SEQ ID NO:105
MRLTITMNGRQGPVSLPLHYQHLLQGLLYRSLESKQLATFLHEIGFRHEKRSFKLFTFSR
LFGRHEVDRVKKTIRFLDEFQWHIDTILPELTEQLGQQLLLRREIWLYDQPVEVKSVKMDKVEIR
QSTIEVAMLSPLTVYSTYETIDRRKKTHFFGPDDEVFPHLIELNFRHKYQAYYGVPPVERLSIQP
VHVHQRHRVVTLFKDMYITGWLGHYRLSSSPEQLTFLYHVGLGSRNSQGFGMFCLTGK UniProtKB/TrEMBL Accession No. B1SSR3 (B1SSR3_9BACI)
*Geobacillus sp.* WCH70
SEQ ID NO:106
MRISCSFETDKIPIHYRMAMVSIIKEALRISDEEYYHRLYQRGQRTKPFVFSTYLKNFHI
INHEIELDGITLTVSSPDHEFLLNLYNGLQKNQAFSYKDYHFVKKKIAVVKEKQVTSPSVVFRTL
SPILIEDEKGNPIAPDDASYEGHVNYVADMILSQYRGKGLYAPLSIKPIYFKKVVVKESNHEFAA
THGNDEYLYFTAYHGLFAITGHPGDLQLLYQLGLSKRRNQGFGQLEIEEVRG UniProtKB/TrEMBL Accession No. B1ST90 (B1ST90_9BACI)
*Geobacillus sp.* WCH70
SEQ ID NO:107
MRLTIVMSGRDNPVTLPLHYQQQLQGLLYHSLRNPKFSQFLHEVGFRKEKRSFKLFTFSRLYGPH
QLNFERKTITFYEEFYWHVGTVLPELTQELGEYLLLHPDVQIGGQPVEVQRIDVEKRDIEGEEIE
IEMLSPLTVYSTYETVDGSKKTQFFSPYDEVFSHLVELNFRNKYEAYYGVPPKERLFIEPIRVTE
KHKVVTIFKGFYITAWLGHYRLRSSPGNLTFLYRVGIGGRNSQGFGMFRLLSER UniProtKB/TrEMBL Accession No. A7GQ92 (A7GQ92_BACCN)
*Bacillus cereus* subsp. *cytotoxis* (strain NVH 391-98)
SEQ ID NO:108
MRLHIKLQTNRFPISYRMMMVSFIKEALKLSDAAYFQQIYQESKANRPFSYGVYIHDYKLNATEF
HIKGYVGLTITSPDAQFMLHFYNGLMKMNDFRYKGFSLKRMKVQMVNSADINQNHVYFKTLSPLL
IRDKHAKPIFIDDDKFEKELNYISDTVLKEFRGYGLKQPLIFTSKNMKKVVVKEKIHSDHDTLFF
TGYHGIFSLQGAVEDLKILSEIGLGFRSSQGFGAVEVV UniProtKB/TrEMBL Accession No. A2U7V5 (A2U7V5_BACCO)
*Bacillus coagulans* 36D1
SEQ ID NO:109
MKLIVTFSANDNALKLPLNYQQMLQGFIYRNLLDPDFSRFLHNHGFLNGKRIFKLFVFSQLFGKY
SLLKETKEIVFKGPVTWHVGSVVPEFIKGFGRSLLTSGHLELNGQEMKVEEVTYRQDTPESEKCR
IRMLSPITVYSTYQNQNGKKITQYFDPKDPAFTYLVEENIKKKYAAFYQKDTQDLFFKIQPVRVT
EKDKRITRYKGFIINGWGGIYVIEGSPNLLSFAESTGLGSKNSQGFGMFEVIHQQL

*Figure 16C*

UniProtKB/TrEMBL Accession No. Q4EVR3 (Q4EVR3_LISMO)
*Listeria monocytogenes* str. 1/2a F6854
SEQ ID NO:110
MRLKINCDFDSKIISKDFQSKVVSLFKAGIMKSSPERYENLFGGNKHKQYTFSVYLPKPQNKGAE
IQLNEANCIINFSTGDAETGIIFYNALMSLRGSKVLFGAGNHITVKNIQIVPEKK
IIGKRTILRTLSPVVSRDHNRETFKNWFYSFEDEEFEPTLKRNMLPYLMDAFGEQARYDLEKLKI
TPISMKKVVVYCHEIHIESSVGIFELEAEAYLQKYLVENGIGTMTGSGFGMIEQF UniProtKB/TrEMBL Accession No. A3FY01 (A3FY01_LISMO)
*Listeria monocytogenes* J0161
SEQ ID NO:111
MRLKINCDFDSKIISKDFQSKVVSLFKAGIMKSSPERYENLFGGNKHKQYTFSVYLPKPQNKGAE
IQLNEANCIINFSTGDAETGIIFYNALMSLRGSKVLFGAGNHITVKNIQIVPEKK
IIGKRTILRTLSPVVSRDHNRETFKNWFYSFEDEEFEPTLKRNMLPYLMDAFGEQARYDLEKLKI
TPISMKKVVVYCHEIHIESSVGIFELEAEAYLQKYLVENGIGTMTGSGFGMIEQF UniProtKB/TrEMBL Accession No. A4DBL9 (A4DBL9_LISMO)
*Listeria monocytogenes* FSL N1-017
SEQ ID NO:112
MRLKINCDFDSKIIPKDFQSKVVSLFKAGIMKSSPERYENLFGGNKHKQYTFSVYLPKPQNKGAE
IQLNEANCIINFSTGDAETGIIFYNALISLRGSKILFGAGNNITIKNIQIVPEKKIIGNRTILRT
LSPVVSRDHNRETFKNWFYSFEDEEFEPTLKRNMLPYLIDAFGEQARYDLEKLKITPISMKKVVV
YCHEIHIESSVGIFELEAEAYLQKYLVENGLGTMTGSGFGMIEQL UniProtKB/TrEMBL Accession No. A4DS64 (A4DS64_LISMO)
*Listeria monocytogenes* F6900
SEQ ID NO:113
MRLKINCDFDSKIISKDFQSKVVSLFKAGIMKSSPERYENLFGGNKHKQYTFSVYLPKPQNKGAE
IQLNEANCIINFSTGDAETGIIFYNALMSLRGSKVLFGAGNHITVKNIQIVPEKK
IIGKRTILRTLSPVVSRDHNRETFKNWFYSFEDEEFEPTLKRNMLPYLMDAFGEQARYDLEKLKI
TPISMKKVVVYCHEIHIESSVGIFELEAEAYLQKYLVENGIGTMTGSGFGMIEQF UniProtKB/TrEMBL Accession No. A3FZX3 (A3FZX3_LISMO)
*Listeria monocytogenes* J2818
SEQ ID NO:114
MRLKINCDFDSKIISKDFQSKVVSLFKAGIMKSSPERYENLFGGNKHKQYTFSVYLPKPQNKGAE
IQLNEANCIINFSTGDAETGIIFYNALMSLRGSKVLFGAGNHITVKNIQIVPEKK
IIGKRTILRTLSPVVSRDHNRETFKNWFYSFEDEEFEPTLKRNMLPYLMDAFGEQARYDLEKLKI
TPISMKKVVVYCHEIHIESSVGIFELEAEAYLQKYLVENGIGTMTGSGFGMIEQF UniProtKB/TrEMBL Accession No. A3CNA0 (A3CNA0_STRSV)
*Streptococcus sanguinis* (strain SK36)
SEQ ID NO:115
MKKIRLHLSKVSLKDDDLVCKLQGFLMEKLSDDFASFLHQQETNPYSMNLRSEREESIWTVNLLS
EEAEQQILPQLLSLEMIKLETYSEEILVKNIEIQSLSSQSLLEVFQGDEASHLIS
LNFYTPTTFKRQGQFVLFPDTRLIFQSLMQKYSRLVEGKAEIEEETLEFLAEHSQISSYRLKSHY
FPIHGRKYPAFEGRVTIRIQGASTLKAYAQMLLRFGEYSGVGAKCSLGMGGMRIEERKT

*Figure 16m*

UniProtKB/TrEMBL Accession No. Q5M4I8 (Q5M4I8_STRT2)
*Streptococcus thermophilus* (strain ATCC BAA-250 / LMG 18311)
SEQ ID NO:116
MKKLVFTFKRIDHPAQDLAVKFHGFLMEQLDSDYVDYLHQQQTNPYATKVIQGKENTQWVVHLLT
DDIEDKVFMTLLQIKEVSLNDLPKLSVEKVEIQELGADKLLEIFNSEENQTYFSIIFETPTGFKS
QGSYVIFPSMRLIFQSLMQKYGRLVENQPEIEEDTLDYLSEHSTITNYRLETSYFRVHRQRIPAF
RGKLTFKVQGAQTLKAYVKMLLTFGEYSGLGMKTSLGMGGIKLEERKD UniProtKB/TrEMBL Accession No. Q03KT3 (Q03KT3_STRTD)
*Streptococcus thermophilus* (strain ATCC BAA-491 / LMD-9)
SEQ ID NO:117
MKKLVFTFKRIDHPAQDLAVKFHGFLMEQLDSDYVDYLHQQQTNPYATKVIQGKENTQWVVHLLT
DDIEDKVFMTLLQIKEVSLNDLPKLSVEKVEIQELGTDKLLEIFNSEENQTYFSIIFETPTGFKS
QGSYVIFPSMRLIFQSLMQKYGRLVENQPEIEEDTLDYLSEHSTITNYRLETSYFRVHRQRIPAF
RGKLTFKVQGAKTLKAYVKMLLTFGEYSGLGMKTSLGMGGIKLEERKD UniProtKB/TrEMBL Accession No. Q2RHQ5 (Q2RHQ5_MOOTA)
*Moorella thermoacetica* (strain ATCC 39073)
SEQ ID NO:118
MVLPLDFRRHFISLIKTLAGTSALAARFTLEKPGYSPYVFSVEFNKIIDIDTRQREITARPPILV
TISTGLFDVMTTFSNGAIAMKGRETVLGLYLKDIYLLPLKQIQTGEQEFRIAGHAVFRGVRHYVD
GSDVRELEEAINTHLYKRYSFLIQQYHLDYHSRVSPVKVLGPPSYHKGVCFHYGGQLTTLQGRIH
LKSTPETLQFLYDFGLGIRTGQGFGLLEVGD UniProtKB/TrEMBL Accession No. Q3AA62 (Q3AA62_CARHZ)
NCBI GI No. gi:78044781
*Carboxydothermus hydrogenoformans* (strain Z-2901 / DSM 6008)
SEQ ID NO:119
MRALIKFEVRSKALLPYNYQHALTALIYRGLGVESAKLATFLHDIGFRKGKKTFKFFTFSPLSFT
NYKTTKEGIIVFPGTASFTVSSPLPEFIDYLTSGLWALRNFKIITLPVSIIEIAAIPLRNFTDEE
LFTLKSPLVLAIKSQEKATPTYLSYVEDKALYKEKLLNNLKNKYLVYYGCEPRIDYFDFAFDERH
FQTKLPTRLITYKDQKIRGLCAPFKIKTNPELISLGYYAGFGEKNSMGFGFVE UniProtKB/TrEMBL Accession No. Q3AA81 (Q3AA81_CARHZ)
NCBI GI No. gi:78043250
*Carboxydothermus hydrogenoformans* (strain Z-2901 / DSM 6008)
SEQ ID NO:120
MRIEVLLKPREKAVFLPFNYQYQITSAIYETIAKSSPEFARKLHDEGFGERRFKFFTFSQ
ILAKRKKLAPDGFWIIGECSLKISSPLYEFLLHLLNGLFKDHKFIIGREEFTVKGAFIRENPEIK
PGQTFVCLSPIVVSTLKEGYTKPYYIRYTEEPELFSEKIRQNLLRKFATYYGRLPVDDRLFFFFD
EEYLQKNKGTKLIHYRDQKILGYLAPFTVEGSAELIAFGYDVGFGEKNSMGFGCAEVK

*Figure 16n*

UniProtKB/TrEMBL Accession No. Q8R6W6 (Q8R6W6_THETN)
NCBI GI No. gi:20809011
*Thermoanaerobacter tengcongensis*
SEQ ID NO:121
MRITLEFTGEKNLILPIHYNYIVQGLLYDLMGDTDFAAFLHDVGFQYEKRRFKLFTFSRI
EGEFQIVEKPNGQKKIIIKPPFKFTVASPLEEVIIDISKNILKREYCHFNGQKFTLNSLNIENPP
IFKEKARIKFISPVVMYTTLRNGEKKYTYYYSPWDEKFSPLLLNNLVKKYELVYKIKPKNPHFKL
IPLTEKEDRRYSKVIKYKNVYVKGWMGIYDVETTPELLELAYYTGLGAKNSQGFGCFEIIG UniProtKB/TrEMBL Accession No. Q8R6W9 (Q8R6W9_THETN)
NCBI GI No. gi:20809008
*Thermoanaerobacter tengcongensis*
SEQ ID NO:122
MQLIVTFTASGPIFLPVHYGHLLQALIYNQMDNPTIRHYLHEHGFPLGKRHFKLFTFSRL
QGRELTYEKESKRLIFTPPLRLVICSPLDFLLQELGTGFLRQGKVRIGEAVLEVQNMSVG
AQQVLSTSIRVRMLSPLVVYSTLEKEGGDRYVYYYTPFEERFSQLVGDNLKKKYLIVHGNFPYSL
NFNIRPLRVREKDFKVTYFKNTIVKGWMGDYELEGEPKLLQLALDAGLGSKNSQGYGCCRLLEEG
KTYKGGEKSG UniProtKB/TrEMBL Accession No. B0K556 (B0K556_THEPX)
*Thermoanaerobacter sp.* (strain X514)
SEQ ID NO:123
MRITLEFVGEKNLVLPIHYNYIVQGFLYDLMGDSEFAAFLHDEGFQYEKRKFKLFTFSRI
EGEFKILTDSKGQKKISIKPPFKFTVASPLDEFIFDISKNALKKEYCHFNGQKFILNSLNIDNPP
VFKNKARIKFISPVVMYTTLKDGDIKYTYYYSPWDEKFSPLLLNNLLKKYELVYKIKAEDPYFKL
YPLSEKEDRRYSKMIKYKNVYVKGWMGIYDVESSPELLELAYYTGLGAKNSQGFGCFEIIG UniProtKB/TrEMBL Accession No. B0KB23 (B0KB23_THEP3)
NCBI GI No. gi:167036552
*Thermoanaerobacter pseudethanolicus* (strain ATCC 33223 / 39E)
SEQ ID NO:124
MRITLEFVGEKNLVLPIHYNYIVQGFLYDLMGDSEFAAFLHDEGFQYEKRKFKLFTFSRI
EGEFKILTDSKGQKKISIKPPFKFTVASPLDEFIFDISKNALKKEYCHFNGQKFILNSLNIDNPP
VFKNKARIKFISPVVMYTTLKDGDIKYTYYYSPWDEKFSPLLLNNLLKKYELVYKIKAEDPYFKL
YPLSEKEDRRYSKMIKYKNVYVKGWMGIYDVESSPELLELAYYTGLGAKNSQGFGCFEIIG UniProtKB/TrEMBL Accession No. A4XIJ2 (A4XIJ2_CALS8)
NCBI GI No. gi:146296147
*Caldicellulosiruptor saccharolyticus* (strain ATCC 43494 / DSM 8903)
SEQ ID NO:125
MRIKVDFESQNLIELPIHYNYFVQSMIYNTIEDKIYATFLHDKGYEVDLKNFKLFSFSRLEGPFK
IVGEGSNKKIIFDKKVSLTVSSPVEDFVTKFSTGLLKKDQIYLKDNILYVTSANM
LRKPKFSSFHKIKMLSPMCAYKTIRNENSEYKHFFTPFEDEFYNLISQNLMKKCKLLIKD
FDEKSFRFDLKPLKVEEKSHFKPMLFKKTPIKGWLGFYTIETDPKIMEVAYYCGLGSKNSQGFGL
FEIIE

*Figure 16o*

UniProtKB/TrEMBL Accession No. A4XM43 (A4XM43_CALS8)
*Caldicellulosiruptor saccharolyticus* (strain ATCC 43494 / DSM 8903)
SEQ ID NO:126
MRAKFIFEVHNGFNETKELPVYYRTLFMAFLKKALSSYNEEYFKRLYWWEDKKNKWQKPFVYAVN
LPNMNFSDDKVLFRGDIVLNLSTSDYEFFVNIYNSLISSKLYPHKLTNNCEIKLRRAYLIKEPEQ
FSSTMTFKTFSPVVIEKKEGDDKIPILPYDEGFEEVLNDVIDFEIRNIRILRGQNRGLYKRISFK
PINVKKIVVKHKISEFVENTGKEIMYLTGFGGIFELSGHPDDLKEIYQNGLGFRRGQGFGFIEVV
R UniProtKB/TrEMBL Accession No. B0AAF2 (B0AAF2_9CLOT)
*Clostridium bartlettii* DSM 16795
SEQ ID NO:127
MEFTVDKKQKIDYNIGSVLQGIMMTFLDRDYGEVLHRQSLMPYSQHFETKDGKYYWIINALTEEA
KENIICKILDSDKRSLDLTYRKSKLNIERLIFEEVNLFKDRGEKDIVLNFKTPTSFKRTSGGYEI
FPNVRHIFNSLINKYEMFEMNNLDDSLFSKINKKEDFLEDIIKNVDIVGY
NLKTEKFGIKGNYIPGFMGKVNIKVKGSAEFKNNISKLLQFGEYSGVGLKCTMGMGVMEIL UniProtKB/TrEMBL Accession No. Q894R6 (Q894R6_CLOTE)
*Clostridium tetani*
SEQ ID NO:128
MKIYELTLKVFLLKDIKSDESLEKISNLIDKSLSKDGKLLDFHERNTYKNYTFNSLYPIE
KDKIYNEGKIYSVQIRTVDESLIQYFKKNLTNEYTEYIKALTLECRVIPQRYIEKIYSITPVIIK
TEKGYWKGNLSLGEFEERIKNNLIKKYNSFFNTKIDERFTLFRTINLINNKPISCSYKDINILGD
KITLIIDENEMAQKLACFSLGSGVGEMNARGYGFVNYKWL UniProtKB/TrEMBL Accession No. Q895X4 (Q895X4_CLOTE)
*Clostridium tetani*
SEQ ID NO:129
MRFCLTLHLKEKIFLIEYRKVILSYIKNAISKCNNGKYYECFFKDTKQKDYCFSVILPNP
TFTKNEIILNGNEIKVLFSTNNNSKIGFILFSAFIAQKNKPYPLPNNNSMILKNINNKKQEEIFN
SKAIFKTTLGSGLCVRDHDKEENKDTYYVYTDEKFREKLKVVLIKQILKAGFTEEEANDIKVNPI
QCKKVVVKHYRRYIDTTTGLFEIQANNKILQHFYDVGIGSRKSMGFGMID
LVTQDLL UniProtKB/TrEMBL Accession No. Q0SUG5 (Q0SUG5_CLOPS)
*Clostridium perfringens* (strain SM101 / Type A)
SEQ ID NO:130
MKILVAGKMKNKKISLSYRMFILSMIKKIISDFDEIYFEEMFFYEGKKTKKTKPFTFSVFFKDYK
INRDFVDVEGEVKIVISTPDIKLNMVLFNGFMKMKEYGDFEKTSVRIEKERKVEE
NEAIFKTLSPIFIKDTNNKALEIEDENYNKELNYFANLSLKSFRGYGLKEELVFTPLKMK
KVVVKEEISGFKEKTNKKYIYFNSYSGVFHLRGDKDDLNLLKELGLGCRRNSGLGSIDLI

*Figure 16p*

UniProtKB/TrEMBL Accession No. B1R9P1 (B1R9P1_CLOPE)
*Clostridium perfringens* B str. ATCC 3626
SEQ ID NO:131
MKILVAGKMKNKKISLSYRMFILSMIKKIISDFDQSYFEEMFFYEGKKTKKTKPFTFSVF
FKDYKINRDFVDVEGEVKIVISTPDIKLNMVLFNGFMKMKEYGDFEKTSVRIEKERKVEENEAIF
KTLSPIFIKDANNKAIEIEDENYNKELNYFANLSLKSFRGYGLKEELVFTPLKMKKVVVKEEISG
FKEKTNKKYIYFNSYSGVFHLRGDKDDLNLLKELGLGCRRNSGLGSIDLI UniProtKB/TrEMBL Accession No. B1RMM0 (B1RMM0_CLOPE)
*Clostridium perfringens* NCTC 8239
SEQ ID NO:132
MKVFELTVKCYLNNNIKQEDVSGQIGFLLDLILGKDKKFLKIHKSNTFKNYVFNGFYPLEREKIY
KEEYIYTFQIRTIDAGLANYLKENLTKVNSNCINVLRVSIEEKEFKKINKLYSIT
PAIMKNDFGYWKNNISIDEYKNRINQNLIKKYNSYMDESLHDDFELIKNIKFINKKPIRF
SYKGVRVLGDKVELEISDNEKAQLLAYMSLGTGILELNARGMGYVNFK UniProtKB/TrEMBL Accession No. A0Q258 (A0Q258_CLONN)
*Clostridium novyi* (strain NT)
SEQ ID NO:133
MEVFEEKVKVYLLNDVRREYMSVKIAQIIDKILCKSEEFSKFHEENKFKMYCFNGFYPIEKSEVY
KKGKIYDFSIRTVDESLAKFIKENLVNEYTECIKVLTIQEKIIHERYIEKIYSIMPVILKTTQGY
WRKNLRLEDFERLIKENLIKKYNQYYNTKIDENFSLYDNLIFNNNKPVPM
KCKNITLLGDKITLFISSNETAQKLAHFALGVALGENSARGAGFCNYKWL UniProtKB/TrEMBL Accession No. Q182E2 (Q182E2_CLOD6)
*Clostridium difficile* (strain 630)
SEQ ID NO:134
MSRISIFMESCNGKFPNENSMLSVSFIKNILNAENKDFAKNIFNYGEERKNNKQIKDINT
AIYIPNLIRSKNELLVDGDIIFNISFYNYSMFSKLYNGILKVKELEYKGYRFKIKNIKIHKEHEI
KENGVIFKTMSPIIVKNKEGKYLDVEDSNYIECLNYIANLTLESIRGSGLRKPLEFIPLNFKKRV
LKEKIRGFKEREFYYINAYAGTFFLKGNMEDLNALYKMGIGYRRTENAGMVDILK UniProtKB/TrEMBL Accession No. Q184H4 (Q184H4_CLOD6)
*Clostridium difficile* (strain 630)
SEQ ID NO:135
MKMKIEFSTGCIPISYNSLFMSIIKEAIRKSNEDYYKNMYYYKEKNNKKTKNFTFSVYIK
KYSIEGDNFIIEDKVILNISTPDLELGFHIYNGLMTSKKCLYKDYELTRIRIDLSREKKVTEERV
LFNALSPICVKSKEGKFLEITDDRYIEELNYITNEVVKNYRGNGLKRKLEFENVGFKKVVVKESL
REFKKITGKEYQYINGYKGKFILKGDIDDLNLIYNLGIGFRRAQGFGDVDILEWR UniProtKB/TrEMBL Accession No. A7GFB2 (A7GFB2_CLOBL)
*Clostridium botulinum* (strain Langeland / NCTC 10281 / Type F)
SEQ ID NO:136
MEFWELIVTAMLKKDIYFEDCGYIIGKNINKSMLWDKDLKEVHPKKQYKNYVFNSFYPIERDKFY
KKDRLYIFNIRGLSKEFIDKIETCLCNLESNDFNVISTSKKEIKQRYIKELYTQT
PLIITVDDKPWLQNDGDLDLFKQRLEDNLEKKYKSFFNEDIDVKGKFIKSIEFKNRKPMHYNYKN
GKKLLANKVSIQIEDNEEAQKVAFLARAIGLGEKNPSIGAGFCK

*Figure 16q*

UniProtKB/TrEMBL Accession No. A7FZJ4 (A7FZJ4_CLOB1)
*Clostridium botulinum* (strain ATCC 19397 / Type A)
SEQ ID NO:137
MEFCELIATVMLKKDIYFEDCGYIIGKNINKSMLLDKDLKEIHPKKQYKNYVFNSFYPIE
RDKFYKKDRLYIFNIRGLSKEFIDKIETCLCNLESNDFNVISTSKKEIKQRYIKELYTQTPLIIT
VDDKPWLQNDGDLDLFKQRLEDNLEKKYKSFFNEDIDVKGKFIKSIEFKNRKPMHYNYKNGIKLL
ANKVSIQIKDNEEAQKVAFLARAIGLGEKNPSIGAGFCK UniProtKB/TrEMBL Accession No. A5I3V0 (A5I3V0_CLOBH)
*Clostridium botulinum* (strain Hall / ATCC 3502 / NCTC 13319 / Type A)
SEQ ID NO:138
MEFCELIATVMLKKDIYFEDCGYIIGKNINKSMLLDKDLKEIHPKKQYKNYVFNSFYPIE
RDKFYKKDRLYIFNIRGLSKEFIDKIETCLCNLESNDFNVISTSKKEIKQRYIKELYTQTPLIIT
VDDKPWLQNDGDLDLFKQRLEDNLEKKYKSFFNEDIDVKGKFIKSIEFKNRKPMHYNYKNGIKLL
ANKVSIQIKDNEEAQKVAFLARAIGLGEKNPSIGAGFCK UniProtKB/TrEMBL Accession No. B1L2N1 (B1L2N1_CLOBM)
*Clostridium botulinum* (strain Loch Maree / Type A3)
SEQ ID NO:139
MRTIVFFSTVIDMLSYYELLLEIKLNKDIHFSKSYEMLSKFFNRVMLTDNYLKTLHERKGVKLYS
FSGLYPAATNQIYKRNALYKIRIRSFDPEFICAMQFSLSQIQDNDINIISIKFIKNQQQFITELV
SINPVIFSIWEKQNYWQIGDNIDLLGKQLTNNLLHKYNTISCNKLTTQDTIFHCLNITNNKTIYI
PYKKGLLLGNKLKIQVKEDDISQTLATVALGAGIGEKNSIGMGFCYGH UniProtKB/TrEMBL Accession No. B1B9J7 (B1B9J7_CLOBO)
*Clostridium botulinum* C str. Eklund
SEQ ID NO:140
MRIRCEYKTEKLPVAYNMLFLSLIKESLKKSDEDYLRKLYFYKGDKVNKKPKNFCFSVYLKDFVK
KEDIFQINDRIIFNISSPDYEFMLKVYNGLLDFSTFRYKDYNINKVRINLLKEKVINKSSAVFST
MSPICIKNKQGNMISIDDDQYEKELNYIESKSLEGFRGYGLVEALKFSPI
FMKKKIVKEDIRNFRENTNKPYYYVNSYAGTFKLKGNTKDLNDYLMGIGFKRGQGFGMIEIIE UniProtKB/TrEMBL Accession No. B1IGS6 (B1IGS6_CLOBK)
*Clostridium botulinum* (strain Okra / Type B1)
SEQ ID NO:141
MEFWELIATVMLKKDIYFEDCGYIIGKNINKSMLLDNDLKKIHPKKQYKNYVFNSFYPIERDKFY
KKDRLYIFNIRGLSKEFIDKIETCLCNLESNDFNVISTSKKEIKRRYIKELYTQT
PLIITVDDKPWLQKDGDLDLFKQRLEDNLEKKYKSFFNEDIDVKDKFINSIEFKNRKPMHYNYKN
GIKLLANKVSVQIEDNEEAQKVAFLAKATGLGEKNSSIGAGFCK UniProtKB/TrEMBL Accession No. B1IP19 (B1IP19_CLOBK)
*Clostridium botulinum* (strain Okra / Type B1)
SEQ ID NO:142
MLSKFFNRVMLTDNYLKTLHERKGVKLYSFSGLYPAATNQIYKRNALYKIRIRSFDPEFICAMQF
SLSQIQDNDINIISIKFIKNQQQFITELVSINPVIFSIWEKQNYWQIGDNIDLLGKQLTNNLLHK
YNTISCNKLTTQDTIFHCLNITNNKTIYIPYKKGLLLGNKLKIQVKEDDISQTLATVALGAGIGE
KNSIGMGFCYGH

*Figure 16r*

UniProtKB/TrEMBL Accession No. B1QMY6 (B1QMY6_CLOBO)
*Clostridium botulinum* Bf
SEQ ID NO:143
MELWELIATVMLKKDIYFEDCGYIIGKNINKSMLLDKDLKEVHPKKQYKNYVFNSFYPIERDKFY
KKDRLYIFNIRGLSKEFIDKIETCLCNLESNDFNVISTSKKEIKQRYIKELYTQTPLIITVDDKP
WLQKDGDLDLFKQRLEDNLEKKYKSFFNEDIDVKDKFINSIEFKNRKPMHYNYKNGIKLLANKVS
IQIEDNEEAQKVAFLARAVGLGEKNSAIGAGFCK UniProtKB/TrEMBL Accession No. B1QPD6 (B1QPD6_CLOBO)
*Clostridium botulinum* Bf
SEQ ID NO:144
MRPIVFFSTVIGMLSYYELLLEIKLSKDIHFSKSYEILSKFFNRVMLTDNYLKTLHERKG
VKLYSFSGLYPAATNQIYKRNALYKIRIRSFDPEFICAMQFSLSQIQDNDINIISIKFIKNQQQF
IAELVSINPVIFSIWEKQNYWQIGDNIDLLGKQLTNNLLHKYNIISCNKLTTQDTIFHCLSITNN
KTIYIPYKKGLLLGNKLKIQVKEDDISQTLATVALGAGIGEKNSIGMGFCYGH UniProtKB/TrEMBL Accession No. A3DHS6 (A3DHS6_CLOTH)
NCBI GI No. gi:125974788
*Clostridium thermocellum* (strain ATCC 27405 / DSM 1237)
SEQ ID NO:145
MRFKVGIEFDESLELPFNYNKILQGFIYRNIMDKDLARFIHDRGFSYEKRKYKMFTFSRL
QGKFSIDSKKKKIIYQSPVELVVSSCYEDFFIDLSLSLLRRDVEIAGHKAYVSKMDIIMEEPKSI
QKIRMLSPVTAYSTLDDKRTVYFSPYNHDFKRIIKENLIKKYKAFYKDDSKDNVDFDIELVSDKY
AKVISSYDGFIIEGWMGDFVLKGDQEVIKLAYDAGIGGKNSQGFGCFKLI UniProtKB/TrEMBL Accession No. A7VC49 (A7VC49_9CLOT)
*Clostridium sp.* L2-50
SEQ ID NO:146
MILTYYKRNAILIIQSQINYEGGEKMYQIKLRFKLEFPFLPKEMDRLFTSFLKAATKNIS
EDLYQRLYDKSRSIMKAFTYSYYLPGAKFTDDKILLDKNEFMVFFTDADDKEFLYLFNAFQTMKF
RHYSMNKNSMQLISVYIQNINDIIDDEIIIKMQSPLLARYHDNDTNSDSYYTFDKDEFSDVVKEN
VKIFIQRMNIPVETDDFSIQAIKGKKVIIPVFGRNTDASLGIFKLKGSVALLNVLQRSGIGVRRS
TGNGKFEVLG UniProtKB/TrEMBL Accession No. A6TQ80 (A6TQ80_ALKMQ)
*Alkaliphilus metalliredigens* (strain QYMF)
SEQ ID NO:147
MQTPNTTIKMKGGGEVRFGVEIFLEKEMLPKDKNRIILSIIKNCFSSCNKEYYKALYKDT
PNQTKDFTFSLYLGDCKFLREEILVPSKKIYLNFSTYHNEDGIMFFNSMLMNKGKAFSIR
DNTYTIGKINLKREKLITEHQVIFKTMSPIVAREHQGDNKKTWYHSLNTEEGQAVFLENLQYQLK
DAFGEGILMDSRKLSIEVSQDNKEVKVKNYGIEILSNLAKIRIQGAPYILDYLYKAGIGSKRGSG
FGMVDIV

*Figure 16s*

UniProtKB/TrEMBL Accession No. Q0AW55 (Q0AW55_SYNWW)
*Syntrophomonas wolfei* subsp. wolfei (strain Goettingen)
SEQ ID NO:148
MMLQKIILQCKYGGEQRASYNWGSLFHGILVKSLPSDIAEMLHENHLRPFSQYVLSSSNQELTWN
IGLWDAEIANHIIQAVLPLVQIELQHKATTLEVTGVKRSSQNEYEYFNHYFATENPCRRYEIEFL
TPCTHKQDGSYVLFPTPELIVKSLNNRYCAFMQDVSLDAPEAMEQIAKHIHIVRYSLHSAVFYLE
RTKITGYMGRITVVISGTEQLARLAGALLSFAEYSGLGIKTALGMGGVKIRALA UniProtKB/TrEMBL Accession No. B0M919 (B0M919_9FIRM)
*Anaerostipes caccae* DSM 14662
SEQ ID NO:149
MNHSLQGNRYDRYYQHVYDTRVHTKERGGAVDLKVFEIRLKVYLLEDIPVEAVQKKTAALIDICL
SRDEALLKFHETNQFKNYSFGNPYPLEKDKIYKKDKVYVITIRTIDPQLAKVFSEKLIHERSDEM
QALTCEIKIIPKENKIIDTIYSISPVIVKAERYWRGVFSLQEYEKRLTVNLVKKYNAFCDTKINE
DFEFIRMIEVKNRTPITVSYKKIKLLGDKIALKVADNELSQELSYMTLGTGLGEINARGAGFVNY
RWM UniProtKB/TrEMBL Accession No. B0MG00 (B0MG00_9FIRM)
*Anaerostipes caccae* DSM 14662
SEQ ID NO:150
MRLELQLDLEKPELSKDYRRIVLSYLKFALSECNDGKYFEKYFKDTIQKDYCFSVLMKGPKFSKD
KILLEEPRIKILFSCDDRRKTGLILFSAFLGIKNRNFPLANNNAMVLKRIDQKSEKLITESTVYM
QTVLGNGLCIREHDRETNRDRFITFEDEDFKEKASEVLSVQAKLAGFSDKKASGISLEPVQCKKV
VVLHYGVYIDVTVGIIKMTGDPDVLQYLYSAGAGSKHSAGFGALNVLRQGESI UniProtKB/TrEMBL Accession No. A4J1X6 (A4J1X6_DESRM)
NCBI GI No. gi:134298408
*Desulfotomaculum reducens* (strain MI-1)
SEQ ID NO:151
MRLQLLLDSENPVLLATNYQQQIQGLIYNLLTDPLMQAFLHDHGFDYNQRRFKLFTFSRLMGKSY
FNQQDKTLRITPPVLLYISSPWTEFLENLANSLLARGFIQIGKNQLQVKEIKLAVTPPFNQDQSY
PVKMLSPVTMYSTLETREGSKKTYYYSPTEREFTRLIAQNLVKKASAFYGEDWSKLFFCIEVANS
FRASQQKIIIYKGTVIKGWLGNYHISGHPKMLKLAYESGIGSKNSQGFGLFELCNNG UniProtKB/TrEMBL Accession No. A4J507 (A4J507_DESRM)
*Desulfotomaculum reducens* (strain MI-1)
SEQ ID NO:152
MLTALQVELEAVADGALPVGNALYIHGLFFRLLQEVNINISDYLHNVQSIKPYTLSTLQGVKQNK
GWCSVCQGKKYRFRATFMQEEVFLNFYEVVYSYYVNKKTVKIGNIDFLVSKIDLERTNKFEDLIG
NEVNLQKFEIDFLSPTNFRVNGIQHIFPDSHTVFKSYKNRWNTFCPNHLIFPEHDLSLIYDGCYS
VRYNLHTEIIEMGKYKMVGFKGTCRYEINPKLSGELRDRASGLLKFARYCGTGYKTTMGLGQTKV
SFMIK

*Figure 16t*

UniProtKB/TrEMBL Accession No. Q18ZU7 (Q18ZU7_DESHD)
*Desulfitobacterium hafniense* (strain DCB-2)
SEQ ID NO:153
MNLEIYFKPLREPVVLPIHYNYLVQAALYNSIDQELAAFLHEKGYSDGNRAFKLFCFSLI
QGVYQMDRVNKRIAFEGELKLTVSSPLQDFCQSLVNVLLTKGVMRLGAQELEIDRISAGQYKVRE
NKVMVRTLSPVVLYSTLLRPDGRKYTVYFQPGETDYSRLFNENLRKKYRALYGSEGPEGEVEIRP
LGIQRMRIVNYKNTVIKGYAGKLLLSGPKELLQLAVDGGIGSKNSQGFGCVEIING UniProtKB/TrEMBL Accession No. Q24TS7 (Q24TS7_DESHY)
*Desulfitobacterium hafniense* (strain Y51)
SEQ ID NO:154
MLIQAIPRKDGERQKMNLEIYFKPLREPVVLPIHYNYLVQAALYNSIDQELAAFLHEKGYSDGNR
AFKLFCFSLIQGVYQMDRVKKRIAFEGELKLTVSSPLQDFCQSLVNVLLTKGVMRLGAQELEIDR
ISAGQYEVREHKVMVRTLSPVVLYSTLLRPDGRKYTVYFQPGETDYSRLFNENLRKKYRALYGSE
GPEGEVEIRPLGIQRMRIVNYKNTVIKGYAGKLLLSGPKELLQLAVDGGIGSKNSQGFGCVEIIN
G UniProtKB/TrEMBL Accession No. A5D0Y7 (A5D0Y7_PELTS)
NCBI GI No. gi:147678256
*Pelotomaculum thermopropionicum* (strain DSM 13744 / JCM 10971 / SI)
SEQ ID NO:155
MHAYLKMRMDPSSPAIPIHYNYLIQAAIYAVLPEEMAARLHNEGFAAGKRSFKMFSFSRLMGRFI
LDKTAGTISFPEEISFVITSPDMGFFLALINNLLTRGQIQVGQSLLLIDEIRFDE
QVADGEVLTVRTLSPVVAYSTLLRPEGGKYTCYYQPGEGEFDKLITANLAKKYEAFYRSRPPEGN
VRARPLDRPRLHVTTYKGTVVKGYTCRLKLNGPRELLQMALDAGLGGKGSQGYGCVEKVVGRKGS
Q UniProtKB/TrEMBL Accession No. A5D0Y8 (A5D0Y8_PELTS)
*Pelotomaculum thermopropionicum* (strain DSM 13744 / JCM 10971 / SI)
SEQ ID NO:156
MQLTVTFHAPSEVAVPVHYGVLLQGLIYRQMQNPALRRYLHEHGFPLEKRRFKLFTFSRLMGRSA
RFDRAGGSIVFVPPLQLVICSPISFILQELGNGFLQQGQVRLGDARLEVKEMAAASPRVSSSSIR
VRMLSPVVMYSTAGAENGRSYTYYYSPFEPRFAELIGANLAKKHLLIHGRRAEADGFDIRPAEVR
EKDFKITRYKDTIVKGWLGEYYLNGDPELLQVALDAGLGAKNSQGYGCCELVI UniProtKB/TrEMBL Accession No. B1I5K4 (B1I5K4_DESAP)
NCBI GI No. gi:169831963
*Desulforudis audaxviator* (strain MP104C)
SEQ IDNO:157
MQLTIFFSAPGPVAIPVQYGHLLQGLIYRRMDNPVLRSYLHEHGFALEKRRFKLFTFSRL
MGQAVTYDQAAGRLVLTPPLRLVICSPIPFILQELGTGFLRQGRVRLGDAHLEVKKMATAAPWVT
RETLQVRMLSPLVVYSTLSGVDGRNYTYYYSPFEPRFTELVASNLAKKHFLVYGQPARAEGFAIR
PVRVEDRDLKVTYYKDTVIKGWMGEYELSGDLELLQLALDAGLGSKNSQGYGCCNLVEKASQVSS
RYRRNSNIM

*Figure 16u*

UniProtKB/TrEMBL Accession No. A8SM91 (A8SM91_9FIRM)
Parvimonas micra ATCC 33270
SEQ ID NO:158
MKIVLKFKTDNNFIPKDYHRFCIKFFKTAVSNYSDGNFFEKFFGDDYIKSDEKKYSWAVKFFKPK
FFSNRIEVGENNFEITFKAPKTDVGTIFFNSFLEYKDKEFKISENNFIVLTDAKIVNEKKIVGNC
ARFKFCSPLVIREHNREDNTDRHITVEDEDFFDKFKENLKIHFPNYSNAIDDMKMDISEMKKAVV
LFYGLYIDVSLGVIEIKADNNLLNEMLISSIGSKNASGFGLLQLIESWEMI UniProtKB/TrEMBL Accession No. B0N6L1 (B0N6L1_9FIRM)
Clostridium ramosum DSM 1402
SEQ ID NO:159
MESIEMDVYEIKIKLYLLKDIKIEETQTYLAYFIDSVMVKDNMFLGIHETNQYKFYTFDS
LYPLAKNGVYQKDNSYMFRIRTLDYQLAQYLYDTLAKNRTKEFQGLTAEVKIIKPKLIKKIYTLT
PVILKTEQGYWKNSIKTEDFEKRLKTNLIKKYKDITGEEINEDFQLYYQINFKNKVPVSRKYKGI
KLLGDMIELEIAENDNAQKLAFLAIGSGLLEMNARGFGFVNYIYY UniProtKB/TrEMBL Accession No. A0YIK9 (A0YIK9_9CYAN)
Lyngbya sp. PCC 8106
SEQ ID NO:160
MKRSFKKNTSLSWSADTELVGLVLALRPTGADLLYPQYTIGLHAWFLDQVRQTSPDLSAYLHDGE
SEKPFTISGLEGALKLSGKHLQLQPEQTYFWSITALSKPVVQWLVEWVKCLPTQVELRNAPLTIQ
SCQMALAPTTYRQLFDAPTPKPAKVNLSFMSPTSFRRKGHHFPLPLPTNLFHSYLRRWNDFSNLP
VEQESFLDWVDESVIIQRHQIASTKVAAGKRGMVTGFTGAIELSLSKKSSLASTQNQQLFYALGR
FAPYCGTGHKTTFGLGQTRFEWQIEETEMIPTSSQQLGERIAELAEQFTIQRKRTGGTRTQKIAE
TWATILARREDGESLQAIAVDLEMPYETVKTYAKLARRALRQPD UniProtKB/TrEMBL Accession No. A0YW92 (A0YW92_9CYAN)
Lyngbya sp. PCC 8106
SEQ ID NO:161
MPYSLVLNLIPLSSISPTYLSGRHLHALFLTLVSSVDKQLGDYLHEPKTEKSFTLSPLQTCSKHR
RVEQTLQWEHSQPISVGTPCWWRISLLDEGLFSKLTHLWLNLNPDQPWHLGSANLKITSVLATPQ
STQPWANTCSYSQLYQQASNSDRSMTLIFCTPTAFRQGKFDTSLPTAEII
FNSLLNRWNKYSGIEFKQLPLNSIFPSFFNIKTEMVADSRSKFIGCVGKVNYRLLGNVEP
EIIQQVNTLADFAFYCGVGRKTPMGMGMLRRLQKEGTGDRGQGTESLRRL UniProtKB/TrEMBL Accession No. A8YLQ9 (A8YLQ9_MICAE)
Microcystis aeruginosa PCC 7806
SEQ ID NO:162
MPYSLVLNLTPRSPIYPNFLTGRHLHALFLTLVSSVDQELGKILHAAEADKAFTLSPLQI
QSRGKITINSPQWRHEREIASETPCWWRISLLDDRLFGKLTSLWLNLNPKQPWHLGSADLVITSV
LATPQSVQPWANSCTYQYLYENASETNREFDFLFATPVTFRQGKFDSALPTRELVFNSLLNRWNR
YSGIPFDSIALESIFPSFFDIQTKLADEAYKNQSFGCVGEIHYRLLGEVEPAKIKAINVLADFAL
YAGVGRKTTMGMGMTRRIAKEKR

*Figure 16v*

UniProtKB/TrEMBL Accession No. B0JKW7 (B0JKW7_MICAN)
*Microcystis aeruginosa* (strain NIES-843)
SEQ ID NO:163
MPYSLVLNLTPRSPIYPNFLTGRHLHALFLTLVSSVDQELGKILHTAEADKAFTLSPLQM
QSGGKTINSPQWRYERPIAPETPCWWRISLLDDRLFGKLTPLWLNLNPKHPWHLGSADLVITSVL
ATPQSVQPWANSCTYQYLYENASETNREFDFLFATPVTFRQGKFDSALPTRELVFNSLLNRWNRY
SAIPFDSIVLESIFPSFFDIQTKLADEAYKNQSFGCVGEIHYRLLGEVEPAKIKAINVLADFALY
AGVGRKTTMGMGMTRRIAKEKR UniProtKB/TrEMBL Accession No. Q6ZED0 (Q6ZED0_SYNY3)
*Synechocystis* sp. (strain PCC 6803)
SEQ ID NO:164
MVDLKSLAGAEMVGLRWQLRFDRPCRLESHYVKGLHAWFLHQVQAIDPDVSAWLHDGQGEKPFTI
SRLIGPTLWQEGHWHWQINKTYHWQLNLLSGALIEALQPWLARLPNKIVLARQTLWVEAVDCYLA
PHNYQQLWPQGALPRRQEFTFTSPTSFRRQGNHYPLPEPRNVLQSYLRRWNDFSGLAFEPEPFLD
YWVPQNVVIDRHWLESVKTTAGKQGSVVGFVGAVSLVLTPQARNDGDDYGRLFHALCRYGPYCGT
GHKTTFGLGQTMAGWATPDLKTFACLQEDLQTQVLTQRIDQCASLLLAQRQRTGGQRAQEICHTL
ATIFVRREQGESLQEIALDLQLPYETARTYSKRAKRALANVQ UniProtKB/TrEMBL Accession No. Q6ZEI4 (Q6ZEI4_SYNY3)
*Synechocystis* sp. (strain PCC 6803)
SEQ ID NO:165
MFDDRYSLYSVVIELGAAKKGFPTGILGRALHSQVLEWLKIGEPSLAEELHQSQISPFSI
SPLIGKRRSKLTEEGDRFFFRISLLNGSLLQPLLKGLEQQDKQIVMLDKFAFRLCHIHILPGSHS
LARASSYALTTQAPTSSKITLKFHSATSFKIDRNTIQPFPLGDSVFNSLLRRWNHFAPEELYFPS
VSWQIPVAAFELKTYSVQLKKSEIGSEGWVTYLFPDQEQAKIASVLSQFAFFAGVGRKTSMGMGQ
VSVNNHG UniProtKB/TrEMBL Accession No. Q2JNR9 (Q2JNR9_SYNJB)
*Synechococcus* sp. (strain JA-2-3B'a(2-13)) (Cyanobacteria
bacterium Yellowstone B-Prime)
SEQ ID NO:166
MLIVAVDWEWAVPMLSFSEPSADREANGKWPTGSELVGITLEVQAPRSYLLDPHYAKGLHAWFLS
QVQETDPQLSAYLHDGESEKPFTLSRLMGPFREQGGRPLIPPHLPFRWWITGLNPPVVEWLRGWC
QRLPTWLELRGSPLQILGWQISIPPRTYRQLLEQPLSPRSWSLSFVSPTSFRHRGHHLPLPIPRN
LFHSYLRRWNDFSGLPIEAEPFLDWVDGEVIIQRHRLESVKTTAGRQGSVTGFIGCVQLAVSSRA
PELLQQQLQALIHLAPYCGTGHKTPFGLGQTRLGWLAEELPASPVPSREEQVAQRIEELSALFLS
QRQRQGGSRAEKTAQLWATILARREGGESLQQIAADLEMPYETVKTYAKLARRSLQSGSQDYSSS
SLP

*Figure 16w*

UniProtKB/TrEMBL Accession No. Q2JVZ0 (Q2JVZ0_SYNJA)
*Synechococcus* sp. (strain JA-3-3Ab) (Cyanobacteria bacterium Yellowstone A-Prime)
SEQ ID NO:167
MLTKLSFSEPPVAGAENSKWPAGSELVGIALEVQAPQPYLLDPHYAKGLHAWFLSQVQETDPQLS
AYLHDGESEKPFTLSRLMGPFREQGGRLLIPPQIPFRWSITALNPQVVEWLREWCRRLPPWLELR
GSPLQILGWKVSAPPRTYRQLLEQPLSPRSWSLSFVSPTSFRHRGHHLPLPIPRNLFHSYLRRWN
DFSGLPIEAEPFLDWVDGEVIIQRHRLESVKTTAGRQGSVTGFIGCVQLAVSSRAPELLQQQLQA
LIHLAPYCGTGHKTPFGLGQTRLGWLAEELPATPVLCREEQLARRIEELSALFLSQRQRQGGSRA
EKTAQLWATILARREGGESLQQIAADLEMPYETVKTYAKLARRSLQSGSQDYSSSSLP UniProtKB/TrEMBL Accession No. A0ZJZ0 (A0ZJZ0_NODSP)
*Nodularia spumigena* CCY9414
SEQ ID NO:168
MVRTAKPTNRQQKPKSSPTATLPTWADNTELVGLEFDLEALTTSSLYSQYTIALHAWFLDQVRQL
DPDLSAYLHDGESEKPFNISALESQLLPTGKQLQLEANQILHWQVNALSAKVAEFLQLWLTQLPQ
TLNLRGATLQIKQVRIAHPPTTYAQLLQPPAKYSQVNLSFISPTSFRRKGHHFPLPVPVNLFHSY
LRRWNDFSQIPISQADFLDWIDENVIIHQHRLESVKVAAGKRGSVTGFTGAISCGLSKAALANTE
FTQLFYALVKLAPYCGTGHKTTFGLGQTSLSWVEPEASSPTQLLTNLLGERIEELTAIFTAQRKR
SGGDRTDKIAATWATILARREMGESLKLIAEDLEMPVDTVKTYTKLARRSLKDADL UniProtKB/TrEMBL Accession No. Q3M5G3 (Q3M5G3_ANAVT)
*Anabaena variabilis* (strain ATCC 29413 / PCC 7937)
SEQ ID NO:169
MPHSLVLNLLPQSPIPPQYITGRHLHALFLTLVSSVDSTLGDRLHDSTADKAFTLSPLQI
KGEERGRYKSKIPHGQSLQYFHQQAIPAGTPCWWRISLLDDTLFSQLTQLWLNLNPSHPWHLGPA
NLYITSIQGTPQSTQPWANATTYAQLYEQAGESNDVRSLVNNRTLNFTFTTPTAFRQGKFDTTLP
TRECVFNSLLSRWNKYSGIEFSEIAIESIFPSFLNIHTEILADSRSKFIG
ILGEINYRILGDIEPIQIKQINALADFAMYAGIGRKTTMGMGMIRRLYSA UniProtKB/TrEMBL Accession No. B2ITK0 (B2ITK0_NOSP7)
*Nostoc punctiforme* (strain ATCC 29133 / PCC 73102)
SEQ ID NO:170
MPHSLVLNLLPQSPIPPQYLTGRHLHALFLTLVSSVDSTLGDRLHDSTADKAFTLSPLQI
SNTNSPLLKGGKGGSKLQYSHQQPIPAGTPCWWRISLLDDTLFGKLTQLWLNLNPNRPWHLGPAD
LYITSIQGTPQSIQPWANANTYAQLYEEASDGNSSINLTFSTPTAFRQGQYDTTLPTRESVFNSL
LSRWNKYSGIEFSQIAIESIFPSFVNIHTEILADSRSKFIGIIGEVTYKILGAVEPIQIKQINAL
ADFALYTGVGRKTTMGMGMTRQMYSP UniProtKB/TrEMBL Accession No. Q8YWN8 (Q8YWN8_ANASP)
*Anabaena* sp. (strain PCC 7120)
SEQ ID NO:171
MPHSLVLNLLPQSPIPPQYLTGRHLHALFLTLVSSVDSTLGDRLHDSTADKAFTLSPLQI
QGEERGRYKSKIPNSYSLQYLHQQAIPAGTPCWWRISLLDDTLFSQLTQLWLNLNPNHPWHLGPA
NLYITSIQGTPQSTQPWANAITYTQLYEQAGENNDLRSLGNNHTLNFTFTTPTAFRQGKFDTTLP
TRECVFNSLLSRWNKYSGIEFSEIALEAIFPSFLNIHTEILADSRSKFIG
ILGEINYRILGDIEPIQIKQINALADFAMYAGVGRKTTMGMGMIRRLYSS

*Figure 16x*

UniProtKB/TrEMBL Accession No. Q8YWW2 (Q8YWW2_ANASP)
*Anabaena* sp. (strain PCC 7120)
SEQ ID NO:172
MPRAATTPKRKPRAKSAPTSLVPTWADETELVGLVFDLEATDSGSLYSQYTIGLHAWFLHQVQQV
DPDLSAYLHDGESEKPFNISALEGQLLPSGKQLRLEAKQTYHWHINALSQKVALFLKEWLTNLPK
TIELSGTPLQIKQVSIAHAPTTYAQLLQPSTQPSLVNLSFVSPTSFRRKGHHFPLPVPENLFHSY
LRRWNDFSNMLVNQESFLEWIDENVIIHQHRLQSEKVAAGKRGSVTGFTGAISLGLSRAGLANAD
FTKLFYALVQLSPYCGTGHKTTFGLGQTRLDWLEQKPTTSAQLLENILAERIEELTEIFTAQRKR
KGGDRTDKIAATWATVLARRDMGDSLQAIADDLEMPLLTVKTYVKLARKALK UniProtKB/TrEMBL Accession No. A7I0F8 (A7I0F8_CAMHC)
*Campylobacter hominis* (strain ATCC BAA-381 / LMG 19568 / NCTC
13146 / CH001A)
SEQ ID NO:173
MLIYELNVTVKLKKAVKFSQIPGFLSKNINYSFLLDKNLKNLHSKNHIKPYSLSFLQSHE
GRKDLFDVNEIAFFKIRSVFPEFIESMKYCLENSKGFDFQVLGTLTTDFAPTNIQSLYTM
SPAVVTISIDNKSYCWTKKDSDILTLKNSLETNLKNKFSLFVNDSVSFNDDIIELIEIKNDKPFM
FPYKGGKIFAYRYKVYFANNSYARELAKIALALGLGEKGSLTFGFCEKGR UniProtKB/TrEMBL Accession No. A0RNQ1 (A0RNQ1_CAMFF)
*Campylobacter fetus* subsp. fetus (strain 82-40)
SEQ ID NO:174
MKIYQLKVFLKLNQNVDFVNSPEFLSSNLHKSMLGDEALRSIHMQRYLKPYSIGFLYGMKGKKDG
FTSGEDMYFYVRSIDESFISKLRICLENSKNLGFNVYASKLEVLDSKRIDCLYTMSPATVVLKEG
DKTIPWRRENSDIAALKDALILNLKNKYEYFLDKKIEITDDIIELIEIKTNRAFAFKYKNGKIYA
YRYQIHFSGNKTAQEFANIAMILGVGVKNTLGFGFCMRSKNVV

*Figure 16y*

UniProtKB/TrEMBL Accession No. A0YIK9 (A0YIK9_9CYAN)
*Lyngbya* sp. PCC 8106
SEQ ID NO:175
MKRSFKKNTSLSWSADTELVGLVLALRPTGADLLYPQYTIGLHAWFLDQVRQTSPDLSAYLHDGE
SEKPFTISGLEGALKLSGKHLQLQPEQTYFWSITALSKPVVQWLVEWVKCLPTQVELRNAPLTIQ
SCQMALAPTTYRQLFDAPTPKPAKVNLSFMSPTSFRRKGHHFPLPLPTNLFHSYLRRWNDFSNLP
VEQESFLDWVDESVIIQRHQIASTKVAAGKRGMVTGFTGAIELSLSKKSSLASTQNQQLFYALGR
FAPYCGTGHKTTFGLGQTRFEWQIEETEMIPTSSQQLGERIAELAEQFTIQRKRTGGTRTQKIAE
TWATILARREDGESLQAIAVDLEMPYETVKTYAKLARRALRQPD UniProtKB/TrEMBL Accession No. A0YW92 (A0YW92_9CYAN)
*Lyngbya* sp. PCC 8106
SEQ ID NO:176
MPYSLVLNLIPLSSISPTYLSGRHLHALFLTLVSSVDKQLGDYLHEPKTEKSFTLSPLQTCSKHR
RVEQTLQWEHSQPISVGTPCWWRISLLDEGLFSKLTHLWLNLNPDQPWHLGSANLKITSVLATPQ
STQPWANTCSYSQLYQQASNSDRSMTLIFCTPTAFRQGKFDTSLPTAEII
FNSLLNRWNKYSGIEFKQLPLNSIFPSFFNIKTEMVADSRSKFIGCVGKVNYRLLGNVEP
EIIQQVNTLADFAFYCGVGRKTPMGMGMLRRLQKEGTGDRGQGTESLRRL UniProtKB/TrEMBL Accession No. A8YLQ9 (A8YLQ9_MICAE)
*Microcystis aeruginosa* PCC 7806
SEQ ID NO:177
MPYSLVLNLTPRSPIYPNFLTGRHLHALFLTLVSSVDQELGKILHAAEADKAFTLSPLQI
QSRGKITINSPQWRHEREIASETPCWWRISLLDDRLFGKLTSLWLNLNPKQPWHLGSADLVITSV
LATPQSVQPWANSCTYQYLYENASETNREFDFLFATPVTFRQGKFDSALPTRELVFNSLLNRWNR
YSGIPFDSIALESIFPSFFDIQTKLADEAYKNQSFGCVGEIHYRLLGEVEPAKIKAINVLADFAL
YAGVGRKTTMGMGMTRRIAKEKR UniProtKB/TrEMBL Accession No. B0JKW7 (B0JKW7_MICAN)
*Microcystis aeruginosa* (strain NIES-843)
SEQ ID NO:178
MPYSLVLNLTPRSPIYPNFLTGRHLHALFLTLVSSVDQELGKILHTAEADKAFTLSPLQM
QSGGKTINSPQWRYERPIAPETPCWWRISLLDDRLFGKLTPLWLNLNPKHPWHLGSADLVITSVL
ATPQSVQPWANSCTYQYLYENASETNREFDFLFATPVTFRQGKFDSALPTRELVFNSLLNRWNRY
SAIPFDSIVLESIFPSFFDIQTKLADEAYKNQSFGCVGEIHYRLLGEVEPAKIKAINVLADFALY
AGVGRKTTMGMGMTRRIAKEKR UniProtKB/TrEMBL Accession No. Q6ZED0 (Q6ZED0_SYNY3)
*Synechocystis* sp. (strain PCC 6803)
SEQ ID NO:179
MVDLKSLAGAEMVGLRWQLRFDRPCRLESHYVKGLHAWFLHQVQAIDPDVSAWLHDGQGEKPFTI
SRLIGPTLWQEGHWHWQINKTYHWQLNLLSGALIEALQPWLARLPNKIVLARQTLWVEAVDCYLA
PHNYQQLWPQGALPRRQEFTFTSPTSFRRQGNHYPLPEPRNVLQSYLRRWNDFSGLAFEPEPFLD
YWVPQNVVIDRHWLESVKTTAGKQGSVVGFVGAVSLVLTPQARNDGDDYGRLFHALCRYGPYCGT
GHKTTFGLGQTMAGWATPDLKTFACLQEDLQTQVLTQRIDQCASLLLAQRQRTGGQRAQEICHTL
ATIFVRREQGESLQEIALDLQLPYETARTYSKRAKRALANVQ

*Figure 17a*

UniProtKB/TrEMBL Accession No. Q6ZEI4 (Q6ZEI4_SYNY3)
*Synechocystis* sp. (strain PCC 6803)
SEQ ID NO:180
MFDDRYSLYSVVIELGAAKKGFPTGILGRALHSQVLEWLKIGEPSLAEELHQSQISPFSI
SPLIGKRRSKLTEEGDRFFFRISLLNGSLLQPLLKGLEQQDKQIVMLDKFAFRLCHIHILPGSHS
LARASSYALTTQAPTSSKITLKFHSATSFKIDRNTIQPFPLGDSVFNSLLRRWNHFAPEELYFPS
VSWQIPVAAFELKTYSVQLKKSEIGSEGWVTYLFPDQEQAKIASVLSQFAFFAGVGRKTSMGMGQ
VSVNNHG UniProtKB/TrEMBL Accession No. Q2JNR9 (Q2JNR9_SYNJB)
*Synechococcus* sp. (strain JA-2-3B'a(2-13)) (Cyanobacteria
bacterium Yellowstone B-Prime)
SEQ ID NO:181
MLIVAVDWEWAVPMLSFSEPSADREANGKWPTGSELVGITLEVQAPRSYLLDPHYAKGLHAWFLS
QVQETDPQLSAYLHDGESEKPFTLSRLMGPFREQGGRPLIPPHLPFRWWITGLNPPVVEWLRGWC
QRLPTWLELRGSPLQILGWQISIPPRTYRQLLEQPLSPRSWSLSFVSPTSFRHRGHHLPLPIPRN
LFHSYLRRWNDFSGLPIEAEPFLDWVDGEVIIQRHRLESVKTTAGRQGSVTGFIGCVQLAVSSRA
PELLQQQLQALIHLAPYCGTGHKTPFGLGQTRLGWLAEELPASPVPSREEQVAQRIEELSALFLS
QRQRQGGSRAEKTAQLWATILARREGGESLQQIAADLEMPYETVKTYAKLARRSLQSGSQDYSSS
SLP UniProtKB/TrEMBL Accession No. Q2JVZ0 (Q2JVZ0_SYNJA)
*Synechococcus* sp. (strain JA-3-3Ab) (Cyanobacteria bacterium
Yellowstone A-Prime)
SEQ ID NO:182
MLTKLSFSEPPVAGAENSKWPAGSELVGIALEVQAPQPYLLDPHYAKGLHAWFLSQVQETDPQLS
AYLHDGESEKPFTLSRLMGPFREQGGRLLIPPQIPFRWSITALNPQVVEWLREWCRRLPPWLELR
GSPLQILGWKVSAPPRTYRQLLEQPLSPRSWSLSFVSPTSFRHRGHHLPLPIPRNLFHSYLRRWN
DFSGLPIEAEPFLDWVDGEVIIQRHRLESVKTTAGRQGSVTGFIGCVQLAVSSRAPELLQQQLQA
LIHLAPYCGTGHKTPFGLGQTRLGWLAEELPATPVLCREEQLARRIEELSALFLSQRQRQGGSRA
EKTAQLWATILARREGGESLQQIAADLEMPYETVKTYAKLARRSLQSGSQDYSSSSLP UniProtKB/TrEMBL Accession No. A0ZJZ0 (A0ZJZ0_NODSP)
*Nodularia spumigena* CCY9414
SEQ ID NO:183
MVRTAKPTNRQQKPKSSPTATLPTWADNTELVGLEFDLEALTTSSLYSQYTIALHAWFLDQVRQL
DPDLSAYLHDGESEKPFNISALESQLLPTGKQLQLEANQILHWQVNALSAKVAEFLQLWLTQLPQ
TLNLRGATLQIKQVRIAHPPTTYAQLLQPPAKYSQVNLSFISPTSFRRKGHHFPLPVPVNLFHSY
LRRWNDFSQIPISQADFLDWIDENVIIHQHRLESVKVAAGKRGSVTGFTGAISCGLSKAALANTE
FTQLFYALVKLAPYCGTGHKTTFGLGQTSLSWVEPEASSPTQLLTNLLGERIEELTAIFTAQRKR
SGGDRTDKIAATWATILARREMGESLKLIAEDLEMPVDTVKTYTKLARRSLKDADL

*Figure 17b*

UniProtKB/TrEMBL Accession No. Q3M5G3 (Q3M5G3_ANAVT)
Anabaena variabilis (strain ATCC 29413 / PCC 7937)
SEQ ID NO:184
MPHSLVLNLLPQSPIPPQYITGRHLHALFLTLVSSVDSTLGDRLHDSTADKAFTLSPLQI
KGEERGRYKSKIPHGQSLQYFHQQAIPAGTPCWWRISLLDDTLFSQLTQLWLNLNPSHPWHLGPA
NLYITSIQGTPQSTQPWANATTYAQLYEQAGESNDVRSLVNNRTLNFTFTTPTAFRQGKFDTTLP
TRECVFNSLLSRWNKYSGIEFSEIAIESIFPSFLNIHTEILADSRSKFIG
ILGEINYRILGDIEPIQIKQINALADFAMYAGIGRKTTMGMGMIRRLYSA UniProtKB/TrEMBL Accession No. B2ITK0 (B2ITK0_NOSP7)
Nostoc punctiforme (strain ATCC 29133 / PCC 73102)
SEQ ID NO:185
MPHSLVLNLLPQSPIPPQYLTGRHLHALFLTLVSSVDSTLGDRLHDSTADKAFTLSPLQI
SNTNSPLLKGGKGGSKLQYSHQQPIPAGTPCWWRISLLDDTLFGKLTQLWLNLNPNRPWHLGPAD
LYITSIQGTPQSIQPWANANTYAQLYEEASDGNSSINLTFSTPTAFRQGQYDTTLPTRESVFNSL
LSRWNKYSGIEFSQIAIESIFPSFVNIHTEILADSRSKFIGIIGEVTYKI
LGAVEPIQIKQINALADFALYTGVGRKTTMGMGMTRQMYSP UniProtKB/TrEMBL Accession No. Q8YWN8 (Q8YWN8_ANASP)
Anabaena sp. (strain PCC 7120)
SEQ ID NO:186
MPHSLVLNLLPQSPIPPQYLTGRHLHALFLTLVSSVDSTLGDRLHDSTADKAFTLSPLQI
QGEERGRYKSKIPNSYSLQYLHQQAIPAGTPCWWRISLLDDTLFSQLTQLWLNLNPNHPWHLGPA
NLYITSIQGTPQSTQPWANAITYTQLYEQAGENNDLRSLGNNHTLNFTFTTPTAFRQGKFDTTLP
TRECVFNSLLSRWNKYSGIEFSEIALEAIFPSFLNIHTEILADSRSKFIG
ILGEINYRILGDIEPIQIKQINALADFAMYAGVGRKTTMGMGMIRRLYSS UniProtKB/TrEMBL Accession No. Q8YWW2 (Q8YWW2_ANASP)
Anabaena sp. (strain PCC 7120)
SEQ ID NO:187
MPRAATTPKRKPRAKSAPTSLVPTWADETELVGLVFDLEATDSGSLYSQYTIGLHAWFLHQVQQV
DPDLSAYLHDGESEKPFNISALEGQLLPSGKQLRLEAKQTYHWHINALSQKVALFLKEWLTNLPK
TIELSGTPLQIKQVSIAHAPTTYAQLLQPSTQPSLVNLSFVSPTSFRRKGHHFPLPVPENLFHSY
LRRWNDFSNMLVNQESFLEWIDENVIIHQHRLQSEKVAAGKRGSVTGFTGAISLGLSRAGLANAD
FTKLFYALVQLSPYCGTGHKTTFGLGQTRLDWLEQKPTTSAQLLENILAERIEELTEIFTAQRKR
KGGDRTDKIAATWATVLARRDMGDSLQAIADDLEMPLLTVKTYVKLARKALK

*Figure 17c*

SEQ ID NO:1
TTATACTCCAGTTTTTAATTCCTCTCTACTGTTGAATGTTATCTTTTCTTGCTCTTCAGCCTCCT
TCGTCGTTTTATTGCCCTCAACCTTAACCATTCCGAAGCCCAGGGAATTCTTTTCTCCGAACCCT
ACTTCGTATCCAACTTTTAGGAGGTCATCATTTCCATAAGCCCTAAACACCAAATGCCACGCAGT
CTGGTAAATCCCCGGTTTTATTCTAAATCGCTTTGGTTTTGCAATTAAAACCTCCATTTCAAATT
CACTGGGAGGTTTATCTCCATAGGCCATAACGTACTTATCCTGCAGGTCGTCTTTTATAATAGAG
TAGAACTCTTTTTCCATTGGGGGAACGTCATATGACTTGCCTTTTCTTACTACTGTAACGGCTAT
TGGGGAGAGCGTTACAAAGGTTGAACCGTTGAACTTCTTGGGCTCTCTTAAAACCTTAATTTCAT
GAAGATAAAACCTCTCATCCCACAGCCTAACTTCTGGGTTCATTAACAATCCATTCACCAAGGCC
TCAGCTATCTCAGGGACGCAAGTAGAAAAGTAGAAAAATCCTTTTTTATATCCTAGGAAATATGG
CAAGCCTTTGGGATGTTCTCTTTTTTCGGCCATAAAAAGTGAATACGTAAAGAGTTTAGGGCCCT
TAACTTCATGGAGATATGTTGCAAGCTTCGGATTGGAAGATTTAATAGCGTTGTATATTAAACCC
TGGAGGTAGTATTGATGATTGTAGGGTACTTTAAATGCCCTATCCTTATCCTCTGGAACTAGTCT
TATTAAAAACCTCAT

SEQ ID NO:2
MRFLIRLVPEDKDRAFKVPYNHQYYLQGLIYNAIKSSNPKLATYLHEVKGPKLFTYSLFMAEKRE
HPKGLPYFLGYKKGFFYFSTCVPEIAEALVNGLLMNPEVRLWDERFYLHEIKVLREPKKFNGSTF
VTLSPIAVTVVRKGKSYDVPPMEKEFYSIIKDDLQDKYVMAYGDKPPSEFEMEVLIAKPKRFRIK
PGIYQTAWHLVFRAYGNDDLLKVGYEVGFGEKNSLGFGMVKVEGNKTTKEAEEQEKITFNSREEL
KTGV

*Figure 18*

```
TIGR01877: domain 1 of 1, from 44 to 236: score 230.5, E = 4.9e-66
             *->elhdkkkfKpFtfSvlfgekrkiekgnkkkilefegpysfyiSspdd
                +lh+ k++K+Ft+S+++ ekr+++kg    +++ +++++fy+S++ +
     Cas6  44    YLHEVKGPKLFTYSLFMAEKREHPKG--LPYFLGYKKGFFYFSTCVP  88 elieslyngllknpefkigntsfevkeikvlpepklaiftdessevtfkt
                e++e+l+ngll+npe+++++ +f+++eikvl epk    +++    tf t
     Cas6  89   EIAEALVNGLLMNPEVRLWDERFYLHEIKVLREPK---KFNG---STFVT 132 lSPivirtklrpkpkekkkryyllpddelFfesLkenlikkyllfygelp
                lSPi +   r++     k y+++p +++F+ ++k+ l++ky ++yg++p
     Cas6  133  LSPIAVTVV-RKG-----KSYDVPPMEKEFYSIIKDDLQDKYVMAYGDKP 176 eeerefefeplklfkkvgyrlkvvrikygrykgdkkikgfagegvfrlkg
                +   efe+e+l   k+     k++rik      +i+ +a++ vfr+  g
     Cas6  177  PS--EFEMEVLI-AKP-----KRFRIKP-------GIYQTAWHLVFRAYG 211 dplreeireLLkfayyaGlGektsqGFGmve<-*
                ++        +LLk++y++G+Gek+s+GFGmv+
     Cas6  212  ND------DLLKVGYEVGFGEKNSLGFGMVK    236

PF01881: domain 1 of 1, from 95 to 238: score 217.5, E = 4.1e-62
             *->yeGLldrpeNQYIirignvkFkVeevkvLKekelkkknsGskFkTLS
                ++GLl  pe   +r++ + F++ e+   K++ ++kk++Gs+F+TLS
     Cas6  95     VNGLLMNPE----VRLWDERFYLHEI---KVLREPKKFNGSTFVTLS 134

PIviktvGseeggylKeyDlyPddekFyerLreNlvkKYvafyGeepkde
                PI+++   + ++g  K yD+ P + +Fy  +++ l +KYv+  yG ++++
     Cas6  135  PIAVT---VVRKG--KSYDVPPMEKEFYSIIKDDLQDKYVMAYG-DKPPS 178 dFefeplkvKpkRnrvkiPKEGvdiYvRavemvveFkveGdsWkLLEKik
                Fe+e+l++KpkR+r+k       ++iY+ a+++v F+++G
     Cas6  179  EFEMEVLIAKPKRFRIK-----PGIYQTAWHLV--FRAYGN--------- 212

IkpEERkLirFGYdcGFGEKNSlGFGMVkvi<-*
                ++    L+++GY++GFGEKNSlGFGMVkv+
     Cas6  213  --DD---LLKVGYEVGFGEKNSLGFGMVKVE    238
```

*Figure 19*

SEQUENCE LISTING

<160> NUMBER OF SEQ ID NOS: 242

<210> SEQ ID NO 1
<211> LENGTH: 795

<210> SEQ ID NO 1
<211> LENGTH: 795
<212> TYPE: DNA
<213> ORGANISM: Pyrococcus furiosus

<400> SEQUENCE: 1

```
ttatactcca gtttttaatt cctctctact gttgaatgtt atcttttctt gctcttcagc      60
ctccttcgtc gttttattgc cctcaacctt aaccattccg aagcccaggg aattcttttc     120
tccgaaccct acttcgtatc aacttttag gaggtcatca tttccataag ccctaaacac     180
caaatgccac gcagtctggt aaatccccgg ttttattcta aatcgctttg gttttgcaat     240
taaaacctcc atttcaaatt cactgggagg tttatctcca taggccataa cgtacttatc     300
ctgcaggtcg tcttttataa tagagtagaa ctcttttttcc attgggggaa cgtcatatga     360
cttgcctttt cttactactg taacggctat tggggagagc gttacaaagg ttgaaccgtt     420
gaacttcttg ggctctctta aaaccttaat ttcatgaaga taaaacctct catcccacag     480
cctaacttct gggttcatta acaatccatt caccaaggcc tcagctatct cagggacgca     540
agtagaaaag tagaaaaatc ctttttttata tcctaggaaa tatggcaagc ctttgggatg     600
ttctcttttt tcggccataa aaagtgaata cgtaaagagt ttagggcccct aacttcatg     660
gagatatgtt gcaagcttcg gattggaaga tttaatagcg ttgtatatta aaccctggag     720
gtagtattga tgattgtagg gtactttaaa tgccctatcc ttatcctctg gaactagtct     780
tattaaaaac ctcat                                                      795
```

<210> SEQ ID NO 2
<211> LENGTH: 264
<212> TYPE: PRT
<213> ORGANISM: Pyrococcus furiosus

<400> SEQUENCE: 2

```
Met Arg Phe Leu Ile Arg Leu Val Pro Glu Asp Lys Asp Arg Ala Phe
1               5                   10                  15
Lys Val Pro Tyr Asn His Gln Tyr Tyr Leu Gln Gly Leu Ile Tyr Asn
            20                  25                  30
Ala Ile Lys Ser Ser Asn Pro Lys Leu Ala Thr Tyr Leu His Glu Val
        35                  40                  45
Lys Gly Pro Lys Leu Phe Thr Tyr Ser Leu Phe Met Ala Glu Lys Arg
    50                  55                  60
Glu His Pro Lys Gly Leu Pro Tyr Phe Leu Gly Tyr Lys Lys Gly Phe
65                  70                  75                  80
Phe Tyr Phe Ser Thr Cys Val Pro Glu Ile Ala Glu Ala Leu Val Asn
                85                  90                  95
Gly Leu Leu Met Asn Pro Glu Val Arg Leu Trp Asp Glu Arg Phe Tyr
            100                 105                 110
Leu His Glu Ile Lys Val Leu Arg Glu Pro Lys Lys Phe Asn Gly Ser
        115                 120                 125
Thr Phe Val Thr Leu Ser Pro Ile Ala Val Thr Val Arg Lys Gly
    130                 135                 140
Lys Ser Tyr Asp Val Pro Pro Met Glu Lys Glu Phe Tyr Ser Ile Ile
145                 150                 155                 160
Lys Asp Asp Leu Gln Asp Lys Tyr Val Met Ala Tyr Gly Asp Lys Pro
                165                 170                 175
Pro Ser Glu Phe Glu Met Glu Val Leu Ile Ala Lys Pro Lys Arg Phe
            180                 185                 190
Arg Ile Lys Pro Gly Ile Tyr Gln Thr Ala Trp His Leu Val Phe Arg
        195                 200                 205
```

Ala Tyr Gly Asn Asp Asp Leu Leu Lys Val Gly Tyr Glu Val Gly Phe
            210                 215                 220

Gly Glu Lys Asn Ser Leu Gly Phe Gly Met Val Lys Val Glu Gly Asn
225                 230                 235                 240

Lys Thr Thr Lys Glu Ala Glu Glu Gln Glu Lys Ile Thr Phe Asn Ser
                    245                 250                 255

Arg Glu Glu Leu Lys Thr Gly Val
            260

<210> SEQ ID NO 3
<211> LENGTH: 271
<212> TYPE: PRT
<213> ORGANISM: Korarchaeum cryptofilum

<400> SEQUENCE: 3

Met Ile Ser Ile Ile Glu Val Glu Ala Thr Ser Gln Gly Asp Gly Val
1               5                   10                  15

Ile Pro Phe Thr Gly Pro Phe Phe Arg Ala Ala Val Leu Arg Ser Ile
            20                  25                  30

Ser Ser Gln Asp Pro Leu Leu Ala Lys Ala Leu Glu Leu Ser Ser Lys
        35                  40                  45

Lys Ile Phe Val Glu Ala Leu Arg Lys Glu Arg Lys Gln Met Pro Cys
50                  55                  60

Gly Ser Leu Glu Glu Pro Val Tyr Met Gly Ser Glu Tyr Arg Gly Ser
65                  70                  75                  80

Ile Ile Ile Phe Asn Asp Asn Val Ile Ser Asp Ala Ile Lys Ser Trp
                85                  90                  95

Val Phe Lys Lys Pro Thr Ile Thr Ile Lys Asp Ile Pro Phe Lys Val
            100                 105                 110

Thr Ser Tyr Ser Gln Gln Glu Ile Asn Ile Leu Asp Phe Ile Gln Glu
        115                 120                 125

Ser Pro Cys Arg Asn Phe Arg Leu Arg Phe Leu Thr Pro Thr Cys Phe
130                 135                 140

Lys Arg Thr Thr Ser Gln Tyr Cys Tyr Leu Tyr Pro Asn Pro Arg Leu
145                 150                 155                 160

Ile Val Ser Ser Leu Ala Ser Ala Trp Asn Ala Leu Ser Pro Lys Lys
                165                 170                 175

Gly Pro Glu Thr Arg Leu Val Ala Thr Trp Ala Asp Leu Ser Val Val
            180                 185                 190

Glu Thr Gly Tyr Glu Leu Cys Thr Thr Lys Pro Val Glu Met Ser Gly
        195                 200                 205

Glu Lys Thr Phe Val Gly Phe Met Gly Trp Val Asn Tyr Lys Val Ile
210                 215                 220

Asp His Pro Glu Trp His Arg Ser Ser His Glu Glu Met Ala Thr Trp
225                 230                 235                 240

Leu Ala Thr Tyr Leu Met Phe Gly Glu Leu Ile Gly Val Gly Tyr Met
                245                 250                 255

Arg Asn Met Gly Phe Gly Arg Ile Lys Phe Glu Val Lys Arg Lys
            260                 265                 270

<210> SEQ ID NO 4
<211> LENGTH: 210
<212> TYPE: PRT
<213> ORGANISM: Metallosphaera sedula

<400> SEQUENCE: 4

```
Met Ser Phe Leu Val Arg Gly Thr Val Pro Val His Tyr Asn Tyr Leu
1               5                   10                  15

Ile Gln Ser Ala Ile Tyr His Arg Leu Pro Thr Arg Leu Ser Arg Ala
                20                  25                  30

Leu His Asn Lys Gly Val Val Glu Gly Pro Arg Arg Phe Lys Met Phe
            35                  40                  45

Thr Phe Ser Arg Leu Tyr Gly Asp Phe Thr Arg Ser Asp Glu Gly Leu
        50                  55                  60

Val Tyr Arg Asp Arg Ala Tyr Leu Cys Phe Ser Ser Pro Leu Glu Arg
65                  70                  75                  80

Val Val Met Glu Val Tyr Arg Ser Phe Leu Arg Asp Pro Val Leu Arg
                85                  90                  95

Leu Gly Gly Ser Glu Leu Asn Leu Glu Val Met Asn Val Val Glu Pro
            100                 105                 110

Pro Glu Leu Gly Ser Lys Thr Val Val Tyr Thr Leu Ser Pro Ile Ala
        115                 120                 125

Val Tyr Arg Lys Ser Glu Val Gly Thr Arg Tyr Tyr Ser Pro Tyr Glu
130                 135                 140

Lys Glu Trp Glu Leu Leu Ile Ser Leu Asn Ser Leu Arg Lys Tyr His
145                 150                 155                 160

Ala Leu Arg Arg Arg Tyr Leu Lys Thr Gly Leu Val Val Arg Pro Leu
                165                 170                 175

Lys Ala Gly Leu Ser Arg Val Lys Tyr Lys Asp Asn Val Val Phe Ala
            180                 185                 190

Trp Arg Gly Gly Ile Arg Asp Glu Gly Thr Lys Val Pro Ala Asp Gly
        195                 200                 205

Gly Leu
    210

<210> SEQ ID NO 5
<211> LENGTH: 285
<212> TYPE: PRT
<213> ORGANISM: Sulfolobus tokodaii

<400> SEQUENCE: 5

Met Val Glu Phe Phe Ser Glu Lys Ile Val Lys Val Glu Phe Ser Ala
1               5                   10                  15

Val Pro Glu Ser Asp Val Ile Leu Pro Pro Leu Ser Ser Lys Val Val
                20                  25                  30

Lys Asn Leu Ile Leu Ser Ser Lys Leu Leu Pro Ser Leu Ser Ser Leu
            35                  40                  45

Val Gln Ser Gly Met Lys Asn Lys Pro Leu Phe Ile Ser Asn Leu Gly
        50                  55                  60

Lys Asn Gly Phe Arg Leu Phe Ser Thr Gly Lys Pro Val Ser Val Lys
65                  70                  75                  80

Ala Gly Glu Ile Leu Asn Phe Phe Ile Ser Phe Pro Tyr Tyr Asp Gly
                85                  90                  95

Phe Phe Thr Glu Leu Ser Ser Gly Ser Phe Glu Thr Gly Tyr Gly Lys
            100                 105                 110

Phe Phe Ile Glu Leu Glu Gln Leu Glu Val Ile Glu Leu Ser Ser Ile
        115                 120                 125

Lys Gly Val Ser Glu Gly Asn Phe Tyr Val Lys Phe Val Thr Pro Ala
130                 135                 140

Leu Leu Ser Ser Lys Val Leu Leu Pro Pro Ser Leu Lys Glu Lys Tyr
```

```
            145                 150                 155                 160
Lys Asn Val Asn Pro Gly Tyr Ser Leu Ile Pro Ser Val Gly Leu Val
                    165                 170                 175

Val Ser Tyr Ala Tyr Arg Val Tyr Arg Ala Leu Tyr Gly Asn Thr Ser
                180                 185                 190

Asn Met Glu Leu Asp Ser Lys Ser Phe Arg Leu Gly Val Leu Ser Asn
            195                 200                 205

Ser Leu Ser Arg Val Ile Gly Tyr Lys Leu Lys Pro Leu Thr Val Val
        210                 215                 220

Ile Gly Asn Asp Asn Lys Gly Arg Leu Arg Thr Ser Arg Gly Phe Val
225                 230                 235                 240

Gly Trp Met Glu Phe Asp Ile Pro Tyr Lys Lys Leu Lys Lys Ala Ile
                245                 250                 255

Ser Lys Tyr Leu Ile Ile Ala Ser Tyr Leu Gly Ile Gly Lys Ser Arg
                260                 265                 270

Gly Ile Gly Leu Gly Glu Val Val Lys Ile Lys Ser
                275                 280                 285

<210> SEQ ID NO 6
<211> LENGTH: 245
<212> TYPE: PRT
<213> ORGANISM: Sulfolobus tokodaii

<400> SEQUENCE: 6

Met Gln Pro Phe Thr Ser Lys Val Ser Arg Ile Val Met Asn Asn Tyr
1               5                   10                  15

Pro Ser Tyr Val Lys Ile Ser Glu Ser Ser Glu Pro Leu Lys Pro Val
                20                  25                  30

Arg Val Thr Val Ile Lys Asp Glu Glu Gly Arg Ser Ile Phe Lys Gly
            35                  40                  45

Met Asp Lys Asn Val Leu Arg Leu Lys Pro Gln Ile Asn Tyr Phe Phe
        50                  55                  60

Asp Leu Thr Ser Leu Asp Ile Asn Leu Phe Glu Glu Ile Val Ser Asn
65                  70                  75                  80

Pro Tyr Phe Asn Thr Lys Val Tyr Ser Thr Glu Ala Ser Val Glu Val
                85                  90                  95

Gly Glu Thr Lys Val Phe Glu Glu Val Glu Ile Glu Asp Ser Lys Ala
                100                 105                 110

Tyr Lys Ile Glu Phe Lys Thr Pro Thr Leu Ile Gln Pro Pro Arg Pro
            115                 120                 125

Asn Phe Lys Arg Lys Lys Asn Arg Tyr Leu Leu Phe Pro Phe Ser Pro
        130                 135                 140

Tyr Phe Leu Val Ser Ile Gln Arg His Trp Asn Lys Tyr Gln Glu Lys
145                 150                 155                 160

Lys Ile Ile Ile Ser Tyr Ser Arg Ala Leu Tyr Tyr Phe Lys Glu Val
                165                 170                 175

Asp Tyr Asn Leu Lys Pro Val Thr Val Ile Tyr Asp Lys Ser Lys Val
                180                 185                 190

Arg Gly Phe Val Gly Trp Thr Leu Phe Thr Leu Glu Ala Arg Lys Asn
            195                 200                 205

Ser Ser Leu Arg Glu Gly Ile Arg Lys Leu Leu Ala Tyr Ser Asn Tyr
        210                 215                 220

Ile Gly Val Gly Lys Ser Arg Ala Ile Gly Phe Gly Glu Val Met Val
225                 230                 235                 240
```

```
Lys Gly Val Arg Lys
            245
```

<210> SEQ ID NO 7
<211> LENGTH: 255
<212> TYPE: PRT
<213> ORGANISM: Sulfolobus tokodaii

<400> SEQUENCE: 7

```
Met Ile Tyr Leu Ala Ile Phe Lys Val Ser Ala Asp Arg Asp Thr Ile
1               5                   10                  15

Ile Pro Pro Phe Ser Ser Lys Leu Ser Arg Ser Ile Leu Ala His Ile
            20                  25                  30

Ser Ser Ser Tyr Ala Lys Val Met Glu Ser Arg Gln Pro Phe Lys Pro
        35                  40                  45

Ile Arg Val Thr Val Leu Lys Asp Ser Lys Gly Phe Pro Leu Ile Ala
    50                  55                  60

Phe Asn Gly Arg Lys Thr Ile Leu Arg Ala Asn Glu Ile Tyr Ser Phe
65                  70                  75                  80

Ser Phe Ser Thr Thr Ser Asn Asp Ile Ala Asn Asp Leu Ile Arg Arg
                85                  90                  95

Asp Met Ile Asp Ile Lys Ile Trp Asn Ser Thr Phe Thr Ile Glu Leu
            100                 105                 110

Thr Ser Leu Lys Ile Val Glu Glu Ile Glu Tyr Ile Asp Ser Asp Phe
        115                 120                 125

Tyr Arg Val Asn Phe Ile Thr Pro Thr Leu Leu Gln Pro Pro Lys Phe
    130                 135                 140

Gly Lys Met Asn Arg Phe Leu Leu Phe Pro Tyr Ala His Phe Phe Leu
145                 150                 155                 160

Leu Ser Ile Ala Arg His Trp Asn Ala Asn Met Lys Thr Lys Ile Lys
                165                 170                 175

Leu Ser Ser Leu Lys Thr Leu Tyr Tyr Phe Lys Glu Ile Asp His Arg
            180                 185                 190

Ile Trp Pro Val Thr Thr Ile Tyr Asp Gly His Pro Ile Arg Gly Phe
        195                 200                 205

Trp Gly Trp Val Leu Tyr Lys Ile Glu Gly Glu Arg Glu Asn Ile Ile
    210                 215                 220

Arg Leu Leu Asn Tyr Ala Asn Tyr Phe Gly Ala Gly Lys Ser Arg Ser
225                 230                 235                 240

Ile Gly Phe Gly Glu Ile Glu Ala Leu Pro Thr Gly Phe Leu Ala
                245                 250                 255
```

<210> SEQ ID NO 8
<211> LENGTH: 289
<212> TYPE: PRT
<213> ORGANISM: Sulfolobus solfataricus

<400> SEQUENCE: 8

```
Met Pro Leu Ile Phe Lys Ile Gly Tyr Asn Val Ile Pro Leu Gln Asp
1               5                   10                  15

Val Ile Leu Pro Thr Pro Ser Ser Lys Val Leu Lys Tyr Leu Ile Gln
            20                  25                  30

Ser Gly Lys Leu Ile Pro Ser Leu Lys Asp Leu Ile Thr Ser Arg Asp
        35                  40                  45

Lys Tyr Lys Pro Ile Phe Ile Ser His Leu Gly Phe Asn Gln Arg Arg
    50                  55                  60
```

```
Ile Phe Gln Thr Asn Gly Asn Leu Lys Thr Ile Thr Lys Gly Ser Arg
 65                  70                  75                  80

Leu Ser Ser Ile Ile Ala Phe Ser Thr Gln Ala Asn Val Leu Ser Glu
                 85                  90                  95

Val Ala Asp Glu Gly Ile Phe Glu Thr Val Tyr Gly Lys Phe His Ile
            100                 105                 110

Met Ile Glu Ser Ile Glu Ile Val Glu Val Glu Lys Leu Lys Glu Glu
        115                 120                 125

Val Glu Lys His Met Asn Asp Asn Ile Arg Val Arg Phe Val Ser Pro
    130                 135                 140

Thr Leu Leu Ser Ser Lys Val Leu Leu Pro Pro Ser Leu Ser Glu Arg
145                 150                 155                 160

Tyr Lys Lys Ile His Ala Gly Tyr Ser Thr Leu Pro Ser Val Gly Leu
                165                 170                 175

Ile Val Ala Tyr Ala Tyr Asn Val Tyr Cys Asn Leu Ile Gly Lys Lys
            180                 185                 190

Glu Val Glu Val Arg Ala Phe Lys Phe Gly Ile Leu Ser Asn Ala Leu
        195                 200                 205

Ser Arg Ile Ile Gly Tyr Asp Leu His Pro Val Thr Val Ala Ile Gly
    210                 215                 220

Glu Asp Ser Lys Gly Asn Leu Arg Lys Ala Arg Gly Val Met Gly Trp
225                 230                 235                 240

Ile Glu Phe Asp Ile Pro Asp Glu Arg Leu Lys Arg Arg Ala Leu Asn
                245                 250                 255

Tyr Leu Leu Thr Ser Ser Tyr Leu Gly Ile Gly Arg Ser Arg Gly Ile
            260                 265                 270

Gly Phe Gly Glu Ile Arg Leu Glu Phe Arg Lys Ile Glu Glu Lys Glu
        275                 280                 285

Gly

<210> SEQ ID NO 9
<211> LENGTH: 287
<212> TYPE: PRT
<213> ORGANISM: Sulfolobus solfataricus

<400> SEQUENCE: 9

Met Pro Leu Ile Phe Lys Ile Gly Tyr Asn Val Ile Pro Leu Gln Asp
 1               5                  10                  15

Val Ile Leu Pro Thr Pro Ser Ser Lys Val Leu Lys Tyr Leu Ile Gln
                 20                  25                  30

Ser Gly Lys Leu Leu Pro Ser Leu Asn Asn Leu Ile Thr Ser Arg Asp
             35                  40                  45

Lys Tyr Lys Pro Ile Phe Ile Ser His Leu Gly Leu Asn Gln Arg Arg
         50                  55                  60

Ile Phe Gln Thr Asn Gly Asn Leu Lys Thr Ile Ser Arg Gly Ser Lys
 65                  70                  75                  80

Leu Ser Ser Thr Ile Ala Phe Ser Thr Gln Val Asn Val Leu Pro Glu
                 85                  90                  95

Leu Asp Glu Gly Val Phe Glu Thr Ile Tyr Gly Lys Phe His Ile Thr
            100                 105                 110

Ile Glu Ser Val Glu Ile Val Glu Val Glu Lys Leu Lys Glu Glu Val
        115                 120                 125

Glu Lys His Met Asn Asp Asn Ile Arg Val Arg Phe Ile Ser Pro Thr
    130                 135                 140
```

```
Leu Leu Ser Ser Lys Val Leu Pro Pro Ser Leu Glu Arg Tyr
145                 150                 155                 160

Lys Arg Val Asn Ala Gly Tyr Ser Thr Leu Pro Ser Val Gly Leu Ile
                165                 170                 175

Val Ala Tyr Ala Tyr Asn Val Tyr Cys Asn Leu Ile Gly Lys Lys Glu
            180                 185                 190

Val Glu Val Arg Ala Phe Lys Phe Gly Val Ile Ser Asn Ala Leu Ser
        195                 200                 205

Arg Ile Ile Gly Tyr Asp Leu His Pro Val Thr Ile Val Ile Gly Glu
    210                 215                 220

Asp Ser Lys Gly Asn Leu Arg Lys Ala Arg Gly Val Met Gly Trp Ile
225                 230                 235                 240

Glu Phe Asp Ile Pro Asp Glu Lys Leu Lys Arg Arg Ala Leu Arg Tyr
                245                 250                 255

Leu Leu Ala Ser Ser Tyr Leu Gly Ile Gly Arg Ser Arg Gly Ile Gly
                260                 265                 270

Phe Gly Glu Ile Lys Leu Glu Phe Ile Lys Arg Glu Glu Asn His
                275                 280                 285

<210> SEQ ID NO 10
<211> LENGTH: 263
<212> TYPE: PRT
<213> ORGANISM: Sulfolobus solfataricus

<400> SEQUENCE: 10

Met Gln Asn Thr Lys Cys Val Ile Ser Asp Ile Thr Gln His Ser Tyr
1               5                   10                  15

Thr Phe Ser Gly Arg Phe Asp Met Ile Val Ala Glu Ile Phe Val Lys
                20                  25                  30

Pro Glu Ser Asp Ala Ile Ile Pro Phe Ser Ser Lys Val Gly Lys Ser
            35                  40                  45

Leu Leu Leu Asp Pro Lys Asn Val Ser Ile Ser Pro Leu Lys Tyr Lys
        50                  55                  60

Gly Lys Tyr Leu Ile Lys Tyr Gly Ser Val Leu Thr Phe Leu Glu Val
65                  70                  75                  80

Ile Gly Gly Asn Val Tyr Ser Phe Glu Val Gly Gly Asp Glu Arg Asn
                85                  90                  95

Val Tyr Ser Ala Leu Ile Asn Leu Gly Asp Lys Ser Leu Leu Phe Asn
            100                 105                 110

Thr Tyr Trp Lys Val Val Asp Val Glu Val His Glu Val Glu Val Ser
        115                 120                 125

Ser Ile Pro Lys Asn Phe Gly Val Asp Ile Leu Thr Pro Ala Leu Ile
    130                 135                 140

Val Ser Pro Tyr Val Lys Glu Lys Arg Lys Val Phe Thr Asn Lys Ser
145                 150                 155                 160

Glu Tyr Val Phe Phe Asn Asn Ile Ile Asp Ala Thr Gly Phe Asn Arg
                165                 170                 175

Gly Asp Val Lys Leu Ser Glu Val Ile Ser Arg Phe Ala Gln Leu Leu
            180                 185                 190

Trp Glu Glu Pro Ser Ile Ile Gly Tyr Ala Asn Val Arg Tyr Gly Asp
        195                 200                 205

Lys Leu Val Ile Gly Met Ile Gly Lys Leu Arg Tyr Ser Val Lys Gly
    210                 215                 220

Glu Asp Glu Val Leu Ile Lys Val Leu Glu Asp Ala Ile Val Arg Gly
225                 230                 235                 240
```

Ile Gly Ser Ser Arg Arg Asn Gly Phe Gly Val Val Arg Ile Lys Gly
                245                 250                 255

Val Glu Ala Ser Trp Leu Arg
            260

<210> SEQ ID NO 11
<211> LENGTH: 261
<212> TYPE: PRT
<213> ORGANISM: Sulfolobus solfataricus

<400> SEQUENCE: 11

Met Ile Tyr Thr Leu Thr Phe Arg Leu Lys Pro Ser Asn Asp Val Ile
1               5                   10                  15

Ile Pro Pro Phe Ser Ser Lys Leu Ser Arg Thr Leu Phe Leu Ser Phe
            20                  25                  30

Ser Pro Thr Tyr Ser Lys Ile Ile Glu Ser Lys Glu Pro Asn Lys Pro
        35                  40                  45

Leu Arg Ile Thr Val Val Lys Asp Gln Gly Lys Pro Leu Tyr Ser Asn
    50                  55                  60

Gly Lys Ser Lys Val Val Leu Lys Ala Glu Asn Thr Tyr Thr Phe Ile
65                  70                  75                  80

Val Asn Thr Leu Leu Glu Asp Val Val Lys Glu Val Ile Arg Val Glu
                85                  90                  95

Ser Val Asn Arg Glu Ile Tyr Asn Thr Ser Phe His Val Glu Leu Val
            100                 105                 110

Asn Val Ser Val Lys Glu Asn Val Met Ala Glu Asp Ala Arg Phe Tyr
        115                 120                 125

Arg Val His Phe Lys Thr Pro Thr Leu Leu Gln Pro Pro Arg Pro Arg
    130                 135                 140

Met Lys Arg Lys Glu Asn Arg Tyr Val Leu Phe Pro Tyr Val Pro Leu
145                 150                 155                 160

Leu Phe Tyr Ser Ile Ala Ser His Trp Asn Arg Tyr Met Asp Lys Lys
                165                 170                 175

Ile Val Gly Val Thr Gly Ser Lys Thr Leu Tyr Tyr Phe Arg Glu Val
            180                 185                 190

Asn Tyr Arg Ile Arg Pro Met Thr Ala Tyr Tyr Gly Asn Ile Pro Asn
        195                 200                 205

Lys Gly Phe Val Gly Trp Val Phe Glu Leu Ser Ala Arg Lys Gly
    210                 215                 220

Ser Lys Ile Arg Glu Asn Ile Arg Arg Leu Leu Asp Tyr Val Asn Tyr
225                 230                 235                 240

Phe Gly Val Gly Lys Ser Arg Asn Ile Gly Phe Gly Glu Val Glu Val
                245                 250                 255

Lys Ser Leu Asn Gly
            260

<210> SEQ ID NO 12
<211> LENGTH: 233
<212> TYPE: PRT
<213> ORGANISM: Sulfolobus solfataricus

<400> SEQUENCE: 12

Met Phe Leu Ser Phe Ser Pro Thr Tyr Ser Lys Ile Thr Glu Ser Lys
1               5                   10                  15

Glu Pro His Lys Pro Leu Arg Ile Thr Val Ile Lys Asp His Gly Lys
            20                  25                  30

Pro Leu Tyr Ser Thr Gly Lys Asn Lys Ile Val Leu Lys Thr Glu Asn
         35                  40                  45

Thr Tyr Thr Phe Thr Val Asn Thr Leu Leu Glu Asp Val Val Lys Glu
 50                  55                  60

Val Val Lys Thr Glu Ser Val Asn Lys Glu Ile Tyr Asn Thr Lys Phe
 65                  70                  75                  80

His Val Glu Leu Glu Asn Ile Ile Val Lys Glu Glu Phe Lys Ile Asn
                 85                  90                  95

Asp Ala Arg Phe Tyr Lys Ile His Phe Lys Thr Pro Thr Leu Leu Gln
             100                 105                 110

Pro Pro Arg Pro Ser Ile Lys Arg Lys Gly Asn Arg Tyr Val Leu Phe
         115                 120                 125

Pro Tyr Val Pro Leu Leu Phe Tyr Ser Ile Ala Ser His Trp Asn Arg
 130                 135                 140

Tyr Met Asn Asn Lys Ile Val Gly Val Thr Gly Ser Lys Thr Leu Tyr
145                 150                 155                 160

Tyr Phe Arg Glu Val Asn Tyr Lys Ile Arg Pro Leu Thr Ala Tyr Tyr
                 165                 170                 175

Gly Asn Ile Pro Asn Lys Gly Phe Val Gly Trp Val Leu Phe Glu Leu
             180                 185                 190

Lys Ala Arg Lys Gly Ser Asn Leu Arg Glu Asn Ile Arg Arg Leu Leu
         195                 200                 205

Asp Tyr Ala Asn Tyr Phe Gly Ile Gly Lys Ser Arg Asn Ile Gly Phe
 210                 215                 220

Gly Glu Val Asp Val Arg Pro Leu Glu
225                 230

<210> SEQ ID NO 13
<211> LENGTH: 270
<212> TYPE: PRT
<213> ORGANISM: Sulfolobus acidocaldarius

<400> SEQUENCE: 13

Met Ser Tyr Thr Ile Ile Val Ile Phe Tyr Thr Ser Phe Glu Ile Thr
1                5                  10                  15

Thr Asp His Asp Ile Ile Leu Pro Pro Phe Thr Ser Lys Leu Ser Arg
                 20                  25                  30

Leu Ile Leu Val Lys Leu Ser Asp Thr Tyr Ser Lys Leu Gln Tyr Gln
         35                  40                  45

Asn Thr Ser Tyr Lys Pro Leu Arg Val Thr Val Ile Lys Asp Pro Glu
 50                  55                  60

Gly Arg Pro Val Tyr Ala Arg Gly Arg Gly Lys Ser Ile Ile Asn Gly
 65                  70                  75                  80

Asn Gln Ser Tyr Ser Phe Thr Phe Ser Phe Gln Asp Glu Asn Ile Phe
                 85                  90                  95

Arg Glu Ile Met Glu Lys Val Gln Thr Thr Val Glu Ala Trp Asn Thr
             100                 105                 110

Lys Phe Gln Val Asn Leu Lys Asp Ile Lys Val Asp Gln Thr Glu
         115                 120                 125

Ser Leu Arg Ser Glu Ser Lys Leu Tyr Arg Met Glu Phe Leu Thr Pro
 130                 135                 140

Thr Leu Leu Gln Pro Ile Arg Pro Asn Leu Lys Arg Lys Asp Asn Arg
145                 150                 155                 160

Phe Val Leu Phe Pro Tyr Val Pro Ile Leu Leu Phe Ser Ile Val Lys

```
                165                 170                 175
His Trp Asn Gln Asn Met Asp Gln Lys Ile His Gly Val Thr Gly Leu
            180                 185                 190

Lys Thr Leu Tyr Tyr Met Arg Glu Val Asp Tyr Arg Leu Arg Pro Val
        195                 200                 205

Thr Thr Tyr Tyr Asp Gly Lys Pro Val Arg Gly Phe Thr Gly Trp Thr
    210                 215                 220

Val Phe Glu Leu Arg Ser Lys Arg Asn Ser Lys Ile Thr Arg Asn Val
225                 230                 235                 240

Gln Lys Leu Leu Glu Tyr Ala Asn Tyr Phe Gly Val Gly Lys Ser Arg
            245                 250                 255

Ala Ile Gly Phe Gly Glu Val Asn Val Lys Val Ile Asp Glu
        260                 265                 270

<210> SEQ ID NO 14
<211> LENGTH: 243
<212> TYPE: PRT
<213> ORGANISM: Aeropyrum pernix

<400> SEQUENCE: 14

Met Val Ile Gly Leu Tyr Lys Val Ser Leu Ile Leu Glu Ser Thr Arg
1               5                   10                  15

Pro Leu Pro Leu Leu Ser Trp Ser Gly Val Val Ala Ala Arg Ile Val
            20                  25                  30

Lys Glu Cys Ile Gly Gly Arg Glu Gly Leu Val Ser Val Glu Pro Leu
        35                  40                  45

Gln Lys Glu Gly Gln Pro Leu Asn Ala Ser Pro Ser Lys Pro Ser Thr
    50                  55                  60

Ile Glu Glu Pro Asn Ile Leu Leu Gly Ala Thr Leu Asn Thr Thr Gly
65                  70                  75                  80

Phe Tyr Arg Leu Arg Ser Ser Leu Pro Gly Cys Leu Asp Arg Trp Gly
            85                  90                  95

Phe Arg Val Ile Ser Phe Glu Val Glu Arg Trp Val Pro Arg Leu Pro
        100                 105                 110

Arg Arg Val Thr Thr Ser Arg Asp Ala Ile Glu Phe Thr Val Glu Tyr
    115                 120                 125

Trp Pro Thr Ile Tyr Met Phe Arg Ser Arg Pro Ile Leu Tyr Pro Ser
130                 135                 140

Pro Gln Arg Leu Val Tyr Ser Val Phe Ser Ala Leu Ala Arg His Thr
145                 150                 155                 160

Gly Leu Ser Leu Lys Gly Tyr Ala Asn Thr Leu Ala Ser Asn Val Glu
            165                 170                 175

Leu Leu Gly Trp Asn Gly Arg Val Gly Leu Tyr Ser Ile Gly Arg Asp
        180                 185                 190

Arg Lys Val Arg Ala Phe Tyr Gly Arg Ala Thr Tyr Ala Ala Thr Ala
    195                 200                 205

Arg Tyr Val Glu Leu Leu Gln Leu Val Met Glu Ala Ala Gln Val Leu
210                 215                 220

His Val Gly Lys Ser Arg Gly Ile Gly Phe Gly Ala Val Lys Thr Gly
225                 230                 235                 240

Ser Ile Met

<210> SEQ ID NO 15
<211> LENGTH: 292
<212> TYPE: PRT
```

<213> ORGANISM: Pyrobaculum arsenaticum

<400> SEQUENCE: 15

```
Met Glu Pro Arg Phe Glu Arg Pro Ile Leu Met Ala Ser Ser Gly
1               5                   10                  15

Gly Val Ala Tyr Leu Arg Val Arg Pro Leu Trp Ala Val Ser Val
                20                  25                  30

Leu Val Arg Gly Arg Pro Thr Glu Ala Val Ala Met Val Gly Phe Thr
            35                  40                  45

Gly Thr Val Ala Gln Ser Leu Val Val Ser Leu Leu Gly Gly Glu Leu
        50                  55                  60

His Asp Ala Arg Pro Lys Ser Phe Ser Val Thr Pro Phe Phe Val Asn
65                  70                  75                  80

Gly Arg Pro Ala Val Asp Lys Ala Val Ala Gly Pro Gly Asp Ile Leu
                85                  90                  95

Glu Leu Arg Ala Ala Phe Ala Gln Arg Glu Leu Ala Glu Arg Phe Ile
            100                 105                 110

Ala Glu Val Ala Lys Gly Tyr Thr Leu Phe Gly Arg Arg Val Val Val
        115                 120                 125

Glu Glu Leu Glu Phe Tyr Asp Val Phe Ser Gln Pro Leu Pro Glu Ala
130                 135                 140

Gln Cys Phe Lys Leu Glu Phe Leu Thr Pro Leu Arg Phe Ala Val Lys
145                 150                 155                 160

Pro Leu Tyr Arg Arg Ser Arg Ala Val Phe Asp Phe Leu Pro Arg Pro
                165                 170                 175

Leu Ser Val Phe Lys Ser Ala Val Arg His Gly Arg Ala Leu Gly Leu
            180                 185                 190

Leu Lys Leu Gly Ala Pro Phe Leu Arg Trp Val His Thr Tyr Val Ala
        195                 200                 205

Leu Thr Asp Phe Gly Cys Arg Gly Arg Cys Val Val Thr Val Lys Leu
210                 215                 220

Pro Asn Gly Gly Val Ala Arg Gly Phe Val Gly Trp Ala Leu Tyr Arg
225                 230                 235                 240

Ser Phe Gly Lys Arg Arg Ile Ala Asp Leu Trp Arg Ala Leu Arg Val
                245                 250                 255

Ala Glu Ala Phe Asn Leu Gly Thr Gly Arg Gly Met Gly Leu Gly Val
            260                 265                 270

Val Arg Val Thr Pro Leu Asp Cys Pro Gly Asn Gly Pro Ala Ala Gln
        275                 280                 285

Arg Gly Asp Ala
    290
```

<210> SEQ ID NO 16
<211> LENGTH: 269
<212> TYPE: PRT
<213> ORGANISM: Pyrobaculum calidifontis

<400> SEQUENCE: 16

```
Met Ala Tyr Val Val Arg Val Val Leu Ala Ala Arg Glu Gly Phe Ser
1               5                   10                  15

Leu Gly Gly Phe Thr Gly Thr Val Glu Ser Leu Val Leu Arg Leu
                20                  25                  30

Thr Asp Pro Ser Leu His Gly Ala Gly Pro Lys Pro Phe Ser Val Thr
            35                  40                  45

Pro Leu Phe Val Gly Gly Arg Pro Val Val Asp Leu Ala Val Val Gly
```

```
        50                  55                  60
Pro Gly Asp Leu Leu Glu Phe Arg Val Gly Phe Ala Gly Glu Gly Leu
 65                  70                  75                  80

Ala Arg Gly Phe Val Glu Arg Leu Leu Gly Gly Val Glu Leu Phe
                 85                  90                  95

Gly Arg Arg Val Glu Val Ala Glu Val Glu Met Arg Asp Val Trp Leu
                100                 105                 110

Asp Pro Leu Pro Glu Ala Arg Cys Phe Lys Leu Glu Phe Leu Thr Pro
                115                 120                 125

Thr Arg Phe Ala Val Pro Pro Leu Tyr Lys Arg Arg Ala Leu Phe
            130                 135                 140

Asp Phe Leu Pro Arg Pro Leu Thr Leu Phe Lys Ser Ala Val Arg His
145                 150                 155                 160

Gly Arg Glu Leu Gly Leu Leu Lys Leu Gly Ala Pro Phe Leu Arg Trp
                165                 170                 175

Val Tyr Thr Tyr Val Ala Leu Thr Asp Val Gly Cys Trp Cys Arg Arg
                180                 185                 190

Arg Gly Ser Cys Val Arg Thr Val Lys Leu Pro Asn Gly Gly Val Ala
            195                 200                 205

Arg Gly Phe Val Gly Trp Ala Leu Tyr Arg Ile Tyr Gly Lys Arg Arg
210                 215                 220

Leu Ala Asp Val Trp Lys Thr Ile Arg Leu Met Glu Ala Phe Asn Val
225                 230                 235                 240

Gly Thr Gly Arg Gly Met Gly Leu Gly Val Val Arg Ala Thr Pro Leu
                245                 250                 255

Pro Cys Pro Gly Glu Thr Ala Lys Asp Gly Gly Gln Arg
                260                 265

<210> SEQ ID NO 17
<211> LENGTH: 254
<212> TYPE: PRT
<213> ORGANISM: Pyrobaculum aerophilum

<400> SEQUENCE: 17

Met Ser Val Val Val Arg Gly Arg Ser Pro Glu Ala Ile Pro Leu
 1               5                  10                  15

Leu Gly Phe Thr Gly Thr Val Val Glu Ser Leu Val Val Ser Leu Leu
                 20                  25                  30

Gly Arg Glu Leu His Asp Val Lys Pro Lys Pro Phe Ser Val Thr Pro
             35                  40                  45

Phe Phe Val Gly Gly Arg Pro Ala Val Asp Lys Ala Met Val Ala Pro
 50                  55                  60

Gly Asp Leu Leu Glu Phe Arg Val Ser Phe Ala Gly Arg Glu Leu Ala
 65                  70                  75                  80

Glu Lys Phe Ile Ala Lys Ile Met Gln Gly Tyr Thr Leu Phe Gly Arg
                 85                  90                  95

Arg Val Val Glu Glu Leu Glu Phe Tyr Asp Val Phe Ser Gln Pro
                100                 105                 110

Thr Pro Gln Thr Gly Cys Phe Lys Leu Glu Phe Leu Thr Pro Leu Arg
                115                 120                 125

Phe Ala Val Lys Pro Leu Tyr Lys Arg Lys Ala Ile Phe Asp Phe
            130                 135                 140

Leu Pro Arg Pro Leu Ser Val Phe Lys Ser Ala Val Lys His Gly Arg
145                 150                 155                 160
```

```
Glu Leu Gly Leu Leu Arg Leu Gly Ala Pro Phe Leu Arg Trp Val His
            165                 170                 175

Thr Tyr Val Ala Leu Thr Asp Phe Gly Cys Pro Gly Arg Cys Ile Ile
        180                 185                 190

Thr Val Arg Leu Pro Asn Gly Gly Ile Ala Arg Gly Phe Val Gly Trp
        195                 200                 205

Ala Leu Tyr Arg Ala Phe Gly Lys Arg Leu Ala Asp Met Trp Lys
    210                 215                 220

Thr Leu Arg Phe Ala Glu Ala Phe Asn Ile Gly Ser Gly Arg Gly Met
225                 230                 235                 240

Gly Leu Gly Val Val Arg Ala Thr Pro Leu Glu Cys Pro Ser
            245                 250
```

<210> SEQ ID NO 18
<211> LENGTH: 262
<212> TYPE: PRT
<213> ORGANISM: Pyrobaculum aerophilum

<400> SEQUENCE: 18

```
Met Arg Ala Val Trp Arg Val Arg Val Leu Gly Arg Leu Ala Gly Gly
1               5                   10                  15

Val Val Leu Thr Gly Phe Ser Gly Thr Leu Val Glu Ser Leu Val Val
            20                  25                  30

Ser Arg Leu Gly Gly Trp Leu His Asp Ala Lys Pro Lys Pro Phe Ala
        35                  40                  45

Val Ser Pro Leu Phe Ala Gly Arg Pro Val Leu Asp Gly Ala Ala
    50                  55                  60

Leu Gly Gln Gly Thr Glu Val Glu Phe Arg Val Gly Phe Ala Asp Glu
65                  70                  75                  80

Leu Leu Ala Leu Arg Phe Val Asp Ser Leu Ser Gly Val Thr Leu
                85                  90                  95

Phe Gly Lys Pro Leu Glu Leu Ala Glu Leu Glu Phe Arg Asp Val Ser
            100                 105                 110

Ser Glu Pro Leu Pro Ser Thr Pro Cys Phe Lys Val Glu Phe Leu Ser
        115                 120                 125

Pro Thr Arg Phe Ala Val Lys Pro Leu Tyr Lys Arg Arg Ala Leu
    130                 135                 140

Phe Asp Phe Thr Pro Arg Pro Leu Asn Leu Phe Lys Ser Ala Val Arg
145                 150                 155                 160

Gln Gly Arg Ala Leu Gly Leu Leu Arg Leu Gly Gly Pro Phe Leu Arg
                165                 170                 175

Trp Val Tyr Thr Tyr Val Ala Leu Thr Asp Phe Gly Cys Trp Gly Lys
            180                 185                 190

Cys Val Arg Thr Val Lys Leu Gly Gly Val Ala Arg Gly Phe
        195                 200                 205

Val Gly Trp Ala Leu Tyr Arg Ala Phe Gly Arg Arg Leu Ala Asp
    210                 215                 220

Val Trp Arg Ala Leu Arg Val Ala Glu Val Phe Asn Val Gly Thr Gly
225                 230                 235                 240

Arg Gly Met Gly Leu Gly Ala Val Arg Val Thr Pro Leu Glu Cys Pro
                245                 250                 255

Gly Ala Thr Asp Arg Gly
            260
```

<210> SEQ ID NO 19

```
<211> LENGTH: 246
<212> TYPE: PRT
<213> ORGANISM: Pyrobaculum aerophilum

<400> SEQUENCE: 19

Met Trp Arg Glu Val Glu Ile Glu Leu Val Thr Ser Ala Pro Cys Pro
1               5                   10                  15

Leu Thr Gly Trp Ser Gly Ser Val Ala Tyr Lys Thr Leu Leu Glu Leu
            20                  25                  30

Ile Arg Arg Glu Ala Glu Pro Lys Gly Lys Ile Phe Ala His Pro Leu
        35                  40                  45

Tyr Arg Gly Asp Arg Pro Ile Leu Ser Gly Val Glu Gly Arg Ala Val
    50                  55                  60

Val Leu Glu Pro Met Thr Gln Val Lys Ile Arg Ala Val Leu Thr Glu
65                  70                  75                  80

Gln Asp Leu Phe Tyr Leu Leu Ser Ala Val Ser Lys Ala Glu Pro Thr
                85                  90                  95

Ser Ser Thr Cys Pro Met Ser Pro Ala Ala Leu Arg Phe Ser Pro Leu
            100                 105                 110

Glu Leu Lys Leu Gly Glu Gly His Gly Phe Ala Val Val Lys Leu Arg
        115                 120                 125

Phe Tyr Pro Thr Ala Phe Met Phe His Gly Arg Asp Val Leu Tyr Pro
    130                 135                 140

Ser Pro Gln Arg Met Ala Tyr Ser Leu Ala Lys Ala Tyr Lys Glu Leu
145                 150                 155                 160

Phe Gly Val Asp Ile Lys Pro Ile Ala Asp Arg Ala Pro Thr Ala Leu
                165                 170                 175

Glu Ile Val Gly Met Arg Thr Lys Ala Val Arg Val Asn Ile Gly Asp
            180                 185                 190

Ser Arg Leu Val Pro Ala Phe Leu Gly Arg Ala Gln Leu Ala Val Phe
        195                 200                 205

Gly Asn Val Asp Ala Trp Leu Ser Leu Leu Lys Leu Gly Glu Ser Val
    210                 215                 220

Gly Val Gly Ile Ser Arg Ala Ile Gly Phe Gly Lys Tyr Lys Ile Glu
225                 230                 235                 240

Glu Val Val Leu His Ala
                245

<210> SEQ ID NO 20
<211> LENGTH: 222
<212> TYPE: PRT
<213> ORGANISM: Pyrobaculum islandicum

<400> SEQUENCE: 20

Met Tyr Asn Phe Phe Leu Thr Ala Leu Arg Arg Val Ala Glu Pro Lys
1               5                   10                  15

Gly Arg Val Phe Ala His Pro Leu Tyr His Gly Gly Ala Pro Val Leu
            20                  25                  30

Ser Gly Leu Asn Gly Ser Gln Lys Ala Phe Glu Pro Gly Ala Ala Phe
        35                  40                  45

Glu Leu Arg Ala Leu Leu Leu Glu His Asp Ala Arg Leu Leu Leu Asp
    50                  55                  60

Ser Leu Ala Ala Glu Pro Arg Val Glu Val Gly Cys Val Leu Glu Val
65                  70                  75                  80

Ser Gly Ile Asp Ile Val Pro Ala Asp Gly Lys Leu Glu Glu Arg His
                85                  90                  95
```

Gly Met Ala Val Val Glu Leu Val Phe Tyr Pro Thr Val Phe Met Phe
            100                 105                 110

His Gly Arg Asp Val Leu Tyr Pro Ser Pro Gln Arg Leu Ala Tyr Ser
            115                 120                 125

Leu Ala Lys Thr Tyr Tyr Gln Leu Tyr Gly Val Ser Leu Lys Glu Leu
        130                 135                 140

Ala Asp Arg Ala Pro Thr Ala Leu Glu Leu Val Gly Met Arg Ile Lys
145                 150                 155                 160

Thr Gly Trp Leu Asn Ile Gly Glu Ala Arg Lys Val Pro Val Phe Tyr
                165                 170                 175

Gly Arg Ala Arg Leu Ala Ile Tyr Gly Asp Val Gly Met Trp Leu Ser
            180                 185                 190

Leu Leu Lys Leu Gly Glu Leu Thr Gly Val Gly Ile Ser Arg Ala Ile
        195                 200                 205

Gly Leu Gly Lys Tyr Arg Ile Glu Lys Val Glu Ile Leu Ile
    210                 215                 220

<210> SEQ ID NO 21
<211> LENGTH: 266
<212> TYPE: PRT
<213> ORGANISM: Thermoproteus neutrophilus

<400> SEQUENCE: 21

Met Arg Ile Val Ala Val Arg Ala Arg Ala Gly Ser Ala Phe Ala Val
1               5                   10                  15

Ser Gly Phe Ser Gly Thr Val Val Glu Ser Leu Val Leu Lys Thr Leu
            20                  25                  30

Gly Arg Pro Asp Leu His Asp Ala Arg Val Lys Pro Phe Ser Val Trp
        35                  40                  45

Pro Leu Leu His Arg Gly Arg Pro Val Leu Trp Gly Ala Ala Val Ala
    50                  55                  60

Pro Gly Asp Pro Val Glu Val Arg Val Gly Phe Ala Asp Asp Asp Met
65                  70                  75                  80

Ala Ser Gln Phe Ala Ala Ala Ala Gly Gly Gly Leu Gln Leu Phe
                85                  90                  95

Gly Ala Arg Leu Asp Pro Glu Ala Val Glu Met Arg Asp Ala His His
            100                 105                 110

Asp Leu Pro Gln Glu Gln Cys Phe Lys Leu Glu Phe Leu Ser Pro Leu
        115                 120                 125

Arg Phe Ala Thr Pro Pro Leu Tyr Arg Arg Ser Lys Pro Ile Tyr Glu
    130                 135                 140

Phe Phe Pro Arg Pro Leu Ser Leu Phe Lys Ser Ala Val Lys His Gly
145                 150                 155                 160

Arg Ala Leu Gly Val Thr Lys Leu Gly Ala Pro Phe Leu Arg Trp Val
                165                 170                 175

Tyr Thr Tyr Val Ala Leu Thr Asp Phe Gly Cys His Ser Arg Cys Val
            180                 185                 190

Ala Thr Val Lys Leu Pro Gly Gly Ile Ala Arg Gly Phe Leu Gly
        195                 200                 205

Trp Ala Leu Tyr Arg Ala Tyr Gly Lys Arg Arg Ile Thr Asp Leu Trp
    210                 215                 220

Lys Thr Ile Arg Leu Met Glu Thr Leu Asn Val Gly Thr Gly Arg Ser
225                 230                 235                 240

Met Gly Leu Gly Ala Val Lys Ala Thr Pro Leu Lys Cys Pro Asn Gln

```
                        245                 250                 255

Gln Pro Thr Glu Lys Pro Thr Tyr Pro Ile
                260                 265

<210> SEQ ID NO 22
<211> LENGTH: 242
<212> TYPE: PRT
<213> ORGANISM: Methanobrevibacter smithii

<400> SEQUENCE: 22

Met Arg Leu Glu Ile Ile Leu Lys Gly Lys Asn Asn Phe Lys Val Pro
1               5                   10                  15

Phe Asn Tyr Asn His Ile Leu Ser Ala Ile Ile Tyr Asn Lys Ile Ala
            20                  25                  30

Asp Leu Asn Phe Ala Asn Glu Leu His Ser Ser Lys Ser Phe Lys Phe
        35                  40                  45

Phe Thr Phe Ser Gln Ile Tyr Ile Pro Lys Arg Arg Ile Val Lys Asp
    50                  55                  60

Gly Ile Ile Ala Lys Asp Gly Val Ile Ser Phe Tyr Ile Ser Ser Pro
65                  70                  75                  80

Asn Asp Phe Leu Ile Lys Ser Leu Val Asp Gly Phe Leu Glu Asp Leu
                85                  90                  95

Glu Ile Ser Phe Gln Asn Gln Lys Leu Thr Ile Gln Lys Ile Glu Ala
            100                 105                 110

Leu Lys Thr Pro Glu Phe Ser Ser Lys Ser Glu Phe Lys Thr Leu Ala
        115                 120                 125

Pro Ile Ile Val Arg Thr Lys Lys Glu Ile Asn Gly Glu Leu Lys Ile
    130                 135                 140

Trp Asp Leu Ala Pro Ser Asp Lys Phe Phe Lys Ser Leu Glu Asn Asn
145                 150                 155                 160

Leu Ile Lys Lys Tyr Ile Lys Phe Asn Asn Leu Thr Lys Thr Asp Lys
                165                 170                 175

Lys Ile Asn Ile Tyr Ser Asp Met Asn Phe Val Lys Arg Lys Arg Ile
            180                 185                 190

Ser Ile Asn Lys Gly Asn Ala Thr Thr His His Arg Ala Tyr Met Met
        195                 200                 205

Asp Leu Ile Leu Glu Gly Asp Leu Asp Leu Ile Glu Phe Ala Tyr Asp
    210                 215                 220

Val Gly Ile Gly Glu Lys Asn Ser Met Gly Phe Gly Met Ile Lys Leu
225                 230                 235                 240

Leu Glu

<210> SEQ ID NO 23
<211> LENGTH: 247
<212> TYPE: PRT
<213> ORGANISM: Methanosphaera stadtmanae

<400> SEQUENCE: 23

Met Arg Ile Glu Ile Tyr Leu Glu Ser Lys Asp Lys Lys Asn Thr Leu
1               5                   10                  15

Ile Lys Tyr Asn Tyr Asn Tyr Met Leu Ser Ser Ala Ile Tyr Ser Lys
            20                  25                  30

Phe Val Asp Leu Glu Phe Phe Arg Asn Leu His Glu Ser Glu Ser Phe
        35                  40                  45

Lys Phe Phe Asn Phe Ser Lys Leu Tyr Ile Lys His Ile Asn Asn Ser
    50                  55                  60
```

```
Asn Ser Glu Gly Leu Ile Ala Asn Lys Gly Lys Val Lys Phe Ile Leu
 65                  70                  75                  80

Ser Ser Pro Asn Gln Tyr Ile Ile Thr Asn Phe Leu Ser Gly Cys Leu
                 85                  90                  95

Glu Asn Pro Glu Leu Arg Ile Gly Lys Asn Ile Tyr Lys Ile Thr Gln
            100                 105                 110

Ile Lys Glu Ile Lys Asp Pro Lys Ile His Lys Lys Glu Glu Ile Asn
        115                 120                 125

Thr Leu Ser Pro Ile Ile Thr Arg Thr Lys Glu Glu Ile Glu Gly Lys
    130                 135                 140

Leu Lys Ile Arg Asp Leu Ala Pro Ser Pro His Phe Phe Arg Asn Leu
145                 150                 155                 160

Glu Lys Asn Leu Ile Arg Lys Tyr Ile Leu Phe Asn Asn Ile Glu Asn
                165                 170                 175

Thr Asn Leu Lys Val Asn Ile Ser Ser Glu Met Arg Tyr Val Lys Glu
            180                 185                 190

Lys Arg Ile Leu Ile Glu Lys Tyr Gly Tyr Lys Thr Tyr Asn Arg Cys
        195                 200                 205

Tyr Leu Met Asn Leu Ser Ile Glu Gly Asp Ala Glu Leu Ile Lys Phe
    210                 215                 220

Ala Tyr Asp Thr Gly Ile Gly Glu Lys Asn Ser Met Gly Phe Gly Met
225                 230                 235                 240

Ile Lys Ile Lys Glu Asn Lys
                245

<210> SEQ ID NO 24
<211> LENGTH: 235
<212> TYPE: PRT
<213> ORGANISM: Methanosphaera stadtmanae

<400> SEQUENCE: 24

Met Arg Leu Ile Ile Lys Phe Asn Pro Leu Ser Asp Cys Lys Tyr Asp
  1               5                  10                  15

Ala Ile Gly Lys Tyr Asp Ile Gln Gly Phe Ile Tyr Ser Leu Leu Lys
                 20                  25                  30

Asp Thr Glu Phe Lys Asn Tyr His Asp Ile Lys Gly Phe Lys Phe Phe
             35                  40                  45

Thr Phe Ser Asn Ile Phe Pro Val Cys Asp Phe Lys Gln Asp Asn Leu
         50                  55                  60

Lys Thr Ile Ile Ile Ser Ser Pro Ser Ser Ala Phe Ile Lys Val Leu
 65                  70                  75                  80

Tyr Tyr Gln Leu Ser Asn Leu Glu Ile Phe Arg Leu Asn Lys Tyr Tyr
                 85                  90                  95

Met Glu Lys Tyr Lys Val Lys Leu Ile Lys Asn Asn Lys Cys Ser Asn
            100                 105                 110

Ser Ile Ile Thr Gly Thr Pro Ile Val Leu Phe Glu Asn Asn Tyr Glu
        115                 120                 125

Asn Arg Tyr Tyr Ser Phe Asn Gln Lys Leu Asp Phe Asn Phe Phe
    130                 135                 140

Asn Arg Leu Lys Glu Asn Ala Leu Lys Lys Tyr Thr Ala Tyr Thr Gln
145                 150                 155                 160

Asp Glu Ile Asn Leu Glu Ser Asp Leu Phe Asp Ser Phe Glu Phe Asn
                165                 170                 175

Arg Glu Val Ser Met Arg Ile Ile Met Lys Asn Gln Thr Phe Ile Ile
```

```
            180                 185                 190
Ile Gly Ser Leu Trp Lys Val Leu Glu Lys Asn Ile Ala Arg Glu Asp
        195                 200                 205

Arg Lys Phe Tyr Asn Phe Leu Phe Asp Cys Gly Leu Gly Glu Lys Asn
    210                 215                 220

Ser Leu Gly Met Gly Phe Ile Asn Asn Arg Arg
225                 230                 235

<210> SEQ ID NO 25
<211> LENGTH: 154
<212> TYPE: PRT
<213> ORGANISM: Methanobacterium thermoautotrophicum

<400> SEQUENCE: 25

Met Glu Gly Phe Ile Asp Arg Pro Glu Ile Asp Phe Leu Arg Arg Ser
1               5                   10                  15

Val Asn Val Glu Tyr Val Glu Phe Leu Glu Pro Pro Glu Phe Arg Arg
            20                  25                  30

Asn Met Lys Phe Arg Thr Leu Ser Pro Ile Ile Ile Lys Thr Val Arg
        35                  40                  45

Glu Glu Asp Gly Val Leu Lys Gln Trp Asp Val Asn Pro Asn Asp Leu
50                  55                  60

Lys Phe Tyr Glu Asn Leu Gln Asn Asn Leu Val Arg Lys Tyr Arg Glu
65                  70                  75                  80

Phe Tyr Gly Asp Tyr Asp Gly Asp Glu Tyr Leu Arg Leu Val Pro Tyr
                85                  90                  95

Gln Arg Ser Ile Lys Arg Lys Arg Ile Met Ile Pro Lys Glu Gly Ala
            100                 105                 110

Glu Thr Tyr His Arg Ala Tyr His Met Lys Phe Arg Val Glu Gly Asp
        115                 120                 125

Pro Arg Leu Ile Glu Phe Gly Tyr Asp Cys Gly Phe Gly Glu Lys Asn
    130                 135                 140

Ser Met Gly Phe Gly Met Val Val Thr Ser
145                 150

<210> SEQ ID NO 26
<211> LENGTH: 254
<212> TYPE: PRT
<213> ORGANISM: Methanocaldococcus jannaschii

<400> SEQUENCE: 26

Met Arg Glu Ser Met Arg Ile Glu Leu Glu Leu Gln Thr Asp Asn Phe
1               5                   10                  15

Thr Val Ile Pro Tyr Asn His Gln Tyr Tyr Leu Ala Ser Ala Ile Tyr
            20                  25                  30

Asn Lys Ile His Ser Ala Asn Pro Ala Tyr Ala Lys Arg Leu His Asn
        35                  40                  45

Tyr Gln Lys Phe Lys Phe Thr Phe Ser Leu Leu Gln Ile Arg Lys
    50                  55                  60

Arg Val Ile Arg Lys Glu Gly Ile Glu Thr Ile Asp Gly Lys Ala Tyr
65                  70                  75                  80

Leu Tyr Ile Ser Ser Pro Asn Asn Glu Phe Ile Glu Asn Phe Val Ala
                85                  90                  95

Gly Leu Leu Glu Asp Gly Lys Leu Arg Val Gly Asn Val Glu Phe Phe
            100                 105                 110

Val Arg Lys Ala Lys Ile Leu Pro Ile Pro Lys Lys Phe Asn Ile Leu
```

```
                115                 120                 125
Lys Thr Ile Ser Pro Ile Tyr Leu Lys Thr Met Ile Glu Thr Glu Asp
    130                 135                 140
Gly Leu Lys Thr Tyr Asp Leu Leu Pro Asn Asn Ser Lys Phe Tyr Glu
145                 150                 155                 160
Asn Leu Lys Asn Asn Leu Lys Lys Lys Tyr Glu Ala Phe Tyr Asn Glu
                165                 170                 175
Lys Cys Asp Met Asn Phe Glu Phe Glu Val Leu Lys Phe Arg Pro Lys
            180                 185                 190
Arg Met Arg Ile Lys Asn Asp Ile Tyr Cys Arg Cys Ser Glu Met Val
        195                 200                 205
Phe Lys Val Trp Gly Asp Tyr Asp Leu Ile Lys Phe Gly Tyr Glu Cys
    210                 215                 220
Gly Phe Gly Glu Lys Asn Ser Met Gly Phe Gly Met Val Val Asn Val
225                 230                 235                 240
Glu Asp Lys Asn Gln Lys Asn Lys Lys Leu Lys Thr Lys Ile
                245                 250

<210> SEQ ID NO 27
<211> LENGTH: 241
<212> TYPE: PRT
<213> ORGANISM: Methanocaldococcus jannaschii

<400> SEQUENCE: 27

Met Arg Leu Lys Leu Ser Leu Thr Pro Lys Gln Asp Phe Ser Phe Asp
1               5                   10                  15
Lys Ile Asn Lys His Thr Ile Gln Gly Phe Ile Tyr Ser Leu Leu Lys
                20                  25                  30
Asp Thr Glu Phe Gly Glu Met His Asn Gln Pro Arg Phe Lys Phe Trp
            35                  40                  45
Cys Phe Ser Asp Ile Phe Pro Pro Asn Asp Phe Val Lys Gly Glu Asp
    50                  55                  60
Lys Tyr Leu Leu Ile Ser Ser Pro Arg Glu Glu Phe Ile Asn Val Leu
65                  70                  75                  80
Tyr Glu Arg Leu Asp Asn Leu Glu Glu Val Asn Leu Asn Asn Phe Lys
                85                  90                  95
Phe Glu Val Ser Glu Leu Lys Lys Phe Asp Leu Lys Val Lys Asn Lys
                100                 105                 110
Phe Ile Thr Gly Ser Pro Ile Val Leu Tyr Lys Asp Lys Asp Arg Gly
            115                 120                 125
Glu Tyr Ile Lys Phe Tyr Asp Asp Asp Phe Asp Leu Met Phe Phe Val
    130                 135                 140
Gln Arg Leu Gln Asp Asn Ala Val Lys Lys Tyr Lys Ala Phe Tyr Asn
145                 150                 155                 160
Glu Glu Pro Val Leu Asn Gly Phe Ile Phe Asp Arg Ile Ser Pro Arg
                165                 170                 175
Val Arg Asn Gly Arg Val Asp Val Tyr Val Arg Ile Ala Lys Lys Gly
            180                 185                 190
Arg Glu Phe Leu Val Val Gly Thr Thr Trp Lys Leu Leu Glu Lys Ile
        195                 200                 205
Lys Ile Arg Lys Glu Glu Arg Lys Phe Tyr Lys Phe Ile Met Asp Cys
    210                 215                 220
Gly Leu Gly Glu Lys Asn Ser Leu Gly Phe Gly Phe Ile Asn Pro Ile
225                 230                 235                 240
```

Lys

<210> SEQ ID NO 28
<211> LENGTH: 250
<212> TYPE: PRT
<213> ORGANISM: Methanococcus voltae A3

<400> SEQUENCE: 28

Met Arg Ile Ser Ile Asn Leu Lys Cys Glu Lys Asn Thr Thr Ile Pro
1               5                   10                  15

Phe Asn Tyr Gln Tyr Gln Leu Ser Thr Ala Leu Tyr Asn Cys Met Tyr
            20                  25                  30

Asp Asn Asn Lys Glu Phe Ala Glu Asn Leu His Lys Ser Lys Asp Phe
        35                  40                  45

Lys Phe Phe Thr His Ser Trp Leu Phe Met Pro Asn Ser Lys Val Gly
50                  55                  60

Lys Asn Gly Ile Ile Cys Lys Asp Gly Asn Ala Phe Phe Lys Val Ser
65                  70                  75                  80

Ser Pro Asn Asp Glu Leu Met Thr His Leu Leu Gln Gly Leu Phe Lys
                85                  90                  95

Val Gly Tyr Met Gln Ile Asn Asn Thr Lys Leu Asp Val Val Gly Val
            100                 105                 110

Leu Asn Glu Lys Gly Tyr Asn Ser Asn Ile Lys Lys Met Lys Thr Ile
        115                 120                 125

Ser Pro Val Leu Leu Arg Thr Lys Lys Glu Arg Asn Gly Ile Asp Asn
130                 135                 140

Thr Glu Gly Leu Lys Ile Tyr Asp Ile Leu Pro Gln Glu Asn Ser Glu
145                 150                 155                 160

Lys Phe His Glu Asn Leu Lys Asn Asn Leu Lys Arg Lys Tyr Ser Leu
                165                 170                 175

Phe Tyr Asp Lys Asp Tyr Glu Asn Cys Asp Leu Asp Phe Asp Ile Asn
            180                 185                 190

Ile Ser Glu Ala Lys Ser Lys Arg Val Lys Ile Lys Asp Ser Phe Gln
        195                 200                 205

Arg Cys Ser Asn Leu Lys Phe Glu Ile Ser Gly Asp Glu Asp Leu Ile
210                 215                 220

Lys Phe Ala Tyr Glu Cys Gly Leu Gly Glu Leu Asn Ser Met Gly Phe
225                 230                 235                 240

Gly Met Ile Asp Lys Tyr Ser Tyr Lys Cys
                245                 250

<210> SEQ ID NO 29
<211> LENGTH: 270
<212> TYPE: PRT
<213> ORGANISM: Haloarcula marismortui

<400> SEQUENCE: 29

Met Arg Ile Leu Ala Arg Leu Ser Ala Arg Thr Asp Ala Ala Tyr Asp
1               5                   10                  15

Asn Thr Tyr His Asn Lys Leu Gln Gly Arg Ile Trp Gln Ala Leu Glu
            20                  25                  30

Asp Ser Lys Tyr Asp Ala Leu His Asp Lys Asn Gln Pro Lys Pro Phe
        35                  40                  45

Val Tyr Ser Asn Pro Phe Pro Pro Gln Asp Met Asp Glu Gly Asp Glu
50                  55                  60

Arg Thr Leu Leu Val Ala Ser Pro Glu Glu Ser Leu Leu Ala His Ile

```
                65                  70                  75                  80
Ala Glu Asp Leu Thr His Asp Arg Glu Leu Asn Ile Gly Glu Met Pro
                    85                  90                  95

Phe His Val Asp Lys Val Ser Pro Leu Ala Pro Asp Val Gly Glu Pro
                100                 105                 110

Gly Thr Ser Gly Thr Ile Glu Thr Gly Thr Gly Leu Leu Val Arg Ile
                115                 120                 125

Pro Pro Trp Arg Phe Asp Asp Tyr Gly Met Asp Val Asn His Asp Gln
        130                 135                 140

Ala Glu Phe Trp Arg Pro Glu His Thr Leu Glu Pro Phe Arg Thr Gln
145                 150                 155                 160

Leu Glu Ala Asn Leu Asp Lys Lys His Arg Leu Tyr Met Pro Asp Tyr
                165                 170                 175

Leu Ala Gly Pro Ser Asp Val Asp Gly Asp Leu Phe Ser Tyr Glu
                180                 185                 190

Leu Ile Lys Thr Phe Ala Ile Pro Val Thr Pro Thr Thr Gly Arg Thr
                195                 200                 205

Glu Glu Trp Val Leu Ser Lys Trp Arg Phe Asp Tyr Thr Val Arg Asp
        210                 215                 220

Asp Asp His Arg Arg His Leu Asn Leu Ala Leu Asp Val Gly Leu Gly
225                 230                 235                 240

Glu Arg Asn Ser Leu Gly Phe Gly Phe Ile Asn Ile Thr Asp Gln Thr
                245                 250                 255

Arg Pro Asp Glu Thr Glu Leu Glu Gly Glu Asn Ala Phe Pro
                260                 265                 270

<210> SEQ ID NO 30
<211> LENGTH: 261
<212> TYPE: PRT
<213> ORGANISM: Halorubrum lacusprofundi

<400> SEQUENCE: 30

Met Ala His Leu Ser Ala Arg Ala Asp Thr Ala Tyr Gln Asp Asp Tyr
1               5                   10                  15

His His Lys Leu Arg Gly Arg Leu Trp Asn Ala Leu Asp Gly Thr Glu
                20                  25                  30

Tyr Gly Glu Arg His Asp Ser Gly Glu Pro Pro Gly Phe Ala Tyr Ser
            35                  40                  45

Asn Pro Phe Pro Pro His Asp Met Gln Glu Gly Asp Glu Arg Lys Leu
    50                  55                  60

Ile Val Ser Ser Val Glu Asp Gly Leu Leu Ala His Val Ala Ala Asp
65                  70                  75                  80

Leu Leu Glu Glu Pro Glu Phe Asn Ile Gly Glu Met Pro Phe His Val
                85                  90                  95

Asp Asp Val Thr Ser Phe Thr Pro Asp Val Gly Glu Pro Gly Thr Gln
                100                 105                 110

Gly Ile Ile Glu Ser Gly Thr Gly Leu Leu Ile Arg Ile Pro Pro Trp
            115                 120                 125

Arg Cys Glu Glu Tyr Gly Ile Asp His Pro Gly Asp Thr Ala Val
        130                 135                 140

Phe Trp Gln Pro Glu His Thr Thr Glu Pro Leu Ile Thr Gln Leu Arg
145                 150                 155                 160

Ala Asn Leu Asp Lys Lys His Gly Leu Phe Cys Pro Asp Tyr Leu Pro
                165                 170                 175
```

```
Gly Pro Ser Glu Arg Asp Thr Glu Leu Phe Asp Ser Tyr Glu Leu Ile
            180                 185                 190

Lys Thr Phe Ser Ile Pro Val Thr Val Thr Glu Gly Thr Gln Met Thr
        195                 200                 205

Tyr Val Leu Ser Lys Trp Arg Phe Gly Tyr Thr Val Gln Asp Asp His
210                 215                 220

His Arg Arg His Leu Asn Leu Ala Leu Asp Thr Gly Leu Gly Glu Arg
225                 230                 235                 240

Asn Ser Leu Gly Leu Gly Phe Ile Asn Ile Thr Asp Lys Thr Ala Pro
                245                 250                 255

Trp Glu Val Ser Ser
            260

<210> SEQ ID NO 31
<211> LENGTH: 229
<212> TYPE: PRT
<213> ORGANISM: Picrophilus torridus

<400> SEQUENCE: 31

Met Lys Leu Val Ile Glu Leu Thr Gln Asn Gln Lys Thr Ile Ser Tyr
1               5                   10                  15

Ser Asp Ile Tyr Ser Ile Phe Glu Asn Ile Phe Glu Ile Gly Arg
                20                  25                  30

Ser Lys Pro Leu Ile Lys Ser Ala Met Ile Asp Asp Phe Pro Tyr Tyr
            35                  40                  45

Cys Gly Ser His Pro Leu Pro Tyr Lys Gly Arg Ile Ser Asn Asn Thr
        50                  55                  60

Ile Ser Tyr Gly Lys Tyr Arg Ile Tyr Ile Ser Ser Gly Tyr Tyr Lys
65                  70                  75                  80

Ile Ile Asp Asp Ile Met Asp Ala Ile Lys Ser Gly Asn Val Lys His
                85                  90                  95

Arg Leu Met Arg Ile Asn Ser Val Lys Met Glu Asn Asn Asn Cys Phe
            100                 105                 110

Phe Asp Thr Val Asn Met Ile Ser Arg Ser Pro Val Ile Ile Lys Tyr
        115                 120                 125

Asn Gly Glu Tyr Ile Asp Ala Asn Asn Arg Asn Phe Val Asp Ala Ile
130                 135                 140

Lys Asn Asp Ile Ile Lys Lys Tyr Ser Phe Thr Gly Leu Asn Gly Tyr
145                 150                 155                 160

Ile Asp Phe Ile Lys Ile Ile His Phe Lys Thr Leu Asn Leu Arg Ile
                165                 170                 175

Asn Asn Glu Asp Ile Lys Ala Ser Met Ile Lys Phe Thr Ile Met Ser
            180                 185                 190

Asp Asn Lys Ile Ile Asn Asn Ile Leu Asn Thr Gly Ile Gly Glu Leu
        195                 200                 205

Thr Lys Ser Gly Phe Gly Phe Ile Asp Glu Glu Arg Ile Pro Leu Asp
210                 215                 220

Phe Gly Ile Met Tyr
225

<210> SEQ ID NO 32
<211> LENGTH: 240
<212> TYPE: PRT
<213> ORGANISM: Picrophilus torridus

<400> SEQUENCE: 32
```

Met Arg Ile Lys Ile Lys Phe Tyr Thr Glu Glu Pro Ile Pro Asn
1               5                   10                  15

Tyr Asn Phe Asn Lys Tyr Asp Phe Gln Gly Met Ile Tyr Ser Ser Leu
                20                  25                  30

Leu Asp Ala Gly Val Thr Asp Ile His Asp Gly Asn Ser Ile Arg Phe
            35                  40                  45

Phe Ser Phe Ser Asp Val Phe Pro Tyr Asn Tyr Val Lys Lys Asp Leu
50                  55                  60

Ile Tyr Asn Phe Met Ile Ser Ser Pro Val Asp Arg Ile Ile Asn Ser
65                  70                  75                  80

Ile Tyr Asp Val Leu Asn Lys Asn Lys Tyr Phe Tyr Leu Ser Gly Tyr
                85                  90                  95

Lys Phe Asn Ile Ala Glu Ile Lys Lys Phe Asp Val Asn Ile Ser Lys
                100                 105                 110

Ser Phe Ile Thr Gly Ser Pro Ile Val Leu Tyr Leu Asp Asn Arg Lys
            115                 120                 125

Asn Arg Tyr Phe Ser Ile Arg Asn Gly Asp Ser Ile Ala Phe Phe Ile
        130                 135                 140

Lys Arg Leu Lys Glu Asn Ala Ile Lys Lys Phe Asn Ile Phe Tyr Asn
145                 150                 155                 160

Asp Glu Ile Ser Met Asn His Leu Leu Phe Asp Lys Met Lys Phe His
                165                 170                 175

Lys Glu Val Ser Val Leu Leu Asn Lys Gly Thr Lys Asn Phe Asn Ile
                180                 185                 190

Ile Gly Thr Met Trp Tyr Lys Leu Asp Leu Leu Arg Leu Arg Arg Ser
            195                 200                 205

Glu Val Lys Phe Tyr Lys Phe Ile Met Asp Ala Gly Leu Gly Glu Lys
        210                 215                 220

Asn Ser Leu Gly Phe Gly Phe Ile Asn Pro Val Val Asn Asn Gly Gln
225                 230                 235                 240

<210> SEQ ID NO 33
<211> LENGTH: 233
<212> TYPE: PRT
<213> ORGANISM: Picrophilus torridus

<400> SEQUENCE: 33

Met Lys Ser Ala Ile Leu Lys Phe Arg Ser Glu Asn Lys Gln Gln Ile
1               5                   10                  15

Pro Phe Glu His Asn Tyr Tyr Leu Gly Ile Ala Ile Gln Lys Lys Tyr
                20                  25                  30

Asn Gln Leu Met Tyr Ser Glu Lys Ile Glu Met His Ser Gly Leu Gln
            35                  40                  45

Asn Asn Tyr Thr Ile Ser Ser Ile Ile Thr Lys Asp Ala Glu Ile Arg
50                  55                  60

Asp Asp Gly Ile Tyr Thr Lys Asn Phe Phe Ile Val Leu Arg Ser Leu
65                  70                  75                  80

Glu Asp Glu Phe Ile Asn Arg Leu Lys Val Ser Phe Ser Ser Tyr Pro
                85                  90                  95

Glu Ile Arg Ile Gly Asn Ser Val Phe Ser Ile Val Gly Ile Lys Asp
                100                 105                 110

Thr Lys Arg Val Asp Phe Ser Ser Asp Ile Tyr Phe Lys Ser Leu Ser
            115                 120                 125

Pro Ile Leu Ile Arg Tyr Ser Lys Lys Leu Asp Asn Phe Val Thr Gln
        130                 135                 140

Lys Asn Glu Ile Glu Pro Asn Leu Lys Ala Trp Met Ile Asn Ala Tyr
145                 150                 155                 160

Tyr Lys Asn Thr Gly Arg Lys Pro Glu Thr Asn Phe Ser Ile Asp Ile
                165                 170                 175

Asp Lys Val Lys Val Lys Ser Val Ile Val Ser Lys Asn Arg Ile Lys
            180                 185                 190

Leu Arg Ala Pro Leu Ile Tyr Gly Arg Phe Arg Ser Ala Asp Pro Glu
        195                 200                 205

Met Leu Glu Met Phe Tyr Tyr Lys Gly Met Gly Ser Lys Thr Gly Leu
    210                 215                 220

Gly Leu Gly Cys Trp Glu Ala Tyr Gln
225                 230

<210> SEQ ID NO 34
<211> LENGTH: 237
<212> TYPE: PRT
<213> ORGANISM: Thermoplasma volcanium

<400> SEQUENCE: 34

Met Arg Leu Lys Val Thr Phe Tyr Thr Lys Asp Asp Glu Asn Tyr Glu
1               5                   10                  15

Phe Asn Lys Tyr Asp Ile Gln Gly Met Ile Tyr Ser Ala Leu Leu Asp
                20                  25                  30

Ala Gly Met Thr Glu Ile His Ala Gly Asn Lys Ile Arg Phe Phe Cys
            35                  40                  45

Phe Ser Asp Ile Phe Pro Ser Asn Ile Leu Lys Asp Phe Leu Phe
50                  55                  60

Asn Phe Ile Ile Ser Ser Pro Asp Ser Asn Ile Ile Lys Asn Ile Tyr
65                  70                  75                  80

Asn Ile Leu Asp Lys Asn Lys Ile Phe Tyr Leu Ser Gly Tyr Lys Phe
                85                  90                  95

His Ile Ala Glu Ile Lys Glu Phe Asp Ile Asn Ile Ser Lys Asp Phe
            100                 105                 110

Ile Thr Gly Ser Pro Val Val Leu Tyr Leu Asp Asn Lys Lys Asn Lys
        115                 120                 125

Tyr Phe Ser Ile Lys Asp Asp Ser Ile Ala Phe Phe Leu Arg Arg Leu
    130                 135                 140

Lys Glu Asn Ala Ile Lys Lys Phe Asn Leu Tyr Tyr His Glu Asn Ile
145                 150                 155                 160

Asn Ile Asn His Leu Ile Phe Asp Lys Leu Lys Phe His Arg Glu Val
                165                 170                 175

Ala Leu Leu Leu Arg Lys Gly Lys Thr Ser Phe Asn Ile Ile Gly Thr
            180                 185                 190

Thr Trp Tyr Asn Leu His Leu Asn Lys Leu Asn Arg Asp Glu Ile Lys
        195                 200                 205

Phe Tyr Asn Phe Ile Met Asp Ala Gly Ile Gly Glu Lys Asn Ser Leu
    210                 215                 220

Gly Phe Gly Phe Leu Asn Pro Val Arg Asn Tyr Gly Gln
225                 230                 235

<210> SEQ ID NO 35
<211> LENGTH: 257
<212> TYPE: PRT
<213> ORGANISM: Pyrococcus kodakaraensis

<400> SEQUENCE: 35

```
Met Arg Ile Lys Leu Leu Arg Phe Lys Pro Pro Phe Leu Ile Pro
1               5                   10                  15

Tyr Asn Tyr Pro Arg Tyr Leu Tyr Ser Phe Leu Arg Ala Ile Glu
                20                  25                  30

Leu Ala Asp Lys Glu Val Ala Gly Arg Ile His Asn Asn Lys Arg Asp
            35                  40                  45

Ile Lys Phe Val Ala Ser Lys Phe Met Pro Ile Gly Ser Thr Lys Arg
50                  55                  60

Leu Glu Gln Gly Leu Leu Val Glu Ser Gly Thr Val Glu Leu Tyr Val
65                  70                  75                  80

Gly Ser Thr Glu Asp Ile Ile Leu Glu Ser Leu Val Arg Gly Leu Gly
                    85                  90                  95

Gln Gly Val Gly Met Leu His Val Arg Gly Gln Arg Leu Leu Ser Tyr
                100                 105                 110

Glu Ala Glu Leu Glu Glu Ile Pro Lys His Leu Ser Gly Lys Arg Phe
            115                 120                 125

Lys Thr Leu Ser Pro Val Ser Val Tyr His Asn Asn Pro Pro Asn Gly
130                 135                 140

Phe Arg Gln Trp Asp Leu Ser Pro Val Gly Pro Pro Asn Ser Pro Phe
145                 150                 155                 160

Glu Asn Glu Pro Lys Val Trp Lys Glu Leu Leu Phe Glu Asn Leu Lys
                165                 170                 175

Ser Lys Tyr Met Met Val Tyr Gly Glu Pro Tyr Gly Ser Phe Asp
                180                 185                 190

Ile Arg Val Leu Thr Lys Lys Pro Lys Ser Arg Arg Leu Leu Val Lys
            195                 200                 205

Ile Asp Glu Arg Thr Gly Lys Pro Ile Tyr Ala Arg Val Trp Glu Phe
210                 215                 220

Asp Phe Lys Met Trp Gly Glu Glu Leu Leu Arg Val Ala Tyr Glu
225                 230                 235                 240

Leu Gly Ile Gly Met Arg Asn Pro His Gly Phe Gly Met Val Glu Val
                245                 250                 255

Ile

<210> SEQ ID NO 36
<211> LENGTH: 263
<212> TYPE: PRT
<213> ORGANISM: Pyrococcus kodakaraensis

<400> SEQUENCE: 36

Met Val Arg Phe Leu Ile Arg Leu His Pro Glu Asn Glu Pro Phe Arg
1               5                   10                  15

Ile Pro Phe Ser His Gln His Tyr Leu Gln Gly Leu Ile Tyr Arg Arg
                20                  25                  30

Ile Gln Arg Val Asn Pro Asp Leu Ser Leu Arg Leu His Asn Pro Lys
            35                  40                  45

Val Pro Lys Leu Phe Thr Tyr Ser Leu Phe Met Gly Glu Arg Arg Glu
50                  55                  60

Leu Ala Glu Asp Lys Ser Ser Leu Leu Gly Arg Gly Lys Gly Phe Phe
65                  70                  75                  80

Tyr Phe Ser Thr Val Val Pro Glu Ile Ala Glu Ala Phe Ile Gly Gly
                85                  90                  95

Leu Leu Gln Asn Pro Glu Val Glu Leu Trp Arg Glu Lys Phe Thr Val
                100                 105                 110
```

-continued

```
Glu Glu Val Lys Ala Leu Ala Glu Pro Glu Arg Leu Ser Gly Lys Lys
            115                 120                 125

Phe Val Thr Leu Ser Pro Ile Ala Val Thr Thr Lys Arg Ile Gln Phe
        130                 135                 140

Gly Lys Pro Arg Ser Tyr Asp Leu Ser Pro Arg Glu Pro Glu Phe Tyr
145                 150                 155                 160

Glu Leu Val Arg Glu Asn Leu Arg Glu Lys Tyr Val Leu Ile Tyr Gly
                165                 170                 175

Ser Lys Pro Pro Glu Asp Phe Glu Met Arg Val Leu Asn Ala Lys Pro
            180                 185                 190

Lys Arg Phe Glu Val Lys Pro Gly Ile Phe Gln Ile Ala Trp His Leu
        195                 200                 205

Val Phe Arg Ala Tyr Gly Asp Glu Gly Leu Leu Arg Thr Gly Tyr Leu
    210                 215                 220

Ala Gly Phe Gly Glu Lys Asn Ser Ile Gly Phe Gly Met Val Lys Val
225                 230                 235                 240

Asp Ala Arg Lys Glu Arg Val Lys Lys Trp Lys Gly Gly Ala Asp
                245                 250                 255

His Gln Lys Gly Lys Glu Ala
            260

<210> SEQ ID NO 37
<211> LENGTH: 249
<212> TYPE: PRT
<213> ORGANISM: Pyrococcus kodakaraensis

<400> SEQUENCE: 37

Met Arg Ile Glu Ile Lys Leu Arg Pro Ala Glu Val Gly Thr Ile Leu
1               5                   10                  15

Pro Phe Asn Tyr Asn Tyr Glu Val Tyr Ser Gln Leu Leu Glu Lys Val
            20                  25                  30

Tyr Leu Val Ser Pro Glu Leu Gly Lys Glu Val Glu Ser Ser Gly Val
        35                  40                  45

Asp Tyr Phe Thr Phe Ser Arg Ile Met Val Arg Lys Arg Glu Leu Ile
    50                  55                  60

Pro Glu Ala Gly Ile Arg Val Leu Ser Asp Asp Val Ser Leu Tyr Val
65                  70                  75                  80

Ser Ser His Ser Ala Asp Val Ile His Ala Ile Ala Glu Gly Phe Leu
                85                  90                  95

Asp Asp Pro Leu Leu Lys Ile Leu Asp Ala Thr Phe Ile Ala Asp Asp
            100                 105                 110

Val Lys Val Leu Lys Glu Pro Glu Leu Lys Gly Pro Val Leu Phe Ser
        115                 120                 125

Thr Leu Ser Pro Ile Leu Val Arg Thr Val Lys Phe Val Asn Gly Arg
    130                 135                 140

Met Lys Val Trp Asp Leu Tyr Pro Asp Glu Met Phe Phe Asp Lys
145                 150                 155                 160

Leu Arg Lys Ile Met Leu Met Arg Tyr Ser Ser Ile Tyr Gly Arg Met
                165                 170                 175

Pro Glu Asn Lys Glu Phe Lys Ile Glu Val Leu Lys Phe Lys Pro Val
            180                 185                 190

Arg Ile Leu Val Arg Asp Thr Tyr Tyr Arg Ser Ser Leu Met Val Phe
        195                 200                 205

Lys Tyr Ser Gly Ser Pro Glu Leu Ala Trp Leu Gly Tyr Glu Thr Gly
```

```
                    210                 215                 220
Phe Gly Glu Lys Thr Arg Tyr Gly Phe Gly Met Val Lys Val Ile Asp
225                 230                 235                 240

Ser Glu Gln Gly Gln Glu Gly Gln Glu
                245
```

<210> SEQ ID NO 38
<211> LENGTH: 239
<212> TYPE: PRT
<213> ORGANISM: Pyrococcus abyssi

<400> SEQUENCE: 38

```
Met Arg Ile Glu Ile Lys Leu Leu Pro Leu Thr Glu Thr Pro Ile Leu
1               5                   10                  15

Pro Phe Asn Tyr Asn Tyr Asp Val Tyr Thr Gln Ile Val Asn Lys Val
                20                  25                  30

Asn Ser Ile Glu Pro Lys Val Ala Gly Leu Leu Ser Ser Pro His Gly
            35                  40                  45

Phe Trp Thr Phe Ser Arg Ile Ile Arg Lys Arg Lys Ile Ile Pro
    50                  55                  60

Glu Lys Gly Ile Glu Ile Leu Ser Asp Asp Val Ser Leu Tyr Val Ser
65                  70                  75                  80

Ser Ser Asn Glu Glu Ile Ile Arg Ala Ile Ala Glu Ala Val Glu Lys
                85                  90                  95

Ser Pro Glu Phe Lys Ile Gly Asn Val Ser Phe Leu Val Gly Asp Val
                100                 105                 110

Lys Ala Ile Lys Ile Lys Glu Ile Gly Lys Glu Asn Val Phe Ser Thr
            115                 120                 125

Leu Ser Pro Ile Val Val Arg Thr Ile Lys Phe Glu Gly Asp Lys Leu
    130                 135                 140

Arg His Trp Asp Leu Tyr Pro His Asp Glu Met Phe Met Asp Lys Leu
145                 150                 155                 160

Arg Lys Val Met Leu Leu Arg Phe Asn Glu Ile Met Gly Tyr Ser Pro
                165                 170                 175

Glu Asp Lys Glu Phe Gln Ile Glu Val Leu Lys Phe Lys Pro Thr Arg
                180                 185                 190

Leu Ile Val Gly Asn Ser Tyr Ile Arg Gly Ser Leu Met Val Phe Lys
            195                 200                 205

Tyr Thr Gly Ser Glu Glu Ile Ala Arg Phe Gly Tyr Glu Asn Gly Phe
    210                 215                 220

Gly Glu Lys Thr Asn Leu Gly Phe Gly Met Val Lys Leu Ile Glu
225                 230                 235
```

<210> SEQ ID NO 39
<211> LENGTH: 262
<212> TYPE: PRT
<213> ORGANISM: Pyrococcus abyssi

<400> SEQUENCE: 39

```
Met Arg Phe Leu Ile Arg Val Arg Pro Glu Glu Arg Lys Phe Lys Val
1               5                   10                  15

Pro Tyr Asn His Gln Tyr Tyr Leu Gln Gly Leu Ile Tyr Asn Arg Ile
                20                  25                  30

Lys Met Val Asn Pro Arg Leu Ser Thr Phe Leu His Glu Thr Arg Gly
            35                  40                  45

Pro Lys Met Phe Thr Tyr Ser Leu Phe Met Thr Glu Lys Arg Lys His
```

```
              50                  55                  60
Pro Lys Gly Leu Pro Tyr Phe Leu Gly Phe Lys Arg Gly Phe Phe Tyr
 65                  70                  75                  80

Phe Ser Thr Cys Ile Pro Glu Ile Ala Glu Ala Phe Ile Thr Gly Leu
                     85                  90                  95

Phe Arg Glu Pro Glu Ile Val Leu Trp Gly Arg Phe Tyr Leu Glu
                100                 105                 110

Glu Val Lys Thr Leu Arg Glu Pro Thr Lys Phe Ser Gly Ser Thr Phe
            115                 120                 125

Ile Thr Leu Ser Pro Val Ala Val Thr Met Val Lys Glu Gly Lys Arg
        130                 135                 140

Tyr Asp Val Ser Pro Leu Glu Glu Phe Tyr Thr Leu Ile Lys Glu
145                 150                 155                 160

Asn Leu Lys Asp Lys Tyr Val Met Ile Lys Gly Glu Lys Pro Pro Asp
                165                 170                 175

Asp Phe Glu Met Glu Val Ile Val Ala Lys Pro Lys Arg Phe Glu Val
                180                 185                 190

Lys Pro Gly Ile Tyr Gln Met Ala Trp His Leu Val Phe Lys Ala Tyr
            195                 200                 205

Gly Asp Asp Glu Leu Ile Lys Val Gly Tyr Val Val Gly Phe Gly Glu
        210                 215                 220

Lys Asn Ser Leu Gly Phe Gly Met Val Lys Val Glu Asn Asn Arg Glu
225                 230                 235                 240

Glu Lys Gly Met Gly Val Gln Glu Arg Met Leu Phe Lys Asn Glu Asp
                245                 250                 255

Gly Leu Lys Thr Gly Pro
                260

<210> SEQ ID NO 40
<211> LENGTH: 242
<212> TYPE: PRT
<213> ORGANISM: Pyrococcus horikoshii

<400> SEQUENCE: 40

Met Ile Tyr Met Arg Leu Lys Leu Ser Phe Ile Tyr Asp Gly Asp Lys
  1               5                  10                  15

Phe Gln Pro Asn Lys His Ala Val Gln Gly Phe Ile Tyr Asn Met Leu
                 20                  25                  30

Arg Gly Thr Glu Tyr Glu Asp Arg His Asn Arg Gly Phe Lys Phe
             35                  40                  45

Phe Thr Phe Ser Asp Val Phe Arg Asp Ser Lys Gly Tyr Tyr Ser Leu
         50                  55                  60

Leu Ile Ala Ser Pro Asp Ser Gly Phe Ile Asn Ala Leu Tyr Leu Ser
 65                  70                  75                  80

Leu Lys Asp Arg Asp His Val Tyr Ile Gly Lys Asp Glu Ile Lys Leu
                 85                  90                  95

Val Glu Val Lys Lys Phe Lys Leu Lys Leu Lys Arg Ala Phe Gln Thr
                100                 105                 110

Gly Ser Pro Val Val Ile Tyr Lys Asp Ser Arg Lys Asn Glu Tyr Phe
            115                 120                 125

Lys Leu His Glu His Arg Asp Leu Leu Phe Phe Leu Gln Arg Leu Lys
        130                 135                 140

Glu Asn Ala Glu Lys Lys Phe Asn Ser Phe Tyr Gly Asp Glu Phe His
145                 150                 155                 160
```

```
Leu Glu Gly Leu Ile Phe Asp Arg Val Ile Pro Lys Val Arg Lys Asn
            165                 170                 175
Gly Lys Val Asp Val Tyr Val Lys Val Lys Asn Gly Val Pro Phe
        180                 185                 190
Pro Val Ile Gly Thr Asn Trp Glu Leu Leu Glu Lys Glu Arg Ile Lys
        195                 200                 205
Pro Glu Glu Arg Arg Phe Tyr Arg Phe Ile Met Asp Cys Gly Leu Gly
    210                 215                 220
Glu Lys Asn Ser Leu Gly Phe Gly Phe Leu Asn Pro Ile Lys Gly Val
225                 230                 235                 240
Lys Asn

<210> SEQ ID NO 41
<211> LENGTH: 239
<212> TYPE: PRT
<213> ORGANISM: Pyrococcus horikoshii

<400> SEQUENCE: 41

Met Arg Ile Glu Val Lys Leu Leu Pro Leu Lys Asp Asn Pro Ile Leu
1               5                   10                  15
Pro Phe Asn Tyr Asn Tyr Glu Val Tyr Ser Gln Ile Leu Glu Lys Val
            20                  25                  30
Asn Ser Ile Glu Pro Thr Ile Ala Lys Leu Leu Ser Ser Pro His Gly
        35                  40                  45
Phe Trp Thr Phe Ser Arg Ile Val Arg Lys Arg Lys Ile Leu Pro
    50                  55                  60
Asp Lys Gly Ile Glu Ile Leu Ser Asp Val Ser Leu Tyr Ile Ser
65                  70                  75                  80
Ser Ser Asn Glu Asp Ile Ile Arg Ala Ile Ala Glu Ala Val Glu Lys
                85                  90                  95
Ser Pro Glu Phe Lys Ile Gly Glu Leu Ser Phe Leu Val Gly Asp Ile
            100                 105                 110
Lys Ala Ile Lys Val Lys Glu Leu Gly Lys Glu Asn Val Phe Ser Thr
        115                 120                 125
Leu Ser Pro Ile Val Val Arg Thr Val Lys Phe Glu Gly Asn Lys Leu
    130                 135                 140
Arg His Trp Asp Leu Tyr Pro His Asp Glu Leu Phe Met Asp Arg Leu
145                 150                 155                 160
Arg Lys Val Met Ile Leu Arg Tyr Ser Glu Val Met Gly Glu Thr Pro
                165                 170                 175
Lys Asp Arg Asp Phe Thr Ile Glu Val Leu Lys Phe Lys Pro Thr Arg
            180                 185                 190
Leu Met Val Gly Ser Ser Tyr Ile Arg Gly Ser Leu Met Val Phe Arg
        195                 200                 205
Tyr Ala Gly Ser Glu Glu Ile Ala Arg Phe Gly Tyr Glu Asn Gly Phe
    210                 215                 220
Gly Glu Lys Thr Gly Leu Gly Phe Gly Met Val Lys Leu Ile Glu
225                 230                 235

<210> SEQ ID NO 42
<211> LENGTH: 267
<212> TYPE: PRT
<213> ORGANISM: Pyrococcus horikoshii

<400> SEQUENCE: 42

Met Ile Ile Met Arg Phe Leu Ile Lys Val Lys Pro Glu Glu Arg Lys
```

```
                1               5               10              15

Phe Arg Val Pro Tyr Asn His Gln Tyr Phe Leu Gln Gly Leu Ile Tyr
                        20                  25                  30

Asn Arg Ile Lys Leu Thr Asn Pro Arg Leu Ser Thr Phe Leu His Glu
                        35                  40                  45

Thr Lys Gly Pro Lys Leu Phe Thr Tyr Ser Leu Phe Met Thr Glu Arg
                50                  55                  60

Arg Glu His Pro Lys Gly Leu Pro Tyr Phe Leu Gly Tyr Arg Arg Gly
        65                  70                  75                  80

Phe Phe Tyr Phe Ser Thr Cys Ile Pro Glu Ile Ala Glu Ala Phe Ile
                        85                  90                  95

Thr Gly Leu Phe Arg Glu Pro Glu Ile Thr Leu Trp Gly Glu Lys Phe
                        100                 105                 110

Tyr Leu Glu Glu Val Lys Thr Leu Lys Glu Pro Lys Lys Phe Ser Gly
                        115                 120                 125

Ser Thr Phe Ile Thr Leu Ser Pro Ile Ala Val Thr Met Glu Lys Gly
                130                 135                 140

Gly Lys Arg Tyr Asp Val Ser Pro Leu Glu Glu Phe Tyr Ala Leu
        145                 150                 155                 160

Ile Arg Glu Asn Leu Lys Asp Lys Tyr Val Met Ile Lys Gly Glu Lys
                        165                 170                 175

Pro Pro Asp Asp Phe Glu Met Glu Ile Ile Ala Ala Lys Pro Lys Arg
                        180                 185                 190

Phe Glu Val Lys Pro Gly Ile Tyr Gln Met Ala Trp His Leu Val Phe
                        195                 200                 205

Arg Ala Tyr Gly Asp Asp Glu Leu Ile Arg Val Gly Tyr Val Val Gly
                210                 215                 220

Phe Gly Glu Lys Asn Ser Leu Gly Phe Gly Met Val Lys Val Asp Glu
        225                 230                 235                 240

Gln Arg Lys Arg Lys Asn Ile Gly Ser Phe Gln Glu Ser Met Ser
                        245                 250                 255

Phe Asn Glu Asn Arg Glu Leu Glu Thr Gly Thr
                260                 265

<210> SEQ ID NO 43

<400> SEQUENCE: 43

000

<210> SEQ ID NO 44
<211> LENGTH: 241
<212> TYPE: PRT
<213> ORGANISM: Pyrococcus furiosus

<400> SEQUENCE: 44

Met Arg Ile Glu Ile Lys Leu Leu Pro Leu Gln Asp Asn Pro Val Ile
        1               5               10              15

Pro Phe Asn Tyr Asn Tyr Glu Leu Tyr Ser Gln Ile Val Glu Lys Ala
                        20                  25                  30

Gly Ala Ile Glu Pro Arg Ile Val Lys Leu Leu Glu Ser Pro His Gly
                        35                  40                  45

Tyr Trp Thr Phe Ser Arg Ile Ile Ile Arg Lys Arg Glu Ile Ile Pro
                50                  55                  60

Glu Lys Gly Ile Lys Ile Leu Ser Asp Asp Ile Ser Leu Tyr Ile Ser
        65                  70                  75                  80
```

```
Ser Ser Asn Lys Glu Ile Ile Lys Gly Ile Val Gly Ile Glu Lys
            85                  90                  95

Ser Pro Glu Phe Lys Ile Gly Asp Val Gly Phe Leu Val Ala Asp Ile
            100                 105                 110

Lys Ala Leu Lys Ser Lys Glu Ile Lys Asn Val Asn Ile Phe Ser Thr
            115                 120                 125

Leu Ser Pro Ile Val Val Arg Thr Val Lys Phe Glu Gly Asp Lys Leu
            130                 135                 140

Lys His Trp Asp Leu Tyr Pro His Asp Glu Leu Phe Leu Asp Arg Leu
145                 150                 155                 160

Arg Lys Val Met Leu Leu Arg Tyr His Glu Val Met Gly Asp Leu Pro
                165                 170                 175

Glu Asp Lys Asp Phe Arg Ile Glu Leu Ile Lys Phe Lys Pro Thr Arg
            180                 185                 190

Leu Ile Val Lys Asp Ser Tyr Ile Arg Gly Ser Leu Met Val Phe Arg
            195                 200                 205

Tyr Tyr Gly Ser Lys Glu Ile Ala Lys Phe Gly Tyr Glu Asn Gly Phe
            210                 215                 220

Gly Glu Lys Thr Asn Leu Gly Phe Gly Met Val Lys Ile Ile Glu Glu
225                 230                 235                 240

Gln

<210> SEQ ID NO 45
<211> LENGTH: 289
<212> TYPE: PRT
<213> ORGANISM: Archaeoglobus fulgidus

<400> SEQUENCE: 45

Met Ser Phe Ser Leu Gln Leu Thr Arg Leu Lys Ala Arg Leu Tyr Phe
1               5                   10                  15

Pro Gln Tyr His Leu Pro Pro Phe Leu Gly Asn Lys Phe Arg Gly Gly
            20                  25                  30

Phe Gly Ser Val Leu Leu Lys Ala Val Cys Ser Tyr Leu Lys Pro Ser
        35                  40                  45

Cys Asn Ile Cys Lys Ser Val Asp Asp Cys Leu Tyr His Ala Leu Tyr
50                  55                  60

Thr Arg Asp Arg Gln Lys Arg Gly Arg Ser Gln Pro Val Arg Pro Ile
65                  70                  75                  80

Val Phe Ile Pro Pro Phe Phe Gly Arg Ser Val Ser Gly Arg Gly Glu
            85                  90                  95

Leu Thr Leu Tyr Ile Asn Val Phe Gly Asp Tyr Val Lys Tyr Leu Pro
            100                 105                 110

His Ile Ile Tyr Gly Leu Arg Tyr Leu Gly Lys Met Gly Leu Asn Ala
        115                 120                 125

Thr Ser Lys Tyr Glu Ile Val Ser Ile Ser Asp Ala Ile Ser Gly Lys
            130                 135                 140

Glu Val Tyr Asp Gly Glu Thr Val Phe Val Glu Asn Leu Ser Ser Ile
145                 150                 155                 160

Glu Leu Gly Lys Ile Lys Pro Arg Glu Val Lys Glu Ile Glu Val
                165                 170                 175

Asp Tyr Leu Thr Pro Met Glu Ala Lys Thr Pro Ile Asn Leu Pro Phe
            180                 185                 190

Leu Ile His Ile Val Arg Arg Arg Leu Ile Leu Phe Val Asn Glu Tyr
            195                 200                 205
```

-continued

```
Gly Ser Gly Glu Val Pro Glu Phe Tyr Cys Glu Ala Glu Thr Leu Glu
        210                 215                 220

Ser Ser Trp Glu Lys His Glu Leu His His Arg Ser Lys Arg Gln Gly
225                 230                 235                 240

Leu Arg Ser Phe Phe Gly Val Thr Gly Arg Ala Arg Tyr Ser Ile Ser
                245                 250                 255

Glu Ile Asp Asp Asn Ala Leu Thr Leu Leu Ser Ile Gly Glu Leu Ile
            260                 265                 270

Gly Gly Gly Ala Lys Ala Ser Phe Gly Met Gly Phe Phe Arg Ile Arg
            275                 280                 285

Ser
```

<210> SEQ ID NO 46
<211> LENGTH: 241
<212> TYPE: PRT
<213> ORGANISM: Archaeoglobus fulgidus

<400> SEQUENCE: 46

```
Met Arg Leu Lys Ile Ser Leu Leu Ser Pro Ala Asp Ser Phe Glu Ile
1               5                   10                  15

Asp Leu Asn His Ser Tyr His Leu Ala Ser Ala Ile Tyr Arg Ala Ile
            20                  25                  30

Glu Arg Ala Asp Pro Ser Leu Ser Ile Glu Leu His Lys Pro Asp Val
        35                  40                  45

Pro Lys Phe Phe Thr Phe Ser Lys Leu Phe Ile Pro Lys Arg Lys Phe
    50                  55                  60

Arg Ile Glu Gly Glu Lys Met Val Ser Asp Cys Glu Glu Ala Tyr Phe
65                  70                  75                  80

Phe Phe Ser Thr Leu Arg Asn Glu Val Ala Ala Ser Leu Val Glu Gly
                85                  90                  95

Leu Leu Ser Lys Pro Glu Ile Arg Ile Cys Gly Val Asp Phe Ile Val
            100                 105                 110

Ser Glu Val Ser Val Leu Pro Glu Arg Glu Val Lys Gly Arg Glu Lys
        115                 120                 125

Phe Val Thr Leu Ser Pro Ile Tyr Ala Ser Thr Ser Val Gly Glu Asn
    130                 135                 140

Gly Arg Arg Arg Ile Phe Asp Leu Tyr Pro Lys Asp Ser Lys Phe Tyr
145                 150                 155                 160

Glu Val Ile Leu Gln Asn Leu Val Lys Lys Tyr Val Leu Tyr Tyr Lys
                165                 170                 175

Ser Ala Pro Glu Asn Leu Asp Phe His Met Lys Pro Leu Asn Val Lys
            180                 185                 190

Ala Lys Arg Ile Arg Leu Lys Asp Thr Phe His Arg Cys Val Glu Met
        195                 200                 205

Val Phe Lys Ala Glu Gly Ser Pro Glu Leu Leu Asp Val Gly Tyr Lys
    210                 215                 220

Ala Gly Phe Gly Ser Lys Asn Ser Met Gly Phe Gly Met Val Lys Val
225                 230                 235                 240

Val
```

<210> SEQ ID NO 47
<211> LENGTH: 246
<212> TYPE: PRT
<213> ORGANISM: Methanosarcina acetivorans

<400> SEQUENCE: 47

Met Arg Cys Arg Val Ser Ile Arg Lys Ile Ser Pro Tyr Pro Leu His
1               5                   10                  15

Tyr Asp Tyr Gln Tyr Gly Leu Ala Ser Met Leu Tyr Ser Lys Leu Ala
            20                  25                  30

Thr Ser Asn Val Glu Leu Ala Ala Lys Thr His Ser Lys Gln Gly Phe
        35                  40                  45

Lys Phe Tyr Thr Phe Ser Asn Leu Val Leu Asp Asp Arg Ile Pro Glu
    50                  55                  60

Lys Asn Gly Leu Asn Phe Lys Thr Ala His Phe Phe Leu Ser Ser Pro
65                  70                  75                  80

Asp Pro Glu Phe Ile Arg Ser Phe Ala Glu Gly Leu Leu Leu Glu Pro
                85                  90                  95

Glu Phe Phe Leu Gly Asn Asn Glu Asn Lys Val Ser Phe Ile Ile Glu
            100                 105                 110

Arg Ile Glu Val Leu Pro Ala Val His Phe Ser Asp Met Cys Thr Phe
        115                 120                 125

Arg Thr Leu Ser Pro Ile Tyr Leu Lys Thr Leu Arg Lys Gln Asn Asp
    130                 135                 140

Lys Leu Val Glu Phe Asp Leu Tyr Pro Lys Asp Ser Lys Phe His Glu
145                 150                 155                 160

Asn Leu His Lys Asn Leu Val Ala Arg Tyr Glu Glu Phe Tyr Gly Ser
                165                 170                 175

Lys Ile Glu Lys Asp Phe Phe Glu Ile Leu Asn Ile Pro Asn Phe Lys
            180                 185                 190

Pro Lys Arg Val Lys Ile Glu Asn Asn Tyr Arg Arg Cys Ser Leu Met
        195                 200                 205

Asp Phe Ser Ile Ser Ala Asn Pro Glu Leu Leu Lys Phe Ala Tyr Asp
    210                 215                 220

Ala Gly Leu Gly Glu Lys Asn Ala Met Gly Phe Gly Cys Leu Asp Leu
225                 230                 235                 240

Leu Gln Val Asn Thr Lys
                245

<210> SEQ ID NO 48
<211> LENGTH: 246
<212> TYPE: PRT
<213> ORGANISM: Methanosarcina barkeri

<400> SEQUENCE: 48

Met Arg Cys Arg Val Ser Val Arg Lys Ile Ser Pro Glu Pro Leu His
1               5                   10                  15

Tyr Asp Tyr Gln Tyr Gly Leu Ala Ser Met Leu Tyr Ser Lys Leu Ala
            20                  25                  30

Thr Ser Asn Ile Glu Leu Ala Asn Lys Ile His Ser Lys Lys Gly Phe
        35                  40                  45

Lys Phe Tyr Thr Phe Ser Asn Leu Ile Leu Glu Asp Lys Ile Pro Glu
    50                  55                  60

Lys Asn Gly Leu Asn Phe Lys Lys Ala His Phe Phe Leu Ser Ser Pro
65                  70                  75                  80

Asp Pro Glu Phe Ile Arg Ser Phe Ala Glu Gly Leu Leu Ile Glu Pro
                85                  90                  95

Glu Phe Phe Leu Gly Asn Asn Gly Asn Lys Ser Asn Phe Val Ile Glu
            100                 105                 110

```
Arg Ile Glu Val Leu Pro Leu Ile His Phe Ser Asp Thr Cys Thr Phe
            115                 120                 125

Arg Thr Leu Ser Pro Ile Tyr Leu Lys Thr Gln Arg Lys Gln Asp Asp
    130                 135                 140

Arg Leu Val Glu Phe Asp Leu Tyr Pro Lys Asp Ser Lys Phe His Glu
145                 150                 155                 160

Asn Leu His Lys Asn Leu Val Ala Arg Tyr Glu Glu Phe Tyr Gly Ser
                165                 170                 175

Lys Ile Asp Lys Asp Phe Phe Glu Val Ile Lys Ile Pro Ser Phe Lys
            180                 185                 190

Pro Lys Arg Val Lys Ile Glu Asn Asn Tyr Arg Arg Cys Ser Leu Met
        195                 200                 205

Asn Leu Tyr Leu Ser Ala Asn Pro Glu Leu Leu Gln Phe Ala Tyr Asp
    210                 215                 220

Ala Gly Leu Gly Glu Lys Asn Ala Met Gly Phe Gly Cys Val Asn Val
225                 230                 235                 240

Leu Glu Val Lys Gln Lys
                245

<210> SEQ ID NO 49
<211> LENGTH: 241
<212> TYPE: PRT
<213> ORGANISM: Methanococcoides burtonii

<400> SEQUENCE: 49

Met Arg Cys Lys Val Thr Ile Leu Lys Thr Thr Asn Ser His Ile His
1               5                   10                  15

Tyr Asp Tyr Gln Tyr Gly Leu Ala Ser Met Leu Tyr Ala Arg Leu Ala
            20                  25                  30

Asn Ala Asn Ile Thr Leu Ala Asn Glu Ile His Ser His Gln Gly Phe
        35                  40                  45

Lys Phe Tyr Thr Phe Ser Asn Leu Ile Ile Glu Asp Trp Ile Pro Asn
    50                  55                  60

Lys Arg Gly Leu Asp Phe Asn Lys Ala His Phe Phe Ile Ser Ser Pro
65                  70                  75                  80

Asp Leu Glu Phe Ile Arg Ser Phe Thr Glu Gly Leu Leu Leu Glu Pro
                85                  90                  95

Glu Phe Phe Leu Gly Arg Asp Lys Lys Ala Asn Phe Ile Ile Glu Arg
            100                 105                 110

Ile Glu Ile Met Pro Asn Leu Glu Ile Ser Glu Ser Cys Lys Phe Thr
        115                 120                 125

Thr Leu Ser Pro Ile Tyr Val Lys Thr Met Arg Lys Lys Asn Asp Lys
    130                 135                 140

Leu Val Glu Ile Asp Leu Tyr Pro Lys Asp Ser Lys Phe Tyr Glu Asn
145                 150                 155                 160

Ile His Thr Asn Leu Thr Ala Arg Tyr Glu Glu Tyr Gly His Lys
                165                 170                 175

Val Glu His Asp Tyr Phe Asp Val Leu Glu Val Lys Asp Phe Lys Pro
            180                 185                 190

Lys Arg Val Ser Ile Gly Asn Ser Phe Arg Arg Cys Ser Leu Met Lys
        195                 200                 205

Leu Glu Leu Glu Ala Ser Pro Glu Leu Ile Lys Phe Ala Tyr Asp Ala
    210                 215                 220

Gly Leu Gly Glu Lys Asn Ala Met Gly Phe Gly Cys Leu Glu Leu Val
225                 230                 235                 240
```

Lys

<210> SEQ ID NO 50
<211> LENGTH: 250
<212> TYPE: PRT
<213> ORGANISM: Fusobacterium nucleatum

<400> SEQUENCE: 50

Met Arg Phe Ile Leu Asn Phe Glu Leu Asp Thr Val Ile Ile Pro Val
1               5                   10                  15

Glu Ile Lys Arg Thr Ile Ile Ser Phe Phe Lys Lys Ser Leu Thr Glu
            20                  25                  30

Ala His Asn Ser Lys Tyr Tyr Pro Glu Phe Phe Thr Gly Thr Gln Ile
        35                  40                  45

Lys Asp Tyr Ser Phe Ser Val Ile Phe Pro Leu Asp Lys Tyr Phe Gly
    50                  55                  60

Glu Glu Ile Tyr Leu Lys Arg Pro Glu Met Lys Val Leu Val Ser Cys
65                  70                  75                  80

Ser Glu Lys Asn Asn Ile Gly Phe Leu Leu Val Asn Val Phe Leu Ser
                85                  90                  95

Gln Arg Asn Lys Lys Phe Pro Leu Pro Lys Asp Thr His Met Ile Leu
            100                 105                 110

Lys Asp Val Arg Ile Ile Glu Glu Lys Ile Ile Lys Glu Glu Glu Ala
        115                 120                 125

Val Phe Gln Thr Thr Ile Gly Gly Val Val Val Arg Glu His Asn
    130                 135                 140

Lys Glu Glu Asn Lys Asp Ile Tyr Tyr Ser Val Gly Asn Glu Arg Phe
145                 150                 155                 160

Glu Glu Val Leu Asn Trp Leu Met Lys Glu Arg Phe Lys Arg Leu Arg
                165                 170                 175

Tyr Pro Glu Asp Ile Phe Lys Asp Phe Ser Cys Glu Leu Leu Glu Gly
            180                 185                 190

Arg Lys Ile Val Val Lys His Phe Asp Leu Lys Phe Pro Val Thr Thr
        195                 200                 205

Gly Arg Phe Lys Val Lys Ala Pro Lys Ile Leu Leu Glu Glu Ile Tyr
    210                 215                 220

Arg Thr Gly Met Gly Ser Arg Leu Ser Gln Gly Phe Gly Leu Leu Glu
225                 230                 235                 240

Tyr Leu Gly Gly Glu Ile Lys Asp Glu Val
                245                 250

<210> SEQ ID NO 51
<211> LENGTH: 250
<212> TYPE: PRT
<213> ORGANISM: Fusobacterium nucleatum

<400> SEQUENCE: 51

Met Arg Phe Ile Leu Ser Phe Glu Leu Asp Thr Val Lys Leu Pro Ile
1               5                   10                  15

Glu Ile Arg Arg Thr Val Ile Ser Phe Phe Lys Lys Ser Leu Thr Glu
            20                  25                  30

Ala His Asn Ser Lys Tyr Tyr Pro Asp Phe Phe Thr Gly Thr Gln Ile
        35                  40                  45

Lys Asp Tyr Ser Phe Ser Val Ile Phe Pro Leu Asp Lys Tyr Phe Arg
    50                  55                  60

```
Glu Glu Ile Tyr Leu Lys Lys Pro Glu Met Lys Val Val Ser Cys
 65                  70                  75                  80

Ser Glu Lys Asn Asn Ile Gly Phe Leu Leu Val Asn Val Phe Leu Ser
                 85                  90                  95

Gln Arg Asn Lys Lys Phe Pro Leu Pro Lys Asp Thr Cys Met Ile Leu
            100                 105                 110

Lys Asp Val Arg Ile Ile Glu Glu Lys Ile Ile Arg Gly Glu Glu Ala
        115                 120                 125

Val Phe Gln Thr Thr Ile Gly Gly Val Val Arg Glu His Asn
    130                 135                 140

Lys Glu Glu Asn Lys Asp Ile Tyr Tyr Ser Val Gly Asn Glu Arg Phe
145                 150                 155                 160

Glu Glu Val Leu Asn Trp Leu Met Lys Glu Arg Phe Lys Arg Leu Gly
                165                 170                 175

Tyr Pro Glu Asp Ile Phe Lys Asp Phe Ser Cys Glu Leu Leu Asp Gly
            180                 185                 190

Arg Lys Ile Val Val Lys His Phe Asp Leu Lys Phe Pro Val Thr Thr
        195                 200                 205

Gly Lys Phe Lys Val Lys Ala Pro Lys Ile Leu Leu Glu Glu Ile Tyr
    210                 215                 220

Arg Thr Gly Met Gly Ser Arg Leu Ser Gln Gly Phe Gly Leu Leu Glu
225                 230                 235                 240

Tyr Leu Gly Gly Glu Ile Lys Asp Glu Val
                245                 250

<210> SEQ ID NO 52
<211> LENGTH: 261
<212> TYPE: PRT
<213> ORGANISM: Microscilla marina

<400> SEQUENCE: 52

Met Arg Tyr Lys Ile Thr Leu Lys Thr Thr Asp Ala Tyr Thr Val Ile
  1               5                  10                  15

Pro Ile Asn Tyr Gln Tyr Glu Leu Ser Ser Cys Ile Leu Gly Ile Cys
                 20                  25                  30

Lys Asp Ala Asn Thr Lys Tyr Gln Arg Phe Leu Lys Gln His Lys Leu
             35                  40                  45

Pro Ala Arg Arg Lys Asn Phe Gln Trp Phe Ser Phe Ser Asn Leu Tyr
         50                  55                  60

Val Pro Arg Arg Glu Ile Phe Ala Asp Arg Leu Gln Val Ile Ser Pro
 65                  70                  75                  80

Lys Ile Ser Phe Ile Ile Ser Phe Tyr Leu Asp Pro Ser Ala Glu Arg
                 85                  90                  95

Phe Ile Lys Asp Leu Phe Leu Asp Arg Gln Met Tyr Leu Gly Asp Lys
            100                 105                 110

Phe Ser Gln Ala Arg Phe Ile Val Glu Asn Val Glu Pro Leu Pro Leu
        115                 120                 125

Arg Met Pro Ser Thr Thr Val Ser Phe Lys Thr Leu Ser Pro Leu Leu
    130                 135                 140

Ile Ser Lys Leu Asn Asn Arg Gly Asn Val Asp Tyr Leu Pro Pro Glu
145                 150                 155                 160

His Pro Glu Tyr Glu Asn Leu Phe Leu Gln Ala Leu Leu Gly Lys Tyr
                165                 170                 175

Val Lys Val Leu Gln Glu Thr Asn Gln Thr Pro Glu Ser Ser Thr His
            180                 185                 190
```

```
Gln Arg Ile Glu Phe Glu Val Asn His Tyr Lys Lys Ile Lys Ser Arg
        195                 200                 205

Leu Ile Thr Val Lys Ala His Thr Thr Asn Glu Ala Arg Ile Arg Gly
210                 215                 220

Phe Met Tyr Glu Phe Arg Leu Thr Ala Pro Lys Glu Ile Ile Glu Leu
225                 230                 235                 240

Gly Leu Leu Thr Gly Phe Gly Glu Lys Asn Arg Leu Gly Phe Gly Ala
                245                 250                 255

Cys Glu Thr Val Tyr
            260

<210> SEQ ID NO 53
<211> LENGTH: 263
<212> TYPE: PRT
<213> ORGANISM: Microscilla marina

<400> SEQUENCE: 53

Met Arg Phe Arg Leu Thr Leu Arg Arg Leu Ser Thr Pro Cys Asn Ile
1               5                   10                  15

Pro Ile Asn Tyr Gln Ser Tyr Ile Ser Ala Asn Ile Tyr Arg Leu Leu
            20                  25                  30

Glu Leu Ala Asp Ala Gln Tyr Ala Ala Phe Leu His Asp Lys Gly Tyr
        35                  40                  45

Glu Gly Glu Gly Lys Arg Phe Lys Tyr Phe Thr Phe Gly Gln Leu Lys
    50                  55                  60

Ile Pro Arg Gly Lys Trp Gln Met Arg Glu Ser Arg Met Leu Ile Asn
65                  70                  75                  80

Ala Pro Val Val His Leu Glu Thr Ser Phe Leu Val Asp Lys Thr Val
                85                  90                  95

Glu Lys Phe Val Ala Gly Val Phe Gln Asp Gln His Leu Tyr Ile Asn
            100                 105                 110

Asp Ala Phe Ala His Asn Asp Phe Leu Ile Glu Gln Ile Glu Met Leu
        115                 120                 125

Pro Thr Val Ala Phe Gly Glu Met Met Arg Phe Ser Cys Gln Ser Pro
    130                 135                 140

Leu Ile Ile Thr Arg Lys Asn Lys His Asn Lys His Cys Thr Tyr Leu
145                 150                 155                 160

Ala Pro Gly Asp Ala Leu Tyr His Glu Ile Phe Ile Glu Asn Leu Arg
                165                 170                 175

Ser Lys His Gln Thr Tyr Leu Ser Gln Gln Leu Pro His Asn Gly Ser
            180                 185                 190

Asn Thr Gln Ile Pro Pro Gln Leu Glu Val Leu Asn Asn Gly Lys Met
        195                 200                 205

Ser Ser Lys Leu Ile Thr Leu Lys Pro Trp Leu Lys Gln Gly Ile Lys
    210                 215                 220

Val Lys Gly Cys Leu Phe Asp Phe Glu Leu Thr Ala Pro Pro Glu Met
225                 230                 235                 240

Leu Lys Val Gly Phe Tyr Gly Phe Gly Ser Asn Cys Ala Gln Gly
                245                 250                 255

Phe Gly Met Val Glu Val Ile
            260

<210> SEQ ID NO 54
<211> LENGTH: 287
<212> TYPE: PRT
```

-continued

<213> ORGANISM: Algoriphagus

<400> SEQUENCE: 54

Met Pro Phe His His Gln Tyr Ile Leu Ala Gln Phe Leu Lys Gly Leu
1               5                   10                  15

Ile Val Lys Gly Gly Arg Glu Glu Phe Tyr Asn Tyr Asn Phe Asn
            20                  25                  30

Phe Ser Gly Leu Lys Gly Gln Thr Lys Val Ser Arg Ser Gly Leu His
        35                  40                  45

Tyr Tyr Ser Ser Leu Val Thr Leu Val Leu Ser Ser Gln Ser Glu Asp
    50                  55                  60

Phe Met Asp Tyr Leu Leu Glu Gln Val Phe Ala Thr Pro Lys Val Glu
65                  70                  75                  80

Leu Gly Asn Leu Ile Leu Val Pro Glu Tyr Thr Glu Ile Glu Ile Glu
                85                  90                  95

Pro Val Leu Glu Thr Ser Asn Lys Phe Val Cys Ile Ser Pro Leu Val
            100                 105                 110

Leu Ile Thr Pro Ala Phe Asn Glu Glu Ala Gly Lys Arg Phe Ile Ser
        115                 120                 125

Pro Asp Ser Asp Glu Phe Ser Asp Leu Leu Tyr Glu Ser Thr Leu Thr
    130                 135                 140

Arg Met Glu Lys Ser Gly Trp Tyr Thr Pro Glu Gln Met Glu Ser Phe
145                 150                 155                 160

Phe Lys Phe Gln Val Val Pro Asp Met Val Tyr Val Asn Lys Leu Lys
                165                 170                 175

Glu Gln Gln Lys Lys Phe Ala Arg Ile Tyr Ala Val Tyr Asp Met Asp
            180                 185                 190

Val Lys Tyr Glu Val Arg Gly Tyr Thr Leu Pro Phe Thr Leu Tyr Ala
        195                 200                 205

Ala Pro Glu Val Gln Asp Phe Val Phe Lys Cys Gly Leu Gly Ala Phe
    210                 215                 220

Thr His Lys Gly Phe Gly Met Leu Asp Leu Ala Thr His Pro Pro Gly
225                 230                 235                 240

Ser Arg Thr Lys Thr Tyr Lys Phe Lys Arg Glu Gly Phe Val Pro Tyr
                245                 250                 255

Lys Pro Asn Glu Arg Val Arg Gln Asn Val Ala Pro Ala Glu Gly
            260                 265                 270

Glu Glu Lys Glu Ser Asp Ser Gly Ser Glu Glu Lys Ser Glu Ser
        275                 280                 285

<210> SEQ ID NO 55
<211> LENGTH: 223
<212> TYPE: PRT
<213> ORGANISM: Bacteroides fragilis

<400> SEQUENCE: 55

Met Arg Ile Arg Ile Lys Thr Thr Ser Asn Glu Lys Ile Leu Pro Phe
1               5                   10                  15

Asp Tyr Gln Gly Lys Leu Ile Gly Val Ile His Lys Trp Leu Gly Asn
            20                  25                  30

Asn Glu Leu His Asp Lys Ile Ser Leu Tyr Ser Phe Ser Trp Leu Leu
        35                  40                  45

Gly Gly Val Met Val Asp Lys Lys Gly Tyr Val Phe Pro Asn Gly Ala
    50                  55                  60

Glu Leu Leu Ile Ser Phe His Glu Asp Gln His Leu Lys Lys Ile Ile

```
                65                  70                  75                  80
Asp Ser Ile Leu Leu Asp Pro Glu Ile Phe Tyr Gly Leu Cys Val Lys
                    85                  90                  95

Asp Ile Thr Ile Val Gly Ser Pro Val Phe Thr Glu Pro Gln Arg
                100                 105                 110

Phe Phe Leu Ala Ser Pro Ile Phe Ile Lys Arg Arg Ile Glu Glu Ile
                115                 120                 125

Met Gly Tyr Lys Tyr Tyr Phe Tyr Asp Asp Gln Glu Ser Asn Gln Leu
    130                 135                 140

Met Thr Glu Thr Leu Lys His Lys Met Arg Glu Ala Gly Leu Pro Glu
145                 150                 155                 160

Asp Asp Thr Leu Arg Val Glu Phe Asp Ile Ser Tyr Ser Lys Lys Lys
                165                 170                 175

Lys Lys Met Val Thr Ile His Gly Ile Lys Ser Ile Ala Asn Met Cys
                180                 185                 190

Pro Val Ile Ile His Gly Thr Gln Thr Ser Lys Arg Phe Ala Trp Val
                195                 200                 205

Val Gly Leu Gly Asn Gly Thr Gly Ser Gly Tyr Gly Ala Leu Ile
    210                 215                 220

<210> SEQ ID NO 56
<211> LENGTH: 223
<212> TYPE: PRT
<213> ORGANISM: Bacteroides fragilis

<400> SEQUENCE: 56

Met Arg Ile Arg Ile Lys Thr Thr Ser Asn Glu Lys Ile Leu Pro Phe
1               5                   10                  15

Asp Tyr Gln Gly Lys Leu Ile Gly Val Ile His Lys Trp Leu Gly Asn
                20                  25                  30

Asn Glu Leu His Asp Lys Ile Ser Leu Tyr Ser Phe Ser Trp Leu Leu
            35                  40                  45

Gly Gly Val Met Val Asp Lys Lys Gly Tyr Val Phe Pro Asn Gly Ala
        50                  55                  60

Glu Leu Leu Ile Ser Phe His Glu Asp Gln His Leu Lys Lys Ile Ile
65                  70                  75                  80

Asp Ser Ile Leu Leu Asp Ser Glu Ile Phe Tyr Gly Leu Cys Val Lys
                    85                  90                  95

Asp Ile Thr Ile Val Gly Ser Pro Val Phe Thr Glu Pro Gln Arg
                100                 105                 110

Phe Phe Leu Ala Ser Pro Ile Phe Ile Lys Arg Arg Ile Glu Glu Ile
                115                 120                 125

Met Gly Tyr Lys Tyr Tyr Phe Tyr Asp Asp Gln Glu Ser Asn Gln Leu
    130                 135                 140

Met Thr Glu Thr Leu Lys His Lys Met Arg Glu Ala Gly Leu Pro Glu
145                 150                 155                 160

Asp Asp Thr Leu Arg Val Glu Phe Asp Ile Ser Tyr Ser Lys Lys Lys
                165                 170                 175

Lys Lys Met Val Thr Ile His Gly Ile Lys Ser Ile Ala Asn Met Cys
                180                 185                 190

Pro Val Ile Ile His Gly Thr Gln Thr Ser Lys Arg Phe Ala Trp Val
                195                 200                 205

Val Gly Leu Gly Asn Gly Thr Gly Ser Gly Tyr Gly Ala Leu Ile
    210                 215                 220
```

<210> SEQ ID NO 57
<211> LENGTH: 221
<212> TYPE: PRT
<213> ORGANISM: Porphyromonas gingivalis

<400> SEQUENCE: 57

Met Arg Ile Glu Leu Ser Ile Lys Ala Asp Asp Ser Leu Val Ser Phe
1               5                   10                  15

Ser His Gln His Leu Leu Val Gly Thr Leu Gln Lys Trp Leu Gly Glu
            20                  25                  30

Asn Asp Met His Gly Lys Ser Ile Ser Tyr Ser Phe Ser Arg Leu Asn
        35                  40                  45

Gly Gly Lys Leu Val Ser Glu Leu Asn Ser Ile Leu Phe Ala Asp Trp
    50                  55                  60

Ala Asn Met Phe Val Ser Ala His Asp Pro Glu Leu Ile Arg Arg Met
65                  70                  75                  80

Leu Ala Gly Ile Arg Gln Asp Pro Glu Met Phe Lys Ser Leu Cys Val
                85                  90                  95

Arg Glu Val Thr Val Ile Glu Asp Pro Asp Met Thr Asp Arg Glu Ile
            100                 105                 110

Phe Phe Pro Ala Ser Pro Ile Leu Leu Lys Arg Trp Arg Glu Asp Asn
        115                 120                 125

Gly Phe Asp His Ile Val Tyr Thr Asp Glu Ala Ala Asn Ala Leu Leu
    130                 135                 140

Thr Glu Asn Leu Arg Lys Lys Leu Gln Ala Val Gly Ile Asp Asp Pro
145                 150                 155                 160

Thr Ala Thr Ala Ser Phe Val Pro Asp Gln Gly Lys Ala Lys Val Met
                165                 170                 175

Leu Ile Asp Tyr Arg Gly Val Lys Asn Lys Ala Ser Trp Cys Pro Ile
            180                 185                 190

Arg Ile Ile Gly Asn Ala Glu Thr Lys Leu Phe Ala Trp Asn Ala Gly
        195                 200                 205

Ile Gly Asn Ser Thr Gly Ile Gly Phe Gly Ala Ile Lys
    210                 215                 220

<210> SEQ ID NO 58
<211> LENGTH: 221
<212> TYPE: PRT
<213> ORGANISM: Porphyromonas gingivalis

<400> SEQUENCE: 58

Met Arg Ile Glu Leu Ser Ile Lys Ala Asp Asp Ser Leu Val Ser Phe
1               5                   10                  15

Ser His Gln His Leu Leu Val Gly Thr Leu Gln Lys Trp Leu Gly Glu
            20                  25                  30

Asn Asp Met His Gly Lys Ser Ile Ser Tyr Ser Phe Ser Arg Leu Asn
        35                  40                  45

Gly Gly Lys Phe Val Ser Glu Leu Asn Ser Ile Leu Phe Thr Asp Trp
    50                  55                  60

Ala Asn Met Phe Val Ser Ala His Asp Pro Glu Leu Ile Arg Arg Met
65                  70                  75                  80

Leu Ala Gly Ile Arg Gln Asp Pro Glu Met Phe Lys Ser Leu Cys Val
                85                  90                  95

Arg Glu Val Thr Val Ile Glu Asp Pro Asp Met Thr Asp Arg Glu Ile
            100                 105                 110

```
Phe Phe Pro Ala Gly Pro Ile Leu Leu Lys Arg Trp Arg Glu Asp Asn
            115                 120                 125

Gly Phe Asp His Ile Val Tyr Thr Asp Glu Ala Asn Ala Leu Leu
    130                 135                 140

Thr Glu Asn Leu Arg Lys Lys Leu Gln Ala Val Gly Ile Asp Asp Pro
145                 150                 155                 160

Thr Ala Thr Ala Ser Phe Val Pro Asp Gln Gly Lys Ala Lys Val Met
                165                 170                 175

Leu Ile Asp Tyr Arg Gly Val Lys Asn Lys Ala Ser Trp Cys Pro Ile
            180                 185                 190

Arg Ile Ile Gly Asn Ala Glu Thr Lys Leu Phe Ala Trp Asn Ala Gly
            195                 200                 205

Ile Gly Asn Ser Thr Gly Ile Gly Phe Gly Ala Ile Lys
            210                 215                 220

<210> SEQ ID NO 59
<211> LENGTH: 265
<212> TYPE: PRT
<213> ORGANISM: Prosthecochloris aestuarii

<400> SEQUENCE: 59

Met Arg Ile Thr Leu Gln Leu Ser His Arg Ser Arg His Leu Thr Leu
1               5                   10                  15

Pro Val Asn Ile Asn His Leu Val Ser Ser Leu Ile Tyr Asn Ile Val
            20                  25                  30

Ser Asn Ser Ser Ser Glu Phe Ala Glu Lys Leu His Glu Gln Gly Tyr
        35                  40                  45

Arg Leu Glu Lys Arg Thr Phe Lys Leu Phe Thr Phe Ser Pro Leu Ile
    50                  55                  60

Pro Ala Gly His Arg Arg Trp Arg Met Asn Gly Asp Gly Thr Met Thr
65                  70                  75                  80

Thr Asp Ala Gln Ser Val Ser Leu Leu Ile Ser Ser Gly Lys Ala Glu
                85                  90                  95

Phe Val Glu His Leu Val Val Gly Leu Leu His Gln Pro Leu Val Gln
            100                 105                 110

Ile Gly Ala Gln Arg Phe Arg Val Glu Thr Val Lys Lys Leu Asp Pro
            115                 120                 125

Pro Gln Leu Ser Asp Asp Met Ala Cys Ile Met Met Ser Pro Leu Val
        130                 135                 140

Cys Ser Ala Lys Arg Asp Gly Asp Lys Tyr Pro Arg Phe Leu Leu Gln
145                 150                 155                 160

Asp Asp Glu Glu Phe Glu Arg Val Leu Leu Glu Asn Leu Leu Gly Lys
                165                 170                 175

Tyr Glu Ala Met His Gly Lys Pro Tyr Glu Gly Arg Ala Glu Leu His
            180                 185                 190

Phe Asp Val Ala Lys Glu Tyr Ile Glu Arg Arg Asn Gly Ala Ile Thr
            195                 200                 205

Lys Leu Ile Thr Leu Lys Glu Gly Ser Pro Asp Glu Thr Lys Val Arg
    210                 215                 220

Gly Thr Leu Ala Pro Phe Arg Leu Arg Val Ala Arg Pro Leu Met Glu
225                 230                 235                 240

Val Gly Tyr Asp Cys Gly Phe Gly Gly Leu Asn Ala Gln Gly Phe Gly
                245                 250                 255

Met Val Lys Met Ser Asn Leu Thr Ser
            260                 265
```

<210> SEQ ID NO 60
<211> LENGTH: 218
<212> TYPE: PRT
<213> ORGANISM: Chloroherpeton thalassium

<400> SEQUENCE: 60

```
Met Arg Leu Tyr Leu Lys Leu Ser Lys Asn Thr Asp Pro Val Pro Phe
1               5                   10                  15

Glu His Asn Ser Val Leu Ala Gly Ile Phe His Lys Trp Val Asn Asp
            20                  25                  30

Ala Glu Ile His Asp Ser Leu Ser Leu Tyr Ser Phe Ser Trp Leu Arg
        35                  40                  45

Gly Gly Gly Val Asn Asn Asn Leu Asp Phe Pro Lys Gly Gly Tyr
    50                  55                  60

Trp Phe Ile Ser Ile Tyr Asp Ser Glu Thr Leu Met Lys Ile Ile Lys
65                  70                  75                  80

Gln Ile Gln Ile Asn Pro Asn Ile Ala Tyr Gly Met Thr Val Lys Glu
                85                  90                  95

Val Val Ile Phe Glu Thr Pro Glu Phe Ser Ser Glu Gln Arg Phe Met
            100                 105                 110

Leu Ala Thr Pro Ile Phe Ile Lys Arg Thr Met Asp Lys Lys Ser Ile
        115                 120                 125

His Tyr Leu Tyr Phe Asp Asn Glu Ser Asp Lys Leu Met Thr Glu Thr
    130                 135                 140

Leu Lys Thr Lys Leu Lys Lys Ala Gly Ile Asn Asp Glu Ser Leu Lys
145                 150                 155                 160

Ile Ser Phe Asp Arg Ser Tyr Asp Lys Ala Lys Val Lys Leu Ile Ser
                165                 170                 175

Tyr Lys Gly Ile Lys Asn Lys Ala Asn Leu Cys Pro Val Ile Ile Thr
            180                 185                 190

Gly Lys Pro Glu Thr Leu Ala Phe Ala Trp Asn Val Gly Ile Gly Asn
        195                 200                 205

Ser Thr Gly Ile Gly Phe Gly Ala Leu Leu
    210                 215
```

<210> SEQ ID NO 61
<211> LENGTH: 267
<212> TYPE: PRT
<213> ORGANISM: Chloroherpeton thalassium

<400> SEQUENCE: 61

```
Met Arg Ile Lys Ile Val Leu Lys Gln Arg Lys Val Glu Glu Leu
1               5                   10                  15

Pro Ile Asn Thr Gly Tyr Leu Ile Ala Ser Ser Ile Tyr His Thr Leu
            20                  25                  30

Ser Leu Ala Ser Glu Ser Tyr Ala Thr Asp Leu His Glu Ile Gly Tyr
        35                  40                  45

Gly Lys Gln Gly Glu Arg Arg His Phe Lys His Phe Thr Phe Ser Asn
    50                  55                  60

Ile Gln Phe Pro Lys Lys Glu Ile His Lys Lys Ile Ile Ser Tyr
65                  70                  75                  80

Ser Asn Tyr Ile Phe Phe Met Ile Ser Ser Pro Lys Glu Glu Phe Leu
                85                  90                  95

Gln Asn Leu Val Met Gly Leu Phe Gln Asp Gly Leu Phe Arg Ile Ala
            100                 105                 110
```

```
Gln Ser Tyr Phe Glu Lys Glu Leu Ile Glu Thr Leu Pro Glu Pro Ile
            115                 120                 125

Phe Glu Asn Lys Met Ser Phe Ser Met Met Ser Pro Leu Thr Leu Ser
130                 135                 140

Ile Ser Glu Asn Val Glu Asn Gly Val Arg Arg Lys His Tyr Leu Arg
145                 150                 155                 160

Ala His Asp Glu Arg Phe Pro Ile Leu Ile Arg Gln Asn Leu Met Ala
                165                 170                 175

Lys Tyr Glu Ser Leu Thr Gly Glu Asn Phe Gly Phe Asp Glu Ala Asp
            180                 185                 190

Phe Gln Phe Glu Phe Asp Gln Ala Tyr Ile Gln Lys Gln Glu Lys Lys
        195                 200                 205

Gly Arg Ser Ile Glu Lys Leu Ile Thr Ile Ala Ala Gly Ser Glu Lys
    210                 215                 220

Gln Thr Arg Ile Lys Ala Leu Glu Cys Pro Phe Thr Ile Thr Ala His
225                 230                 235                 240

Pro Glu Leu Ile Lys Ile Gly Tyr Glu Cys Gly Phe Gly Asp Ser Asn
                245                 250                 255

Ser Met Gly Phe Gly Met Val Lys Glu Met Lys
            260                 265

<210> SEQ ID NO 62
<211> LENGTH: 263
<212> TYPE: PRT
<213> ORGANISM: Chlorobaculum parvum

<400> SEQUENCE: 62

Met Arg Ile Thr Leu Glu Leu Ser His Arg Arg Ser Phe Val Thr Val
1               5                   10                  15

Pro Ile Asn His Ser Ser Leu Ile Ser Ser Leu Ile Tyr Asn Val Ile
            20                  25                  30

Asp Arg Ser Ser Glu Tyr Ala Glu Arg Leu His Glu Gln Gly Tyr
        35                  40                  45

Arg Leu Glu Asn Arg Ala Phe Lys Leu Phe Thr Phe Ser Pro Leu Asn
50                  55                  60

Pro Gly His His Arg Lys Trp Val Met His Glu Asn Gly Thr Met Ser
65                  70                  75                  80

Thr Gly Glu Lys Arg Leu Tyr Leu Thr Ile Ser Ser Pro Lys Glu Glu
            85                  90                  95

Phe Ile Glu His Leu Ile Leu Gly Leu Leu His Glu Pro Phe Val Ser
            100                 105                 110

Val Gly Lys Glu Arg Phe Arg Val Glu Thr Val Arg Lys Leu Asp Ala
            115                 120                 125

Pro Leu Phe Ser Gly Asp Met Arg Phe Val Met Leu Ser Pro Leu Val
            130                 135                 140

Cys Ala Thr Lys Ser Glu Ala Asp Gln Tyr Pro Gln Tyr Leu Phe Pro
145                 150                 155                 160

Gly Asp Pro Asp Phe Lys Arg Val Leu Val Ala Asn Leu Cys Arg Lys
                165                 170                 175

Tyr Glu Val Leu His Gly Lys Pro Ile Ala Cys Asp Glu Asn Asp Val
            180                 185                 190

Met Phe Glu Leu Asp Arg Asp Tyr Val Ala Lys Val His Gly Lys Val
        195                 200                 205

Gln Lys Leu Ile Thr Leu Lys Glu Gly Arg Ser Asp Glu Ser Lys Val
```

```
                  210                 215                 220
Lys Gly Thr Leu Ala Pro Phe Arg Leu Val Ala Pro Thr Glu Leu Ile
225                 230                 235                 240

Glu Val Gly Tyr Glu Cys Gly Phe Gly Glu Lys Asn Ala Gln Gly Phe
                245                 250                 255

Gly Met Val Lys Ala Ile Asn
                260

<210> SEQ ID NO 63
<211> LENGTH: 267
<212> TYPE: PRT
<213> ORGANISM: Chlorobium phaeobacteroides

<400> SEQUENCE: 63

Met Arg Ile Thr Leu Glu Leu Ser His Arg Asn Ser Ser Ile Thr Leu
1               5                   10                  15

Pro Ile Asn Asn Ser Tyr Leu Leu Ser Ser Leu Ile Tyr Asn Ile Val
                20                  25                  30

Asp Lys Ser Ser Glu Tyr Ala Gly Arg Leu His Ala Gln Gly Tyr
                35                  40                  45

Arg Leu Gln Asn Lys Ala Phe Lys Leu Phe Ala Phe Ser Pro Leu Cys
    50                  55                  60

Pro Ala Asn Arg Arg Lys Trp Glu Met Gln Asp Asp Gly Thr Met Ser
65                  70                  75                  80

Thr Arg Glu Arg Val Leu His Phe Thr Ile Ser Ser Pro Lys Ser Glu
                85                  90                  95

Phe Ile Glu His Leu Val Val Gly Leu Leu His Glu Pro Tyr Val Phe
                100                 105                 110

Val Gly Arg Glu Arg Phe Arg Val Glu Cys Val Arg Arg Leu Asp Cys
            115                 120                 125

Pro Glu Ile Ser Gly Asp Met Arg Phe Ile Ala Leu Ser Pro Val Val
    130                 135                 140

Cys Ala Thr Lys His Ala Gly Asp Leu Tyr Ala Gln Tyr Leu Phe Pro
145                 150                 155                 160

Gly Asp Asp Asp Phe Glu Arg Val Leu Phe Asp Asn Leu Cys Arg Lys
                165                 170                 175

Phe Glu Ala Leu His Gly Arg Arg Phe Asp Gly Asp Asn Gly Asn Phe
            180                 185                 190

His Phe Thr Leu Asp Gln Asp Tyr Val Val Arg Lys Asn Gly Lys Val
        195                 200                 205

Gln Lys Leu Ile Thr Ile Lys Glu Gly Lys Pro Asp Glu Thr Arg Val
    210                 215                 220

Lys Gly Leu Leu Ala Pro Phe Arg Leu Val Ala Pro Ala Glu Leu Met
225                 230                 235                 240

Glu Val Gly Tyr Glu Cys Gly Phe Gly Glu Arg Asn Ser Gln Gly Phe
                245                 250                 255

Gly Leu Val Lys Val Asp Asp Cys Val Arg Cys
            260                 265

<210> SEQ ID NO 64
<211> LENGTH: 266
<212> TYPE: PRT
<213> ORGANISM: Chlorobium limicola

<400> SEQUENCE: 64

Met Arg Leu Lys Leu Thr Leu Arg Gln Gln Arg Pro Val Glu Arg Ile
```

```
               1               5                  10                 15
            Pro Leu Asn His Ser His His Leu Ala Ala Val Ile Tyr Ser Thr Leu
                         20                 25                 30

Ser Lys Ser Ser Ser Glu Phe Ala Thr Val Leu His Asp Lys Gly Tyr
                     35                 40                 45

Ala Pro Glu Gly Ser Arg Gln Lys Phe Lys Tyr Phe Thr Phe Ser Ser
                 50                 55                 60

Leu Gln Ile Pro Ile Arg Thr Ile Asp Ser Gly Glu Ile Val Ser Arg
            65                  70                 75                 80

Ser Arg Gln Ile Thr Phe Tyr Leu Ser Ser Pro Lys Glu Glu Phe Leu
                             85                 90                 95

Gln His Leu Ile Leu Gly Leu Phe Ala Glu Gly Ser Leu Arg Ile His
                        100                105                110

Asn Ala Val Phe Ser Lys Glu Cys Ile Glu Lys Leu Pro Glu Pro Glu
                        115                120                125

Trp Thr Glu Asn Met Thr Phe Ser Met Leu Ser Pro Leu Ala Val Ser
                    130                135                140

Val Tyr Arg Asp Pro Ser Ala Gly Met Asn Thr Lys Glu Tyr Leu Arg
            145                 150                155                160

Tyr Asp Asp Ser Arg Leu Ser Asp Met Leu Leu His Asn Leu Gln Ala
                            165                170                175

Lys Tyr Arg Gly Leu Phe Gly Cys Glu Pro Pro Glu Asn Asp Ile Pro
                        180                185                190

Phe Ser Val Arg Phe Glu Glu Ala Tyr Leu Lys Arg Val Arg Glu Lys
                    195                200                205

Gly Arg Ser Val Glu Lys Leu Ile Thr Ile Lys Asp Tyr Ser Gly Lys
                210                215                220

Glu Thr Arg Val Lys Ala Ile Gln Cys Pro Phe Thr Val Thr Gly Asp
            225                 230                235                240

Pro Glu Leu Ile Lys Val Gly Tyr Glu Cys Gly Phe Gly Glu Asn Asn
                            245                250                255

Pro Met Gly Phe Gly Met Val Lys Val Ser
                        260                265

<210> SEQ ID NO 65
<211> LENGTH: 264
<212> TYPE: PRT
<213> ORGANISM: Pelodictyon phaeoclathratiforme

<400> SEQUENCE: 65

Met Arg Ile Thr Leu Glu Leu Ser His Arg Lys Arg Thr Val Thr Leu
1               5                  10                 15

Pro Ile Asn Asn Ser His Leu Ile Ser Ser Leu Ile Tyr Asn Ile Val
            20                 25                 30

Asp Lys Ser Ser Ser Glu Tyr Ala Glu Arg Leu His Asp Gln Gly Tyr
        35                 40                 45

Arg Leu Gln Asn Arg Ala Phe Lys Leu Phe Thr Phe Ser Pro Leu Tyr
    50                 55                 60

Pro Gly Asn Arg His Lys Trp Val Met His Glu Asn Gly Thr Met Ser
65                  70                 75                 80

Thr Ala Asp Ala Leu Leu His Val Thr Ile Ser Ser Pro Lys Glu Glu
                85                 90                 95

Phe Val Glu His Leu Val Ile Gly Leu Leu Gln Glu Pro Tyr Val Trp
            100                105                110
```

```
Val Gly Asn Glu Arg Phe Arg Val Glu Thr Val Arg Lys Leu Asp Gln
            115                 120                 125

Pro Glu Leu Ser Asp Asp Met Glu Phe Val Met Leu Ser Pro Leu Val
            130                 135                 140

Cys Thr Thr Lys Gly Glu Ala Asp His Tyr Pro Gln Tyr Leu Tyr Pro
145                 150                 155                 160

Gly Asp Pro Glu Phe Glu Arg Val Leu Leu Glu Asn Leu Cys Arg Lys
                165                 170                 175

Tyr Gln Val Leu His Gly Arg Ser Phe Val Cys Glu Ser Gly Gln Phe
            180                 185                 190

Gly Phe Ala Ile Asp Glu Ala Tyr Val Glu Arg Met Gln Gly Lys Val
            195                 200                 205

Gln Lys Leu Ile Thr Leu Lys Glu Gly Arg Ser Asp Glu Thr Lys Ile
            210                 215                 220

Lys Gly Thr Leu Ala Pro Phe Arg Leu Arg Ala Pro Arg Glu Leu Met
225                 230                 235                 240

Glu Val Gly Tyr Ala Cys Gly Phe Gly Leu Lys Asn Ser Met Gly Phe
                245                 250                 255

Gly Met Val Lys Val Asp Glu Ala
            260

<210> SEQ ID NO 66
<211> LENGTH: 239
<212> TYPE: PRT
<213> ORGANISM: Thermus thermophilus

<400> SEQUENCE: 66

Met Val Leu Ala Ala Leu Val Leu Val Leu Glu Gly Glu Gly Leu Pro
1               5                   10                  15

Glu Pro Leu Gly Leu Arg Gly Phe Phe Tyr Gly Leu Leu Arg Glu Val
            20                  25                  30

Ala Pro Glu Val His Asp Gln Gly Glu Asn Pro Phe Ala Leu Gly Phe
            35                  40                  45

Gly Gly Arg Glu Gly Ala Ser Trp Ala Arg Val Ser Leu Leu Val Glu
        50                  55                  60

Glu Leu Tyr Ala Arg Leu Ala Pro Arg Leu Tyr Ala Leu Glu Gly Glu
65                  70                  75                  80

Glu Val Arg Leu Gly Pro Pro Phe Arg Val Arg Ala Val Leu Gln Glu
                85                  90                  95

Gly His Pro Trp Ala Gly Val Ser Thr Tyr Pro Arg Leu Phe Gln Gly
            100                 105                 110

Pro Pro Ser Arg Asp Leu Ala Leu Arg Phe Ala Ser Pro Thr Phe Phe
            115                 120                 125

Arg Arg Lys Gly Val His Tyr Pro Val Pro Glu Pro Arg Leu Val Leu
            130                 135                 140

Glu Ser Leu Leu Arg Arg Leu Glu Ala Phe Gly Pro Leu Lys Ala Pro
145                 150                 155                 160

Glu Gly Val Arg Glu Ala Leu Leu Glu Arg Thr Thr Val Arg Ser Leu
                165                 170                 175

Glu Gly Arg Thr Leu Pro Ala Arg Thr Glu Val Asp Thr Ala Gly Phe
            180                 185                 190

Val Gly Arg Val Val Tyr His Leu Pro Arg Ala Thr Glu Glu Glu Ala
            195                 200                 205

Leu Trp Leu Ser Ala Leu Gly Arg Phe Ala Phe Tyr Ser Gly Val Gly
            210                 215                 220
```

```
Ala Lys Thr Ser Leu Gly Tyr Gly Arg Ala Arg Ala Glu Ser Ala
225                 230                 235
```

<210> SEQ ID NO 67
<211> LENGTH: 264
<212> TYPE: PRT
<213> ORGANISM: Thermus thermophilus

<400> SEQUENCE: 67

```
Met Pro Gln Ala Val Val Leu Glu Leu Val Gly Glu Lys Pro Pro Leu
1               5                   10                  15

Tyr Pro Ala Arg Tyr Ala His Gly Leu Phe Phe Ala Leu Leu Ser Arg
            20                  25                  30

Val Ser Pro Glu Leu Ala Gln Lys Leu His Glu Ala Pro Arg Lys Pro
        35                  40                  45

Phe Thr Leu Ala Pro Leu Pro Arg Ala Gly Pro Glu Gly Ala Thr Leu
    50                  55                  60

Lys Gly Thr Leu Arg Leu Arg Leu Thr Thr Leu Asp Asp Gly Leu Phe
65                  70                  75                  80

Ala Pro Phe Leu Arg Ala Leu Leu Glu Ala Ala Pro Asp Gly Leu Pro
                85                  90                  95

Leu Gly Asp Ser Ser Tyr Arg Leu Ala Arg Val Leu Ala Thr Arg Glu
            100                 105                 110

Gly His Pro Leu Ala Gly Ala Thr Ser Trp Glu Leu Lys Glu Ala
            115                 120                 125

Pro Lys Arg Glu Lys Val Thr Phe Arg Phe Leu Thr Pro Thr Val Phe
    130                 135                 140

Ala Thr Ser Lys Pro Gly Gly Arg Thr Arg Tyr Thr Pro Leu Pro Asp
145                 150                 155                 160

Pro Arg Leu Ile Ala Gly Ser Leu Leu Asp Lys Trp Gln Ala His Ser
                165                 170                 175

Pro Phe Pro Tyr Asn Pro Lys Glu Glu Ala Ala Leu Arg Gly Leu Phe
            180                 185                 190

Glu Leu Asp Leu Glu Val Ala Gly Phe Arg Asn Leu Arg Phe His Arg
            195                 200                 205

Val Gln Ala Gly Lys Gly Phe Phe Pro Gly Phe Thr Gly Glu Met Thr
    210                 215                 220

Leu Arg Leu Trp Ser Gln Ser Leu Glu Ala Arg Glu Ala Leu Gly Arg
225                 230                 235                 240

Leu His Ala Leu Ala Phe Phe Ser Gly Val Gly Ala Lys Thr Pro Tyr
                245                 250                 255

Gly Met Gly Leu Ala Val Pro Leu
            260
```

<210> SEQ ID NO 68
<211> LENGTH: 264
<212> TYPE: PRT
<213> ORGANISM: Thermus thermophilus

<400> SEQUENCE: 68

```
Met Pro Gln Ala Val Val Leu Glu Leu Val Gly Glu Lys Pro Pro Leu
1               5                   10                  15

Tyr Pro Ala Arg Tyr Ala His Gly Leu Phe Phe Ala Leu Leu Ser Arg
            20                  25                  30

Val Ser Pro Glu Leu Ala Gln Lys Leu His Glu Ala Pro Arg Lys Pro
        35                  40                  45
```

```
Phe Thr Leu Ala Pro Leu Pro Arg Ala Gly Pro Glu Gly Ala Thr Leu
    50                  55                  60

Lys Gly Thr Leu Arg Leu Arg Leu Thr Thr Leu Asp Asp Gly Leu Phe
 65                  70                  75                  80

Ala Pro Phe Leu Arg Ala Leu Leu Glu Ala Ala Pro Asp Gly Leu Pro
                 85                  90                  95

Leu Gly Asp Ser Ser Tyr Arg Leu Ala Arg Val Leu Ala Thr Arg Glu
                100                 105                 110

Gly His Pro Leu Ala Gly Ala Thr Ser Trp Glu Glu Leu Lys Glu Ala
                115                 120                 125

Pro Lys Arg Glu Lys Ala Thr Phe Arg Phe Leu Thr Pro Thr Val Phe
    130                 135                 140

Ala Thr Ser Lys Pro Gly Gly Arg Thr Arg Tyr Thr Pro Leu Pro Asp
145                 150                 155                 160

Pro Arg Leu Ile Ala Gly Ser Leu Leu Asp Lys Trp Gln Ala His Ser
                165                 170                 175

Pro Phe Pro Tyr Asn Pro Lys Glu Glu Ala Ala Leu Arg Glu Leu Phe
                180                 185                 190

Glu Leu Asp Leu Glu Val Ala Gly Phe Arg Asn Leu Arg Phe His Arg
                195                 200                 205

Val Gln Ala Gly Lys Gly Phe Phe Pro Gly Phe Thr Gly Glu Ala Thr
    210                 215                 220

Leu Arg Leu Trp Ser Gln Ser Leu Glu Ala Gln Glu Ala Leu Gly Arg
225                 230                 235                 240

Leu His Ala Leu Ala Phe Phe Ser Gly Val Gly Ala Lys Thr Pro Tyr
                245                 250                 255

Gly Met Gly Leu Ala Val Pro Leu
                260

<210> SEQ ID NO 69
<211> LENGTH: 239
<212> TYPE: PRT
<213> ORGANISM: Thermus thermophilus

<400> SEQUENCE: 69

Met Val Leu Ala Ala Leu Val Leu Val Leu Glu Gly Glu Gly Leu Pro
1               5                   10                  15

Glu Pro Leu Gly Leu Arg Gly Phe Phe Tyr Gly Leu Leu Arg Glu Val
                20                  25                  30

Ala Pro Glu Val His Asp Gln Gly Glu Asn Pro Phe Ala Leu Gly Phe
            35                  40                  45

Gly Gly Arg Glu Gly Ala Ala Trp Ala Arg Val Ser Leu Leu Val Glu
    50                  55                  60

Gly Leu Tyr Ala Arg Leu Ala Pro Arg Leu Tyr Ala Leu Glu Gly Glu
 65                  70                  75                  80

Glu Val Arg Leu Gly Pro Pro Phe Arg Val Arg Ala Val Leu Gln Glu
                 85                  90                  95

Gly His Pro Trp Ala Gly Val Ser Thr Tyr Pro Arg Leu Phe Gln Gly
                100                 105                 110

Pro Pro Ser Arg Asp Leu Ala Leu Arg Phe Ala Ser Pro Thr Phe Phe
                115                 120                 125

Arg Arg Lys Gly Val His Tyr Pro Val Pro Glu Pro Arg Leu Val Leu
    130                 135                 140

Glu Ser Leu Leu Arg Arg Leu Glu Ala Phe Gly Pro Leu Lys Ala Pro
```

```
                145                 150                 155                 160
Glu Gly Val Arg Glu Ala Leu Leu Arg Thr Thr Val Arg Ser Leu
                165                 170                 175

Glu Gly Arg Thr Leu Pro Ala Arg Thr Glu Val Asp Thr Ala Gly Phe
                180                 185                 190

Val Gly Arg Val Val Tyr His Leu Pro Arg Ala Thr Glu Glu Ala
                195                 200                 205

Leu Trp Leu Ser Ala Leu Gly Arg Phe Ala Phe Tyr Ser Gly Val Gly
210                 215                 220

Ala Lys Thr Ser Leu Gly Tyr Gly Arg Ala Arg Ala Glu Ser Ala
225                 230                 235

<210> SEQ ID NO 70
<211> LENGTH: 247
<212> TYPE: PRT
<213> ORGANISM: Aquifex aeolicus

<400> SEQUENCE: 70

Met Arg Val Lys Ala Tyr Leu Glu Val Pro Lys Glu Ile Ser Ile Phe
1               5                   10                  15

Tyr Arg Arg Ser Phe Leu Ser Leu Ile Lys Lys Ala Leu Glu Lys Glu
                20                  25                  30

Asp Glu Asn Tyr Ala Lys Asp Leu Phe Gln Lys Lys Asn Phe Lys Pro
            35                  40                  45

Phe Thr Phe Cys Val Phe Phe Glu Asn Ile Arg Ile Asn Gly Glu Ile
    50                  55                  60

Leu Glu Asn Asn Gly Lys Ala Ile Met Thr Val Ser Ser Gly Ser Pro
65                  70                  75                  80

Asp Phe Phe His Arg Phe Tyr Asn Gly Leu Lys Lys Leu Arg Glu Tyr
                85                  90                  95

Asn Gly Arg Tyr Thr Asn Gly Asn Ile Lys Val Lys Val Leu Met
                100                 105                 110

Cys Glu Glu Glu Gln Ile Thr Lys Pro Arg Gln Thr Phe Arg Thr Leu
            115                 120                 125

Ser Pro Ile Val Val Ile Asn Arg Asp Lys Lys Pro Val Leu Pro Ser
    130                 135                 140

Lys Leu Gly Asn Arg Asn Asp Asp Phe Ile Leu Tyr Asp Asp Gly Ala
145                 150                 155                 160

Phe Thr Gln Glu Leu Arg Tyr Ser Leu Lys Cys Ile Phe Asn Gly Leu
                165                 170                 175

Pro Glu Leu Lys Phe Glu His Gln Glu Gly Lys Lys Ser Val Val Lys
            180                 185                 190

His Val Val Gly Asn Arg Glu Asn Glu Lys Val Ile Lys Ile Val Ala
    195                 200                 205

Tyr Gln Gly Val Phe Thr Leu Glu Gly Asp Pro Tyr Val Leu Asn Glu
210                 215                 220

Val Tyr Lys Tyr Gly Leu Gly Phe Arg Arg Tyr Gln Gly Phe Gly Cys
225                 230                 235                 240

Leu Glu Leu Val Lys Glu Ser
                245

<210> SEQ ID NO 71
<211> LENGTH: 247
<212> TYPE: PRT
<213> ORGANISM: Aquifex aeolicus
```

<400> SEQUENCE: 71

```
Met Arg Phe Leu Ile Lys Met Glu Asn Leu Lys Glu Pro Ala Lys
1               5                   10                  15

Val Arg Leu Asp Tyr Arg Ser Arg Phe Ile Ser Leu Leu Lys Ser Val
                20                  25                  30

Leu Gly Glu Glu Tyr Tyr Ser Asn His Lys Ile Lys Pro Phe Thr Phe
                35                  40                  45

Ala Val Phe Phe Gly Lys Glu Ala Lys Ile Ser Asn Gly Tyr Ile Glu
            50                  55                  60

Asn Val Arg Thr Ile Asn Phe Arg Phe Ser Ser Gly Asp Phe Leu Thr
65                  70                  75                  80

Ile Ala Lys Phe Tyr Asn Gly Ile Leu Gln Leu Lys Lys Asn Gln Tyr
                85                  90                  95

Ile His Pro Ile Gly Thr Gly Lys Phe Lys Ile Asp Phe Arg Pro
            100                 105                 110

Glu Lys Glu Arg Glu Ile Ile Gly Phe Phe Lys Thr Leu Ser Pro Ile
                115                 120                 125

Val Ile Glu Arg Ile Gly Ser Lys Pro Lys Asp Ser Pro Glu Glu Arg
            130                 135                 140

Tyr Ile Thr Pro Asp Glu Glu Ser Phe Glu Glu Ser Leu Val Glu Asn
145                 150                 155                 160

Ile Tyr Arg Arg Tyr Ile Ala Ile Met Gly Ser Glu Pro Gln Phe Ser
                165                 170                 175

Lys Phe Lys Phe Ile Pro Val Lys Val Lys Glu Tyr Val Arg His
                180                 185                 190

Tyr Gly Gly Ile Val Lys Thr Phe Ile Gly Lys Phe Lys Ile Glu Thr
            195                 200                 205

Asp Ser Lys Asp Leu Leu Glu Phe Ile Tyr Lys Tyr Gly Leu Gly Val
            210                 215                 220

Arg Thr Gly Gln Gly Phe Gly Tyr Leu Glu Val Glu Asp Glu Lys Arg
225                 230                 235                 240

Thr Ser Lys Asn Ile Asn Ile
                245
```

<210> SEQ ID NO 72
<211> LENGTH: 238
<212> TYPE: PRT
<213> ORGANISM: Hydrogenivirga

<400> SEQUENCE: 72

```
Met Arg Phe Leu Leu Lys Leu Lys Ser Val Ser Asp Ala Pro Val Arg
1               5                   10                  15

Val Gly Ile Asp Tyr Arg Arg Arg Phe Ile Ser Leu Leu Lys Arg Ile
                20                  25                  30

Leu Glu Asp Glu Tyr Asp Lys Val Lys Thr Arg Pro Tyr Thr Phe Ala
                35                  40                  45

Val Tyr Phe Gly Lys Glu Ala Lys Ile Thr Lys Asp Phe Ile Glu Gly
            50                  55                  60

Ile Arg His Ile Asn Phe Arg Phe Ser Thr Gly Asp Ser Ile Leu Ala
65                  70                  75                  80

Val Lys Phe Tyr Asn Gly Ala Leu Ala Leu Lys Lys Gln Lys Ala Asp
                85                  90                  95

His Ala Ile Gly Glu Gly Arg Phe Ala Val Glu Trp Ile Arg Gln Glu
            100                 105                 110
```

```
Glu Glu Lys Asp Pro Thr Gly Val Tyr Arg Thr Leu Ser Pro Val Val
            115                 120                 125

Val Glu Arg Met Gly Phe Ser Ser Pro Lys Pro Thr Glu Arg Tyr Ile
        130                 135                 140

Ile Pro Ser Glu Glu Gly Phe Glu Glu Ser Leu Leu Glu Asn Ile Leu
145                 150                 155                 160

Arg Arg Tyr Arg Asp Ile Arg Gly Thr Asp Leu Lys Val Asn Arg Phe
                165                 170                 175

Ser Phe Glu Gly Leu Lys Thr Lys Glu Glu Phe Ile Lys His Tyr Gly
            180                 185                 190

Gly Tyr Leu Arg Gly Phe Ile Gly Lys Phe Lys Ile Val Ser Asp Ser
        195                 200                 205

Gln Glu Leu Leu Arg Phe Ile Tyr Gln Tyr Gly Leu Gly Leu Arg Thr
    210                 215                 220

Gly Gln Gly Phe Gly Tyr Leu Glu Val Glu Asp Gly Lys Ala
225                 230                 235
```

```
<210> SEQ ID NO 73
<211> LENGTH: 242
<212> TYPE: PRT
<213> ORGANISM: Hydrogenivirga

<400> SEQUENCE: 73

Met Ile Val Lys Ile Asn Leu Ile Gly Glu Glu Ala Ile Ala Leu Pro
1               5                   10                  15

Lys Ser Tyr Asn His Ile Leu Gln Ala Phe Phe Tyr Ser Asn Met Asp
            20                  25                  30

Pro Val Leu Ser Lys Phe Leu His Asp Ile Gly Phe Thr His Gly Lys
        35                  40                  45

Arg Arg Phe Lys Leu Phe Thr Phe Ser Lys Val Ile Gly Lys Ile Thr
    50                  55                  60

Arg Arg Asp Lys Arg Gly Phe Val Phe Ser Pro Asp Val Thr
65                  70                  75                  80

Leu Tyr Phe Ala Ser Pro Leu Ile Asp Ile Val Ser Ser Ser Val Lys
                85                  90                  95

Thr Phe Leu Lys Arg Gly Asn Leu Phe Leu Gly Arg Asn Thr Val Ser
            100                 105                 110

Leu Ser Ser Ile Glu Leu Val Lys Pro Glu Val Asp Gly Glu Met Thr
        115                 120                 125

Val Arg Cys Leu Ser Pro Ile Thr Val Tyr Arg Thr Pro Lys Gly Glu
    130                 135                 140

Lys Arg Phe Gln Tyr Leu Ser Pro Trp Gln Asp Glu Phe Tyr Glu Leu
145                 150                 155                 160

Leu Arg Lys Asn Leu Val Lys Lys Tyr Glu Leu Val Tyr Ser Lys Ser
                165                 170                 175

Tyr Lys Gly Glu Leu Glu Ile Glu Pro Val Lys Val Ile Glu Gly Tyr
            180                 185                 190

Arg Lys Lys Val Leu Tyr Arg Gly Thr Leu Val Glu Ala Trp Glu Gly
        195                 200                 205

Tyr Tyr Lys Leu Lys Gly Asn Glu Asp Met Leu Arg Leu Ala Leu Glu
    210                 215                 220

Ala Gly Leu Gly Ala Lys Asn Ser Gln Gly Phe Gly Met Val Glu Arg
225                 230                 235                 240

Val Leu
```

```
<210> SEQ ID NO 74
<211> LENGTH: 258
<212> TYPE: PRT
<213> ORGANISM: Hydrogenivirga

<400> SEQUENCE: 74

Met Pro Ile Arg Cys Ser Val Cys Phe Val Pro Glu Lys Pro Ile Ser
1               5                   10                  15

Pro Glu Val Leu Lys Pro Lys Tyr Val His Gly Ile Phe Phe Ser Leu
            20                  25                  30

Leu Glu Glu Gly Leu Ala Glu Arg Met His Arg Gly Arg Val Lys Pro
        35                  40                  45

Phe Ala Leu Arg Phe Gln Arg Leu Met Arg Ala Glu Glu Leu Asp
    50                  55                  60

Arg Phe Phe Leu Glu Val Ser Phe Leu Gln Glu Leu Phe Pro Ser
65                  70                  75                  80

Phe Leu Ser Ser Leu Ile Leu Arg Glu Ser Gln Pro Thr Ile Asn Gly
                85                  90                  95

Leu Ser Leu Arg Tyr Leu Lys Lys Pro Tyr Ile Lys Glu Glu Asn Val
            100                 105                 110

Lys Ser Tyr Ser Arg Ile Tyr Glu Glu Ala Gln Pro Arg Asp Thr Ile
        115                 120                 125

Val Leu Asp Phe Leu Thr Pro Thr Ser Phe Lys Arg Gly Ser Phe Asp
    130                 135                 140

Tyr Pro Leu Pro Glu Pro Arg Leu Ile Phe Arg Gly Leu Ile Arg Lys
145                 150                 155                 160

Trp Gln Ile Phe Ser Asp Leu Lys Ile Asp Leu Asp Leu Arg Glu Val
                165                 170                 175

Val Asp Asn His Ile His Ile Ala Gly Ala Trp Ile Arg Thr Arg Lys
            180                 185                 190

Met Glu Leu Ser Asp Arg Ala Lys Phe Thr Gly Phe Thr Gly Arg Val
        195                 200                 205

Val Leu Tyr Ala Asp Val Arg Lys Glu Ala Val Leu Lys Trp Leu Asn
    210                 215                 220

Ala Leu Ala Ala Phe Gly Glu Phe Ala Gly Val Gly Arg Lys Thr Thr
225                 230                 235                 240

Met Gly Phe Gly Ala Val Arg Val Gly Glu Pro Glu Pro Asp Glu Val
                245                 250                 255

Ser Glu

<210> SEQ ID NO 75
<211> LENGTH: 265
<212> TYPE: PRT
<213> ORGANISM: Hydrogenivirga

<400> SEQUENCE: 75

Met Arg Met Lys Ile Tyr Ile Lys Thr Asn Lys Thr Pro Ile Leu Tyr
1               5                   10                  15

Lys His Lys Val Met Ser Leu Leu Lys Glu Ala Leu Lys Lys Ser Asp
            20                  25                  30

Lys Asp Tyr Lys Asp Phe Leu Tyr Lys Gly Lys Ile Thr Lys Pro Phe
        35                  40                  45

Ser Phe Asn Leu Val Leu Pro Pro Lys Arg Lys Pro Ile Lys Ala Lys
    50                  55                  60

Ile Gln Ile Asp Glu Asn Phe Thr Ile Glu Asp Thr Val Phe Glu Ile
```

```
                65                  70                  75                  80
        Glu Glu Gly Tyr Leu Ser Leu Phe Val Ser Ala Leu Asp Tyr Arg Phe
                        85                  90                  95

Leu Ile Ser Leu Phe Asn Gly Leu Lys Arg Leu His Thr Phe Asn Phe
                    100                 105                 110

Ser Ser Asp Thr Asn Met Leu Val Asp Gly Lys Ile Thr Trp Glu
                    115                 120                 125

Ile Lys Lys Val Ser Pro Ile Asn Glu Lys Pro Ile Lys Ser Arg His
                130                 135                 140

Ile Val Phe Lys Thr Asn Ser Pro Ile Val Glu Asn Gly Asn Asp
        145                 150                 155                 160

Lys Pro Val Leu Phe Ser Asp Lys Asn Phe Glu Tyr His Leu Asn Glu
                        165                 170                 175

Ile Thr Asp Arg Ile Leu Lys Ser Pro His Ile Lys Gly Lys Gly Leu
                    180                 185                 190

Glu Glu Pro Leu Lys Phe Lys Pro Ile Lys Met Asn Lys Gln Val Ile
                    195                 200                 205

Lys His Thr Leu Lys Ala Phe Arg Glu Lys Thr Gly Lys Pro Ile Met
                210                 215                 220

Tyr Leu Thr Gly Asn Ser Gly Ile Phe Lys Leu Ser Gly His Pro Lys
        225                 230                 235                 240

Asp Leu Glu Ile Leu Tyr Lys Ile Gly Ile Gly Asn Arg Thr Gly Gln
                        245                 250                 255

Gly Phe Gly Met Val Glu Val Leu Gly
                    260                 265

<210> SEQ ID NO 76
<211> LENGTH: 252
<212> TYPE: PRT
<213> ORGANISM: Sulfurihydrogenibium

<400> SEQUENCE: 76

Met Arg Val Lys Ile Pro Ile Thr Thr Glu Lys Val Pro Ile Ile Phe
1               5                   10                  15

Arg Gln Arg Val Leu Ala Phe Ile Lys Glu Ala Leu Ala Gln Ala Asp
                20                  25                  30

Lys Asp Tyr Lys Glu Ser Met Tyr Ser Val Arg Met Pro Lys Ala Tyr
            35                  40                  45

Thr Phe Asn Leu Val Phe Asp Arg Thr Asn Pro Lys Glu Glu Glu Ile
        50                  55                  60

Ser Leu Asp Glu Lys Phe Lys Ile Lys Asp Lys Val Phe Tyr Gln Asp
65                  70                  75                  80

Arg Pro Val Phe Leu Tyr Ile Ser Ser Asn Asp Tyr Gln Phe Leu Ile
                85                  90                  95

Asn Leu Phe Asn Gly Met Lys Lys Ile Lys Ile Phe Asp Phe Asn Lys
            100                 105                 110

Phe Asp Asn Ile Tyr Trp Gln Val Gly Lys Pro Val Ile Leu Arg Glu
        115                 120                 125

Lys Ile Ile Phe Asn Asp Glu Ile Ile Phe Lys Thr Asn Ala Pro Phe
    130                 135                 140

Ile Ile Glu Thr Lys Asp Asp Arg Pro Val Val Phe Ser Asp Glu Asn
145                 150                 155                 160

Phe Gln Thr Glu Leu Asn Asn Val Met Glu Arg Ile Phe Arg Lys Leu
                165                 170                 175
```

Asp Asn Arg Gly Leu Lys Gln Pro Leu Glu Phe Tyr Pro Ile Lys Met
            180                 185                 190

Lys Lys Glu Val Ile Lys His Thr Leu Arg Gly Phe Arg Glu Lys Thr
        195                 200                 205

Gly Lys Pro Ile Met Tyr Ile Thr Gly Asn Ser Gly Ile Phe Arg Leu
    210                 215                 220

Lys Gly His Pro Glu Asp Leu Gln Thr Ile Tyr Gln Ile Gly Leu Gly
225                 230                 235                 240

Asn Arg Thr Gly Gln Gly Phe Gly Met Val Ser Thr
                245                 250

<210> SEQ ID NO 77
<211> LENGTH: 286
<212> TYPE: PRT
<213> ORGANISM: Chloroflexus aggregans

<400> SEQUENCE: 77

Met Pro Gln Ala Ile Val Phe Thr Leu Arg Pro Ala Gly Ala Gly Arg
1               5                   10                  15

Ala Pro Gly Asn Leu Ser Arg Ala Ala His Ala Ala Val Leu Arg Leu
            20                  25                  30

Ile Gln Arg Ala Asp Pro Gln Leu Ala Ala Arg Ile His Asp Asp Asp
        35                  40                  45

Gly Arg Lys Pro Leu Thr Val Ser Asn Val Trp Gly Leu Gly Gly Gly
    50                  55                  60

Pro Ser Val Leu Val Asp Pro Glu Arg Asp Tyr His Leu Arg Val Thr
65                  70                  75                  80

Leu Leu Ser Thr Glu Leu Glu Gln Ile Ala Val Glu Trp Thr Pro Glu
                85                  90                  95

Arg Ile Gly Ala Leu Glu Leu Asp Gly Leu Pro Trp Arg Val Ile Ala
            100                 105                 110

Arg Ala Asp Thr Val Ala Glu His Pro Trp Ala Asn Arg Ala Asp Tyr
        115                 120                 125

Gln Glu Leu Ala Ala Pro Leu Leu Arg Arg Pro Asp Arg Leu Pro Asn
    130                 135                 140

Thr Trp Thr Leu Glu Phe Ala Ala Pro Val Thr Phe Arg Gln Arg Gly
145                 150                 155                 160

Met Thr Met Pro Leu Pro Leu Pro Asp Leu Val Phe Gly Ser Leu Leu
                165                 170                 175

Glu Gln Trp Asn Ala Ser Ala Glu Leu Ala Leu Pro Asp Glu Val Arg
            180                 185                 190

Arg Tyr Ala Thr Glu Cys Leu Ala Ile Ser Arg Phe Asp Leu Arg Ser
        195                 200                 205

Val Ala Val Pro Thr Ser Gly Gly Ala Ile Gln Ile Gly Ala Leu Gly
    210                 215                 220

Arg Cys Thr Tyr Arg Ala Met Thr Gly Asp Arg Tyr Trp Arg Ala Cys
225                 230                 235                 240

Ile Asp Val Leu Ala Ala Phe Ala Phe Tyr Ser Gly Val Gly Ala Gly
                245                 250                 255

Thr Ala Arg Gly Phe Gly Gln Thr Arg Leu Val Pro Ala Pro His Pro
            260                 265                 270

Glu Pro Asn Arg Ser Thr Thr Asn Gly Asp Thr Leu Arg Asp
        275                 280                 285

<210> SEQ ID NO 78

```
<211> LENGTH: 287
<212> TYPE: PRT
<213> ORGANISM: Chloroflexus aurantiacus

<400> SEQUENCE: 78

Met Pro Gln Ala Ile Val Phe Thr Leu Arg Pro Leu Thr Thr Ala Gln
1               5                   10                  15

Val Ala Gly Asn Leu Ser Arg Ala Ala His Ala Ala Ile Leu Arg Leu
            20                  25                  30

Ile Gln Gln Ala Asp Pro Ala Leu Ala Ala Arg Ile His Asp Asp Asn
        35                  40                  45

Gly Arg Lys Pro Leu Thr Val Ser Asn Ile Trp Gly Leu Ala Gly Glu
    50                  55                  60

Pro Lys Val Ile Val Asp Pro Ala Arg Asp Tyr His Leu Arg Val Thr
65                  70                  75                  80

Leu Leu Ser Ala Glu Leu Glu Gln Ile Ala Thr Asp Trp Thr Pro Ala
                85                  90                  95

Ala Leu Ala Pro Leu Asp Leu Asp Gly Leu Ala Trp Arg Ile Thr Ala
            100                 105                 110

Arg Ala Asp Asn Ser Ala Glu His Ser Trp Ala Gly Arg Ala Thr Tyr
        115                 120                 125

Gln Glu Leu Ala Gln Pro Leu Leu Ser Arg Pro Asn Gln Leu Pro Ser
    130                 135                 140

Val Trp Thr Phe Gln Leu Ala Ser Pro Thr Thr Phe Arg Gln Arg Gly
145                 150                 155                 160

Leu Asn Val Pro Leu Pro Leu Pro Asp Leu Val Phe Gly Ser Leu Leu
                165                 170                 175

Glu Gln Trp Asn Ala Ser Ser Glu Leu Ala Leu Pro Asp Glu Val Arg
            180                 185                 190

Arg Phe Ala Ala Glu Cys Leu Ala Ile Asn Arg Tyr Asp Leu Arg Ser
        195                 200                 205

Val Ala Ser Pro Thr Ser Gly Gly Val Ile Gln Ile Gly Ala Val Gly
    210                 215                 220

Arg Cys Ser Phe Arg Ala Ile Asn Pro Asp Arg Tyr Trp Arg Ala Cys
225                 230                 235                 240

Ile Asp Val Leu Ala Arg Phe Ala Phe Phe Ser Gly Ile Gly Ala Gly
                245                 250                 255

Thr Thr Arg Gly Phe Gly Gln Ala Arg Leu Leu Thr Lys Thr Asp Gln
            260                 265                 270

Pro Arg Gln Arg Glu Ala Val Asp Asn Gly Asp Thr Leu Ser Asp
        275                 280                 285

<210> SEQ ID NO 79
<211> LENGTH: 287
<212> TYPE: PRT
<213> ORGANISM: Chloroflexus

<400> SEQUENCE: 79

Met Pro Gln Ala Ile Val Phe Thr Leu Arg Pro Leu Thr Thr Ala Gln
1               5                   10                  15

Val Ala Gly Asn Leu Ser Arg Ala Ala His Ala Ala Ile Leu Arg Leu
            20                  25                  30

Ile Gln Gln Ala Asp Pro Ala Leu Ala Ala Arg Ile His Asp Asp Asn
        35                  40                  45

Gly Arg Lys Pro Leu Thr Val Ser Asn Ile Trp Gly Leu Ala Gly Glu
    50                  55                  60
```

Pro Lys Val Ile Val Asp Pro Ala Arg Asp Tyr His Leu Arg Val Thr
65                  70                  75                  80

Leu Leu Ser Ala Glu Leu Glu Gln Ile Ala Thr Asp Trp Thr Pro Ala
            85                  90                  95

Ala Leu Ala Pro Leu Asp Leu Asp Gly Leu Ala Trp Arg Ile Thr Ala
        100                 105                 110

Arg Ala Asp Asn Ser Ala Glu His Ser Trp Ala Gly Arg Ala Thr Tyr
    115                 120                 125

Gln Glu Leu Ala Gln Pro Leu Leu Ser Arg Pro Asn Gln Leu Pro Ser
130                 135                 140

Val Trp Thr Phe Gln Leu Ala Ser Pro Thr Thr Phe Arg Gln Arg Gly
145                 150                 155                 160

Leu Asn Val Pro Leu Pro Leu Pro Asp Leu Val Phe Gly Ser Leu Leu
                165                 170                 175

Glu Gln Trp Asn Ala Ser Ser Glu Leu Ala Leu Pro Asp Glu Val Arg
            180                 185                 190

Arg Phe Ala Ala Glu Cys Leu Ala Ile Asn Arg Tyr Asp Leu Arg Ser
        195                 200                 205

Val Ala Ser Pro Thr Ser Gly Gly Val Ile Gln Ile Gly Ala Val Gly
    210                 215                 220

Arg Cys Ser Phe Arg Ala Ile Asn Pro Asp Arg Tyr Trp Arg Ala Cys
225                 230                 235                 240

Ile Asp Val Leu Ala Arg Phe Ala Phe Phe Ser Gly Ile Gly Ala Gly
                245                 250                 255

Thr Thr Arg Gly Phe Gly Gln Ala Arg Leu Leu Thr Lys Thr Asp Gln
            260                 265                 270

Pro Arg Gln Arg Glu Ala Val Asp Asn Gly Asp Thr Leu Ser Asp
        275                 280                 285

<210> SEQ ID NO 80
<211> LENGTH: 274
<212> TYPE: PRT
<213> ORGANISM: Herpetosiphon aurantiacus

<400> SEQUENCE: 80

Met Leu Ala Gln Pro Glu Leu Ile Ala Cys Val Leu Glu Leu Thr Ala
1               5                   10                  15

Thr His Gly Thr Gln Leu Glu Arg Thr Gln Gly His Arg Ala His Ala
            20                  25                  30

Leu Phe Leu His Leu Met Gln Glu Ser Asp Pro Val Leu Ala Glu Gln
        35                  40                  45

Leu His Ala Ala Ser Gln Thr Lys Pro Trp Thr Val Thr Pro Leu Pro
    50                  55                  60

Gln Gln Ala Arg Arg Leu His Asn Gly Glu Thr Tyr Pro Leu Arg Ile
65                  70                  75                  80

Ala Phe Leu Gln Ala Ser Leu Tyr Trp Pro Phe Ala Gln Thr Phe Leu
            85                  90                  95

Gln Arg Pro Asn Arg Gln Leu Arg Leu Gly Ser Ser Asn Phe Asn Leu
        100                 105                 110

Gln Ala Ile His Thr Thr Lys Gln His Ser Pro Trp Ala Gly Val Ser
    115                 120                 125

Ser Trp Gln Ser Leu Ile Asp Gln Ala Gln Pro Thr Asp Glu Ile Ser
130                 135                 140

Leu Trp Phe Ala Thr Pro Thr Cys Phe Lys Leu Gly Arg Asp Arg Gln

```
                145                 150                 155                 160
Gly Lys Gln Arg Val Gly Leu Ile Pro Asp Gly Gln Ser Val Phe Gln
                165                 170                 175

Ser Leu Leu Arg Arg Trp Asn Ala Phe Ala Pro Thr Pro Leu Ala Ser
                180                 185                 190

Pro Glu Gln Ile Glu Gln Leu Asp Ile Gln Ile Lys Arg Tyr Gln Leu
                195                 200                 205

Arg Thr Glu Met Leu His Ala Gln Asp Lys Gln Leu Gly Phe Met Gly
                210                 215                 220

Lys Val Ser Tyr Lys Leu Asp Gly Asp Ala His Glu Arg Arg Ile Leu
225                 230                 235                 240

Ala Thr Leu Ala Asp Ala Ala Leu Tyr Leu Gly Ile Gly Ala Lys Thr
                245                 250                 255

Thr Gln Gly Met Gly Leu Val Gln Arg Ile Ser Thr Gln Pro Glu
                260                 265                 270

Gln Ala

<210> SEQ ID NO 81
<211> LENGTH: 253
<212> TYPE: PRT
<213> ORGANISM: Thermotoga lettingae

<400> SEQUENCE: 81

Met Arg Leu Glu Ile Val Phe Lys Thr Ala Asn Ser Phe Ile Pro Ile
1               5                   10                  15

Asn Tyr Gln Tyr Met Leu Cys Ser Phe Val Tyr Lys Arg Leu Lys Tyr
                20                  25                  30

Thr Asp Glu Asn Phe Ala Ser Phe Leu His Glu Glu Gly Phe Asn Gly
            35                  40                  45

Phe Arg Met Phe Thr Phe Ser Gln Leu Phe Phe Glu Asn Ser His Val
        50                  55                  60

Lys Asn Gly Ser Ile Ile Ile Ser Glu Gly Lys Gly Lys Trp Tyr Ile
65                  70                  75                  80

Ser Ser Leu Ser Glu Asp Phe Ile Arg Asn Phe Phe Ser Ser Ile Ile
                85                  90                  95

Glu Asn Pro Phe Ile Glu Leu Glu Gly Val Leu Phe Asn Ile Leu Gln
            100                 105                 110

Val Arg Val Leu Asp Glu Pro Lys Ile Thr Asp Gln Met Lys Phe Ile
        115                 120                 125

Leu Ile Ser Pro Leu Val Val Ser Ile Pro Val Glu Asn Gln Gly Lys
    130                 135                 140

Leu Ser His Lys Tyr Leu Thr Pro Glu Asp Asp Phe Phe Gln Asn Ala
145                 150                 155                 160

Ile Asn Ala Asn Leu Ile Lys Lys Tyr Ser Ala Phe Phe Gly Lys Glu
                165                 170                 175

Ile Ser Ser Lys Val Tyr Ile Gln Pro Asp Trp Asn Tyr Ile Gln Arg
            180                 185                 190

Lys Gly Arg Ile Thr Lys Leu Ile Gln Ile Lys Asn Thr Phe Val Arg
        195                 200                 205

Gly Thr Val Phe Pro Phe Leu Ile Thr Gly Asp Pro Gly Leu Ile Lys
    210                 215                 220

Val Gly Tyr Glu Ala Gly Phe Gly Glu Lys Asn Ser Leu Gly Phe Gly
225                 230                 235                 240

Met Val Lys Val Cys Arg Asn Asp Asn Asn Leu Asn Phe
                245                 250
```

-continued

```
                245                 250

<210> SEQ ID NO 82
<211> LENGTH: 241
<212> TYPE: PRT
<213> ORGANISM: Thermotoga petrophila

<400> SEQUENCE: 82

Met Arg Ile Phe Phe Arg Ile Phe Phe Lys Asp Asn Ser Gln Glu Val
1               5                   10                  15

Phe Pro Val Asp Tyr Arg Arg Ile Phe Met Ser Val Leu Lys Arg Val
            20                  25                  30

Tyr Glu Gly Thr Pro Phe Glu Ile Val Leu Ser His Asp Arg Ile
        35                  40                  45

Pro Lys Pro Tyr Val Phe Ser Val Gly Phe Arg Arg Ile Lys Glu Ile
    50                  55                  60

Ser Gly Asp Ser Ile Met Phe Glu Ser Pro Val Phe Phe Asn Phe Ser
65                  70                  75                  80

Ser Ser Ile Pro Gln Met Ile Gly Tyr Leu Tyr Asn His Ile Asp Arg
                85                  90                  95

Ile Lys Ser Phe Phe Lys Gly Thr Glu Ile Leu Val Asp Leu Pro Ile
            100                 105                 110

Pro Lys Met Ile Thr Ser Glu Lys Val Asn Phe Lys Ile Leu Gly Ser
        115                 120                 125

Ala Val Leu Thr Arg Ser Glu Lys Asp Arg Tyr Tyr Leu Asn Pro Glu
    130                 135                 140

Asp Asp Asp Phe Glu Glu Ala Leu Asn His Ser Leu Lys Val Arg Leu
145                 150                 155                 160

Asp Leu Leu Lys Asp Ile Phe Glu Lys Phe Gly Val Lys Ala Pro Gly
                165                 170                 175

Phe Lys Pro Val Asn Ile Val Ser Lys Asp Leu Lys Lys Val Pro Val
            180                 185                 190

Lys His Tyr Gly Gly Val Leu Glu Ala Phe Ser Gly Thr Ile Thr Leu
        195                 200                 205

Ser Gly Asn Leu Asn Ile Leu Asn Phe Leu Tyr Glu Asn Gly Leu Gly
    210                 215                 220

Val Arg Thr Gly Gln Gly Phe Gly Met Leu Lys Val Val Lys Glu Trp
225                 230                 235                 240

Arg

<210> SEQ ID NO 83
<211> LENGTH: 250
<212> TYPE: PRT
<213> ORGANISM: Thermotoga petrophila

<400> SEQUENCE: 83

Met Arg Leu Lys Val Ser Phe Gln Ala Met Glu Ser Thr Ile Pro Leu
1               5                   10                  15

Asn Tyr Asn Tyr Phe Leu Ser Ser Phe Ile Tyr Lys Arg Leu Ala Ser
            20                  25                  30

Gln Asn Glu Asn Phe Ala Arg Phe Leu His Glu Lys Gly Tyr Gly Lys
        35                  40                  45

Arg Phe Lys Phe Phe Thr Phe Ser Gln Leu Phe Phe Glu Asn Ser Arg
    50                  55                  60

Val Ser Gly Glu Lys Ile Leu Ile Phe Pro Gly Lys Gly Trp Trp Tyr
65                  70                  75                  80
```

```
Ile Ser Ser Pro Val Ile Glu Phe Val Arg Tyr Met Phe Ser Ser Leu
                85                  90                  95

Ser Glu Asp Pro Val Ile Arg Val Glu Lys Thr Glu Phe Ile Val Lys
            100                 105                 110

Ser Ile Asp Ile Glu Asn Ser Leu Pro Asp Gln Ser Glu Tyr His Phe
        115                 120                 125

Val Met Leu Ser Pro Leu Val Val Ser Val Pro Glu Glu Asn Asn Gly
    130                 135                 140

Lys Leu Tyr His Arg Tyr Leu His Pro Glu Glu Glu Phe Tyr Glu
145                 150                 155                 160

Val Phe Arg Lys Asn Leu Val Lys Lys Tyr Arg Ala Phe Tyr Gly Lys
                165                 170                 175

Glu Pro Glu Gly Thr Val Glu Val Ile Pro Asp Trp Asp Tyr Ile Lys
            180                 185                 190

Ser Arg Gln Arg Ile Thr Lys Arg Ile Lys Leu Lys Asn Ala Phe Val
        195                 200                 205

Arg Ala Val Val Phe Pro Phe Lys Ile Arg Gly Glu Lys Lys Leu Val
    210                 215                 220

Glu Ile Gly Tyr Glu Ala Gly Phe Gly Glu Lys Asn Ser Met Gly Phe
225                 230                 235                 240

Gly Met Val Ala Leu Lys Lys Tyr Glu Arg
                245                 250

<210> SEQ ID NO 84
<211> LENGTH: 250
<212> TYPE: PRT
<213> ORGANISM: Thermotoga maritime

<400> SEQUENCE: 84

Met Arg Leu Lys Val Ser Phe Gln Ala Met Glu Ser Thr Val Pro Leu
1               5                   10                  15

Asn Tyr Asn Tyr Phe Leu Ser Ser Phe Ile Tyr Lys Arg Leu Ala Ser
                20                  25                  30

Gln Asn Glu Asn Phe Ala Arg Phe Leu His Glu Lys Gly Tyr Gly Lys
            35                  40                  45

Arg Phe Lys Phe Phe Thr Phe Ser Gln Leu Phe Phe Glu Asn Ser Arg
    50                  55                  60

Val Ser Gly Glu Arg Ile Phe Ile Phe Pro Gly Lys Gly Trp Trp Tyr
65                  70                  75                  80

Ile Ser Ser Pro Val Val Glu Phe Val Arg Tyr Met Phe Ser Ser Leu
                85                  90                  95

Ser Glu Asp Pro Val Ile Arg Val Gly Lys Thr Glu Phe Ile Val Lys
            100                 105                 110

Ser Ile Asp Ile Glu Asn Ser Leu Pro Asp Gln Ser Glu Tyr His Phe
        115                 120                 125

Val Met Leu Ser Pro Leu Val Val Ser Val Pro Glu Glu Asn Asn Gly
    130                 135                 140

Lys Leu Tyr His Arg Tyr Leu His Pro Gly Glu Glu Phe Tyr Glu
145                 150                 155                 160

Val Phe Arg Lys Asn Leu Met Lys Lys Tyr Arg Ala Phe Tyr Gly Lys
                165                 170                 175

Asp Pro Glu Gly Thr Val Glu Val Ile Pro Asp Trp Asp Tyr Ile Lys
            180                 185                 190

Ser Arg His Arg Ile Thr Lys Arg Ile Lys Leu Lys Asn Ala Phe Val
```

```
            195                 200                 205
Arg Ala Val Val Phe Pro Phe Lys Ile Arg Gly Glu Lys Lys Leu Val
        210                 215                 220

Glu Ile Gly Tyr Glu Ala Gly Phe Gly Glu Lys Asn Ser Met Gly Phe
225                 230                 235                 240

Gly Met Val Ala Leu Lys Lys Tyr Glu Arg
                245                 250

<210> SEQ ID NO 85
<211> LENGTH: 250
<212> TYPE: PRT
<213> ORGANISM: Thermotoga

<400> SEQUENCE: 85

Met Arg Leu Lys Val Ser Phe Gln Ala Met Glu Ser Thr Val Pro Leu
1               5                   10                  15

Asn Tyr Asn Tyr Phe Leu Ser Ser Phe Ile Tyr Lys Arg Leu Ala Ser
            20                  25                  30

Gln Asn Glu Asn Phe Ala Arg Phe Leu His Glu Lys Gly Tyr Gly Lys
        35                  40                  45

Arg Phe Lys Phe Phe Thr Phe Ser Gln Leu Phe Phe Glu Asn Ser Arg
    50                  55                  60

Val Ser Gly Glu Arg Ile Phe Ile Phe Pro Gly Lys Gly Trp Trp Tyr
65                  70                  75                  80

Ile Ser Ser Pro Val Val Glu Phe Val Arg Tyr Met Phe Ser Ser Leu
                85                  90                  95

Ser Glu Asp Pro Val Ile Arg Val Gly Lys Thr Glu Phe Ile Val Lys
            100                 105                 110

Ser Ile Asp Ile Glu Asn Ser Leu Pro Asp Gln Ser Glu Tyr His Phe
        115                 120                 125

Ile Met Leu Ser Pro Leu Val Val Ser Val Pro Glu Glu Asn Asn Gly
    130                 135                 140

Lys Leu Tyr His Arg Tyr Leu His Pro Glu Glu Glu Phe Tyr Glu
145                 150                 155                 160

Val Phe Arg Lys Asn Leu Met Lys Lys Tyr Arg Ala Phe Tyr Gly Lys
                165                 170                 175

Asp Pro Glu Gly Thr Val Glu Val Ile Pro Asp Trp Asp Tyr Ile Lys
            180                 185                 190

Ser Arg His Arg Ile Thr Lys Arg Ile Leu Lys Asn Ala Phe Val
        195                 200                 205

Arg Ala Val Val Phe Pro Phe Lys Ile Arg Gly Glu Lys Lys Leu Val
    210                 215                 220

Glu Ile Gly Tyr Glu Ala Gly Phe Gly Glu Lys Asn Ser Met Gly Phe
225                 230                 235                 240

Gly Met Val Ala Leu Lys Lys Tyr Glu Arg
                245                 250

<210> SEQ ID NO 86
<211> LENGTH: 242
<212> TYPE: PRT
<213> ORGANISM: Thermosipho melanesiensis

<400> SEQUENCE: 86

Met Arg Ile Lys Val Gly Phe Ile Ser Ile Glu Asp Ile Ile Leu Pro
1               5                   10                  15

Val Gly Phe Asn Lys Tyr Ile Gln Ala Leu Ile Tyr Asn Leu Phe Ser
```

```
                    20                  25                  30
Asn Ser Leu Arg Arg Phe Val His Glu Glu Gly Phe Arg Ser Lys Arg
                35                  40                  45
Lys Phe Ser Leu Phe Cys Phe Ser Ser Ile Leu Glu Lys Gly Gln Tyr
         50                  55                  60
Phe Lys Arg Met Lys Val Phe Asn Phe Gly Lys Asn Ile Ser Phe Tyr
 65                  70                  75                  80
Ile Ser Ser Pro Val Thr Lys Leu Met Glu Asn Leu Val Leu Asn Leu
                 85                  90                  95
Leu Asn Gly Asp Lys Tyr Phe Leu Gly Glu Asn Asp Ile Tyr Leu Ser
            100                 105                 110
Ser Val Glu Val Val Tyr Lys Glu Ile Ala Lys Asp Ile Leu Lys Val
        115                 120                 125
Asn Ala Leu Thr Pro Ile Glu Val His Gln Thr Tyr Lys Glu Asn Gly
    130                 135                 140
Arg Asn Lys Thr Lys Tyr Phe Ala Pro Phe Glu Arg Glu Phe Ser Lys
145                 150                 155                 160
Leu Ile Asn Leu Asn Leu Lys Ser Lys Trp Glu Ala Phe Tyr Lys Glu
                165                 170                 175
Asn Leu Asp Arg Asp Ile Glu Ile Ile Ser Leu Gly Asn Met Asn Lys
            180                 185                 190
Ser Val Val Tyr Tyr Gly Phe Gly Asp Lys Lys Tyr Val Val Glu Gly
        195                 200                 205
Trp Lys Gly Lys Phe Leu Leu Lys Gly Glu Pro Ser Val Leu Ala Phe
    210                 215                 220
Ala Tyr Asp Ala Gly Leu Gly Ser Lys Asn Ser Gln Gly Phe Gly Phe
225                 230                 235                 240
Ile Glu

<210> SEQ ID NO 87
<211> LENGTH: 243
<212> TYPE: PRT
<213> ORGANISM: Thermosipho melanesiensis

<400> SEQUENCE: 87

Met Arg Leu Arg Val Lys Phe Asn Phe Asp Arg Leu Asn Leu Pro Ile
  1               5                  10                  15
His Tyr Asn His Ile Leu His Ala Thr Ile Leu Asn Met Ile Asn Asn
                 20                  25                  30
Glu Glu Phe Arg Lys Phe Ile His Asp Arg Gly Tyr Lys Phe Glu Lys
             35                  40                  45
Arg Val Phe Lys Leu Tyr Thr Phe Ser Arg Leu Ile Gly Arg Phe Glu
         50                  55                  60
Ile Asp Thr Glu Ile Lys Glu Ile Asn Phe Phe Asp Asn Val Tyr Leu
 65                  70                  75                  80
Tyr Ile Ser Ser Tyr Asp Asp Asn Phe Cys Tyr Tyr Ile Met Glu Lys
                 85                  90                  95
Leu Leu Thr Phe Glu Asn Ile Arg Met Gly Lys Asn Ile Leu Lys Val
            100                 105                 110
Glu Lys Ile Glu Thr Ile Asn Phe Met Pro Thr Asp Thr Leu Lys Val
        115                 120                 125
Val Thr Arg Ser Pro Val Thr Val Tyr Ser Thr Tyr Ile Asp Glu Thr
    130                 135                 140
Gly Lys Lys Lys Thr Leu Phe Tyr His Pro Asp Asp Phe Lys Phe Lys
```

```
145                 150                 155                 160
Glu Ile Val Glu Lys Asn Ile Ile Lys Lys Tyr Arg Ala Leu His Asn
                165                 170                 175

Arg Glu Pro Gln Gly Arg Ile Glu Val Lys His Val Gly Lys Ser Pro
            180                 185                 190

Lys Phe Val Leu Val Phe Tyr Lys Gly Phe Lys Ile Lys Gly Trp Met
        195                 200                 205

Thr Ala Phe Asp Leu Ile Gly Asp Pro Glu Leu Val Lys Ile Ala Tyr
    210                 215                 220

Glu Thr Gly Leu Gly Ser Lys Asn Ser Gln Gly Phe Gly Phe Ile Glu
225                 230                 235                 240

Gln Ile Lys
```

<210> SEQ ID NO 88
<211> LENGTH: 240
<212> TYPE: PRT
<213> ORGANISM: Fervidobacterium nodosum

<400> SEQUENCE: 88

```
Met Arg Gly Ile Leu Thr Leu Lys Leu Asp Lys Pro Leu Thr Leu Pro
1               5                   10                  15

Ile His Tyr Asn His Ile Leu Gln Ala Ala Ile Leu Asn Leu Leu Ser
            20                  25                  30

Asp Glu Asn Tyr Ser Lys Phe Ile His Asp Thr Gly Phe Gln Phe Gly
        35                  40                  45

Lys Arg Arg Phe Lys Met Phe Thr Phe Ser Arg Leu Glu Gly Lys Phe
50                  55                  60

Ser Ile Asp Ile Glu Arg Lys Thr Ile Thr Tyr Phe Glu Arg Ala Tyr
65                  70                  75                  80

Leu His Ile Ser Thr Ile Glu Asp Lys Phe Ile Glu Tyr Val Val Asn
                85                  90                  95

Asn Leu Leu Leu Glu Gly Leu Asp Ile Lys Gly Glu Arg Ile His Val
            100                 105                 110

Asp Lys Ile Glu Leu Lys Ser Asn Thr Thr Asn Phe Gly Lys Ile Ile
        115                 120                 125

Thr Lys Ser Pro Ile Val Ala Tyr Ser Thr Phe Glu Leu Asn Gly Arg
    130                 135                 140

Lys Lys Thr Tyr Tyr Tyr Asn Pro Lys Glu Lys Glu Phe Gln Glu Ile
145                 150                 155                 160

Leu Ala Asn Asn Leu Ile Lys Lys Tyr Ile Ala Tyr Phe Glu Lys Glu
                165                 170                 175

Pro Lys Asn Arg Tyr Phe Glu Ile Thr Pro Val Ser Asn Leu Lys Glu
            180                 185                 190

Ser Ile Val Ile Tyr Lys Gly Thr Val Ile Arg Gly Trp Asn Gly Ile
        195                 200                 205

Phe Gln Ile Asn Gly Ser Asp Glu Leu Ile Asn Ile Ala Tyr Tyr Thr
    210                 215                 220

Gly Leu Gly Ala Lys Asn Ser Gln Gly Phe Gly Cys Phe Glu Phe Ile
225                 230                 235                 240
```

<210> SEQ ID NO 89
<211> LENGTH: 247
<212> TYPE: PRT
<213> ORGANISM: Fervidobacterium nodosum

<400> SEQUENCE: 89

Met Arg Leu Tyr Ile Lys Phe Ser Phe Glu Gln Leu Glu Leu Pro Thr
1               5                   10                  15

Glu Tyr Asn Asn Ile Leu Gln Gly Phe Val Tyr Asn Ile Ile Ser Glu
                20                  25                  30

Glu Lys Tyr Arg Lys Phe Leu His Asp Lys Gly Tyr Gln Leu Gly Lys
            35                  40                  45

Arg Thr Tyr Lys Leu Phe Ser Phe Ser Arg Leu Leu Gly Lys Phe Glu
        50                  55                  60

Leu Asn Lys Glu Asn Lys Thr Ile Lys Phe Leu Asn Glu Ala Lys Leu
65                  70                  75                  80

Ile Ile Ser Ser Tyr Asp Thr Leu Leu Ala Glu Phe Ile Ile Glu Lys
                85                  90                  95

Val Gly Thr Phe Asp Ser Leu Arg Ile Gly Arg Asn Ile Val Arg Pro
                100                 105                 110

Glu Lys Ile Glu Ile Phe Glu Phe Pro Gln Thr Gln Lys Ile Val Val
            115                 120                 125

Ser Thr Lys Ser Pro Ile Thr Val Tyr Ser Thr Ile Glu Lys Asp Asp
        130                 135                 140

Gly Lys Lys Phe Thr Lys Phe His Ser Pro Asn Glu Asp Asp Phe Ile
145                 150                 155                 160

Arg Ile Leu Lys Glu Asn Leu Leu Arg Lys Tyr Gln Thr Ile His Glu
                165                 170                 175

Thr Pro Phe Lys Gly Glu Leu His Ile Glu Asn Ile Ala Glu Lys Pro
                180                 185                 190

Lys Lys Val Ile Leu Gln Tyr Lys Asn Arg Lys Leu Asp Gly Trp Ile
            195                 200                 205

Thr Val Leu Lys Leu Glu Gly Asp Tyr Glu Ile Leu Lys Ile Ala Tyr
        210                 215                 220

Asp Thr Gly Leu Gly Ser Lys Asn Ser Ala Gly Phe Gly Cys Ile Glu
225                 230                 235                 240

Leu Val Asp Lys Val Leu Thr
                245

<210> SEQ ID NO 90
<211> LENGTH: 248
<212> TYPE: PRT
<213> ORGANISM: Petrotoga mobilis

<400> SEQUENCE: 90

Met Arg Leu Asn Val Gln Phe Ser Leu Asn Ser Leu Ile Leu Pro Leu
1               5                   10                  15

Asn Tyr Asn His Ile Ile Gln Ala Phe Ile Leu Asp Leu Ile Asp Asn
                20                  25                  30

Ala Glu Tyr Arg Asn Phe Ile His Asn Glu Gly Phe Ser Tyr Asn Lys
            35                  40                  45

Arg Lys Tyr Lys Leu Phe Ser Phe Ser Arg Leu Ser Gly Lys Phe Ser
        50                  55                  60

Leu Asn Gln Lys Asp Lys Thr Ile Glu Phe Ser Asp Asn Val Ser Leu
65                  70                  75                  80

Lys Ile Ser Ser His Asp Lys Asn Leu Ile Gln Tyr Cys Ala Asp Ser
                85                  90                  95

Leu Leu Phe Lys Asp Asp Phe Glu Leu Leu Gly Gln Lys Ile His Val
                100                 105                 110

Glu Lys Leu Glu Tyr Asp Asp Leu Glu Ile Lys Ser Asp Lys Ile Lys

```
                115                 120                 125
Val Lys Thr Leu Ser Pro Ile Thr Ile Tyr Ser Thr Ile Val Gln Asn
            130                 135                 140

Ser Ser Lys Lys Thr Ile Tyr Phe Ser Pro Ser Glu Asp Gln Phe Ser
145                 150                 155                 160

Lys Leu Ile Lys Glu Asn Leu Ile Lys Lys Tyr Leu Ala Tyr Tyr Asp
                165                 170                 175

Ser Tyr Leu Ser Lys Lys Ile Ser Asn Asp Glu Phe Val Ile Lys Glu
            180                 185                 190

Ala Asp Gln Lys Gly Ser Lys Met Ile Ile Thr Lys Tyr Lys Asn Phe
        195                 200                 205

Ile Ile Lys Gly Trp His Gly Val Phe Glu Ile Gln Gly Asn Pro Ser
    210                 215                 220

Leu Leu Lys Ile Gly Tyr Asp Ser Gly Phe Gly Ala Lys Asn Ser Gln
225                 230                 235                 240

Gly Phe Gly Leu Val Glu Val Ile
                245

<210> SEQ ID NO 91
<211> LENGTH: 261
<212> TYPE: PRT
<213> ORGANISM: Petrotoga mobilis

<400> SEQUENCE: 91

Met Val Ile Lys Leu Val Phe Gly Ala Leu Glu Gly Asp Lys Ile Asp
1               5                   10                  15

Leu Pro Val His Tyr Asn Arg Pro Leu Gln Gly Leu Phe Tyr Tyr Leu
            20                  25                  30

Met Ser Asp Thr Val Pro Lys Tyr His Asp Leu Gly Thr Arg Ser Glu
        35                  40                  45

Asp Lys Lys Leu Lys Leu Phe Thr Phe Ser Arg Ile Tyr Pro Tyr Ser
    50                  55                  60

Ser Phe Lys Val Glu Asn Arg Arg Met Ile Phe Lys Gly Leu Phe Asn
65                  70                  75                  80

Ile Tyr Phe Ala Ser Pro Ile Asp Lys Leu Val Glu Ala Val Leu His
                85                  90                  95

Ser Leu Asn Glu Gln Lys Val Val Arg Ile Glu Lys Asn Tyr Phe Thr
            100                 105                 110

Leu Arg Lys Tyr Glu Val Ile Gln Asn Glu Val Asp Glu Glu Met Leu
        115                 120                 125

Val Lys Thr Leu Ser Pro Ile Thr Ala Tyr Ser Thr Ile Val Leu Pro
    130                 135                 140

Asn Gly Asn Arg Tyr Thr His Tyr Phe Ser Pro Tyr Ser Ser Asp Phe
145                 150                 155                 160

Lys Lys Leu Ile Glu Glu Asn Leu Lys Arg Lys Ala Ser Ala Leu Gly
                165                 170                 175

Ile Val Ile Lys Asn Asn Asn Phe Tyr Ile Glu Pro Tyr Gly Ile Thr
            180                 185                 190

Glu Lys Asn Glu Lys Leu Leu Phe Tyr Lys Asp Ile Ile Lys Gly
        195                 200                 205

Trp Thr Gly Tyr Phe Ile Leu Lys Gly Glu Thr Gln Leu Leu Lys Leu
    210                 215                 220

Ala Leu Asn Ser Gly Leu Gly Ala Lys Asn Ala Gln Gly Phe Gly Met
225                 230                 235                 240
```

Ile Leu Ser Val Glu Lys Asn Ser Ile Arg Glu Arg Ser Phe Leu Glu
                245                 250                 255

Leu Ala Glu Glu Gly
            260

<210> SEQ ID NO 92
<211> LENGTH: 257
<212> TYPE: PRT
<213> ORGANISM: Rubrobacter xylanophilus

<400> SEQUENCE: 92

Met Arg Leu Lys Ile Val Leu Ser Gly Glu Arg Gly His Leu His Leu
1               5                   10                  15

Pro Leu Gln Tyr Asn Ser Ala Val Gln Gly Phe Ile Tyr Ala Asn Leu
            20                  25                  30

Ser Arg Thr Leu Ala Asp Arg Leu His Asn Arg Gly His Thr Tyr Gly
        35                  40                  45

Gln Arg Arg Phe Lys Leu Phe Thr Phe Ser Arg Leu Phe Gly Arg Arg
    50                  55                  60

Glu Ala Gly Glu Gly Gly Ile Ser Phe Arg Gly Pro Val Arg Leu Tyr
65                  70                  75                  80

Leu Gly Ser Ala Glu Ala Val Leu Gly Ser Leu Ala Glu His Leu
                85                  90                  95

Leu Arg Arg Pro Glu Thr Arg Leu Gly Lys Thr Arg Cys Leu Val Glu
            100                 105                 110

Glu Val Gly Val Glu Pro Glu Pro Glu Val Glu Asp Gly Arg Pro Leu
        115                 120                 125

Leu Val Arg Ala Leu Ser Pro Ile Thr Ala Tyr Thr Thr Leu Ala Thr
    130                 135                 140

Pro Glu Gly Arg Lys Lys Thr Tyr Tyr Tyr Ser Pro Gln Glu Glu Glu
145                 150                 155                 160

Trp Gly Val Ala Ile Leu Glu Asn Ile Lys Arg Lys Val Ala Ala Leu
                165                 170                 175

Gly Trp Ala Ala Asp Ala Glu Glu Asp Leu Arg Glu Ala Tyr Val Arg
            180                 185                 190

Pro Arg Arg Val Arg Ser Ser Asp Gln Lys Val Leu Arg Phe Lys Gly
        195                 200                 205

Thr Val Val Lys Gly Trp Met Gly Leu Tyr Glu Leu Lys Met Pro Glu
    210                 215                 220

Pro Tyr Phe Arg Leu Ala Tyr Asp Thr Gly Leu Gly Ser Lys Asn Ser
225                 230                 235                 240

Gln Gly Phe Gly Met Ile Ala Leu Pro His Pro Thr Glu Gly Arg Lys
                245                 250                 255

Arg

<210> SEQ ID NO 93
<211> LENGTH: 314
<212> TYPE: PRT
<213> ORGANISM: Mycobacterium bovis

<400> SEQUENCE: 93

Met Ala Ala Arg Arg Gly Gly Ile Arg Arg Thr Asp Leu Leu Arg Arg
1 5 10 15

Ser Gly Gln Pro Arg Gly Arg His Arg Ala Ser Ala Ala Glu Ser Gly
20 25 30

Leu Thr Trp Ile Ser Pro Thr Leu Ile Leu Val Gly Phe Ser His Arg

```
             35                  40                  45
Gly Asp Arg Arg Met Thr Glu Pro Leu Ser Arg Leu Thr Leu Thr Leu
 50                  55                  60
Glu Val Asp Ala Pro Leu Glu Arg Ala Arg Val Ala Thr Leu Gly Pro
 65                  70                  75                  80
His Leu His Gly Val Leu Met Glu Ser Ile Pro Ala Asp Tyr Val Gln
                 85                  90                  95
Thr Leu His Thr Val Pro Val Asn Pro Tyr Ser Gln Tyr Ala Leu Ala
                100                 105                 110
Arg Ser Thr Thr Ser Leu Glu Trp Lys Ile Ser Thr Leu Thr Asn Glu
            115                 120                 125
Ala Arg Gln Gln Ile Val Gly Pro Ile Asn Asp Ala Ala Phe Ala Gly
        130                 135                 140
Phe Arg Leu Arg Ala Ser Gly Ile Ala Thr Gln Val Thr Ser Arg Ser
145                 150                 155                 160
Leu Glu Gln Asn Pro Leu Ser Gln Phe Ala Arg Ile Phe Tyr Ala Arg
                165                 170                 175
Pro Glu Thr Arg Lys Phe Arg Val Glu Phe Leu Thr Pro Thr Ala Phe
                180                 185                 190
Lys Gln Ser Gly Glu Tyr Val Phe Trp Pro Asp Pro Arg Leu Val Phe
            195                 200                 205
Gln Ser Leu Ala Gln Lys Tyr Gly Ala Ile Val Asp Gly Glu Pro
        210                 215                 220
Asp Pro Gly Leu Ile Ala Glu Phe Gly Gln Ser Val Arg Leu Ser Ala
225                 230                 235                 240
Phe Arg Val Ala Ser Ala Pro Phe Ala Val Gly Ala Ala Arg Val Pro
                245                 250                 255
Gly Phe Thr Gly Ser Ala Thr Phe Thr Val Arg Gly Val Asp Thr Phe
                260                 265                 270
Ala Ser Tyr Ile Ala Ala Leu Leu Trp Phe Gly Glu Phe Ser Gly Cys
            275                 280                 285
Gly Ile Lys Ala Ser Met Gly Met Gly Ala Ile Arg Val Gln Pro Leu
        290                 295                 300
Ala Pro Arg Glu Lys Cys Val Pro Lys Pro
305                 310

<210> SEQ ID NO 94
<211> LENGTH: 314
<212> TYPE: PRT
<213> ORGANISM: Mycobacterium bovis

<400> SEQUENCE: 94

Met Ala Ala Arg Arg Gly G

```
Thr Leu His Thr Val Pro Val Asn Pro Tyr Ser Gln Tyr Ala Leu Ala
            100                 105                 110

Arg Ser Thr Thr Ser Leu Glu Trp Lys Ile Ser Thr Leu Thr Asn Glu
        115                 120                 125

Ala Arg Gln Gln Ile Val Gly Pro Ile Asn Asp Ala Ala Phe Ala Gly
    130                 135                 140

Phe Arg Leu Arg Ala Ser Gly Ile Ala Thr Gln Val Thr Ser Arg Ser
145                 150                 155                 160

Leu Glu Gln Asn Pro Leu Ser Gln Phe Ala Arg Ile Phe Tyr Ala Arg
                165                 170                 175

Pro Glu Thr Arg Lys Phe Arg Val Glu Phe Leu Thr Pro Thr Ala Phe
            180                 185                 190

Lys Gln Ser Gly Glu Tyr Val Phe Trp Pro Asp Pro Arg Leu Val Phe
        195                 200                 205

Gln Ser Leu Ala Gln Lys Tyr Gly Ala Ile Val Asp Gly Glu Pro
    210                 215                 220

Asp Pro Gly Leu Ile Ala Glu Phe Gly Gln Ser Val Arg Leu Ser Ala
225                 230                 235                 240

Phe Arg Val Ala Ser Ala Pro Phe Ala Val Gly Ala Ala Arg Val Pro
                245                 250                 255

Gly Phe Thr Gly Ser Ala Thr Phe Thr Val Arg Gly Val Asp Thr Phe
            260                 265                 270

Ala Ser Tyr Ile Ala Ala Leu Leu Trp Phe Gly Glu Phe Ser Gly Cys
        275                 280                 285

Gly Ile Lys Ala Ser Met Gly Met Gly Ala Ile Arg Val Gln Pro Leu
    290                 295                 300

Ala Pro Arg Glu Lys Cys Val Pro Lys Pro
305                 310

<210> SEQ ID NO 95
<211> LENGTH: 314
<212> TYPE: PRT
<213> ORGANISM: Mycobacterium tuberculosis

<400> SEQUENCE: 95

Met Ala Ala Arg Arg Gly Gly Ile Arg Arg Thr Asp Leu Leu Arg Arg
1               5                   10                  15

Ser Gly Gln Pro Arg Gly Arg His Arg Ala Ser Ala Ala Glu Ser Gly
            20                  25                  30

Leu Thr Trp Ile Ser Pro Thr Leu Ile Leu Val Gly Phe Ser His Arg
        35                  40                  45

Gly Asp Arg Arg Met Thr Glu His Leu Ser Arg Leu Thr Leu Thr Leu
    50                  55                  60

Glu Val Asp Ala Pro Leu Glu Arg Ala Arg Val Ala Thr Leu Gly Pro
65                  70                  75                  80

His Leu His Gly Val Leu Met Glu Ser Ile Pro Ala Asp Tyr Val Gln
                85                  90                  95

Thr Leu His Thr Val Pro Val Asn Pro Tyr Ser Gln Tyr Ala Leu Ala
            100                 105                 110

Arg Ser Thr Thr Ser Leu Glu Trp Lys Ile Ser Thr Leu Thr Asn Glu
        115                 120                 125

Ala Arg Gln Gln Ile Val Gly Pro Ile Asn Asp Ala Ala Phe Ala Gly
    130                 135                 140

Phe Arg Leu Arg Ala Ser Gly Ile Ala Thr Gln Val Thr Ser Arg Ser
145                 150                 155                 160
```

```
Leu Glu Gln Asn Pro Leu Ser Gln Phe Ala Arg Ile Phe Tyr Ala Arg
                165                 170                 175

Pro Glu Thr Arg Lys Phe Arg Val Glu Phe Leu Thr Pro Thr Ala Phe
            180                 185                 190

Lys Gln Ser Gly Glu Tyr Val Phe Trp Pro Asp Pro Arg Leu Val Phe
        195                 200                 205

Gln Ser Leu Ala Gln Lys Tyr Gly Ala Ile Val Asp Gly Glu Glu Pro
    210                 215                 220

Asp Pro Gly Leu Ile Ala Glu Phe Gly Gln Ser Val Arg Leu Ser Ala
225                 230                 235                 240

Phe Arg Val Ala Ser Ala Pro Phe Ala Val Gly Ala Ala Arg Val Pro
                245                 250                 255

Gly Phe Thr Gly Ser Ala Thr Phe Thr Val Arg Gly Val Asp Thr Phe
            260                 265                 270

Ala Ser Tyr Ile Ala Ala Leu Leu Trp Phe Gly Glu Phe Ser Gly Cys
        275                 280                 285

Gly Ile Lys Ala Ser Met Gly Met Gly Ala Ile Arg Val Gln Pro Leu
    290                 295                 300

Ala Pro Arg Glu Lys Cys Val Pro Lys Pro
305                 310

<210> SEQ ID NO 96
<211> LENGTH: 314
<212> TYPE: PRT
<213> ORGANISM: Mycobacterium tuberculosis C

<400> SEQUENCE: 96

Met Ala Ala Arg Arg Gly Gly Ile Arg Arg Thr Asp Leu Leu Arg Arg
1               5                   10                  15

Ser Gly Gln Pro Arg Gly Arg His Arg Ala Ser Ala Ala Glu Ser Gly
            20                  25                  30

Leu Thr Trp Ile Ser Pro Thr Leu Ile Leu Val Gly Phe Ser His Arg
        35                  40                  45

Gly Asp Arg Arg Met Thr Glu His Leu Ser Arg Leu Thr Leu Thr Leu
    50                  55                  60

Glu Val Asp Ala Pro Leu Glu Arg Ala Arg Val Ala Thr Leu Gly Pro
65                  70                  75                  80

His Leu His Gly Val Leu Met Glu Ser Ile Pro Ala Asp Tyr Val Gln
                85                  90                  95

Thr Leu His Thr Val Pro Val Asn Pro Tyr Ser Gln Tyr Ala Leu Ala
            100                 105                 110

Arg Ser Thr Thr Ser Leu Glu Trp Lys Ile Ser Thr Leu Thr Asn Glu
        115                 120                 125

Ala Arg Gln Gln Ile Val Gly Pro Ile Asn Asp Ala Ala Phe Ala Gly
    130                 135                 140

Phe Arg Leu Arg Ala Ser Gly Ile Ala Thr Gln Val Thr Ser Arg Ser
145                 150                 155                 160

Leu Glu Gln Asn Pro Leu Ser Gln Phe Ala Arg Ile Phe Tyr Ala Arg
                165                 170                 175

Pro Glu Thr Arg Lys Phe Arg Val Glu Phe Leu Thr Pro Thr Ala Phe
            180                 185                 190

Lys Gln Ser Gly Glu Tyr Val Phe Trp Pro Asp Pro Arg Leu Val Phe
        195                 200                 205

Gln Ser Leu Ala Gln Lys Tyr Gly Ala Ile Val Asp Gly Glu Glu Pro
```

```
            210                 215                 220
Asp Pro Gly Leu Ile Ala Glu Phe Gly Gln Ser Val Arg Leu Ser Ala
225                 230                 235                 240

Phe Arg Val Ala Ser Ala Pro Phe Ala Val Gly Ala Ala Arg Val Pro
                245                 250                 255

Gly Phe Thr Gly Ser Ala Thr Phe Thr Val Arg Gly Val Asp Thr Phe
                260                 265                 270

Ala Ser Tyr Ile Ala Ala Leu Leu Trp Phe Gly Glu Phe Ser Gly Cys
            275                 280                 285

Gly Ile Lys Ala Ser Met Gly Met Gly Ala Ile Arg Val Gln Pro Leu
            290                 295                 300

Ala Pro Arg Glu Lys Cys Val Pro Lys Pro
305                 310

<210> SEQ ID NO 97
<211> LENGTH: 314
<212> TYPE: PRT
<213> ORGANISM: Mycobacterium tuberculosis

<400> SEQUENCE: 97

Met Ala Ala Arg Arg Gly Gly Ile Arg Arg Thr Asp Leu Leu Arg Arg
1               5                   10                  15

Ser Gly Gln Pro Arg Gly Arg His Arg Ala Ser Ala Ala Glu Ser Gly
                20                  25                  30

Leu Thr Trp Ile Ser Pro Thr Leu Ile Leu Val Gly Phe Ser His Arg
            35                  40                  45

Gly Asp Arg Arg Met Thr Glu His Leu Ser Arg Leu Thr Leu Thr Leu
50              55                  60

Glu Val Asp Ala Pro Leu Glu Arg Ala Arg Val Ala Thr Leu Gly Pro
65                  70                  75                  80

His Leu His Gly Val Leu Met Glu Ser Ile Pro Ala Asp Tyr Val Gln
                85                  90                  95

Thr Leu His Thr Val Pro Val Asn Pro Tyr Ser Gln Tyr Ala Leu Ala
            100                 105                 110

Arg Ser Thr Thr Ser Leu Glu Trp Lys Ile Ser Thr Leu Thr Asn Glu
        115                 120                 125

Ala Arg Gln Gln Ile Val Gly Pro Ile Asn Asp Ala Ala Phe Ala Gly
    130                 135                 140

Phe Arg Leu Arg Ala Ser Gly Ile Ala Thr Gln Val Thr Ser Arg Ser
145                 150                 155                 160

Leu Glu Gln Asn Pro Leu Ser Gln Phe Ala Arg Ile Phe Tyr Ala Arg
                165                 170                 175

Pro Glu Thr Arg Lys Phe Arg Val Glu Phe Leu Thr Pro Thr Ala Phe
            180                 185                 190

Lys Gln Ser Gly Glu Tyr Val Phe Trp Pro Asp Pro Arg Leu Val Phe
        195                 200                 205

Gln Ser Leu Ala Gln Lys Tyr Gly Ala Ile Val Asp Gly Glu Glu Pro
    210                 215                 220

Asp Pro Gly Leu Ile Ala Glu Phe Gly Gln Ser Val Arg Leu Ser Ala
225                 230                 235                 240

Phe Arg Val Ala Ser Ala Pro Phe Ala Val Gly Ala Ala Arg Val Pro
                245                 250                 255

Gly Phe Thr Gly Ser Ala Thr Phe Thr Val Arg Gly Val Asp Thr Phe
            260                 265                 270
```

```
Ala Ser Tyr Ile Ala Ala Leu Leu Trp Phe Gly Glu Phe Ser Gly Cys
            275                 280                 285

Gly Ile Lys Ala Ser Met Gly Met Gly Ala Ile Arg Val Gln Pro Leu
            290                 295                 300

Ala Pro Arg Glu Lys Cys Val Pro Lys Pro
305                 310

<210> SEQ ID NO 98
<211> LENGTH: 314
<212> TYPE: PRT
<213> ORGANISM: Mycobacterium tuberculosis

<400> SEQUENCE: 98

Met Ala Ala Arg Arg Gly Gly Ile Arg Arg Thr Asp Leu Leu Arg Arg
1               5                   10                  15

Ser Gly Gln Pro Arg Gly Arg His Arg Ala Ser Ala Glu Ser Gly
            20                  25                  30

Leu Thr Trp Ile Ser Pro Thr Leu Ile Leu Val Gly Phe Ser His Arg
            35                  40                  45

Gly Asp Arg Arg Met Thr Glu His Leu Ser Arg Leu Thr Leu Thr Leu
50                  55                  60

Glu Val Asp Ala Pro Leu Glu Arg Ala Arg Val Ala Thr Leu Gly Pro
65                  70                  75                  80

His Leu His Gly Val Leu Met Glu Ser Ile Pro Ala Asp Tyr Val Gln
                85                  90                  95

Thr Leu His Thr Val Pro Val Asn Pro Tyr Ser Gln Tyr Ala Leu Ala
            100                 105                 110

Arg Ser Thr Thr Ser Leu Glu Trp Lys Ile Ser Thr Leu Thr Asn Glu
            115                 120                 125

Ala Arg Gln Gln Ile Val Gly Pro Ile Asn Asp Ala Ala Phe Ala Gly
            130                 135                 140

Phe Arg Leu Arg Ala Ser Gly Ile Ala Thr Gln Val Thr Ser Arg Ser
145                 150                 155                 160

Leu Glu Gln Asn Pro Leu Ser Gln Phe Ala Arg Ile Phe Tyr Ala Arg
                165                 170                 175

Pro Glu Thr Arg Lys Phe Arg Val Glu Phe Leu Thr Pro Thr Ala Phe
            180                 185                 190

Lys Gln Ser Gly Glu Tyr Val Phe Trp Pro Asp Pro Arg Leu Val Phe
            195                 200                 205

Gln Ser Leu Ala Gln Lys Tyr Gly Ala Ile Val Asp Gly Glu Glu Pro
            210                 215                 220

Asp Pro Gly Leu Ile Ala Glu Phe Gly Gln Ser Val Arg Leu Ser Ala
225                 230                 235                 240

Phe Arg Val Ala Ser Ala Pro Phe Ala Val Gly Ala Ala Arg Val Pro
                245                 250                 255

Gly Phe Thr Gly Ser Ala Thr Phe Thr Val Arg Gly Val Asp Thr Phe
            260                 265                 270

Ala Ser Tyr Ile Ala Ala Leu Leu Trp Phe Gly Glu Phe Ser Gly Cys
            275                 280                 285

Gly Ile Lys Ala Ser Met Gly Met Gly Ala Ile Arg Val Gln Pro Leu
            290                 295                 300

Ala Pro Arg Glu Lys Cys Val Pro Lys Pro
305                 310

<210> SEQ ID NO 99
```

<211> LENGTH: 314
<212> TYPE: PRT
<213> ORGANISM: Mycobacterium tuberculosis

<400> SEQUENCE: 99

Met Ala Ala Arg Arg Gly Gly Ile Arg Arg Thr Asp Leu Leu Arg Arg
1               5                   10                  15

Ser Gly Gln Pro Arg Gly Arg His Arg Ala Ser Ala Ala Glu Ser Gly
            20                  25                  30

Leu Thr Trp Ile Ser Pro Thr Leu Ile Leu Val Gly Phe Ser His Arg
        35                  40                  45

Gly Asp Arg Arg Met Thr Glu His Leu Ser Arg Leu Thr Leu Thr Leu
    50                  55                  60

Glu Val Asp Ala Pro Leu Glu Arg Ala Arg Val Ala Thr Leu Gly Pro
65                  70                  75                  80

His Leu His Gly Val Leu Met Glu Ser Ile Pro Ala Asp Tyr Val Gln
                85                  90                  95

Thr Leu His Thr Val Pro Val Asn Pro Tyr Ser Gln Tyr Ala Leu Ala
            100                 105                 110

Arg Ser Thr Thr Ser Leu Glu Trp Lys Ile Ser Thr Leu Thr Asn Glu
        115                 120                 125

Ala Arg Gln Gln Ile Val Gly Pro Ile Asn Asp Ala Ala Phe Ala Gly
    130                 135                 140

Phe Arg Leu Arg Ala Ser Gly Ile Ala Thr Gln Val Thr Ser Arg Ser
145                 150                 155                 160

Leu Glu Gln Asn Pro Leu Ser Gln Phe Ala Arg Ile Phe Tyr Ala Arg
                165                 170                 175

Pro Glu Thr Arg Lys Phe Arg Val Glu Phe Leu Thr Pro Thr Ala Phe
            180                 185                 190

Lys Gln Ser Gly Glu Tyr Val Phe Trp Pro Asp Pro Arg Leu Val Phe
        195                 200                 205

Gln Ser Leu Ala Gln Lys Tyr Gly Ala Ile Val Asp Gly Glu Pro
    210                 215                 220

Asp Pro Gly Leu Ile Ala Glu Phe Gly Gln Ser Val Arg Leu Ser Ala
225                 230                 235                 240

Phe Arg Val Ala Ser Ala Pro Phe Ala Val Gly Ala Ala Arg Val Pro
                245                 250                 255

Gly Phe Thr Gly Ser Ala Thr Phe Thr Val Arg Gly Val Asp Thr Phe
            260                 265                 270

Ala Ser Tyr Ile Ala Ala Leu Leu Trp Phe Gly Glu Phe Ser Gly Cys
        275                 280                 285

Gly Ile Lys Ala Ser Met Gly Met Gly Ala Ile Arg Val Gln Pro Leu
    290                 295                 300

Ala Pro Arg Glu Lys Cys Val Pro Lys Pro
305                 310

<210> SEQ ID NO 100
<211> LENGTH: 230
<212> TYPE: PRT
<213> ORGANISM: Salinispora tropica

<400> SEQUENCE: 100

Met Arg Phe Tyr Val Asp Val Ala Gly Pro Asp Ala Ala Leu Pro Trp
1               5                   10                  15

Arg Tyr Val His Gly Val Ala His Ala Val Val Tyr Ser Val Ile Ala
            20                  25                  30

```
Glu Gln Ser Pro Ala Leu Ala Thr Gln Leu His Glu Gly Thr Trp Ala
        35                  40                  45

Pro Ala Asn Ser Pro Arg Pro Val Gly Ile Ser Pro Val Phe Val
 50                  55                  60

Gly Ala Arg Ala Lys Pro Arg Ala Tyr Met Met Ser Gly Lys Gly Arg
 65                  70                  75                  80

Ile Trp Phe Gly Ser Pro Ile Pro Val Leu Ala Ala Leu Leu Ala
                85                  90                  95

Gly Ile Thr Ser Arg Arg Glu Leu Arg Trp Gly Pro Val Thr Leu Thr
                100                 105                 110

Ile Lys Gly Thr Gln Leu Glu Pro Thr Val Asp Ala Glu Ser Ser Thr
            115                 120                 125

Val Leu Glu Thr Arg Ser Pro Val Leu Val Lys Ala Ser Gly Asn Arg
130                 135                 140

Tyr Leu Leu Pro Asp Asp Gly Phe Val Gly Ala Leu Leu Ala Asn
145                 150                 155                 160

Ile Arg His Lys Ala Asp Leu Leu Gly Leu Pro Gly Asp Ala Glu Val
                165                 170                 175

Gln Val Val Ala Ala Gly Pro Arg Arg Arg Phe Asp Val Ser Gly Gly
            180                 185                 190

Ile Arg Ile Gly Ala Thr Ala Thr Val Arg Leu Asp Ala Asp Pro Arg
            195                 200                 205

Leu Ile Ala Ala Leu Arg Glu Trp Gly Leu Gly Leu Ser Thr Ile Gln
210                 215                 220

Gly Phe Gly Trp Val Arg
225                 230

<210> SEQ ID NO 101
<211> LENGTH: 234
<212> TYPE: PRT
<213> ORGANISM: Frankia alni

<400> SEQUENCE: 101

Met Asn Gly Gly Gly Val Arg Phe Arg Val Asp Leu Ala Ala Asp Arg
1               5                   10                  15

Ser Ser Leu Gln Trp Gly Asp Val Phe Thr Pro Ala Arg Ala Leu Ala
            20                  25                  30

Tyr Asp Leu Ile Arg Gly Gln Asp Pro Glu Leu Ala Glu Glu Leu His
        35                  40                  45

Glu Arg Gly Tyr Ala Gly Ser Pro Leu Arg Pro Leu Gly Ile Ser Ala
 50                  55                  60

Pro Gln Phe Arg Gly Ala Pro Lys Ser Arg Gly Val Tyr Ala Thr Ser
 65                  70                  75                  80

Ala Asp Gly Ser Leu Trp Leu Gly Ser Pro Val Pro Arg Val Ala Ser
                85                  90                  95

Ala Leu Leu Ala Gly Ile Ala Gly Arg Gln Thr Leu Arg Trp Ala Ser
                100                 105                 110

Leu Arg Leu Thr Leu Arg Gly Val Gln Leu Glu Pro Thr Pro Asp His
            115                 120                 125

Gln Ala Gly Glu Ala Val Phe Ser Thr Arg Thr Pro Val Leu Leu Lys
130                 135                 140

Trp Glu Asp Arg Tyr Ile His Pro Asp His Pro His Phe Ala Glu Arg
145                 150                 155                 160

Leu Ser His Asn Leu Arg His Lys Ala Asp Leu Leu Gly Leu Pro Ala
```

165                 170                 175
Asp Asn Asp Val Asp Val Leu Ser Ala Gly Pro Pro Arg Lys Phe Leu
            180                 185                 190

Val Gln Arg Ala Pro Arg His Gly Ser Thr Ala Glu Val His Ile Arg
            195                 200                 205

Ala Asn Pro Ala Leu Leu Asp Ala Val Tyr Asp Trp Gly Leu Gly Leu
            210                 215                 220

Gly Thr Asn Gln Gly Phe Gly Trp Ile Arg
225                 230

<210> SEQ ID NO 102
<211> LENGTH: 229
<212> TYPE: PRT
<213> ORGANISM: Frankia sp.

<400> SEQUENCE: 102

Met Arg Phe Arg Val Asp Val Gly Ala Asp Lys Ala Thr Ile Pro Trp
1               5                   10                  15

Arg Asp Val Phe Gly Pro Ala Arg Ala Val Ala Tyr Glu Leu Ile Arg
            20                  25                  30

Gly Gln Asp Ala Asp Leu Ala Glu Glu Leu His Gly Arg Gly Tyr Ala
        35                  40                  45

Gly Ser Ser Leu Arg Pro Leu Gly Leu Ser Ser Pro Tyr Phe Arg Gly
    50                  55                  60

Pro Ala Arg Gly His Asp Val Tyr Arg Ala Ser Lys Asp Gly Thr Val
65                  70                  75                  80

Trp Phe Gly Ser Pro Val Pro Arg Ile Ala Gly Ala Leu Leu Ala Gly
                85                  90                  95

Leu Ala Gly Arg Arg Gln Leu Arg Trp Gly Ser Val Glu Leu Asp Val
            100                 105                 110

His Gly Val Gln Leu Glu Ser Thr Pro Asp His Ser Ser Gly Glu Thr
        115                 120                 125

Val Phe Ser Thr Val Thr Pro Val Leu Ala Arg Tyr Glu Asp Arg Tyr
    130                 135                 140

Ile Phe Pro Asp His Pro Ala Phe Val Ala Thr Leu Val His Asn Leu
145                 150                 155                 160

Ser His Lys Ala Asp Val Leu Gly Leu Pro Asn Glu Val Glu Phe Glu
                165                 170                 175

Val Leu Ser Ala Gly Pro Pro Arg Lys Phe Phe Val Gln His Thr Pro
            180                 185                 190

Arg His Gly Cys Val Val Arg Ala Arg Val His Ala Ala Pro Ala Leu
        195                 200                 205

Leu Asp Ala Leu Tyr Asp Trp Gly Leu Gly Leu Gly Thr Asn Gln Gly
    210                 215                 220

Phe Gly Trp Ile Arg
225

<210> SEQ ID NO 103
<211> LENGTH: 279
<212> TYPE: PRT
<213> ORGANISM: Candidatus Kuenenia stuttgartiensis

<400> SEQUENCE: 103

Met Pro Leu Asp Phe Cys Ile Leu Lys Thr Gln Pro Asn Leu Lys Cys
1               5                   10                  15

Val Gln Tyr Arg Leu Pro Leu Leu Ser Trp Cys Phe Met Arg Leu Lys

```
            20                  25                  30
Ile Ser Leu Leu Ser Asp Lys Glu Ile Ile Leu Pro Lys Glu Phe Asn
                35                  40                  45

Ala Ile Thr Gln Ala Leu Ile Tyr Arg Leu Ile Asp Arg Val Pro Ala
        50                  55                  60

Gln Trp Leu His Glu Gly Gly Phe Lys Val Glu Asn Arg Ser Phe Lys
65                  70                  75                  80

Leu Phe Thr Phe Ser Ser Ile Ile Glu Lys Gly Arg Tyr Gln Ser Ser
                    85                  90                  95

Lys Glu Leu Phe Ile Phe Pro His Met Val Ser Phe Tyr Val Ser Ser
                100                 105                 110

Pro Val Phe Trp Ile Leu Glu Gln Val Ala Lys Asn Thr Val Phe Ser
            115                 120                 125

Glu Lys Leu Leu Phe Gly Lys Asn Leu Met Asn Ile Ser Ser Val Glu
        130                 135                 140

Val Ile Lys Asp Glu Asp Ile Lys Thr Asn Lys Ile Arg Val Asn Ala
145                 150                 155                 160

Leu Thr Pro Ile Glu Thr His Ser Thr Leu Leu Lys Gly Asp Gly Thr
                    165                 170                 175

Lys Lys Thr Tyr Tyr Tyr Ser Pro Thr Glu Ser Glu Tyr Ser Thr Leu
                180                 185                 190

Ile Asn Glu Asn Leu Arg Lys Lys Trp Cys Ala Tyr His Arg Lys Glu
            195                 200                 205

Cys Pro Tyr Ser Ile Lys Thr Glu Pro Val Gln Met Lys Tyr Cys Arg
        210                 215                 220

Glu Arg Ile Arg Ser Phe Lys Asp Thr Val Ile Lys Gly Trp Thr Gly
225                 230                 235                 240

His Phe Trp Leu Glu Gly Glu Pro Glu Phe Leu Gln Phe Ala Leu Ala
                    245                 250                 255

Ala Gly Leu Gly Ser Arg Asn Ser Gly Gly Phe Gly Phe Ile Glu Lys
                260                 265                 270

Val Arg Glu Arg Lys Asp Ile
            275

<210> SEQ ID NO 104
<211> LENGTH: 244
<212> TYPE: PRT
<213> ORGANISM: Staphylococcus epidermidis

<400> SEQUENCE: 104

Met Ile Asn Lys Ile Thr Val Glu Leu Asp Leu Pro Glu Ser Ile Arg
1               5                   10                  15

Phe Gln Tyr Leu Gly Ser Val Leu His Gly Val Leu Met Asp Tyr Leu
                20                  25                  30

Ser Asp Asp Ile Ala Asp Gln Leu His His Glu Phe Ala Tyr Ser Pro
            35                  40                  45

Leu Lys Gln Arg Ile Tyr His Lys Asn Lys Ile Ile Trp Glu Ile
        50                  55                  60

Val Cys Met Ser Asp Asn Leu Phe Lys Glu Val Lys Leu Phe Ser
65                  70                  75              80

Ser Lys Asn Ser Leu Leu Leu Lys Tyr Tyr Gln Thr Asn Ile Asp Ile
                    85                  90                  95

Gln Ser Phe Gln Ile Glu Lys Ile Asn Val Gln Asn Met Met Asn Gln
                100                 105                 110
```

Leu Leu Gln Val Glu Asp Leu Ser Arg Tyr Val Arg Leu Asn Ile Gln
            115                 120                 125

Thr Pro Met Ser Phe Lys Tyr Gln Asn Ser Tyr Met Ile Phe Pro Asp
        130                 135                 140

Val Lys Arg Phe Phe Arg Ser Ile Met Ile Gln Phe Asp Ala Phe Phe
145                 150                 155                 160

Glu Glu Tyr Arg Met Tyr Asp Lys Glu Thr Leu Asn Phe Leu Glu Lys
                165                 170                 175

Asn Val Asn Ile Val Asp Tyr Lys Leu Lys Ser Thr Arg Phe Asn Leu
            180                 185                 190

Glu Lys Val Lys Ile Pro Ser Phe Thr Gly Glu Ile Val Phe Lys Ile
        195                 200                 205

Lys Gly Pro Leu Pro Phe Leu Gln Leu Thr His Phe Leu Leu Lys Phe
210                 215                 220

Gly Glu Phe Ser Gly Ser Gly Ile Lys Thr Ser Leu Gly Met Gly Lys
225                 230                 235                 240

Tyr Ser Ile Ile

<210> SEQ ID NO 105
<211> LENGTH: 248
<212> TYPE: PRT
<213> ORGANISM: Geobacillus thermodenitrificans

<400> SEQUENCE: 105

Met Arg Leu Thr Ile Thr Met Asn Gly Arg Gln Gly Pro Val Ser Leu
1               5                   10                  15

Pro Leu His Tyr Gln His Leu Leu Gln Gly Leu Leu Tyr Arg Ser Leu
            20                  25                  30

Glu Ser Lys Gln Leu Ala Thr Phe Leu His Glu Ile Gly Phe Arg His
        35                  40                  45

Glu Lys Arg Ser Phe Lys Leu Phe Thr Phe Ser Arg Leu Phe Gly Arg
    50                  55                  60

His Glu Val Asp Arg Val Lys Lys Thr Ile Arg Phe Leu Asp Glu Phe
65                  70                  75                  80

Gln Trp His Ile Asp Thr Ile Leu Pro Glu Thr Glu Gln Leu Gly
                85                  90                  95

Gln Gln Leu Leu Leu Arg Arg Glu Ile Trp Leu Tyr Asp Gln Pro Val
            100                 105                 110

Glu Val Lys Ser Val Lys Met Asp Lys Val Glu Ile Arg Gln Ser Thr
        115                 120                 125

Ile Glu Val Ala Met Leu Ser Pro Leu Thr Val Tyr Ser Thr Tyr Glu
    130                 135                 140

Thr Ile Asp Arg Arg Lys Lys Thr His Phe Phe Gly Pro Asp Asp Glu
145                 150                 155                 160

Val Phe Pro His Leu Ile Glu Leu Asn Phe Arg His Lys Tyr Gln Ala
                165                 170                 175

Tyr Tyr Gly Val Pro Pro Val Glu Arg Leu Ser Ile Gln Pro Val His
            180                 185                 190

Val His Gln Arg His Arg Val Val Thr Leu Phe Lys Asp Met Tyr Ile
        195                 200                 205

Thr Gly Trp Leu Gly His Tyr Arg Leu Ser Ser Ser Pro Glu Gln Leu
    210                 215                 220

Thr Phe Leu Tyr His Val Gly Leu Gly Ser Arg Asn Ser Gln Gly Phe
225                 230                 235                 240

```
Gly Met Phe Cys Leu Thr Gly Lys
            245

<210> SEQ ID NO 106
<211> LENGTH: 242
<212> TYPE: PRT
<213> ORGANISM: Geobacillus sp.

<400> SEQUENCE: 106

Met Arg Ile Ser Cys Ser Phe Glu Thr Asp Lys Ile Pro Ile His Tyr
1               5                   10                  15

Arg Met Ala Met Val Ser Ile Ile Lys Glu Ala Leu Arg Ile Ser Asp
            20                  25                  30

Glu Glu Tyr Tyr His Arg Leu Tyr Gln Arg Gly Gln Arg Thr Lys Pro
        35                  40                  45

Phe Val Phe Ser Thr Tyr Leu Lys Asn Phe His Ile Ile Asn His Glu
    50                  55                  60

Ile Glu Leu Asp Gly Ile Thr Leu Thr Val Ser Ser Pro Asp His Glu
65                  70                  75                  80

Phe Leu Leu Asn Leu Tyr Asn Gly Leu Gln Lys Asn Gln Ala Phe Ser
                85                  90                  95

Tyr Lys Asp Tyr His Phe Val Lys Lys Lys Ile Ala Val Val Lys Glu
            100                 105                 110

Lys Gln Val Thr Ser Pro Ser Val Val Phe Arg Thr Leu Ser Pro Ile
        115                 120                 125

Leu Ile Glu Asp Glu Lys Gly Asn Pro Ile Ala Pro Asp Asp Ala Ser
    130                 135                 140

Tyr Glu Gly His Val Asn Tyr Val Ala Asp Met Ile Leu Ser Gln Tyr
145                 150                 155                 160

Arg Gly Lys Gly Leu Tyr Ala Pro Leu Ser Ile Lys Pro Ile Tyr Phe
                165                 170                 175

Lys Lys Val Val Val Lys Glu Ser Asn His Glu Phe Ala Ala Thr His
            180                 185                 190

Gly Asn Asp Glu Tyr Leu Tyr Phe Thr Ala Tyr His Gly Leu Phe Ala
        195                 200                 205

Ile Thr Gly His Pro Gly Asp Leu Gln Leu Leu Tyr Gln Leu Gly Leu
    210                 215                 220

Ser Lys Arg Arg Asn Gln Gly Phe Gly Gln Leu Glu Ile Glu Glu Val
225                 230                 235                 240

Arg Gly

<210> SEQ ID NO 107
<211> LENGTH: 249
<212> TYPE: PRT
<213> ORGANISM: Geobacillus sp.

<400> SEQUENCE: 107

Met Arg Leu Thr Ile Val Met Ser Gly Arg Asp Asn Pro Val Thr Leu
1               5                   10                  15

Pro Leu His Tyr Gln Gln Gln Leu Gln Gly Leu Leu Tyr His Ser Leu
            20                  25                  30

Arg Asn Pro Lys Phe Ser Gln Leu His Glu Val Gly Phe Arg Lys
        35                  40                  45

Glu Lys Arg Ser Phe Lys Leu Phe Thr Phe Ser Arg Leu Tyr Gly Pro
    50                  55                  60

His Gln Leu Asn Phe Glu Arg Lys Thr Ile Thr Phe Tyr Glu Glu Phe
```

-continued

```
65                  70                  75                  80

Tyr Trp His Val Gly Thr Val Leu Pro Glu Leu Thr Gln Glu Leu Gly
                85                  90                  95

Glu Tyr Leu Leu Leu His Pro Asp Val Gln Ile Gly Gly Gln Pro Val
            100                 105                 110

Glu Val Gln Arg Ile Asp Val Glu Lys Arg Asp Ile Glu Gly Glu Glu
        115                 120                 125

Ile Glu Ile Glu Met Leu Ser Pro Leu Thr Val Tyr Ser Thr Tyr Glu
    130                 135                 140

Thr Val Asp Gly Ser Lys Lys Thr Gln Phe Phe Ser Pro Tyr Asp Glu
145                 150                 155                 160
Val Phe Ser His Leu Val Glu Leu Asn Phe Arg Asn Lys Tyr Glu Ala
                165                 170                 175
Tyr Tyr Gly Val Pro Pro Lys Glu Arg Leu Phe Ile Glu Pro Ile Arg
            180                 185                 190

Val Thr Glu Lys His Lys Val Val Thr Ile Phe Lys Gly Phe Tyr Ile
        195                 200                 205

Thr Ala Trp Leu Gly His Tyr Arg Leu Arg Ser Ser Pro Gly Asn Leu
    210                 215                 220

Thr Phe Leu Tyr Arg Val Gly Ile Gly Gly Arg Asn Ser Gln Gly Phe
225                 230                 235                 240
Gly Met Phe Arg Leu Leu Ser Glu Arg
                245

<210> SEQ ID NO 108
<211> LENGTH: 233
<212> TYPE: PRT
<213> ORGANISM: Bacillus cereus

<400> SEQUENCE: 108

Met Arg Leu His Ile Lys Leu Gln Thr Asn Arg Phe Pro Ile Ser Tyr
1               5                   10                  15
Arg Met Met Met Val Ser Phe Ile Lys Glu Ala Leu Lys Leu Ser Asp
            20                  25                  30

Ala Ala Tyr Phe Gln Gln Ile Tyr Gln Glu Ser Lys Ala Asn Arg Pro
        35                  40                  45

Phe Ser Tyr Gly Val Tyr Ile His Asp Tyr Lys Leu Asn Ala Thr Glu
    50                  55                  60

Phe His Ile Lys Gly Tyr Val Gly Leu Thr Ile Thr Ser Pro Asp Ala
65                  70                  75                  80

Gln Phe Met Leu His Phe Tyr Asn Gly Leu Met Lys Met Asn Asp Phe
                85                  90                  95

Arg Tyr Lys Gly Phe Ser Leu Lys Arg Met Lys Val Gln Met Val Asn
            100                 105                 110

Ser Ala Asp Ile Asn Gln Asn His Val Tyr Phe Lys Thr Leu Ser Pro
        115                 120                 125

Leu Leu Ile Arg Asp Lys His Ala Lys Pro Ile Phe Ile Asp Asp Asp
    130                 135                 140

Lys Phe Glu Lys Glu Leu Asn Tyr Ile Ser Asp Thr Val Leu Lys Glu
145                 150                 155                 160

Phe Arg Gly Tyr Gly Leu Lys Gln Pro Leu Ile Phe Thr Ser Lys Asn
                165                 170                 175

Met Lys Lys Val Val Val Lys Glu Lys Ile His Ser Asp His Asp Thr
            180                 185                 190
```

```
Leu Phe Phe Thr Gly Tyr His Gly Ile Phe Ser Leu Gln Gly Ala Val
            195                 200                 205

Glu Asp Leu Lys Ile Leu Ser Glu Ile Gly Leu Gly Phe Arg Ser Ser
210                 215                 220

Gln Gly Phe Gly Ala Val Glu Val Val
225                 230

<210> SEQ ID NO 109
<211> LENGTH: 251
<212> TYPE: PRT
<213> ORGANISM: Bacillus coagulans

<400> SEQUENCE: 109

Met Lys Leu Ile Val Thr Phe Ser Ala Asn Asp Asn Ala Leu Lys Leu
1               5                   10                  15

Pro Leu Asn Tyr Gln Gln Met Leu Gln Gly Phe Ile Tyr Arg Asn Leu
            20                  25                  30

Leu Asp Pro Asp Phe Ser Arg Phe Leu His Asn His Gly Phe Leu Asn
        35                  40                  45

Gly Lys Arg Ile Phe Lys Leu Phe Val Phe Ser Gln Leu Phe Gly Lys
    50                  55                  60

Tyr Ser Leu Leu Lys Glu Thr Lys Glu Ile Val Phe Lys Gly Pro Val
65                  70                  75                  80

Thr Trp His Val Gly Ser Val Val Pro Glu Phe Ile Lys Gly Phe Gly
                85                  90                  95

Arg Ser Leu Leu Thr Ser Gly His Leu Glu Leu Asn Gly Gln Glu Met
            100                 105                 110

Lys Val Glu Glu Val Thr Tyr Arg Gln Asp Thr Pro Glu Ser Glu Lys
        115                 120                 125

Cys Arg Ile Arg Met Leu Ser Pro Ile Thr Val Tyr Ser Thr Tyr Gln
    130                 135                 140

Asn Gln Asn Gly Lys Lys Ile Thr Gln Tyr Phe Asp Pro Lys Asp Pro
145                 150                 155                 160

Ala Phe Thr Tyr Leu Val Glu Glu Asn Ile Lys Lys Tyr Ala Ala
                165                 170                 175

Phe Tyr Gln Lys Asp Thr Gln Asp Leu Phe Phe Lys Ile Gln Pro Val
            180                 185                 190

Arg Val Thr Glu Lys Asp Lys Arg Ile Thr Arg Tyr Lys Gly Phe Ile
        195                 200                 205

Ile Asn Gly Trp Gly Gly Ile Tyr Val Ile Glu Gly Ser Pro Asn Leu
    210                 215                 220

Leu Ser Phe Ala Glu Ser Thr Gly Leu Gly Ser Lys Asn Ser Gln Gly
225                 230                 235                 240

Phe Gly Met Phe Glu Val Ile His Gln Gln Leu
                245                 250

<210> SEQ ID NO 110
<211> LENGTH: 240
<212> TYPE: PRT
<213> ORGANISM: Listeria monocytogenes

<400> SEQUENCE: 110

Met Arg Leu Lys Ile Asn Cys Asp Phe Asp Ser Lys Ile Ile Ser Lys
1               5                   10                  15

Asp Phe Gln Ser Lys Val Val Ser Leu Phe Lys Ala Gly Ile Met Lys
            20                  25                  30
```

Ser Ser Pro Glu Arg Tyr Glu Asn Leu Phe Gly Gly Asn Lys His Lys
            35                  40                  45

Gln Tyr Thr Phe Ser Val Tyr Leu Pro Lys Pro Gln Asn Lys Gly Ala
        50                  55                  60

Glu Ile Gln Leu Asn Glu Ala Asn Cys Ile Ile Asn Phe Ser Thr Gly
65                  70                  75                  80

Asp Ala Glu Thr Gly Ile Ile Phe Tyr Asn Ala Leu Met Ser Leu Arg
                85                  90                  95

Gly Ser Lys Val Leu Phe Gly Ala Gly Asn His Ile Thr Val Lys Asn
            100                 105                 110

Ile Gln Ile Val Pro Glu Lys Lys Ile Ile Gly Lys Arg Thr Ile Leu
        115                 120                 125

Arg Thr Leu Ser Pro Val Val Ser Arg Asp His Asn Arg Glu Thr Phe
    130                 135                 140

Lys Asn Trp Phe Tyr Ser Phe Glu Asp Glu Glu Phe Glu Pro Thr Leu
145                 150                 155                 160

Lys Arg Asn Met Leu Pro Tyr Leu Met Asp Ala Phe Gly Glu Gln Ala
                165                 170                 175

Arg Tyr Asp Leu Glu Lys Leu Lys Ile Thr Pro Ile Ser Met Lys Lys
            180                 185                 190

Val Val Val Tyr Cys His Glu Ile His Ile Glu Ser Ser Val Gly Ile
        195                 200                 205

Phe Glu Leu Glu Ala Glu Ala Tyr Leu Gln Lys Tyr Leu Val Glu Asn
    210                 215                 220

Gly Ile Gly Thr Met Thr Gly Ser Gly Phe Gly Met Ile Glu Gln Phe
225                 230                 235                 240

<210> SEQ ID NO 111
<211> LENGTH: 240
<212> TYPE: PRT
<213> ORGANISM: Listeria monocytogenes

<400> SEQUENCE: 111

Met Arg Leu Lys Ile Asn Cys Asp Phe Asp Ser Lys Ile Ile Ser Lys
1               5                   10                  15

Asp Phe Gln Ser Lys Val Val Ser Leu Phe Lys Ala Gly Ile Met Lys
            20                  25                  30

Ser Ser Pro Glu Arg Tyr Glu Asn Leu Phe Gly Gly Asn Lys His Lys
        35                  40                  45

Gln Tyr Thr Phe Ser Val Tyr Leu Pro Lys Pro Gln Asn Lys Gly Ala
    50                  55                  60

Glu Ile Gln Leu Asn Glu Ala Asn Cys Ile Ile Asn Phe Ser Thr Gly
65                  70                  75                  80

Asp Ala Glu Thr Gly Ile Ile Phe Tyr Asn Ala Leu Met Ser Leu Arg
                85                  90                  95

Gly Ser Lys Val Leu Phe Gly Ala Gly Asn His Ile Thr Val Lys Asn
            100                 105                 110

Ile Gln Ile Val Pro Glu Lys Lys Ile Ile Gly Lys Arg Thr Ile Leu
        115                 120                 125

Arg Thr Leu Ser Pro Val Val Ser Arg Asp His Asn Arg Glu Thr Phe
    130                 135                 140

Lys Asn Trp Phe Tyr Ser Phe Glu Asp Glu Glu Phe Glu Pro Thr Leu
145                 150                 155                 160

Lys Arg Asn Met Leu Pro Tyr Leu Met Asp Ala Phe Gly Glu Gln Ala
                165                 170                 175

```
Arg Tyr Asp Leu Glu Lys Leu Lys Ile Thr Pro Ile Ser Met Lys Lys
            180                 185                 190

Val Val Val Tyr Cys His Glu Ile His Ile Glu Ser Ser Val Gly Ile
            195                 200                 205

Phe Glu Leu Glu Ala Glu Ala Tyr Leu Gln Lys Tyr Leu Val Glu Asn
        210                 215                 220

Gly Ile Gly Thr Met Thr Gly Ser Gly Phe Gly Met Ile Glu Gln Phe
225                 230                 235                 240

<210> SEQ ID NO 112
<211> LENGTH: 240
<212> TYPE: PRT
<213> ORGANISM: Listeria monocytogenes

<400> SEQUENCE: 112

Met Arg Leu Lys Ile Asn Cys Asp Phe Asp Ser Lys Ile Ile Pro Lys
1               5                   10                  15

Asp Phe Gln Ser Lys Val Val Ser Leu Phe Lys Ala Gly Ile Met Lys
            20                  25                  30

Ser Ser Pro Glu Arg Tyr Glu Asn Leu Phe Gly Gly Asn Lys His Lys
        35                  40                  45

Gln Tyr Thr Phe Ser Val Tyr Leu Pro Lys Pro Gln Asn Lys Gly Ala
    50                  55                  60

Glu Ile Gln Leu Asn Glu Ala Asn Cys Ile Ile Asn Phe Ser Thr Gly
65                  70                  75                  80

Asp Ala Glu Thr Gly Ile Ile Phe Tyr Asn Ala Leu Ile Ser Leu Arg
                85                  90                  95

Gly Ser Lys Ile Leu Phe Gly Ala Gly Asn Asn Ile Thr Ile Lys Asn
            100                 105                 110

Ile Gln Ile Val Pro Glu Lys Lys Ile Ile Gly Asn Arg Thr Ile Leu
        115                 120                 125

Arg Thr Leu Ser Pro Val Val Ser Arg Asp His Asn Arg Glu Thr Phe
    130                 135                 140

Lys Asn Trp Phe Tyr Ser Phe Glu Asp Glu Glu Phe Glu Pro Thr Leu
145                 150                 155                 160

Lys Arg Asn Met Leu Pro Tyr Leu Ile Asp Ala Phe Gly Glu Gln Ala
                165                 170                 175

Arg Tyr Asp Leu Glu Lys Leu Lys Ile Thr Pro Ile Ser Met Lys Lys
            180                 185                 190

Val Val Val Tyr Cys His Glu Ile His Ile Glu Ser Ser Val Gly Ile
            195                 200                 205

Phe Glu Leu Glu Ala Glu Ala Tyr Leu Gln Lys Tyr Leu Val Glu Asn
        210                 215                 220

Gly Leu Gly Thr Met Thr Gly Ser Gly Phe Gly Met Ile Glu Gln Leu
225                 230                 235                 240

<210> SEQ ID NO 113
<211> LENGTH: 240
<212> TYPE: PRT
<213> ORGANISM: Listeria monocytogenes

<400> SEQUENCE: 113

Met Arg Leu Lys Ile Asn Cys Asp Phe Asp Ser Lys Ile Ile Ser Lys
1               5                   10                  15

Asp Phe Gln Ser Lys Val Val Ser Leu Phe Lys Ala Gly Ile Met Lys
            20                  25                  30
```

```
Ser Ser Pro Glu Arg Tyr Glu Asn Leu Phe Gly Gly Asn Lys His Lys
        35                  40                  45

Gln Tyr Thr Phe Ser Val Tyr Leu Pro Lys Pro Gln Asn Lys Gly Ala
    50                  55                  60

Glu Ile Gln Leu Asn Glu Ala Asn Cys Ile Ile Asn Phe Ser Thr Gly
65                  70                  75                  80

Asp Ala Glu Thr Gly Ile Ile Phe Tyr Asn Ala Leu Met Ser Leu Arg
                85                  90                  95

Gly Ser Lys Val Leu Phe Gly Ala Gly Asn His Ile Thr Val Lys Asn
                100                 105                 110

Ile Gln Ile Val Pro Glu Lys Lys Ile Ile Gly Lys Arg Thr Ile Leu
                115                 120                 125

Arg Thr Leu Ser Pro Val Val Ser Arg Asp His Asn Arg Glu Thr Phe
                130                 135                 140

Lys Asn Trp Phe Tyr Ser Phe Glu Asp Glu Glu Phe Glu Pro Thr Leu
145                 150                 155                 160

Lys Arg Asn Met Leu Pro Tyr Leu Met Asp Ala Phe Gly Glu Gln Ala
                165                 170                 175

Arg Tyr Asp Leu Glu Lys Leu Lys Ile Thr Pro Ile Ser Met Lys Lys
                180                 185                 190

Val Val Val Tyr Cys His Glu Ile His Ile Glu Ser Ser Val Gly Ile
                195                 200                 205

Phe Glu Leu Glu Ala Glu Ala Tyr Leu Gln Lys Tyr Leu Val Glu Asn
                210                 215                 220

Gly Ile Gly Thr Met Thr Gly Ser Gly Phe Gly Met Ile Glu Gln Phe
225                 230                 235                 240

<210> SEQ ID NO 114
<211> LENGTH: 240
<212> TYPE: PRT
<213> ORGANISM: Listeria monocytogenes

<400> SEQUENCE: 114

Met Arg Leu Lys Ile Asn Cys Asp Phe Asp Ser Lys Ile Ile Ser Lys
1               5                   10                  15

Asp Phe Gln Ser Lys Val Val Ser Leu Phe Lys Ala Gly Ile Met Lys
                20                  25                  30

Ser Ser Pro Glu Arg Tyr Glu Asn Leu Phe Gly Gly Asn Lys His Lys
        35                  40                  45

Gln Tyr Thr Phe Ser Val Tyr Leu Pro Lys Pro Gln Asn Lys Gly Ala
    50                  55                  60

Glu Ile Gln Leu Asn Glu Ala Asn Cys Ile Ile Asn Phe Ser Thr Gly
65                  70                  75                  80

Asp Ala Glu Thr Gly Ile Ile Phe Tyr Asn Ala Leu Met Ser Leu Arg
                85                  90                  95

Gly Ser Lys Val Leu Phe Gly Ala Gly Asn His Ile Thr Val Lys Asn
                100                 105                 110

Ile Gln Ile Val Pro Glu Lys Lys Ile Ile Gly Lys Arg Thr Ile Leu
                115                 120                 125

Arg Thr Leu Ser Pro Val Val Ser Arg Asp His Asn Arg Glu Thr Phe
                130                 135                 140

Lys Asn Trp Phe Tyr Ser Phe Glu Asp Glu Glu Phe Glu Pro Thr Leu
145                 150                 155                 160

Lys Arg Asn Met Leu Pro Tyr Leu Met Asp Ala Phe Gly Glu Gln Ala
```

```
                    165                 170                 175
Arg Tyr Asp Leu Glu Lys Leu Lys Ile Thr Pro Ile Ser Met Lys Lys
                180                 185                 190

Val Val Val Tyr Cys His Glu Ile His Ile Glu Ser Ser Val Gly Ile
            195                 200                 205

Phe Glu Leu Glu Ala Glu Ala Tyr Leu Gln Lys Tyr Leu Val Glu Asn
        210                 215                 220

Gly Ile Gly Thr Met Thr Gly Ser Gly Phe Gly Met Ile Glu Gln Phe
225                 230                 235                 240
```

<210> SEQ ID NO 115
<211> LENGTH: 244
<212> TYPE: PRT
<213> ORGANISM: Streptococcus sanguinis

<400> SEQUENCE: 115

```
Met Lys Lys Ile Arg Leu His Leu Ser Lys Val Ser Leu Lys Asp Asp
1               5                   10                  15

Asp Leu Val Cys Lys Leu Gln Gly Phe Leu Met Glu Lys Leu Ser Asp
            20                  25                  30

Asp Phe Ala Ser Phe Leu His Gln Gln Glu Thr Asn Pro Tyr Ser Met
        35                  40                  45

Asn Leu Arg Ser Glu Arg Glu Ser Ile Trp Thr Val Asn Leu Leu
    50                  55                  60

Ser Glu Glu Ala Glu Gln Gln Ile Leu Pro Gln Leu Leu Ser Leu Glu
65                  70                  75                  80

Met Ile Lys Leu Glu Thr Tyr Ser Glu Glu Ile Leu Val Lys Asn Ile
                85                  90                  95

Glu Ile Gln Ser Leu Ser Ser Gln Ser Leu Leu Glu Val Phe Gln Gly
            100                 105                 110

Asp Glu Ala Ser His Leu Ile Ser Leu Asn Phe Tyr Thr Pro Thr Thr
        115                 120                 125

Phe Lys Arg Gln Gly Gln Phe Val Leu Phe Pro Asp Thr Arg Leu Ile
    130                 135                 140

Phe Gln Ser Leu Met Gln Lys Tyr Ser Arg Leu Val Glu Gly Lys Ala
145                 150                 155                 160

Glu Ile Glu Glu Glu Thr Leu Glu Phe Leu Ala Glu His Ser Gln Ile
                165                 170                 175

Ser Ser Tyr Arg Leu Lys Ser His Tyr Phe Pro Ile His Gly Arg Lys
            180                 185                 190

Tyr Pro Ala Phe Glu Gly Arg Val Thr Ile Arg Ile Gln Gly Ala Ser
        195                 200                 205

Thr Leu Lys Ala Tyr Ala Gln Met Leu Leu Arg Phe Gly Glu Tyr Ser
    210                 215                 220

Gly Val Gly Ala Lys Cys Ser Leu Gly Met Gly Gly Met Arg Ile Glu
225                 230                 235                 240

Glu Arg Lys Thr
```

<210> SEQ ID NO 116
<211> LENGTH: 243
<212> TYPE: PRT
<213> ORGANISM: Streptococcus thermophilus

<400> SEQUENCE: 116

```
Met Lys Lys Leu Val Phe Thr Phe Lys Arg Ile Asp His Pro Ala Gln
1               5                   10                  15
```

```
Asp Leu Ala Val Lys Phe His Gly Phe Leu Met Glu Gln Leu Asp Ser
             20                  25                  30

Asp Tyr Val Asp Tyr Leu His Gln Gln Gln Thr Asn Pro Tyr Ala Thr
         35                  40                  45

Lys Val Ile Gln Gly Lys Glu Asn Thr Gln Trp Val Val His Leu Leu
     50                  55                  60

Thr Asp Asp Ile Glu Asp Lys Val Phe Met Thr Leu Leu Gln Ile Lys
65                  70                  75                  80

Glu Val Ser Leu Asn Asp Leu Pro Lys Leu Ser Val Glu Lys Val Glu
                 85                  90                  95

Ile Gln Glu Leu Gly Ala Asp Lys Leu Leu Glu Ile Phe Asn Ser Glu
            100                 105                 110

Glu Asn Gln Thr Tyr Phe Ser Ile Ile Phe Glu Thr Pro Thr Gly Phe
        115                 120                 125

Lys Ser Gln Gly Ser Tyr Val Ile Phe Pro Ser Met Arg Leu Ile Phe
    130                 135                 140

Gln Ser Leu Met Gln Lys Tyr Gly Arg Leu Val Glu Asn Gln Pro Glu
145                 150                 155                 160

Ile Glu Glu Asp Thr Leu Asp Tyr Leu Ser Glu His Ser Thr Ile Thr
                165                 170                 175

Asn Tyr Arg Leu Glu Thr Ser Tyr Phe Arg Val His Arg Gln Arg Ile
            180                 185                 190

Pro Ala Phe Arg Gly Lys Leu Thr Phe Lys Val Gln Gly Ala Gln Thr
        195                 200                 205

Leu Lys Ala Tyr Val Lys Met Leu Leu Thr Phe Gly Glu Tyr Ser Gly
    210                 215                 220

Leu Gly Met Lys Thr Ser Leu Gly Met Gly Gly Ile Lys Leu Glu Glu
225                 230                 235                 240

Arg Lys Asp

<210> SEQ ID NO 117
<211> LENGTH: 243
<212> TYPE: PRT
<213> ORGANISM: Streptococcus thermophilus

<400> SEQUENCE: 117

Met Lys Lys Leu Val Phe Thr Phe Lys Arg Ile Asp His Pro Ala Gln
1               5                  10                  15

Asp Leu Ala Val Lys Phe His Gly Phe Leu Met Glu Gln Leu Asp Ser
             20                  25                  30

Asp Tyr Val Asp Tyr Leu His Gln Gln Gln Thr Asn Pro Tyr Ala Thr
         35                  40                  45

Lys Val Ile Gln Gly Lys Glu Asn Thr Gln Trp Val Val His Leu Leu
     50                  55                  60

Thr Asp Asp Ile Glu Asp Lys Val Phe Met Thr Leu Leu Gln Ile Lys
65                  70                  75                  80

Glu Val Ser Leu Asn Asp Leu Pro Lys Leu Ser Val Glu Lys Val Glu
                 85                  90                  95

Ile Gln Glu Leu Gly Thr Asp Lys Leu Leu Glu Ile Phe Asn Ser Glu
            100                 105                 110

Glu Asn Gln Thr Tyr Phe Ser Ile Ile Phe Glu Thr Pro Thr Gly Phe
        115                 120                 125

Lys Ser Gln Gly Ser Tyr Val Ile Phe Pro Ser Met Arg Leu Ile Phe
    130                 135                 140
```

```
Gln Ser Leu Met Gln Lys Tyr Gly Arg Leu Val Glu Asn Gln Pro Glu
145                 150                 155                 160

Ile Glu Glu Asp Thr Leu Asp Tyr Leu Ser Glu His Ser Thr Ile Thr
                165                 170                 175

Asn Tyr Arg Leu Glu Thr Ser Tyr Phe Arg Val His Arg Gln Arg Ile
            180                 185                 190

Pro Ala Phe Arg Gly Lys Leu Thr Phe Lys Val Gln Gly Ala Lys Thr
        195                 200                 205

Leu Lys Ala Tyr Val Lys Met Leu Leu Thr Phe Gly Glu Tyr Ser Gly
    210                 215                 220

Leu Gly Met Lys Thr Ser Leu Gly Met Gly Gly Ile Lys Leu Glu Glu
225                 230                 235                 240

Arg Lys Asp

<210> SEQ ID NO 118
<211> LENGTH: 226
<212> TYPE: PRT
<213> ORGANISM: Moorella thermoacetica

<400> SEQUENCE: 118

Met Val Leu Pro Leu Asp Phe Arg Arg His Phe Ile Ser Leu Ile Lys
1               5                   10                  15

Thr Leu Ala Gly Thr Ser Ala Leu Ala Ala Arg Phe Thr Leu Glu Lys
            20                  25                  30

Pro Gly Tyr Ser Pro Tyr Val Phe Ser Val Glu Phe Asn Lys Ile Ile
        35                  40                  45

Asp Ile Asp Thr Arg Gln Arg Glu Ile Thr Ala Arg Pro Pro Ile Leu
    50                  55                  60

Val Thr Ile Ser Thr Gly Leu Phe Asp Val Met Thr Thr Phe Ser Asn
65                  70                  75                  80

Gly Ala Ile Ala Met Lys Gly Arg Glu Thr Val Leu Gly Leu Tyr Leu
                85                  90                  95

Lys Asp Ile Tyr Leu Leu Pro Leu Lys Gln Ile Gln Thr Gly Glu Gln
            100                 105                 110

Glu Phe Arg Ile Ala Gly His Ala Val Phe Arg Gly Val Arg His Tyr
        115                 120                 125

Val Asp Gly Ser Asp Val Arg Glu Leu Glu Glu Ala Ile Asn Thr His
    130                 135                 140

Leu Tyr Lys Arg Tyr Ser Phe Leu Ile Gln Gln Tyr His Leu Asp Tyr
145                 150                 155                 160

His Ser Arg Val Ser Pro Val Lys Val Leu Gly Pro Pro Ser Tyr His
                165                 170                 175

Lys Gly Val Cys Phe His Tyr Gly Gly Gln Leu Thr Thr Leu Gln Gly
            180                 185                 190

Arg Ile His Leu Lys Ser Thr Pro Glu Thr Leu Gln Phe Leu Tyr Asp
        195                 200                 205

Phe Gly Leu Gly Ile Arg Thr Gly Gln Gly Phe Gly Leu Leu Glu Val
    210                 215                 220

Gly Asp
225

<210> SEQ ID NO 119
<211> LENGTH: 248
<212> TYPE: PRT
<213> ORGANISM: Carboxydothermus hydrogenoformans
```

<400> SEQUENCE: 119

```
Met Arg Ala Leu Ile Lys Phe Glu Val Arg Ser Lys Ala Leu Leu Pro
1               5                   10                  15

Tyr Asn Tyr Gln His Ala Leu Thr Ala Leu Ile Tyr Arg Gly Leu Gly
            20                  25                  30

Val Glu Ser Ala Lys Leu Ala Thr Phe Leu His Asp Ile Gly Phe Arg
        35                  40                  45

Lys Gly Lys Lys Thr Phe Lys Phe Phe Thr Phe Ser Pro Leu Ser Phe
50                  55                  60

Thr Asn Tyr Lys Thr Thr Lys Glu Gly Ile Ile Val Phe Pro Gly Thr
65                  70                  75                  80

Ala Ser Phe Thr Val Ser Ser Pro Leu Pro Glu Phe Ile Asp Tyr Leu
                85                  90                  95

Thr Ser Gly Leu Trp Ala Leu Arg Asn Phe Lys Ile Ile Thr Leu Pro
            100                 105                 110

Val Ser Ile Ile Glu Ile Ala Ala Ile Pro Leu Arg Asn Phe Thr Asp
        115                 120                 125

Glu Glu Leu Phe Thr Leu Lys Ser Pro Leu Val Leu Ala Ile Lys Ser
130                 135                 140

Gln Glu Lys Ala Thr Pro Thr Tyr Leu Ser Tyr Val Glu Asp Lys Ala
145                 150                 155                 160

Leu Tyr Lys Glu Lys Leu Leu Asn Asn Leu Lys Asn Lys Tyr Leu Val
                165                 170                 175

Tyr Tyr Gly Cys Glu Pro Arg Ile Asp Tyr Phe Asp Phe Ala Phe Asp
            180                 185                 190

Glu Arg His Phe Gln Thr Lys Leu Pro Thr Arg Leu Ile Thr Tyr Lys
        195                 200                 205

Asp Gln Lys Ile Arg Gly Leu Cys Ala Pro Phe Lys Ile Lys Thr Asn
210                 215                 220

Pro Glu Leu Ile Ser Leu Gly Tyr Ala Gly Phe Gly Glu Lys Asn
225                 230                 235                 240

Ser Met Gly Phe Gly Phe Val Glu
                245
```

<210> SEQ ID NO 120
<211> LENGTH: 248
<212> TYPE: PRT
<213> ORGANISM: Carboxydothermus hydrogenoformans

<400> SEQUENCE: 120

```
Met Arg Ile Glu Val Leu Leu Lys Pro Arg Glu Lys Ala Val Phe Leu
1               5                   10                  15

Pro Phe Asn Tyr Gln Tyr Gln Ile Thr Ser Ala Ile Tyr Glu Thr Ile
            20                  25                  30

Ala Lys Ser Ser Pro Glu Phe Ala Arg Lys Leu His Asp Glu Gly Phe
        35                  40                  45

Gly Glu Arg Arg Phe Lys Phe Phe Thr Phe Ser Gln Ile Leu Ala Lys
50                  55                  60

Arg Lys Lys Leu Ala Pro Asp Gly Phe Trp Ile Ile Gly Glu Cys Ser
65                  70                  75                  80

Leu Lys Ile Ser Ser Pro Leu Tyr Glu Phe Leu Leu His Leu Leu Asn
                85                  90                  95

Gly Leu Phe Lys Asp His Lys Phe Ile Ile Gly Arg Glu Glu Phe Thr
            100                 105                 110
```

```
Val Lys Gly Ala Phe Ile Arg Glu Asn Pro Glu Ile Lys Pro Gly Gln
        115                 120                 125

Thr Phe Val Cys Leu Ser Pro Ile Val Val Ser Thr Leu Lys Glu Gly
    130                 135                 140

Tyr Thr Lys Pro Tyr Tyr Ile Arg Tyr Thr Glu Glu Pro Glu Leu Phe
145                 150                 155                 160

Ser Glu Lys Ile Arg Gln Asn Leu Leu Arg Lys Phe Ala Thr Tyr Tyr
                165                 170                 175

Gly Arg Leu Pro Val Asp Asp Arg Leu Phe Phe Phe Asp Glu Glu
            180                 185                 190

Tyr Leu Gln Lys Asn Lys Gly Thr Lys Leu Ile His Tyr Arg Asp Gln
        195                 200                 205

Lys Ile Leu Gly Tyr Leu Ala Pro Phe Thr Val Glu Gly Ser Ala Glu
        210                 215                 220

Leu Ile Ala Phe Gly Tyr Asp Val Gly Phe Gly Glu Lys Asn Ser Met
225                 230                 235                 240

Gly Phe Gly Cys Ala Glu Val Lys
            245

<210> SEQ ID NO 121
<211> LENGTH: 251
<212> TYPE: PRT
<213> ORGANISM: Thermoanaerobacter tengcongensis

<400> SEQUENCE: 121

Met Arg Ile Thr Leu Glu Phe Thr Gly Glu Lys Asn Leu Ile Leu Pro
1               5                   10                  15

Ile His Tyr Asn Tyr Ile Val Gln Gly Leu Leu Tyr Asp Leu Met Gly
            20                  25                  30

Asp Thr Asp Phe Ala Ala Phe Leu His Asp Val Gly Phe Gln Tyr Glu
        35                  40                  45

Lys Arg Arg Phe Lys Leu Phe Thr Phe Ser Arg Ile Glu Gly Glu Phe
    50                  55                  60

Gln Ile Val Glu Lys Pro Asn Gly Gln Lys Lys Ile Ile Ile Lys Pro
65                  70                  75                  80

Pro Phe Lys Phe Thr Val Ala Ser Pro Leu Glu Glu Val Ile Ile Asp
                85                  90                  95

Ile Ser Lys Asn Ile Leu Lys Arg Glu Tyr Cys His Phe Asn Gly Gln
            100                 105                 110

Lys Phe Thr Leu Asn Ser Leu Asn Ile Glu Asn Pro Pro Ile Phe Lys
        115                 120                 125

Glu Lys Ala Arg Ile Lys Phe Ile Ser Pro Val Val Met Tyr Thr Thr
    130                 135                 140

Leu Arg Asn Gly Glu Lys Lys Tyr Thr Tyr Tyr Ser Pro Trp Asp
145                 150                 155                 160

Glu Lys Phe Ser Pro Leu Leu Leu Asn Asn Leu Val Lys Lys Tyr Glu
                165                 170                 175

Leu Val Tyr Lys Ile Lys Pro Lys Asn Pro His Phe Lys Leu Ile Pro
            180                 185                 190

Leu Thr Glu Lys Glu Asp Arg Arg Tyr Ser Lys Val Ile Lys Tyr Lys
        195                 200                 205

Asn Val Tyr Val Lys Gly Trp Met Gly Ile Tyr Asp Val Glu Thr Thr
    210                 215                 220

Pro Glu Leu Leu Glu Leu Ala Tyr Tyr Thr Gly Leu Gly Ala Lys Asn
```

```
                    225                 230                 235                 240
Ser Gln Gly Phe Gly Cys Phe Glu Ile Ile Gly
                245                 250
```

<210> SEQ ID NO 122
<211> LENGTH: 260
<212> TYPE: PRT
<213> ORGANISM: Thermoanaerobacter tengcongensis

<400> SEQUENCE: 122

```
Met Gln Leu Ile Val Thr Phe Thr Ala Ser Gly Pro Ile Phe Leu Pro
1               5                   10                  15

Val His Tyr Gly His Leu Leu Gln Ala Leu Ile Tyr Asn Gln Met Asp
            20                  25                  30

Asn Pro Thr Ile Arg His Tyr Leu His Glu His Gly Phe Pro Leu Gly
        35                  40                  45

Lys Arg His Phe Lys Leu Phe Thr Phe Ser Arg Leu Gln Gly Arg Glu
    50                  55                  60

Leu Thr Tyr Glu Lys Glu Ser Lys Arg Leu Ile Phe Thr Pro Pro Leu
65                  70                  75                  80

Arg Leu Val Ile Cys Ser Pro Leu Asp Phe Leu Leu Glu Leu Gly
                85                  90                  95

Thr Gly Phe Leu Arg Gln Gly Lys Val Arg Ile Gly Glu Ala Val Leu
            100                 105                 110

Glu Val Gln Asn Met Ser Val Gly Ala Gln Gln Val Leu Ser Thr Ser
        115                 120                 125

Ile Arg Val Arg Met Leu Ser Pro Leu Val Val Tyr Ser Thr Leu Glu
    130                 135                 140

Lys Glu Gly Gly Asp Arg Tyr Val Tyr Tyr Thr Pro Phe Glu Glu
145                 150                 155                 160

Arg Phe Ser Gln Leu Val Gly Asp Asn Leu Lys Lys Tyr Leu Ile
                165                 170                 175

Val His Gly Asn Phe Pro Tyr Ser Leu Asn Phe Asn Ile Arg Pro Leu
            180                 185                 190

Arg Val Arg Glu Lys Asp Phe Lys Val Thr Tyr Phe Lys Asn Thr Ile
        195                 200                 205

Val Lys Gly Trp Met Gly Asp Tyr Glu Leu Glu Gly Glu Pro Lys Leu
    210                 215                 220

Leu Gln Leu Ala Leu Asp Ala Gly Leu Gly Ser Lys Asn Ser Gln Gly
225                 230                 235                 240

Tyr Gly Cys Cys Arg Leu Leu Glu Glu Gly Lys Thr Tyr Lys Gly Gly
                245                 250                 255

Glu Lys Ser Gly
            260
```

<210> SEQ ID NO 123
<211> LENGTH: 251
<212> TYPE: PRT
<213> ORGANISM: Thermoanaerobacter sp.

<400> SEQUENCE: 123

```
Met Arg Ile Thr Leu Glu Phe Val Gly Glu Lys Asn Leu Val Leu Pro
1               5                   10                  15

Ile His Tyr Asn Tyr Ile Val Gln Gly Phe Leu Tyr Asp Leu Met Gly
            20                  25                  30

Asp Ser Glu Phe Ala Ala Phe Leu His Asp Glu Gly Phe Gln Tyr Glu
```

```
            35                  40                  45
Lys Arg Lys Phe Lys Leu Phe Thr Phe Ser Arg Ile Glu Gly Glu Phe
 50                  55                  60
Lys Ile Leu Thr Asp Ser Lys Gly Gln Lys Lys Ile Ser Ile Lys Pro
 65                  70                  75                  80
Pro Phe Lys Phe Thr Val Ala Ser Pro Leu Asp Glu Phe Ile Phe Asp
                     85                  90                  95
Ile Ser Lys Asn Ala Leu Lys Lys Glu Tyr Cys His Phe Asn Gly Gln
                    100                 105                 110
Lys Phe Ile Leu Asn Ser Leu Asn Ile Asp Asn Pro Pro Val Phe Lys
                    115                 120                 125
Asn Lys Ala Arg Ile Lys Phe Ile Ser Pro Val Val Met Tyr Thr Thr
                    130                 135                 140
Leu Lys Asp Gly Asp Ile Lys Tyr Thr Tyr Tyr Ser Pro Trp Asp
145                 150                 155                 160
Glu Lys Phe Ser Pro Leu Leu Asn Asn Leu Leu Lys Lys Tyr Glu
                    165                 170                 175
Leu Val Tyr Lys Ile Lys Ala Glu Asp Pro Tyr Phe Lys Leu Tyr Pro
                    180                 185                 190
Leu Ser Glu Lys Glu Asp Arg Arg Tyr Ser Lys Met Ile Lys Tyr Lys
                    195                 200                 205
Asn Val Tyr Val Lys Gly Trp Met Gly Ile Tyr Asp Val Glu Ser Ser
                    210                 215                 220
Pro Glu Leu Leu Glu Leu Ala Tyr Tyr Thr Gly Leu Gly Ala Lys Asn
225                 230                 235                 240
Ser Gln Gly Phe Gly Cys Phe Glu Ile Ile Gly
                    245                 250

<210> SEQ ID NO 124
<211> LENGTH: 251
<212> TYPE: PRT
<213> ORGANISM: Thermoanaerobacter pseudethanolicus

<400> SEQUENCE: 124

Met Arg Ile Thr Leu Glu Phe Val Gly Glu Lys Asn Leu Val Leu Pro
 1                   5                  10                  15
Ile His Tyr Asn Tyr Ile Val Gln Gly Phe Leu Tyr Asp Leu Met Gly
                    20                  25                  30
Asp Ser Glu Phe Ala Ala Phe Leu His Asp Glu Gly Phe Gln Tyr Glu
                    35                  40                  45
Lys Arg Lys Phe Lys Leu Phe Thr Phe Ser Arg Ile Glu Gly Glu Phe
 50                  55                  60
Lys Ile Leu Thr Asp Ser Lys Gly Gln Lys Lys Ile Ser Ile Lys Pro
 65                  70                  75                  80
Pro Phe Lys Phe Thr Val Ala Ser Pro Leu Asp Glu Phe Ile Phe Asp
                     85                  90                  95
Ile Ser Lys Asn Ala Leu Lys Lys Glu Tyr Cys His Phe Asn Gly Gln
                    100                 105                 110
Lys Phe Ile Leu Asn Ser Leu Asn Ile Asp Asn Pro Pro Val Phe Lys
                    115                 120                 125
Asn Lys Ala Arg Ile Lys Phe Ile Ser Pro Val Val Met Tyr Thr Thr
                    130                 135                 140
Leu Lys Asp Gly Asp Ile Lys Tyr Thr Tyr Tyr Ser Pro Trp Asp
145                 150                 155                 160
```

```
Glu Lys Phe Ser Pro Leu Leu Leu Asn Asn Leu Leu Lys Lys Tyr Glu
            165                 170                 175

Leu Val Tyr Lys Ile Lys Ala Glu Asp Pro Tyr Phe Lys Leu Tyr Pro
        180                 185                 190

Leu Ser Glu Lys Glu Asp Arg Arg Tyr Ser Lys Met Ile Lys Tyr Lys
        195                 200                 205

Asn Val Tyr Val Lys Gly Trp Met Gly Ile Tyr Asp Val Glu Ser Ser
        210                 215                 220

Pro Glu Leu Leu Glu Leu Ala Tyr Tyr Thr Gly Leu Gly Ala Lys Asn
225                 230                 235                 240

Ser Gln Gly Phe Gly Cys Phe Glu Ile Ile Gly
            245                 250

<210> SEQ ID NO 125
<211> LENGTH: 250
<212> TYPE: PRT
<213> ORGANISM: Caldicellulosiruptor saccharolyticus

<400> SEQUENCE: 125

Met Arg Ile Lys Val Asp Phe Glu Ser Gln Asn Leu Ile Glu Leu Pro
1               5                   10                  15

Ile His Tyr Asn Tyr Phe Val Gln Ser Met Ile Tyr Asn Thr Ile Glu
            20                  25                  30

Asp Lys Ile Tyr Ala Thr Phe Leu His Asp Lys Gly Tyr Glu Val Asp
        35                  40                  45

Leu Lys Asn Phe Lys Leu Phe Ser Phe Ser Arg Leu Glu Gly Pro Phe
    50                  55                  60

Lys Ile Val Gly Glu Gly Ser Asn Lys Lys Ile Ile Phe Asp Lys Lys
65                  70                  75                  80

Val Ser Leu Thr Val Ser Ser Pro Val Glu Asp Phe Val Thr Lys Phe
                85                  90                  95

Ser Thr Gly Leu Leu Lys Lys Asp Gln Ile Tyr Leu Lys Asp Asn Ile
            100                 105                 110

Leu Tyr Val Thr Ser Ala Asn Met Leu Arg Lys Pro Lys Phe Ser Ser
        115                 120                 125

Phe His Lys Ile Lys Met Leu Ser Pro Met Cys Ala Tyr Lys Thr Ile
    130                 135                 140

Arg Asn Glu Asn Ser Glu Tyr Lys His Phe Phe Thr Pro Phe Glu Asp
145                 150                 155                 160

Glu Phe Tyr Asn Leu Ile Ser Gln Asn Leu Met Lys Lys Cys Lys Leu
                165                 170                 175

Leu Ile Lys Asp Phe Asp Glu Lys Ser Phe Arg Phe Asp Leu Lys Pro
            180                 185                 190

Leu Lys Val Glu Glu Lys Ser His Phe Lys Pro Met Leu Phe Lys Lys
        195                 200                 205

Thr Pro Ile Lys Gly Trp Leu Gly Phe Tyr Thr Ile Glu Thr Asp Pro
    210                 215                 220

Lys Ile Met Glu Val Ala Tyr Tyr Cys Gly Leu Gly Ser Lys Asn Ser
225                 230                 235                 240

Gln Gly Phe Gly Leu Phe Glu Ile Ile Glu
            245                 250

<210> SEQ ID NO 126
<211> LENGTH: 261
<212> TYPE: PRT
<213> ORGANISM: Caldicellulosiruptor saccharolyticus
```

<400> SEQUENCE: 126

Met Arg Ala Lys Phe Ile Phe Glu Val His Asn Gly Phe Asn Glu Thr
1 5 10 15

Lys Glu Leu Pro Val Tyr Tyr Arg Thr Leu Phe Met Ala Phe Leu Lys
20 25 30

Lys Ala Leu Ser Ser Tyr Asn Glu Glu Tyr Phe Lys Arg Leu Tyr Trp
35 40 45

Trp Glu Asp Lys Lys Asn Lys Trp Gln Lys Pro Phe Val Tyr Ala Val
50 55 60

Asn Leu Pro Asn Met Asn Phe Ser Asp Asp Lys Val Leu Phe Arg Gly
65 70 75 80

Asp Ile Val Leu Asn Leu Ser Thr Ser Asp Tyr Glu Phe Phe Val Asn
85 90 95

Ile Tyr Asn Ser Leu Ile Ser Ser Lys Leu Tyr Pro His Lys Leu Thr
100 105 110

Asn Asn Cys Glu Ile Lys Leu Arg Arg Ala Tyr Leu Ile Lys Glu Pro
115 120 125

Glu Gln Phe Ser Ser Thr Met Thr Phe Lys Thr Phe Ser Pro Val Val
130 135 140

Ile Glu Lys Lys Glu Gly Asp Asp Lys Ile Pro Ile Leu Pro Tyr Asp
145 150 155 160

Glu Gly Phe Glu Glu Val Leu Asn Asp Val Ile Asp Phe Glu Ile Arg
165 170 175

Asn Ile Arg Ile Leu Arg Gly Gln Asn Arg Gly Leu Tyr Lys Arg Ile
180 185 190

Ser Phe Lys Pro Ile Asn Val Lys Lys Ile Val Val Lys His Lys Ile
195 200 205

Ser Glu Phe Val Glu Asn Thr Gly Lys Glu Ile Met Tyr Leu Thr Gly
210 215 220

Phe Gly Gly Ile Phe Glu Leu Ser Gly His Pro Asp Asp Leu Lys Glu
225 230 235 240

Ile Tyr Gln Asn Gly Leu Gly Phe Arg Arg Gly Gln Gly Phe Gly Phe
245 250 255

Ile Glu Val Val Arg
260

<210> SEQ ID NO 127
<211> LENGTH: 240
<212> TYPE: PRT
<213> ORGANISM: Clostridium bartlettii

<400> SEQUENCE: 127

Met Glu Phe Thr Val Asp Lys Lys Gln Lys Ile Asp Tyr Asn Ile Gly
1 5 10 15

Ser Val Leu Gln Gly Ile Met Met Thr Phe Leu Asp Arg Asp Tyr Gly
20 25 30

Glu Val Leu His Arg Gln Ser Leu Met Pro Tyr Ser Gln His Phe Glu
35 40 45

Thr Lys Asp Gly Lys Tyr Tyr Trp Ile Ile Asn Ala Leu Thr Glu Glu
50 55 60

Ala Lys Glu Asn Ile Ile Cys Lys Ile Leu Asp Ser Asp Lys Arg Ser
65 70 75 80

Leu Asp Leu Thr Tyr Arg Lys Ser Lys Leu Asn Ile Glu Arg Leu Ile
85 90 95

```
Phe Glu Glu Val Asn Leu Phe Lys Asp Arg Gly Lys Asp Ile Val
                100                 105                 110

Leu Asn Phe Lys Thr Pro Thr Ser Phe Lys Arg Thr Ser Gly Gly Tyr
            115                 120                 125

Glu Ile Phe Pro Asn Val Arg His Ile Phe Asn Ser Leu Ile Asn Lys
        130                 135                 140

Tyr Glu Met Phe Glu Met Asn Asn Leu Asp Asp Ser Leu Phe Ser Lys
145                 150                 155                 160

Ile Asn Lys Lys Glu Asp Phe Leu Glu Asp Ile Ile Lys Asn Val Asp
                165                 170                 175

Ile Val Gly Tyr Asn Leu Lys Thr Glu Lys Phe Gly Ile Lys Gly Asn
            180                 185                 190

Tyr Ile Pro Gly Phe Met Gly Lys Val Asn Ile Lys Val Lys Gly Ser
        195                 200                 205

Ala Glu Phe Lys Asn Asn Ile Ser Lys Leu Leu Gln Phe Gly Glu Tyr
    210                 215                 220

Ser Gly Val Gly Leu Lys Cys Thr Met Gly Met Gly Val Met Glu Ile
225                 230                 235                 240

<210> SEQ ID NO 128
<211> LENGTH: 230
<212> TYPE: PRT
<213> ORGANISM: Clostridium tetani

<400> SEQUENCE: 128

Met Lys Ile Tyr Glu Leu Thr Leu Lys Val Phe Leu Leu Lys Asp Ile
1               5                   10                  15

Lys Ser Asp Glu Ser Leu Glu Lys Ile Ser Asn Leu Ile Asp Lys Ser
            20                  25                  30

Leu Ser Lys Asp Gly Lys Leu Leu Asp Phe His Glu Arg Asn Thr Tyr
        35                  40                  45

Lys Asn Tyr Thr Phe Asn Ser Leu Tyr Pro Ile Glu Lys Asp Lys Ile
    50                  55                  60

Tyr Asn Glu Gly Lys Ile Tyr Ser Val Gln Ile Arg Thr Val Asp Glu
65                  70                  75                  80

Ser Leu Ile Gln Tyr Phe Lys Lys Asn Leu Thr Asn Glu Tyr Thr Glu
                85                  90                  95

Tyr Ile Lys Ala Leu Thr Leu Glu Cys Arg Val Ile Pro Gln Arg Tyr
            100                 105                 110

Ile Glu Lys Ile Tyr Ser Ile Thr Pro Val Ile Ile Lys Thr Glu Lys
        115                 120                 125

Gly Tyr Trp Lys Gly Asn Leu Ser Leu Gly Glu Phe Glu Glu Arg Ile
    130                 135                 140

Lys Asn Asn Leu Ile Lys Lys Tyr Asn Ser Phe Phe Asn Thr Lys Ile
145                 150                 155                 160

Asp Glu Arg Phe Thr Leu Phe Arg Thr Ile Asn Leu Ile Asn Asn Lys
                165                 170                 175

Pro Ile Ser Cys Ser Tyr Lys Asp Ile Asn Ile Leu Gly Asp Lys Ile
            180                 185                 190

Thr Leu Ile Ile Asp Glu Asn Glu Met Ala Gln Lys Leu Ala Cys Phe
        195                 200                 205

Ser Leu Gly Ser Gly Val Gly Glu Met Asn Ala Arg Gly Tyr Gly Phe
    210                 215                 220

Val Asn Tyr Lys Trp Leu
```

```
                        225                 230

<210> SEQ ID NO 129
<211> LENGTH: 247
<212> TYPE: PRT
<213> ORGANISM: Clostridium tetani

<400> SEQUENCE: 129

Met Arg Phe Cys Leu Thr Leu His Leu Lys Glu Lys Ile Phe Leu Ile
1               5                   10                  15

Glu Tyr Arg Lys Val Ile Leu Ser Tyr Ile Lys Asn Ala Ile Ser Lys
            20                  25                  30

Cys Asn Asn Gly Lys Tyr Tyr Glu Cys Phe Phe Lys Asp Thr Lys Gln
        35                  40                  45

Lys Asp Tyr Cys Phe Ser Val Ile Leu Pro Asn Pro Thr Phe Thr Lys
    50                  55                  60

Asn Glu Ile Ile Leu Asn Gly Asn Glu Ile Lys Val Leu Phe Ser Thr
65                  70                  75                  80

Asn Asn Asn Ser Lys Ile Gly Phe Ile Leu Phe Ser Ala Phe Ile Ala
                85                  90                  95

Gln Lys Asn Lys Pro Tyr Pro Leu Pro Asn Asn Ser Met Ile Leu
            100                 105                 110

Lys Asn Ile Asn Asn Lys Lys Gln Glu Glu Ile Phe Asn Ser Lys Ala
        115                 120                 125

Ile Phe Lys Thr Thr Leu Gly Ser Gly Leu Cys Val Arg Asp His Asp
    130                 135                 140

Lys Glu Glu Asn Lys Asp Thr Tyr Tyr Val Tyr Thr Asp Glu Lys Phe
145                 150                 155                 160

Arg Glu Lys Leu Lys Val Val Leu Ile Lys Gln Ile Leu Lys Ala Gly
                165                 170                 175

Phe Thr Glu Glu Glu Ala Asn Asp Ile Lys Val Asn Pro Ile Gln Cys
            180                 185                 190

Lys Lys Val Val Val Lys His Tyr Arg Arg Tyr Ile Asp Thr Thr Thr
        195                 200                 205

Gly Leu Phe Glu Ile Gln Ala Asn Asn Lys Ile Leu Gln His Phe Tyr
    210                 215                 220

Asp Val Gly Ile Gly Ser Arg Lys Ser Met Gly Phe Gly Met Ile Asp
225                 230                 235                 240

Leu Val Thr Gln Asp Leu Leu
            245

<210> SEQ ID NO 130
<211> LENGTH: 240
<212> TYPE: PRT
<213> ORGANISM: Clostridium perfringens

<400> SEQUENCE: 130

Met Lys Ile Leu Val Ala Gly Lys Met Lys Asn Lys Lys Ile Ser Leu
1               5                   10                  15

Ser Tyr Arg Met Phe Ile Leu Ser Met Ile Lys Ile Ile Ser Asp
            20                  25                  30

Phe Asp Glu Ile Tyr Phe Glu Met Phe Phe Tyr Glu Gly Lys Lys
        35                  40                  45

Thr Lys Lys Thr Lys Pro Phe Thr Phe Ser Val Phe Phe Lys Asp Tyr
    50                  55                  60

Lys Ile Asn Arg Asp Phe Val Asp Val Glu Gly Glu Val Lys Ile Val
```

```
            65                  70                  75                  80
Ile Ser Thr Pro Asp Ile Lys Leu Asn Met Val Leu Phe Asn Gly Phe
                85                  90                  95
Met Lys Met Lys Glu Tyr Gly Asp Phe Glu Lys Thr Ser Val Arg Ile
                100                 105                 110
Glu Lys Glu Arg Lys Val Glu Glu Asn Glu Ala Ile Phe Lys Thr Leu
                115                 120                 125
Ser Pro Ile Phe Ile Lys Asp Thr Asn Lys Ala Leu Glu Ile Glu
                130                 135                 140
Asp Glu Asn Tyr Asn Lys Glu Leu Asn Tyr Phe Ala Asn Leu Ser Leu
145                 150                 155                 160
Lys Ser Phe Arg Gly Tyr Gly Leu Lys Glu Glu Leu Val Phe Thr Pro
                165                 170                 175
Leu Lys Met Lys Lys Val Val Val Lys Glu Glu Ile Ser Gly Phe Lys
                180                 185                 190
Glu Lys Thr Asn Lys Lys Tyr Ile Tyr Phe Asn Ser Tyr Ser Gly Val
                195                 200                 205
Phe His Leu Arg Gly Asp Lys Asp Leu Asn Leu Leu Lys Glu Leu
                210                 215                 220
Gly Leu Gly Cys Arg Arg Asn Ser Gly Leu Gly Ser Ile Asp Leu Ile
225                 230                 235                 240

<210> SEQ ID NO 131
<211> LENGTH: 240
<212> TYPE: PRT
<213> ORGANISM: Clostridium perfringens B

<400> SEQUENCE: 131

Met Lys Ile Leu Val Ala Gly Lys Met Lys Asn Lys Lys Ile Ser Leu
1               5                   10                  15
Ser Tyr Arg Met Phe Ile Leu Ser Met Ile Lys Lys Ile Ile Ser Asp
                20                  25                  30
Phe Asp Gln Ser Tyr Phe Glu Glu Met Phe Phe Tyr Glu Gly Lys Lys
                35                  40                  45
Thr Lys Lys Thr Lys Pro Phe Thr Phe Ser Val Phe Phe Lys Asp Tyr
50                  55                  60
Lys Ile Asn Arg Asp Phe Val Asp Val Glu Gly Glu Val Lys Ile Val
65                  70                  75                  80
Ile Ser Thr Pro Asp Ile Lys Leu Asn Met Val Leu Phe Asn Gly Phe
                85                  90                  95
Met Lys Met Lys Glu Tyr Gly Asp Phe Glu Lys Thr Ser Val Arg Ile
                100                 105                 110
Glu Lys Glu Arg Lys Val Glu Glu Asn Glu Ala Ile Phe Lys Thr Leu
                115                 120                 125
Ser Pro Ile Phe Ile Lys Asp Ala Asn Lys Ala Ile Glu Ile Glu
                130                 135                 140
Asp Glu Asn Tyr Asn Lys Glu Leu Asn Tyr Phe Ala Asn Leu Ser Leu
145                 150                 155                 160
Lys Ser Phe Arg Gly Tyr Gly Leu Lys Glu Glu Leu Val Phe Thr Pro
                165                 170                 175
Leu Lys Met Lys Lys Val Val Val Lys Glu Glu Ile Ser Gly Phe Lys
                180                 185                 190
Glu Lys Thr Asn Lys Lys Tyr Ile Tyr Phe Asn Ser Tyr Ser Gly Val
                195                 200                 205
```

```
Phe His Leu Arg Gly Asp Lys Asp Asp Leu Asn Leu Leu Lys Glu Leu
        210                 215                 220

Gly Leu Gly Cys Arg Arg Asn Ser Gly Leu Gly Ser Ile Asp Leu Ile
225                 230                 235                 240
```

<210> SEQ ID NO 132
<211> LENGTH: 228
<212> TYPE: PRT
<213> ORGANISM: Clostridium perfringens

<400> SEQUENCE: 132

```
Met Lys Val Phe Glu Leu Thr Val Lys Cys Tyr Leu Asn Asn Asn Ile
1               5                   10                  15

Lys Gln Glu Asp Val Ser Gly Gln Ile Gly Phe Leu Leu Asp Leu Ile
            20                  25                  30

Leu Gly Lys Asp Lys Lys Phe Leu Lys Ile His Lys Ser Asn Thr Phe
        35                  40                  45

Lys Asn Tyr Val Phe Asn Gly Phe Tyr Pro Leu Glu Arg Glu Lys Ile
50                  55                  60

Tyr Lys Glu Glu Tyr Ile Tyr Thr Phe Gln Ile Arg Thr Ile Asp Ala
65                  70                  75                  80

Gly Leu Ala Asn Tyr Leu Lys Glu Asn Leu Thr Lys Val Asn Ser Asn
                85                  90                  95

Cys Ile Asn Val Leu Arg Val Ser Ile Glu Lys Glu Phe Lys Lys
            100                 105                 110

Ile Asn Lys Leu Tyr Ser Ile Thr Pro Ala Ile Met Lys Asn Asp Phe
        115                 120                 125

Gly Tyr Trp Lys Asn Asn Ile Ser Ile Asp Glu Tyr Lys Asn Arg Ile
130                 135                 140

Asn Gln Asn Leu Ile Lys Lys Tyr Asn Ser Tyr Met Asp Glu Ser Leu
145                 150                 155                 160

His Asp Asp Phe Glu Leu Ile Lys Asn Ile Lys Phe Ile Asn Lys Lys
                165                 170                 175

Pro Ile Arg Phe Ser Tyr Lys Gly Val Arg Val Leu Gly Asp Lys Val
            180                 185                 190

Glu Leu Glu Ile Ser Asp Asn Glu Lys Ala Gln Leu Leu Ala Tyr Met
        195                 200                 205

Ser Leu Gly Thr Gly Ile Leu Gly Leu Asn Ala Arg Gly Met Gly Tyr
210                 215                 220

Val Asn Phe Lys
225
```

<210> SEQ ID NO 133
<211> LENGTH: 230
<212> TYPE: PRT
<213> ORGANISM: Clostridium novyi

<400> SEQUENCE: 133

```
Met Glu Val Phe Glu Lys Val Lys Val Tyr Leu Leu Asn Asp Val
1               5                   10                  15

Arg Arg Glu Tyr Met Ser Val Lys Ile Ala Gln Ile Ile Asp Lys Ile
            20                  25                  30

Leu Cys Lys Ser Glu Glu Phe Ser Lys Phe His Glu Glu Asn Lys Phe
        35                  40                  45

Lys Met Tyr Cys Phe Asn Gly Phe Tyr Pro Ile Glu Lys Ser Glu Val
50                  55                  60
```

```
Tyr Lys Lys Gly Lys Ile Tyr Asp Phe Ser Ile Arg Thr Val Asp Glu
 65                  70                  75                  80

Ser Leu Ala Lys Phe Ile Lys Glu Asn Leu Val Asn Glu Tyr Thr Glu
                 85                  90                  95

Cys Ile Lys Val Leu Thr Ile Gln Glu Lys Ile Ile His Glu Arg Tyr
            100                 105                 110

Ile Glu Lys Ile Tyr Ser Ile Met Pro Val Ile Leu Lys Thr Thr Gln
        115                 120                 125

Gly Tyr Trp Arg Lys Asn Leu Arg Leu Glu Asp Phe Glu Arg Leu Ile
    130                 135                 140

Lys Glu Asn Leu Ile Lys Lys Tyr Asn Gln Tyr Tyr Asn Thr Lys Ile
145                 150                 155                 160

Asp Glu Asn Phe Ser Leu Tyr Asp Asn Leu Ile Phe Asn Asn Asn Lys
                165                 170                 175

Pro Val Pro Met Lys Cys Lys Asn Ile Thr Leu Leu Gly Asp Lys Ile
            180                 185                 190

Thr Leu Phe Ile Ser Ser Asn Glu Thr Ala Gln Lys Leu Ala His Phe
        195                 200                 205

Ala Leu Gly Val Ala Leu Gly Glu Asn Ser Ala Arg Gly Ala Gly Phe
    210                 215                 220

Cys Asn Tyr Lys Trp Leu
225             230

<210> SEQ ID NO 134
<211> LENGTH: 245
<212> TYPE: PRT
<213> ORGANISM: Clostridium difficile

<400> SEQUENCE: 134

Met Ser Arg Ile Ser Ile Phe Met Glu Ser Cys Asn Gly Lys Phe Pro
  1               5                  10                  15

Asn Glu Asn Ser Met Leu Ser Val Ser Phe Ile Lys Asn Ile Leu Asn
                 20                  25                  30

Ala Glu Asn Lys Asp Phe Ala Lys Asn Ile Phe Asn Tyr Gly Glu Glu
            35                  40                  45

Arg Lys Asn Asn Lys Gln Ile Lys Asp Ile Asn Thr Ala Ile Tyr Ile
 50                  55                  60

Pro Asn Leu Ile Arg Ser Lys Asn Glu Leu Leu Val Asp Gly Asp Ile
 65                  70                  75                  80

Ile Phe Asn Ile Ser Phe Tyr Asn Tyr Ser Met Phe Ser Lys Leu Tyr
                 85                  90                  95

Asn Gly Ile Leu Lys Val Lys Glu Leu Glu Tyr Lys Gly Tyr Arg Phe
            100                 105                 110

Lys Ile Lys Asn Ile Lys Ile His Lys Glu His Glu Ile Lys Glu Asn
        115                 120                 125

Gly Val Ile Phe Lys Thr Met Ser Pro Ile Ile Val Lys Asn Lys Glu
    130                 135                 140

Gly Lys Tyr Leu Asp Val Glu Asp Ser Asn Tyr Ile Glu Cys Leu Asn
145                 150                 155                 160

Tyr Ile Ala Asn Leu Thr Leu Ser Ile Arg Gly Ser Gly Leu Arg
                165                 170                 175

Lys Pro Leu Glu Phe Ile Pro Leu Asn Phe Lys Lys Arg Val Leu Lys
            180                 185                 190

Glu Lys Ile Arg Gly Phe Lys Glu Arg Glu Phe Tyr Tyr Ile Asn Ala
        195                 200                 205
```

```
Tyr Ala Gly Thr Phe Phe Leu Lys Gly Asn Met Glu Asp Leu Asn Ala
            210                 215                 220
Leu Tyr Lys Met Gly Ile Gly Tyr Arg Arg Thr Glu Asn Ala Gly Met
225                 230                 235                 240
Val Asp Ile Leu Lys
                245

<210> SEQ ID NO 135
<211> LENGTH: 245
<212> TYPE: PRT
<213> ORGANISM: Clostridium difficile

<400> SEQUENCE: 135

Met Lys Met Lys Ile Glu Phe Ser Thr Gly Cys Ile Pro Ile Ser Tyr
1               5                   10                  15
Asn Ser Leu Phe Met Ser Ile Ile Lys Glu Ala Ile Arg Lys Ser Asn
            20                  25                  30
Glu Asp Tyr Tyr Lys Asn Met Tyr Tyr Lys Glu Lys Asn Asn Lys
        35                  40                  45
Lys Thr Lys Asn Phe Thr Phe Ser Val Tyr Ile Lys Lys Tyr Ser Ile
50                  55                  60
Glu Gly Asp Asn Phe Ile Ile Glu Asp Lys Val Ile Leu Asn Ile Ser
65                  70                  75                  80
Thr Pro Asp Leu Glu Leu Gly Phe His Ile Tyr Asn Gly Leu Met Thr
                85                  90                  95
Ser Lys Lys Cys Leu Tyr Lys Asp Tyr Glu Leu Thr Arg Ile Arg Ile
            100                 105                 110
Asp Leu Ser Arg Glu Lys Lys Val Thr Glu Arg Val Leu Phe Asn
            115                 120                 125
Ala Leu Ser Pro Ile Cys Val Lys Ser Lys Glu Gly Lys Phe Leu Glu
130                 135                 140
Ile Thr Asp Asp Arg Tyr Ile Glu Glu Leu Asn Tyr Ile Thr Asn Glu
145                 150                 155                 160
Val Val Lys Asn Tyr Arg Gly Asn Gly Leu Lys Arg Lys Leu Glu Phe
                165                 170                 175
Glu Asn Val Gly Phe Lys Lys Val Val Lys Glu Ser Leu Arg Glu
            180                 185                 190
Phe Lys Lys Ile Thr Gly Lys Glu Tyr Gln Tyr Ile Asn Gly Tyr Lys
            195                 200                 205
Gly Lys Phe Ile Leu Lys Gly Asp Ile Asp Leu Asn Leu Ile Tyr
210                 215                 220
Asn Leu Gly Ile Gly Phe Arg Arg Ala Gln Gly Phe Gly Asp Val Asp
225                 230                 235                 240
Ile Leu Glu Trp Arg
                245

<210> SEQ ID NO 136
<211> LENGTH: 229
<212> TYPE: PRT
<213> ORGANISM: Clostridium botulinum

<400> SEQUENCE: 136

Met Glu Phe Trp Glu Leu Ile Val Thr Ala Met Leu Lys Lys Asp Ile
1               5                   10                  15
Tyr Phe Glu Asp Cys Gly Tyr Ile Ile Gly Lys Asn Ile Asn Lys Ser
            20                  25                  30
```

Met Leu Trp Asp Lys Asp Leu Lys Glu Val His Pro Lys Lys Gln Tyr
                35                  40                  45

Lys Asn Tyr Val Phe Asn Ser Phe Tyr Pro Ile Glu Arg Asp Lys Phe
 50                  55                  60

Tyr Lys Lys Asp Arg Leu Tyr Ile Phe Asn Ile Arg Gly Leu Ser Lys
 65                  70                  75                  80

Glu Phe Ile Asp Lys Ile Glu Thr Cys Leu Cys Asn Leu Glu Ser Asn
                 85                  90                  95

Asp Phe Asn Val Ile Ser Thr Ser Lys Lys Glu Ile Lys Gln Arg Tyr
                100                 105                 110

Ile Lys Glu Leu Tyr Thr Gln Thr Pro Leu Ile Ile Thr Val Asp Asp
                115                 120                 125

Lys Pro Trp Leu Gln Asn Asp Gly Asp Leu Asp Leu Phe Lys Gln Arg
130                 135                 140

Leu Glu Asp Asn Leu Glu Lys Lys Tyr Lys Ser Phe Phe Asn Glu Asp
145                 150                 155                 160

Ile Asp Val Lys Gly Lys Phe Ile Lys Ser Ile Glu Phe Lys Asn Arg
                165                 170                 175

Lys Pro Met His Tyr Asn Tyr Lys Asn Gly Lys Lys Leu Leu Ala Asn
                180                 185                 190

Lys Val Ser Ile Gln Ile Glu Asp Asn Glu Glu Ala Gln Lys Val Ala
                195                 200                 205

Phe Leu Ala Arg Ala Ile Gly Leu Gly Glu Lys Asn Pro Ser Ile Gly
210                 215                 220

Ala Gly Phe Cys Lys
225

<210> SEQ ID NO 137
<211> LENGTH: 229
<212> TYPE: PRT
<213> ORGANISM: Clostridium botulinum

<400> SEQUENCE: 137

Met Glu Phe Cys Glu Leu Ile Ala Thr Val Met Leu Lys Lys Asp Ile
 1               5                  10                  15

Tyr Phe Glu Asp Cys Gly Tyr Ile Ile Gly Lys Asn Ile Asn Lys Ser
                20                  25                  30

Met Leu Leu Asp Lys Asp Leu Lys Glu Ile His Pro Lys Lys Gln Tyr
                35                  40                  45

Lys Asn Tyr Val Phe Asn Ser Phe Tyr Pro Ile Glu Arg Asp Lys Phe
 50                  55                  60

Tyr Lys Lys Asp Arg Leu Tyr Ile Phe Asn Ile Arg Gly Leu Ser Lys
 65                  70                  75                  80

Glu Phe Ile Asp Lys Ile Glu Thr Cys Leu Cys Asn Leu Glu Ser Asn
                 85                  90                  95

Asp Phe Asn Val Ile Ser Thr Ser Lys Lys Glu Ile Lys Gln Arg Tyr
                100                 105                 110

Ile Lys Glu Leu Tyr Thr Gln Thr Pro Leu Ile Ile Thr Val Asp Asp
                115                 120                 125

Lys Pro Trp Leu Gln Asn Asp Gly Asp Leu Asp Leu Phe Lys Gln Arg
130                 135                 140

Leu Glu Asp Asn Leu Glu Lys Lys Tyr Lys Ser Phe Phe Asn Glu Asp
145                 150                 155                 160

Ile Asp Val Lys Gly Lys Phe Ile Lys Ser Ile Glu Phe Lys Asn Arg

```
                165                 170                 175
Lys Pro Met His Tyr Asn Tyr Lys Asn Gly Ile Lys Leu Leu Ala Asn
            180                 185                 190
Lys Val Ser Ile Gln Ile Lys Asp Asn Glu Glu Ala Gln Lys Val Ala
            195                 200                 205
Phe Leu Ala Arg Ala Ile Gly Leu Gly Glu Lys Asn Pro Ser Ile Gly
            210                 215                 220
Ala Gly Phe Cys Lys
225

<210> SEQ ID NO 138
<211> LENGTH: 229
<212> TYPE: PRT
<213> ORGANISM: Clostridium botulinum

<400> SEQUENCE: 138

Met Glu Phe Cys Glu Leu Ile Ala Thr Val Met Leu Lys Lys Asp Ile
1               5                   10                  15
Tyr Phe Glu Asp Cys Gly Tyr Ile Ile Gly Lys Asn Ile Asn Lys Ser
                20                  25                  30
Met Leu Leu Asp Lys Asp Leu Lys Glu Ile His Pro Lys Lys Gln Tyr
            35                  40                  45
Lys Asn Tyr Val Phe Asn Ser Phe Tyr Pro Ile Glu Arg Asp Lys Phe
        50                  55                  60
Tyr Lys Lys Asp Arg Leu Tyr Ile Phe Asn Ile Arg Gly Leu Ser Lys
65                  70                  75                  80
Glu Phe Ile Asp Lys Ile Glu Thr Cys Leu Cys Asn Leu Glu Ser Asn
                85                  90                  95
Asp Phe Asn Val Ile Ser Thr Ser Lys Lys Glu Ile Lys Gln Arg Tyr
            100                 105                 110
Ile Lys Glu Leu Tyr Thr Gln Thr Pro Leu Ile Ile Thr Val Asp Asp
        115                 120                 125
Lys Pro Trp Leu Gln Asn Asp Gly Asp Leu Asp Leu Phe Lys Gln Arg
130                 135                 140
Leu Glu Asp Asn Leu Glu Lys Lys Tyr Lys Ser Phe Phe Asn Glu Asp
145                 150                 155                 160
Ile Asp Val Lys Gly Lys Phe Ile Lys Ser Ile Glu Phe Lys Asn Arg
                165                 170                 175
Lys Pro Met His Tyr Asn Tyr Lys Asn Gly Ile Lys Leu Leu Ala Asn
            180                 185                 190
Lys Val Ser Ile Gln Ile Lys Asp Asn Glu Glu Ala Gln Lys Val Ala
            195                 200                 205
Phe Leu Ala Arg Ala Ile Gly Leu Gly Glu Lys Asn Pro Ser Ile Gly
        210                 215                 220
Ala Gly Phe Cys Lys
225

<210> SEQ ID NO 139
<211> LENGTH: 243
<212> TYPE: PRT
<213> ORGANISM: Clostridium botulinum

<400> SEQUENCE: 139

Met Arg Thr Ile Val Phe Phe Ser Thr Val Ile Asp Met Leu Ser Tyr
1               5                   10                  15
Tyr Glu Leu Leu Leu Glu Ile Lys Leu Asn Lys Asp Ile His Phe Ser
```

```
                     20                   25                   30
Lys Ser Tyr Glu Met Leu Ser Lys Phe Phe Asn Arg Val Met Leu Thr
             35                   40                   45
Asp Asn Tyr Leu Lys Thr Leu His Glu Arg Lys Gly Val Lys Leu Tyr
 50                   55                   60
Ser Phe Ser Gly Leu Tyr Pro Ala Ala Thr Asn Gln Ile Tyr Lys Arg
 65                   70                   75                   80
Asn Ala Leu Tyr Lys Ile Arg Ile Arg Ser Phe Asp Pro Glu Phe Ile
                 85                   90                   95
Cys Ala Met Gln Phe Ser Leu Ser Gln Ile Gln Asp Asn Asp Ile Asn
                100                  105                  110
Ile Ile Ser Ile Lys Phe Ile Lys Asn Gln Gln Gln Phe Ile Thr Glu
            115                  120                  125
Leu Val Ser Ile Asn Pro Val Ile Phe Ser Ile Trp Glu Lys Gln Asn
            130                  135                  140
Tyr Trp Gln Ile Gly Asp Asn Ile Asp Leu Leu Gly Lys Gln Leu Thr
145                  150                  155                  160
Asn Asn Leu Leu His Lys Tyr Asn Thr Ile Ser Cys Asn Lys Leu Thr
                165                  170                  175
Thr Gln Asp Thr Ile Phe His Cys Leu Asn Ile Thr Asn Asn Lys Thr
            180                  185                  190
Ile Tyr Ile Pro Tyr Lys Lys Gly Leu Leu Gly Asn Lys Leu Lys
            195                  200                  205
Ile Gln Val Lys Glu Asp Asp Ile Ser Gln Thr Leu Ala Thr Val Ala
        210                  215                  220
Leu Gly Ala Gly Ile Gly Glu Lys Asn Ser Ile Gly Met Gly Phe Cys
225                  230                  235                  240
Tyr Gly His

<210> SEQ ID NO 140
<211> LENGTH: 244
<212> TYPE: PRT
<213> ORGANISM: Clostridium botulinum C

<400> SEQUENCE: 140

Met Arg Ile Arg Cys Glu Tyr Lys Thr Glu Lys Leu Pro Val Ala Tyr
 1               5                  10                  15
Asn Met Leu Phe Leu Ser Leu Ile Lys Glu Ser Leu Lys Lys Ser Asp
            20                   25                   30
Glu Asp Tyr Leu Arg Lys Leu Tyr Phe Tyr Lys Gly Asp Lys Val Asn
        35                   40                   45
Lys Lys Pro Lys Asn Phe Cys Phe Ser Val Tyr Leu Lys Asp Phe Val
 50                   55                   60
Lys Lys Glu Asp Ile Phe Gln Ile Asn Asp Arg Ile Ile Phe Asn Ile
 65                   70                   75                   80
Ser Ser Pro Asp Tyr Glu Phe Met Leu Lys Val Tyr Asn Gly Leu Leu
                85                   90                   95
Asp Phe Ser Thr Phe Arg Tyr Lys Asp Tyr Asn Ile Asn Lys Val Arg
            100                  105                  110
Ile Asn Leu Leu Lys Glu Lys Val Ile Asn Lys Ser Ser Ala Val Phe
            115                  120                  125
Ser Thr Met Ser Pro Ile Cys Ile Lys Asn Lys Gln Gly Asn Met Ile
            130                  135                  140
Ser Ile Asp Asp Asp Gln Tyr Glu Lys Glu Leu Asn Tyr Ile Glu Ser
```

```
            145                 150                 155                 160
Lys Ser Leu Glu Gly Phe Arg Gly Tyr Gly Leu Val Glu Ala Leu Lys
                165                 170                 175

Phe Ser Pro Ile Phe Met Lys Lys Ile Val Lys Glu Asp Ile Arg
            180                 185                 190

Asn Phe Arg Glu Asn Thr Asn Lys Pro Tyr Tyr Tyr Val Asn Ser Tyr
                195                 200                 205

Ala Gly Thr Phe Lys Leu Lys Gly Asn Thr Lys Asp Leu Asn Asp Leu
    210                 215                 220

Tyr Met Leu Gly Ile Gly Phe Lys Arg Gly Gln Gly Phe Gly Met Ile
225                 230                 235                 240

Glu Ile Ile Glu

<210> SEQ ID NO 141
<211> LENGTH: 229
<212> TYPE: PRT
<213> ORGANISM: Clostridium botulinum

<400> SEQUENCE: 141

Met Glu Phe Trp Glu Leu Ile Ala Thr Val Met Leu Lys Lys Asp Ile
1               5                   10                  15

Tyr Phe Glu Asp Cys Gly Tyr Ile Ile Gly Lys Asn Ile Asn Lys Ser
            20                  25                  30

Met Leu Leu Asp Asn Asp Leu Lys Lys Ile His Pro Lys Lys Gln Tyr
        35                  40                  45

Lys Asn Tyr Val Phe Asn Ser Phe Tyr Pro Ile Glu Arg Asp Lys Phe
    50                  55                  60

Tyr Lys Lys Asp Arg Leu Tyr Ile Phe Asn Ile Arg Gly Leu Ser Lys
65                  70                  75                  80

Glu Phe Ile Asp Lys Ile Glu Thr Cys Leu Cys Asn Leu Glu Ser Asn
                85                  90                  95

Asp Phe Asn Val Ile Ser Thr Ser Lys Lys Glu Ile Lys Arg Arg Tyr
            100                 105                 110

Ile Lys Glu Leu Tyr Thr Gln Thr Pro Leu Ile Ile Thr Val Asp Asp
        115                 120                 125

Lys Pro Trp Leu Gln Lys Asp Gly Asp Leu Asp Leu Phe Lys Gln Arg
    130                 135                 140

Leu Glu Asp Asn Leu Glu Lys Lys Tyr Lys Ser Phe Phe Asn Glu Asp
145                 150                 155                 160

Ile Asp Val Lys Asp Lys Phe Ile Asn Ser Ile Glu Phe Lys Asn Arg
                165                 170                 175

Lys Pro Met His Tyr Asn Tyr Lys Asn Gly Ile Lys Leu Leu Ala Asn
            180                 185                 190

Lys Val Ser Val Gln Ile Glu Asp Asn Glu Glu Ala Gln Lys Val Ala
        195                 200                 205

Phe Leu Ala Lys Ala Thr Gly Leu Gly Glu Lys Asn Ser Ser Ile Gly
    210                 215                 220

Ala Gly Phe Cys Lys
225

<210> SEQ ID NO 142
<211> LENGTH: 207
<212> TYPE: PRT
<213> ORGANISM: Clostridium botulinum

<400> SEQUENCE: 142
```

```
Met Leu Ser Lys Phe Phe Asn Arg Val Met Leu Thr Asp Asn Tyr Leu
1               5                   10                  15

Lys Thr Leu His Glu Arg Lys Gly Val Lys Leu Tyr Ser Phe Ser Gly
                20                  25                  30

Leu Tyr Pro Ala Ala Thr Asn Gln Ile Tyr Lys Arg Asn Ala Leu Tyr
            35                  40                  45

Lys Ile Arg Ile Arg Ser Phe Asp Pro Glu Phe Ile Cys Ala Met Gln
50                  55                  60

Phe Ser Leu Ser Gln Ile Gln Asp Asn Asp Ile Asn Ile Ile Ser Ile
65                  70                  75                  80

Lys Phe Ile Lys Asn Gln Gln Gln Phe Ile Thr Glu Leu Val Ser Ile
                85                  90                  95

Asn Pro Val Ile Phe Ser Ile Trp Glu Lys Gln Asn Tyr Trp Gln Ile
                100                 105                 110

Gly Asp Asn Ile Asp Leu Leu Gly Lys Gln Leu Thr Asn Asn Leu Leu
            115                 120                 125

His Lys Tyr Asn Thr Ile Ser Cys Asn Lys Leu Thr Thr Gln Asp Thr
        130                 135                 140

Ile Phe His Cys Leu Asn Ile Thr Asn Asn Lys Thr Ile Tyr Ile Pro
145                 150                 155                 160

Tyr Lys Lys Gly Leu Leu Leu Gly Asn Lys Leu Lys Ile Gln Val Lys
                165                 170                 175

Glu Asp Asp Ile Ser Gln Thr Leu Ala Thr Val Ala Leu Gly Ala Gly
            180                 185                 190

Ile Gly Glu Lys Asn Ser Ile Gly Met Gly Phe Cys Tyr Gly His
            195                 200                 205

<210> SEQ ID NO 143
<211> LENGTH: 229
<212> TYPE: PRT
<213> ORGANISM: Clostridium botulinum

<400> SEQUENCE: 143

Met Glu Leu Trp Glu Leu Ile Ala Thr Val Met Leu Lys Lys Asp Ile
1               5                   10                  15

Tyr Phe Glu Asp Cys Gly Tyr Ile Ile Gly Lys Asn Ile Asn Lys Ser
                20                  25                  30

Met Leu Leu Asp Lys Asp Leu Lys Glu Val His Pro Lys Lys Gln Tyr
            35                  40                  45

Lys Asn Tyr Val Phe Asn Ser Phe Tyr Pro Ile Glu Arg Asp Lys Phe
50                  55                  60

Tyr Lys Lys Asp Arg Leu Tyr Ile Phe Asn Ile Arg Gly Leu Ser Lys
65                  70                  75                  80

Glu Phe Ile Asp Lys Ile Glu Thr Cys Leu Cys Asn Leu Glu Ser Asn
                85                  90                  95

Asp Phe Asn Val Ile Ser Thr Ser Lys Lys Glu Ile Lys Gln Arg Tyr
                100                 105                 110

Ile Lys Glu Leu Tyr Thr Gln Thr Pro Leu Ile Ile Thr Val Asp Asp
            115                 120                 125

Lys Pro Trp Leu Gln Lys Asp Gly Asp Leu Asp Phe Lys Gln Arg
            130                 135                 140

Leu Glu Asp Asn Leu Glu Lys Lys Tyr Lys Ser Phe Asn Glu Asp
145                 150                 155                 160

Ile Asp Val Lys Asp Lys Phe Ile Asn Ser Ile Glu Phe Lys Asn Arg
```

```
                165                 170                 175
Lys Pro Met His Tyr Asn Tyr Lys Asn Gly Ile Lys Leu Leu Ala Asn
                180                 185                 190

Lys Val Ser Ile Gln Ile Glu Asp Asn Glu Glu Ala Gln Lys Val Ala
            195                 200                 205

Phe Leu Ala Arg Ala Val Gly Leu Gly Lys Asn Ser Ala Ile Gly
        210                 215                 220

Ala Gly Phe Cys Lys
225

<210> SEQ ID NO 144
<211> LENGTH: 243
<212> TYPE: PRT
<213> ORGANISM: Clostridium botulinum

<400> SEQUENCE: 144

Met Arg Pro Ile Val Phe Phe Ser Thr Val Ile Gly Met Leu Ser Tyr
1               5                   10                  15

Tyr Glu Leu Leu Leu Glu Ile Lys Leu Ser Lys Asp Ile His Phe Ser
            20                  25                  30

Lys Ser Tyr Glu Ile Leu Ser Lys Phe Phe Asn Arg Val Met Leu Thr
        35                  40                  45

Asp Asn Tyr Leu Lys Thr Leu His Glu Arg Lys Gly Val Lys Leu Tyr
    50                  55                  60

Ser Phe Ser Gly Leu Tyr Pro Ala Ala Thr Asn Gln Ile Tyr Lys Arg
65                  70                  75                  80

Asn Ala Leu Tyr Lys Ile Arg Ile Arg Ser Phe Asp Pro Glu Phe Ile
                85                  90                  95

Cys Ala Met Gln Phe Ser Leu Ser Gln Ile Gln Asp Asn Asp Ile Asn
            100                 105                 110

Ile Ile Ser Ile Lys Phe Ile Lys Asn Gln Gln Gln Phe Ile Ala Glu
        115                 120                 125

Leu Val Ser Ile Asn Pro Val Ile Phe Ser Ile Trp Glu Lys Gln Asn
    130                 135                 140

Tyr Trp Gln Ile Gly Asp Asn Ile Asp Leu Leu Gly Lys Gln Leu Thr
145                 150                 155                 160

Asn Asn Leu Leu His Lys Tyr Asn Ile Ile Ser Cys Asn Lys Leu Thr
                165                 170                 175

Thr Gln Asp Thr Ile Phe His Cys Leu Ser Ile Thr Asn Asn Lys Thr
            180                 185                 190

Ile Tyr Ile Pro Tyr Lys Lys Gly Leu Leu Leu Gly Asn Lys Leu Lys
        195                 200                 205

Ile Gln Val Lys Glu Asp Ile Ser Gln Thr Leu Ala Thr Val Ala
    210                 215                 220

Leu Gly Ala Gly Ile Gly Glu Lys Asn Ser Ile Gly Met Gly Phe Cys
225                 230                 235                 240

Tyr Gly His

<210> SEQ ID NO 145
<211> LENGTH: 240
<212> TYPE: PRT
<213> ORGANISM: Clostridium thermocellum

<400> SEQUENCE: 145

Met Arg Phe Lys Val Gly Ile Glu Phe Asp Glu Ser Leu Glu Leu Pro
1               5                   10                  15
```

```
Phe Asn Tyr Asn Lys Ile Leu Gln Gly Phe Ile Tyr Arg Asn Ile Met
                20                  25                  30

Asp Lys Asp Leu Ala Arg Phe Ile His Asp Arg Gly Phe Ser Tyr Glu
            35                  40                  45

Lys Arg Lys Tyr Lys Met Phe Thr Phe Ser Arg Leu Gln Gly Lys Phe
 50                  55                  60

Ser Ile Asp Ser Lys Lys Lys Ile Tyr Gln Ser Pro Val Glu
 65                  70                  75                  80

Leu Val Val Ser Ser Cys Tyr Glu Asp Phe Phe Ile Asp Leu Ser Leu
                    85                  90                  95

Ser Leu Leu Arg Arg Asp Val Glu Ile Ala Gly His Lys Ala Tyr Val
                100                 105                 110

Ser Lys Met Asp Ile Ile Met Glu Glu Pro Lys Ser Ile Gln Lys Ile
                115                 120                 125

Arg Met Leu Ser Pro Val Thr Ala Tyr Ser Thr Leu Asp Asp Lys Arg
130                 135                 140

Thr Val Tyr Phe Ser Pro Tyr Asn His Asp Phe Lys Arg Ile Ile Lys
145                 150                 155                 160

Glu Asn Leu Ile Lys Lys Tyr Lys Ala Phe Tyr Lys Asp Ser Lys
                    165                 170                 175

Asp Asn Val Asp Phe Asp Ile Glu Leu Val Ser Asp Lys Tyr Ala Lys
                180                 185                 190

Val Ile Ser Ser Tyr Asp Gly Phe Ile Ile Glu Gly Trp Met Gly Asp
                195                 200                 205

Phe Val Leu Lys Gly Asp Gln Glu Val Ile Lys Leu Ala Tyr Asp Ala
                210                 215                 220

Gly Ile Gly Gly Lys Asn Ser Gln Gly Phe Gly Cys Phe Lys Leu Ile
225                 230                 235                 240

<210> SEQ ID NO 146
<211> LENGTH: 265
<212> TYPE: PRT
<213> ORGANISM: Clostridium sp.

<400> SEQUENCE: 146

Met Ile Leu Thr Tyr Tyr Lys Arg Asn Ala Ile Leu Ile Ile Gln Ser
1               5                   10                  15

Gln Ile Asn Tyr Glu Gly Gly Glu Lys Met Tyr Gln Ile Lys Leu Arg
                20                  25                  30

Phe Lys Leu Glu Phe Pro Phe Leu Pro Lys Glu Met Asp Arg Leu Phe
            35                  40                  45

Thr Ser Phe Leu Lys Ala Ala Thr Lys Asn Ile Ser Glu Asp Leu Tyr
 50                  55                  60

Gln Arg Leu Tyr Asp Lys Ser Arg Ser Ile Met Lys Ala Phe Thr Tyr
 65                  70                  75                  80

Ser Tyr Tyr Leu Pro Gly Ala Lys Phe Thr Asp Lys Ile Leu Leu
                    85                  90                  95

Asp Lys Asn Glu Phe Met Val Phe Phe Thr Asp Ala Asp Lys Glu
                100                 105                 110

Phe Leu Tyr Leu Phe Asn Ala Phe Gln Thr Met Lys Phe Arg His Tyr
                115                 120                 125

Ser Met Asn Lys Asn Ser Met Gln Leu Ile Ser Val Tyr Ile Gln Asn
130                 135                 140

Ile Asn Asp Ile Ile Asp Asp Glu Ile Ile Ile Lys Met Gln Ser Pro
```

```
                145                 150                 155                 160
Leu Leu Ala Arg Tyr His Asp Asn Asp Thr Asn Ser Asp Ser Tyr Tyr
                    165                 170                 175

Thr Phe Asp Lys Asp Glu Phe Ser Asp Val Val Lys Glu Asn Val Lys
                180                 185                 190

Ile Phe Ile Gln Arg Met Asn Ile Pro Val Glu Thr Asp Asp Phe Ser
                195                 200                 205

Ile Gln Ala Ile Lys Gly Lys Lys Val Ile Pro Val Phe Gly Arg
            210                 215                 220

Asn Thr Asp Ala Ser Leu Gly Ile Phe Lys Leu Lys Gly Ser Val Ala
225                 230                 235                 240

Leu Leu Asn Val Leu Gln Arg Ser Gly Ile Gly Val Arg Arg Ser Thr
                    245                 250                 255

Gly Asn Gly Lys Phe Glu Val Leu Gly
                260                 265

<210> SEQ ID NO 147
<211> LENGTH: 257
<212> TYPE: PRT
<213> ORGANISM: Alkaliphilus metalliredigens

<400> SEQUENCE: 147

Met Gln Thr Pro Asn Thr Thr Ile Lys Met Lys Gly Gly Gly Glu Val
1               5                   10                  15

Arg Phe Gly Val Glu Ile Phe Leu Glu Lys Glu Met Leu Pro Lys Asp
                20                  25                  30

Lys Asn Arg Ile Ile Leu Ser Ile Lys Asn Cys Phe Ser Ser Cys
            35                  40                  45

Asn Lys Glu Tyr Tyr Lys Ala Leu Tyr Lys Asp Thr Pro Asn Gln Thr
    50                  55                  60

Lys Asp Phe Thr Phe Ser Leu Tyr Leu Gly Asp Cys Lys Phe Leu Arg
65                  70                  75                  80

Glu Glu Ile Leu Val Pro Ser Lys Lys Ile Tyr Leu Asn Phe Ser Thr
                85                  90                  95

Tyr His Asn Glu Asp Gly Ile Met Phe Phe Asn Ser Met Leu Met Asn
                100                 105                 110

Lys Gly Lys Ala Phe Ser Ile Arg Asp Asn Thr Tyr Thr Ile Gly Lys
            115                 120                 125

Ile Asn Leu Lys Arg Glu Lys Leu Ile Thr Glu His Gln Val Ile Phe
130                 135                 140

Lys Thr Met Ser Pro Ile Val Ala Arg Glu His Gln Gly Asp Asn Lys
145                 150                 155                 160

Lys Thr Trp Tyr His Ser Leu Asn Thr Glu Glu Gly Gln Ala Val Phe
                165                 170                 175

Leu Glu Asn Leu Gln Tyr Gln Leu Lys Asp Ala Phe Gly Glu Gly Ile
                180                 185                 190

Leu Met Asp Ser Arg Lys Leu Ser Ile Glu Val Ser Gln Asp Asn Lys
            195                 200                 205

Glu Val Lys Val Lys Asn Tyr Gly Ile Glu Ile Leu Ser Asn Leu Ala
    210                 215                 220

Lys Ile Arg Ile Gln Gly Ala Pro Tyr Ile Leu Asp Tyr Leu Tyr Lys
225                 230                 235                 240

Ala Gly Ile Gly Ser Lys Arg Gly Ser Gly Phe Gly Met Val Asp Ile
                245                 250                 255
```

Val

<210> SEQ ID NO 148
<211> LENGTH: 249
<212> TYPE: PRT
<213> ORGANISM: Syntrophomonas wolfei

<400> SEQUENCE: 148

```
Met Met Leu Gln Lys Ile Ile Leu Gln Cys Lys Tyr Gly Gly Glu Gln
1               5                   10                  15

Arg Ala Ser Tyr Asn Trp Gly Ser Leu Phe His Gly Ile Leu Val Lys
            20                  25                  30

Ser Leu Pro Ser Asp Ile Ala Glu Met Leu His Glu Asn His Leu Arg
        35                  40                  45

Pro Phe Ser Gln Tyr Val Leu Ser Ser Ser Asn Gln Glu Leu Thr Trp
    50                  55                  60

Asn Ile Gly Leu Trp Asp Ala Glu Ile Ala Asn His Ile Ile Gln Ala
65                  70                  75                  80

Val Leu Pro Leu Val Gln Ile Glu Leu Gln His Lys Ala Thr Thr Leu
                85                  90                  95

Glu Val Thr Gly Val Lys Arg Ser Ser Gln Asn Glu Tyr Glu Tyr Phe
            100                 105                 110

Asn His Tyr Phe Ala Thr Glu Asn Pro Cys Arg Arg Tyr Glu Ile Glu
        115                 120                 125

Phe Leu Thr Pro Cys Thr His Lys Gln Asp Gly Ser Tyr Val Leu Phe
    130                 135                 140

Pro Thr Pro Glu Leu Ile Val Lys Ser Leu Asn Asn Arg Tyr Cys Ala
145                 150                 155                 160

Phe Met Gln Asp Val Ser Leu Asp Ala Pro Glu Ala Met Glu Gln Ile
                165                 170                 175

Ala Lys His Ile His Ile Val Arg Tyr Ser Leu His Ser Ala Val Phe
            180                 185                 190

Tyr Leu Glu Arg Thr Lys Ile Thr Gly Tyr Met Gly Arg Ile Thr Val
        195                 200                 205

Val Ile Ser Gly Thr Glu Gln Leu Ala Arg Leu Ala Gly Ala Leu Leu
    210                 215                 220

Ser Phe Ala Glu Tyr Ser Gly Leu Gly Ile Lys Thr Ala Leu Gly Met
225                 230                 235                 240

Gly Gly Val Lys Ile Arg Ala Leu Ala
                245
```

<210> SEQ ID NO 149
<211> LENGTH: 263
<212> TYPE: PRT
<213> ORGANISM: Anaerostipes caccae

<400> SEQUENCE: 149

```
Met Asn His Ser Leu Gln Gly Asn Arg Tyr Asp Arg Tyr Tyr Gln His
1               5                   10                  15

Val Tyr Asp Thr Arg Val His Thr Lys Glu Arg Gly Gly Ala Val Asp
            20                  25                  30

Leu Lys Val Phe Glu Ile Arg Leu Lys Val Tyr Leu Leu Glu Asp Ile
        35                  40                  45

Pro Val Glu Ala Val Gln Lys Lys Thr Ala Ala Leu Ile Asp Ile Cys
    50                  55                  60

Leu Ser Arg Asp Glu Ala Leu Leu Lys Phe His Glu Thr Asn Gln Phe
```

```
            65                  70                  75                  80
Lys Asn Tyr Ser Phe Gly Asn Pro Tyr Pro Leu Glu Lys Asp Lys Ile
                85                  90                  95

Tyr Lys Lys Asp Lys Val Tyr Val Ile Thr Ile Arg Thr Ile Asp Pro
                100                 105                 110

Gln Leu Ala Lys Val Phe Ser Glu Lys Leu Ile His Glu Arg Ser Asp
                115                 120                 125

Glu Met Gln Ala Leu Thr Cys Glu Ile Lys Ile Pro Lys Glu Asn
130                 135                 140

Lys Ile Ile Asp Thr Ile Tyr Ser Ile Ser Pro Val Ile Val Lys Ala
145                 150                 155                 160

Glu Arg Tyr Trp Arg Gly Val Phe Ser Leu Gln Glu Tyr Glu Lys Arg
                165                 170                 175

Leu Thr Val Asn Leu Val Lys Lys Tyr Asn Ala Phe Cys Asp Thr Lys
                180                 185                 190

Ile Asn Glu Asp Phe Glu Phe Ile Arg Met Ile Glu Val Lys Asn Arg
                195                 200                 205

Thr Pro Ile Thr Val Ser Tyr Lys Lys Ile Lys Leu Leu Gly Asp Lys
                210                 215                 220

Ile Ala Leu Lys Val Ala Asp Asn Glu Leu Ser Gln Glu Leu Ser Tyr
225                 230                 235                 240

Met Thr Leu Gly Thr Gly Leu Gly Glu Ile Asn Ala Arg Gly Ala Gly
                245                 250                 255

Phe Val Asn Tyr Arg Trp Met
                260

<210> SEQ ID NO 150
<211> LENGTH: 248
<212> TYPE: PRT
<213> ORGANISM: Anaerostipes caccae

<400> SEQUENCE: 150

Met Arg Leu Glu Leu Gln Leu Asp Leu Glu Lys Pro Glu Leu Ser Lys
1               5                   10                  15

Asp Tyr Arg Arg Ile Val Leu Ser Tyr Leu Lys Phe Ala Leu Ser Glu
                20                  25                  30

Cys Asn Asp Gly Lys Tyr Phe Glu Lys Tyr Phe Lys Asp Thr Ile Gln
            35                  40                  45

Lys Asp Tyr Cys Phe Ser Val Leu Met Lys Gly Pro Lys Phe Ser Lys
50                  55                  60

Asp Lys Ile Leu Leu Glu Pro Arg Ile Lys Ile Leu Phe Ser Cys
65                  70                  75                  80

Asp Asp Arg Arg Lys Thr Gly Leu Ile Leu Phe Ser Ala Phe Leu Gly
                85                  90                  95

Ile Lys Asn Arg Asn Phe Pro Leu Ala Asn Asn Ala Met Val Leu
                100                 105                 110

Lys Arg Ile Asp Gln Lys Ser Glu Lys Leu Ile Thr Glu Ser Thr Val
                115                 120                 125

Tyr Met Gln Thr Val Leu Gly Asn Gly Leu Cys Ile Arg Glu His Asp
                130                 135                 140

Arg Glu Thr Asn Arg Asp Arg Phe Ile Thr Phe Glu Asp Glu Asp Phe
145                 150                 155                 160

Lys Glu Lys Ala Ser Glu Val Leu Ser Val Gln Ala Lys Leu Ala Gly
                165                 170                 175
```

```
Phe Ser Asp Lys Lys Ala Ser Gly Ile Ser Leu Glu Pro Val Gln Cys
                180                 185                 190

Lys Lys Val Val Val Leu His Tyr Gly Val Tyr Ile Asp Val Thr Val
            195                 200                 205

Gly Ile Ile Lys Met Thr Gly Asp Pro Asp Val Leu Gln Tyr Leu Tyr
        210                 215                 220

Ser Ala Gly Ala Gly Ser Lys His Ser Ala Gly Phe Gly Ala Leu Asn
225                 230                 235                 240

Val Leu Arg Gln Gly Glu Ser Ile
                245

<210> SEQ ID NO 151
<211> LENGTH: 252
<212> TYPE: PRT
<213> ORGANISM: Desulfotomaculum reducens

<400> SEQUENCE: 151

Met Arg Leu Gln Leu Leu Asp Ser Glu Asn Pro Val Leu Leu Ala
1               5                   10                  15

Thr Asn Tyr Gln Gln Gln Ile Gln Gly Leu Ile Tyr Asn Leu Leu Thr
            20                  25                  30

Asp Pro Leu Met Gln Ala Phe Leu His Asp His Gly Phe Asp Tyr Asn
        35                  40                  45

Gln Arg Arg Phe Lys Leu Phe Thr Phe Ser Arg Leu Met Gly Lys Ser
    50                  55                  60

Tyr Phe Asn Gln Gln Asp Lys Thr Leu Arg Ile Thr Pro Pro Val Leu
65                  70                  75                  80

Leu Tyr Ile Ser Ser Pro Trp Thr Glu Phe Leu Glu Asn Leu Ala Asn
                85                  90                  95

Ser Leu Leu Ala Arg Gly Phe Ile Gln Ile Gly Lys Asn Gln Leu Gln
            100                 105                 110

Val Lys Glu Ile Lys Leu Ala Val Thr Pro Pro Phe Asn Gln Asp Gln
        115                 120                 125

Ser Tyr Pro Val Lys Met Leu Ser Pro Val Thr Met Tyr Ser Thr Leu
    130                 135                 140

Glu Thr Arg Glu Gly Ser Lys Lys Thr Tyr Tyr Tyr Ser Pro Thr Glu
145                 150                 155                 160

Arg Glu Phe Thr Arg Leu Ile Ala Gln Asn Leu Val Lys Lys Ala Ser
                165                 170                 175

Ala Phe Tyr Gly Glu Asp Trp Ser Lys Leu Phe Phe Cys Ile Glu Val
            180                 185                 190

Ala Asn Ser Phe Arg Ala Ser Gln Gln Lys Ile Ile Ile Tyr Lys Gly
        195                 200                 205

Thr Val Ile Lys Gly Trp Leu Gly Asn Tyr His Ile Ser Gly His Pro
    210                 215                 220

Lys Met Leu Lys Leu Ala Tyr Glu Ser Gly Ile Gly Ser Lys Asn Ser
225                 230                 235                 240

Gln Gly Phe Gly Leu Phe Glu Leu Cys Asn Asn Gly
                245                 250

<210> SEQ ID NO 152
<211> LENGTH: 265
<212> TYPE: PRT
<213> ORGANISM: Desulfotomaculum reducens

<400> SEQUENCE: 152
```

Met Leu Thr Ala Leu Gln Val Glu Leu Glu Ala Val Ala Asp Gly Ala
1               5                   10                  15

Leu Pro Val Gly Asn Ala Leu Tyr Ile His Gly Leu Phe Phe Arg Leu
            20                  25                  30

Leu Gln Glu Val Asn Ile Asn Ile Ser Asp Tyr Leu His Asn Val Gln
        35                  40                  45

Ser Ile Lys Pro Tyr Thr Leu Ser Thr Leu Gln Gly Val Lys Gln Asn
50                  55                  60

Lys Gly Trp Cys Ser Val Cys Gln Gly Lys Lys Tyr Arg Phe Arg Ala
65                  70                  75                  80

Thr Phe Met Gln Glu Glu Val Phe Leu Asn Phe Tyr Glu Val Val Tyr
                85                  90                  95

Ser Tyr Tyr Val Asn Lys Lys Thr Val Lys Ile Gly Asn Ile Asp Phe
            100                 105                 110

Leu Val Ser Lys Ile Asp Leu Glu Arg Thr Asn Lys Phe Glu Asp Leu
        115                 120                 125

Ile Gly Asn Glu Val Asn Leu Gln Lys Phe Glu Ile Asp Phe Leu Ser
    130                 135                 140

Pro Thr Asn Phe Arg Val Asn Gly Ile Gln His Ile Phe Pro Asp Ser
145                 150                 155                 160

His Thr Val Phe Lys Ser Tyr Lys Asn Arg Trp Asn Thr Phe Cys Pro
                165                 170                 175

Asn His Leu Ile Phe Pro Glu His Asp Leu Ser Leu Ile Tyr Asp Gly
            180                 185                 190

Cys Tyr Ser Val Arg Tyr Asn Leu His Thr Glu Ile Ile Glu Met Gly
        195                 200                 205

Lys Tyr Lys Met Val Gly Phe Lys Gly Thr Cys Arg Tyr Glu Ile Asn
    210                 215                 220

Pro Lys Leu Ser Gly Glu Leu Arg Asp Arg Ala Ser Gly Leu Leu Lys
225                 230                 235                 240

Phe Ala Arg Tyr Cys Gly Thr Gly Tyr Lys Thr Thr Met Gly Leu Gly
                245                 250                 255

Gln Thr Lys Val Ser Phe Met Ile Lys
            260                 265

<210> SEQ ID NO 153
<211> LENGTH: 246
<212> TYPE: PRT
<213> ORGANISM: Desulfitobacterium hafniense

<400> SEQUENCE: 153

Met Asn Leu Glu Ile Tyr Phe Lys Pro Leu Arg Glu Pro Val Val Leu
1               5                   10                  15

Pro Ile His Tyr Asn Tyr Leu Val Gln Ala Ala Leu Tyr Asn Ser Ile
            20                  25                  30

Asp Gln Glu Leu Ala Ala Phe Leu His Glu Lys Gly Tyr Ser Asp Gly
        35                  40                  45

Asn Arg Ala Phe Lys Leu Phe Cys Phe Ser Leu Ile Gln Gly Val Tyr
50                  55                  60

Gln Met Asp Arg Val Asn Lys Arg Ile Ala Phe Glu Gly Glu Leu Lys
65                  70                  75                  80

Leu Thr Val Ser Ser Pro Leu Gln Asp Phe Cys Gln Ser Leu Val Asn
                85                  90                  95

Val Leu Leu Thr Lys Gly Val Met Arg Leu Gly Ala Gln Glu Leu Glu
            100                 105                 110

```
Ile Asp Arg Ile Ser Ala Gly Gln Tyr Lys Val Arg Glu Asn Lys Val
            115                 120                 125

Met Val Arg Thr Leu Ser Pro Val Val Leu Tyr Ser Thr Leu Leu Arg
    130                 135                 140

Pro Asp Gly Arg Lys Tyr Thr Val Tyr Phe Gln Pro Gly Glu Thr Asp
145                 150                 155                 160

Tyr Ser Arg Leu Phe Asn Glu Asn Leu Arg Lys Lys Tyr Arg Ala Leu
                165                 170                 175

Tyr Gly Ser Glu Gly Pro Glu Gly Glu Val Glu Ile Arg Pro Leu Gly
                180                 185                 190

Ile Gln Arg Met Arg Ile Val Asn Tyr Lys Asn Thr Val Ile Lys Gly
            195                 200                 205

Tyr Ala Gly Lys Leu Leu Leu Ser Gly Pro Lys Glu Leu Leu Gln Leu
        210                 215                 220

Ala Val Asp Gly Gly Ile Gly Ser Lys Asn Ser Gln Gly Phe Gly Cys
225                 230                 235                 240

Val Glu Ile Ile Asn Gly
                245

<210> SEQ ID NO 154
<211> LENGTH: 261
<212> TYPE: PRT
<213> ORGANISM: Desulfitobacterium hafniense

<400> SEQUENCE: 154

Met Leu Ile Gln Ala Ile Pro Arg Lys Asp Gly Glu Arg Gln Lys Met
1               5                   10                  15

Asn Leu Glu Ile Tyr Phe Lys Pro Leu Arg Glu Pro Val Val Leu Pro
            20                  25                  30

Ile His Tyr Asn Tyr Leu Val Gln Ala Ala Leu Tyr Asn Ser Ile Asp
        35                  40                  45

Gln Glu Leu Ala Ala Phe Leu His Glu Lys Gly Tyr Ser Asp Gly Asn
    50                  55                  60

Arg Ala Phe Lys Leu Phe Cys Phe Ser Leu Ile Gln Gly Val Tyr Gln
65                  70                  75                  80

Met Asp Arg Val Lys Lys Arg Ile Ala Phe Glu Gly Glu Leu Lys Leu
                85                  90                  95

Thr Val Ser Ser Pro Leu Gln Asp Phe Cys Gln Ser Leu Val Asn Val
            100                 105                 110

Leu Leu Thr Lys Gly Val Met Arg Leu Gly Ala Gln Glu Leu Glu Ile
        115                 120                 125

Asp Arg Ile Ser Ala Gly Gln Tyr Glu Val Arg Glu His Lys Val Met
    130                 135                 140

Val Arg Thr Leu Ser Pro Val Val Leu Tyr Ser Thr Leu Leu Arg Pro
145                 150                 155                 160

Asp Gly Arg Lys Tyr Thr Val Tyr Phe Gln Pro Gly Thr Asp Tyr
                165                 170                 175

Ser Arg Leu Phe Asn Glu Asn Leu Arg Lys Lys Tyr Arg Ala Leu Tyr
                180                 185                 190

Gly Ser Glu Gly Pro Glu Gly Glu Val Glu Ile Arg Pro Leu Gly Ile
            195                 200                 205

Gln Arg Met Arg Ile Val Asn Tyr Lys Asn Thr Val Ile Lys Gly Tyr
        210                 215                 220

Ala Gly Lys Leu Leu Leu Ser Gly Pro Lys Glu Leu Leu Gln Leu Ala
```

```
225                 230                 235                 240
Val Asp Gly Gly Ile Gly Ser Lys Asn Ser Gln Gly Phe Gly Cys Val
                245                 250                 255

Glu Ile Ile Asn Gly
            260
```

<210> SEQ ID NO 155
<211> LENGTH: 251
<212> TYPE: PRT
<213> ORGANISM: Pelotomaculum thermopropionicum

<400> SEQUENCE: 155

```
Met His Ala Tyr Leu Lys Met Arg Met Asp Pro Ser Ser Pro Ala Ile
1               5                   10                  15

Pro Ile His Tyr Asn Tyr Leu Ile Gln Ala Ala Ile Tyr Ala Val Leu
                20                  25                  30

Pro Glu Glu Met Ala Ala Arg Leu His Asn Glu Gly Phe Ala Ala Gly
            35                  40                  45

Lys Arg Ser Phe Lys Met Phe Ser Phe Ser Arg Leu Met Gly Arg Phe
    50                  55                  60

Ile Leu Asp Lys Thr Ala Gly Thr Ile Ser Phe Pro Glu Glu Ile Ser
65                  70                  75                  80

Phe Val Ile Thr Ser Pro Asp Met Gly Phe Phe Leu Ala Leu Ile Asn
                85                  90                  95

Asn Leu Leu Thr Arg Gly Gln Ile Gln Val Gly Gln Ser Leu Leu Leu
                100                 105                 110

Ile Asp Glu Ile Arg Phe Asp Glu Gln Val Ala Asp Gly Glu Val Leu
            115                 120                 125

Thr Val Arg Thr Leu Ser Pro Val Val Ala Tyr Ser Thr Leu Leu Arg
    130                 135                 140

Pro Glu Gly Gly Lys Tyr Thr Cys Tyr Tyr Gln Pro Gly Glu Gly Glu
145                 150                 155                 160

Phe Asp Lys Leu Ile Thr Ala Asn Leu Ala Lys Lys Tyr Glu Ala Phe
                165                 170                 175

Tyr Arg Ser Arg Pro Pro Glu Gly Asn Val Arg Ala Arg Pro Leu Asp
            180                 185                 190

Arg Pro Arg Leu His Val Thr Thr Tyr Lys Gly Thr Val Val Lys Gly
    195                 200                 205

Tyr Thr Cys Arg Leu Lys Leu Asn Gly Pro Arg Glu Leu Leu Gln Met
    210                 215                 220

Ala Leu Asp Ala Gly Leu Gly Gly Lys Gly Ser Gln Gly Tyr Gly Cys
225                 230                 235                 240

Val Glu Lys Val Val Gly Arg Lys Gly Ser Gln
                245                 250
```

<210> SEQ ID NO 156
<211> LENGTH: 248
<212> TYPE: PRT
<213> ORGANISM: Pelotomaculum thermopropionicum

<400> SEQUENCE: 156

```
Met Gln Leu Thr Val Thr Phe His Ala Pro Ser Glu Val Ala Val Pro
1               5                   10                  15

Val His Tyr Gly Val Leu Leu Gln Gly Leu Ile Tyr Arg Gln Met Gln
                20                  25                  30

Asn Pro Ala Leu Arg Arg Tyr Leu His Glu His Gly Phe Pro Leu Glu
```

```
                35                  40                  45
Lys Arg Arg Phe Lys Leu Phe Thr Phe Ser Arg Leu Met Gly Arg Ser
 50                  55                  60

Ala Arg Phe Asp Arg Ala Gly Gly Ser Ile Val Phe Val Pro Pro Leu
 65                  70                  75                  80

Gln Leu Val Ile Cys Ser Pro Ile Ser Phe Ile Leu Gln Glu Leu Gly
                 85                  90                  95

Asn Gly Phe Leu Gln Gln Gly Gln Val Arg Leu Gly Asp Ala Arg Leu
                100                 105                 110

Glu Val Lys Glu Met Ala Ala Ser Pro Arg Val Ser Ser Ser Ser
            115                 120                 125

Ile Arg Val Arg Met Leu Ser Pro Val Val Met Tyr Ser Thr Ala Gly
            130                 135                 140

Ala Glu Asn Gly Arg Ser Tyr Thr Tyr Tyr Ser Pro Phe Glu Pro
145                 150                 155                 160

Arg Phe Ala Glu Leu Ile Gly Ala Asn Leu Ala Lys Lys His Leu Leu
                165                 170                 175

Ile His Gly Arg Arg Ala Glu Ala Asp Gly Phe Asp Ile Arg Pro Ala
                180                 185                 190

Glu Val Arg Glu Lys Asp Phe Lys Ile Thr Arg Tyr Lys Asp Thr Ile
            195                 200                 205

Val Lys Gly Trp Leu Gly Glu Tyr Tyr Leu Asn Gly Asp Pro Glu Leu
210                 215                 220

Leu Gln Val Ala Leu Asp Ala Gly Leu Gly Ala Lys Asn Ser Gln Gly
225                 230                 235                 240

Tyr Gly Cys Cys Glu Leu Val Ile
                245

<210> SEQ ID NO 157
<211> LENGTH: 264
<212> TYPE: PRT
<213> ORGANISM: Desulforudis audaxviator

<400> SEQUENCE: 157

Met Gln Leu Thr Ile Phe Phe Ser Ala Pro Gly Pro Val Ala Ile Pro
 1               5                  10                  15

Val Gln Tyr Gly His Leu Leu Gln Gly Leu Ile Tyr Arg Arg Met Asp
                20                  25                  30

Asn Pro Val Leu Arg Ser Tyr Leu His Glu His Gly Phe Ala Leu Glu
            35                  40                  45

Lys Arg Arg Phe Lys Leu Phe Thr Phe Ser Arg Leu Met Gly Gln Ala
 50                  55                  60

Val Thr Tyr Asp Gln Ala Ala Gly Arg Leu Val Leu Thr Pro Pro Leu
 65                  70                  75                  80

Arg Leu Val Ile Cys Ser Pro Ile Pro Phe Ile Leu Gln Glu Leu Gly
                 85                  90                  95

Thr Gly Phe Leu Arg Gln Gly Arg Val Arg Leu Gly Asp Ala His Leu
                100                 105                 110

Glu Val Lys Lys Met Ala Thr Ala Ala Pro Trp Val Thr Arg Glu Thr
            115                 120                 125

Leu Gln Val Arg Met Leu Ser Pro Leu Val Tyr Ser Thr Leu Ser
            130                 135                 140

Gly Val Asp Gly Arg Asn Tyr Thr Tyr Tyr Tyr Ser Pro Phe Glu Pro
145                 150                 155                 160
```

```
Arg Phe Thr Glu Leu Val Ala Ser Asn Leu Ala Lys Lys His Phe Leu
            165                 170                 175

Val Tyr Gly Gln Pro Ala Arg Ala Glu Gly Phe Ala Ile Arg Pro Val
            180                 185                 190

Arg Val Glu Asp Arg Asp Leu Lys Val Thr Tyr Tyr Lys Asp Thr Val
            195                 200                 205

Ile Lys Gly Trp Met Gly Tyr Glu Leu Ser Gly Asp Leu Glu Leu
            210                 215                 220

Leu Gln Leu Ala Leu Asp Ala Gly Leu Gly Ser Lys Asn Ser Gln Gly
225                 230                 235                 240

Tyr Gly Cys Cys Asn Leu Val Glu Lys Ala Ser Gln Val Ser Ser Arg
            245                 250                 255

Tyr Arg Arg Asn Ser Asn Ile Met
            260

<210> SEQ ID NO 158
<211> LENGTH: 246
<212> TYPE: PRT
<213> ORGANISM: Parvimonas micra

<400> SEQUENCE: 158

Met Lys Ile Val Leu Lys Phe Lys Thr Asp Asn Asn Phe Ile Pro Lys
1               5                   10                  15

Asp Tyr His Arg Phe Cys Ile Lys Phe Phe Lys Thr Ala Val Ser Asn
            20                  25                  30

Tyr Ser Asp Gly Asn Phe Phe Glu Lys Phe Gly Asp Asp Tyr Ile
            35                  40                  45

Lys Ser Asp Glu Lys Lys Tyr Ser Trp Ala Val Lys Phe Phe Lys Pro
50                  55                  60

Lys Phe Phe Ser Asn Arg Ile Glu Val Gly Asn Asn Phe Glu Ile
65                  70                  75                  80

Thr Phe Lys Ala Pro Lys Thr Asp Val Gly Thr Ile Phe Phe Asn Ser
            85                  90                  95

Phe Leu Glu Tyr Lys Asp Lys Glu Phe Lys Ile Ser Glu Asn Asn Phe
            100                 105                 110

Ile Val Leu Thr Asp Ala Lys Ile Val Asn Glu Lys Lys Ile Val Gly
            115                 120                 125

Asn Cys Ala Arg Phe Lys Phe Cys Ser Pro Leu Val Ile Arg Glu His
130                 135                 140

Asn Arg Glu Asp Asn Thr Asp Arg His Ile Thr Val Glu Asp Glu Asp
145                 150                 155                 160

Phe Phe Asp Lys Phe Lys Glu Asn Leu Lys Ile His Phe Pro Asn Tyr
            165                 170                 175

Ser Asn Ala Ile Asp Asp Met Lys Met Asp Ile Ser Glu Met Lys Lys
            180                 185                 190

Ala Val Val Leu Phe Tyr Gly Leu Tyr Ile Asp Val Ser Leu Gly Val
            195                 200                 205

Ile Glu Ile Lys Ala Asp Asn Asn Leu Leu Asn Glu Met Leu Ile Ser
            210                 215                 220

Ser Ile Gly Ser Lys Asn Ala Ser Gly Phe Gly Leu Leu Gln Leu Ile
225                 230                 235                 240

Glu Ser Trp Glu Met Ile
            245

<210> SEQ ID NO 159
```

```
<211> LENGTH: 235
<212> TYPE: PRT
<213> ORGANISM: Clostridium ramosum

<400> SEQUENCE: 159
```

| | | | | | | | | | | | | | | |
|---|---|---|---|---|---|---|---|---|---|---|---|---|---|---|
| Met | Glu | Ser | Ile | Glu | Met | Asp | Val | Tyr | Glu | Ile | Lys | Ile | Lys | Leu | Tyr |
| 1 | | | | 5 | | | | | 10 | | | | | 15 | |

| Leu | Leu | Lys | Asp | Ile | Lys | Ile | Glu | Glu | Thr | Gln | Thr | Tyr | Leu | Ala | Tyr |
|---|---|---|---|---|---|---|---|---|---|---|---|---|---|---|---|
| | | | 20 | | | | | 25 | | | | | 30 | | |

| Phe | Ile | Asp | Ser | Val | Met | Val | Lys | Asp | Asn | Met | Phe | Leu | Gly | Ile | His |
|---|---|---|---|---|---|---|---|---|---|---|---|---|---|---|---|
| | | | 35 | | | | | 40 | | | | | 45 | | |

| Glu | Thr | Asn | Gln | Tyr | Lys | Phe | Tyr | Thr | Phe | Asp | Ser | Leu | Tyr | Pro | Leu |
|---|---|---|---|---|---|---|---|---|---|---|---|---|---|---|---|
| | 50 | | | | | 55 | | | | | 60 | | | | |

| Ala | Lys | Asn | Gly | Val | Tyr | Gln | Lys | Asp | Asn | Ser | Tyr | Met | Phe | Arg | Ile |
|---|---|---|---|---|---|---|---|---|---|---|---|---|---|---|---|
| 65 | | | | | 70 | | | | | 75 | | | | | 80 |

| Arg | Thr | Leu | Asp | Tyr | Gln | Leu | Ala | Gln | Tyr | Leu | Tyr | Asp | Thr | Leu | Ala |
|---|---|---|---|---|---|---|---|---|---|---|---|---|---|---|---|
| | | | | 85 | | | | | 90 | | | | | 95 | |

| Lys | Asn | Arg | Thr | Lys | Glu | Phe | Gln | Gly | Leu | Thr | Ala | Glu | Val | Lys | Ile |
|---|---|---|---|---|---|---|---|---|---|---|---|---|---|---|---|
| | | | 100 | | | | | 105 | | | | | 110 | | |

| Ile | Lys | Pro | Lys | Leu | Ile | Lys | Lys | Ile | Tyr | Thr | Leu | Thr | Pro | Val | Ile |
|---|---|---|---|---|---|---|---|---|---|---|---|---|---|---|---|
| | | | 115 | | | | | 120 | | | | | 125 | | |

| Leu | Lys | Thr | Glu | Gln | Gly | Tyr | Trp | Lys | Asn | Ser | Ile | Lys | Thr | Glu | Asp |
|---|---|---|---|---|---|---|---|---|---|---|---|---|---|---|---|
| 130 | | | | | 135 | | | | | 140 | | | | | |

| Phe | Glu | Lys | Arg | Leu | Lys | Thr | Asn | Leu | Ile | Lys | Lys | Tyr | Lys | Asp | Ile |
|---|---|---|---|---|---|---|---|---|---|---|---|---|---|---|---|
| 145 | | | | | 150 | | | | | 155 | | | | | 160 |

| Thr | Gly | Glu | Glu | Ile | Asn | Glu | Asp | Phe | Gln | Leu | Tyr | Tyr | Gln | Ile | Asn |
|---|---|---|---|---|---|---|---|---|---|---|---|---|---|---|---|
| | | | | 165 | | | | | 170 | | | | | 175 | |

| Phe | Lys | Asn | Lys | Val | Pro | Val | Ser | Arg | Lys | Tyr | Lys | Gly | Ile | Lys | Leu |
|---|---|---|---|---|---|---|---|---|---|---|---|---|---|---|---|
| | | | 180 | | | | | 185 | | | | | 190 | | |

| Leu | Gly | Asp | Met | Ile | Glu | Leu | Glu | Ile | Ala | Glu | Asn | Asp | Asn | Ala | Gln |
|---|---|---|---|---|---|---|---|---|---|---|---|---|---|---|---|
| | | | 195 | | | | | 200 | | | | | 205 | | |

| Lys | Leu | Ala | Phe | Leu | Ala | Ile | Gly | Ser | Gly | Leu | Leu | Glu | Met | Asn | Ala |
|---|---|---|---|---|---|---|---|---|---|---|---|---|---|---|---|
| 210 | | | | | 215 | | | | | 220 | | | | | |

| Arg | Gly | Phe | Gly | Phe | Val | Asn | Tyr | Ile | Tyr | Tyr |
|---|---|---|---|---|---|---|---|---|---|---|
| 225 | | | | | 230 | | | | | 235 |

```
<210> SEQ ID NO 160
<211> LENGTH: 369
<212> TYPE: PRT
<213> ORGANISM: Lyngbya sp.

<400> SEQUENCE: 160
```

| Met | Lys | Arg | Ser | Phe | Lys | Lys | Asn | Thr | Ser | Leu | Ser | Trp | Ser | Ala | Asp |
|---|---|---|---|---|---|---|---|---|---|---|---|---|---|---|---|
| 1 | | | | 5 | | | | | 10 | | | | | 15 | |

| Thr | Glu | Leu | Val | Gly | Leu | Val | Leu | Ala | Leu | Arg | Pro | Thr | Gly | Ala | Asp |
|---|---|---|---|---|---|---|---|---|---|---|---|---|---|---|---|
| | | | 20 | | | | | 25 | | | | | 30 | | |

| Leu | Leu | Tyr | Pro | Gln | Tyr | Thr | Ile | Gly | Leu | His | Ala | Trp | Phe | Leu | Asp |
|---|---|---|---|---|---|---|---|---|---|---|---|---|---|---|---|
| | | | 35 | | | | | 40 | | | | | 45 | | |

| Gln | Val | Arg | Gln | Thr | Ser | Pro | Asp | Leu | Ser | Ala | Tyr | Leu | His | Asp | Gly |
|---|---|---|---|---|---|---|---|---|---|---|---|---|---|---|---|
| | 50 | | | | | 55 | | | | | 60 | | | | |

| Glu | Ser | Glu | Lys | Pro | Phe | Thr | Ile | Ser | Gly | Leu | Glu | Gly | Ala | Leu | Lys |
|---|---|---|---|---|---|---|---|---|---|---|---|---|---|---|---|
| 65 | | | | | 70 | | | | | 75 | | | | | 80 |

| Leu | Ser | Gly | Lys | His | Leu | Gln | Leu | Gln | Pro | Glu | Gln | Thr | Tyr | Phe | Trp |
|---|---|---|---|---|---|---|---|---|---|---|---|---|---|---|---|
| | | | | 85 | | | | | 90 | | | | | 95 | |

| Ser | Ile | Thr | Ala | Leu | Ser | Lys | Pro | Val | Val | Gln | Trp | Leu | Val | Glu | Trp |
|---|---|---|---|---|---|---|---|---|---|---|---|---|---|---|---|
| | | | 100 | | | | | 105 | | | | | 110 | | |

Val Lys Cys Leu Pro Thr Gln Val Glu Leu Arg Asn Ala Pro Leu Thr
            115                 120                 125

Ile Gln Ser Cys Gln Met Ala Leu Ala Pro Thr Thr Tyr Arg Gln Leu
            130                 135                 140

Phe Asp Ala Pro Thr Pro Lys Pro Ala Lys Val Asn Leu Ser Phe Met
145                 150                 155                 160

Ser Pro Thr Ser Phe Arg Arg Lys Gly His His Phe Pro Leu Pro Leu
            165                 170                 175

Pro Thr Asn Leu Phe His Ser Tyr Leu Arg Arg Trp Asn Asp Phe Ser
            180                 185                 190

Asn Leu Pro Val Glu Gln Glu Ser Phe Leu Asp Trp Val Asp Glu Ser
            195                 200                 205

Val Ile Ile Gln Arg His Gln Ile Ala Ser Thr Lys Val Ala Ala Gly
            210                 215                 220

Lys Arg Gly Met Val Thr Gly Phe Thr Gly Ala Ile Glu Leu Ser Leu
225                 230                 235                 240

Ser Lys Lys Ser Ser Leu Ala Ser Thr Gln Asn Gln Leu Phe Tyr
            245                 250                 255

Ala Leu Gly Arg Phe Ala Pro Tyr Cys Gly Thr Gly His Lys Thr Thr
            260                 265                 270

Phe Gly Leu Gly Gln Thr Arg Phe Glu Trp Gln Ile Glu Glu Thr Glu
            275                 280                 285

Met Ile Pro Thr Ser Gln Gln Leu Gly Glu Arg Ile Ala Glu Leu
            290                 295                 300

Ala Glu Gln Phe Thr Ile Gln Arg Lys Arg Thr Gly Gly Thr Arg Thr
305                 310                 315                 320

Gln Lys Ile Ala Glu Thr Trp Ala Thr Ile Leu Ala Arg Arg Glu Asp
            325                 330                 335

Gly Glu Ser Leu Gln Ala Ile Ala Val Asp Leu Glu Met Pro Tyr Glu
            340                 345                 350

Thr Val Lys Thr Tyr Ala Lys Leu Ala Arg Arg Ala Leu Arg Gln Pro
            355                 360                 365

Asp

<210> SEQ ID NO 161
<211> LENGTH: 290
<212> TYPE: PRT
<213> ORGANISM: Lyngbya sp.

<400> SEQUENCE: 161

Met Pro Tyr Ser Leu Val Leu Asn Leu Ile Pro Leu Ser Ser Ile Ser
1               5                   10                  15

Pro Thr Tyr Leu Ser Gly Arg His Leu His Ala Leu Phe Leu Thr Leu
            20                  25                  30

Val Ser Ser Val Asp Lys Gln Leu Gly Asp Tyr Leu His Glu Pro Lys
            35                  40                  45

Thr Glu Lys Ser Phe Thr Leu Ser Pro Leu Gln Thr Cys Ser Lys His
        50                  55                  60

Arg Arg Val Glu Gln Thr Leu Gln Trp Glu His Ser Gln Pro Ile Ser
65                  70                  75                  80

Val Gly Thr Pro Cys Trp Trp Arg Ile Ser Leu Leu Asp Glu Gly Leu
            85                  90                  95

Phe Ser Lys Leu Thr His Leu Trp Leu Asn Leu Asn Pro Asp Gln Pro
            100                 105                 110

```
Trp His Leu Gly Ser Ala Asn Leu Lys Ile Thr Ser Val Leu Ala Thr
            115                 120                 125

Pro Gln Ser Thr Gln Pro Trp Ala Asn Thr Cys Ser Tyr Ser Gln Leu
        130                 135                 140

Tyr Gln Gln Ala Ser Asn Ser Asp Arg Ser Met Thr Leu Ile Phe Cys
145                 150                 155                 160

Thr Pro Thr Ala Phe Arg Gln Gly Lys Phe Asp Thr Ser Leu Pro Thr
                165                 170                 175

Ala Glu Ile Ile Phe Asn Ser Leu Leu Asn Arg Trp Asn Lys Tyr Ser
            180                 185                 190

Gly Ile Glu Phe Lys Gln Leu Pro Leu Asn Ser Ile Phe Pro Ser Phe
        195                 200                 205

Phe Asn Ile Lys Thr Glu Met Val Ala Asp Ser Arg Ser Lys Phe Ile
210                 215                 220

Gly Cys Val Gly Lys Val Asn Tyr Arg Leu Leu Gly Asn Val Glu Pro
225                 230                 235                 240

Glu Ile Ile Gln Gln Val Asn Thr Leu Ala Asp Phe Ala Phe Tyr Cys
                245                 250                 255

Gly Val Gly Arg Lys Thr Pro Met Gly Met Gly Met Leu Arg Arg Leu
            260                 265                 270

Gln Lys Glu Gly Thr Gly Asp Arg Gly Gln Gly Thr Glu Ser Leu Arg
        275                 280                 285

Arg Leu
    290

<210> SEQ ID NO 162
<211> LENGTH: 278
<212> TYPE: PRT
<213> ORGANISM: Microcystis aeruginosa

<400> SEQUENCE: 162

Met Pro Tyr Ser Leu Val Leu Asn Leu Thr Pro Arg Ser Pro Ile Tyr
1               5                   10                  15

Pro Asn Phe Leu Thr Gly Arg His Leu His Ala Leu Phe Leu Thr Leu
            20                  25                  30

Val Ser Ser Val Asp Gln Glu Leu Gly Lys Ile Leu His Ala Ala Glu
        35                  40                  45

Ala Asp Lys Ala Phe Thr Leu Ser Pro Leu Gln Ile Gln Ser Arg Gly
    50                  55                  60

Lys Ile Thr Ile Asn Ser Pro Gln Trp Arg His Glu Arg Glu Ile Ala
65                  70                  75                  80

Ser Glu Thr Pro Cys Trp Trp Arg Ile Ser Leu Leu Asp Asp Arg Leu
                85                  90                  95

Phe Gly Lys Leu Thr Ser Leu Trp Leu Asn Leu Asn Pro Lys Gln Pro
            100                 105                 110

Trp His Leu Gly Ser Ala Asp Leu Val Ile Thr Ser Val Leu Ala Thr
            115                 120                 125

Pro Gln Ser Val Gln Pro Trp Ala Asn Ser Cys Thr Tyr Gln Tyr Leu
        130                 135                 140

Tyr Glu Asn Ala Ser Glu Thr Asn Arg Glu Phe Asp Phe Leu Phe Ala
145                 150                 155                 160

Thr Pro Val Thr Phe Arg Gln Gly Lys Phe Asp Ser Ala Leu Pro Thr
                165                 170                 175

Arg Glu Leu Val Phe Asn Ser Leu Leu Asn Arg Trp Asn Arg Tyr Ser
```

```
                    180                 185                 190
Gly Ile Pro Phe Asp Ser Ile Ala Leu Glu Ser Ile Phe Pro Ser Phe
            195                 200                 205

Phe Asp Ile Gln Thr Lys Leu Ala Asp Glu Ala Tyr Lys Asn Gln Ser
        210                 215                 220

Phe Gly Cys Val Gly Glu Ile His Tyr Arg Leu Leu Gly Glu Val Glu
225                 230                 235                 240

Pro Ala Lys Ile Lys Ala Ile Asn Val Leu Ala Asp Phe Ala Leu Tyr
                245                 250                 255

Ala Gly Val Gly Arg Lys Thr Thr Met Gly Met Gly Met Thr Arg Arg
            260                 265                 270

Ile Ala Lys Glu Lys Arg
            275

<210> SEQ ID NO 163
<211> LENGTH: 277
<212> TYPE: PRT
<213> ORGANISM: Microcystis aeruginosa

<400> SEQUENCE: 163

Met Pro Tyr Ser Leu Val Leu Asn Leu Thr Pro Arg Ser Pro Ile Tyr
1               5                   10                  15

Pro Asn Phe Leu Thr Gly Arg His Leu His Ala Leu Phe Leu Thr Leu
            20                  25                  30

Val Ser Ser Val Asp Gln Glu Leu Gly Lys Ile Leu His Thr Ala Glu
        35                  40                  45

Ala Asp Lys Ala Phe Thr Leu Ser Pro Leu Gln Met Gln Ser Gly Gly
    50                  55                  60

Lys Thr Ile Asn Ser Pro Gln Trp Arg Tyr Glu Arg Pro Ile Ala Pro
65                  70                  75                  80

Glu Thr Pro Cys Trp Trp Arg Ile Ser Leu Leu Asp Asp Arg Leu Phe
                85                  90                  95

Gly Lys Leu Thr Pro Leu Trp Leu Asn Leu Asn Pro Lys His Pro Trp
            100                 105                 110

His Leu Gly Ser Ala Asp Leu Val Ile Thr Ser Val Leu Ala Thr Pro
        115                 120                 125

Gln Ser Val Gln Pro Trp Ala Asn Ser Cys Thr Tyr Gln Tyr Leu Tyr
    130                 135                 140

Glu Asn Ala Ser Glu Thr Asn Arg Glu Phe Asp Phe Leu Phe Ala Thr
145                 150                 155                 160

Pro Val Thr Phe Arg Gln Gly Lys Phe Asp Ser Ala Leu Pro Thr Arg
                165                 170                 175

Glu Leu Val Phe Asn Ser Leu Leu Asn Arg Trp Asn Arg Tyr Ser Ala
            180                 185                 190

Ile Pro Phe Asp Ser Ile Val Leu Glu Ser Ile Phe Pro Ser Phe Phe
        195                 200                 205

Asp Ile Gln Thr Lys Leu Ala Asp Glu Ala Tyr Lys Asn Gln Ser Phe
    210                 215                 220

Gly Cys Val Gly Glu Ile His Tyr Arg Leu Leu Gly Glu Val Glu Pro
225                 230                 235                 240

Ala Lys Ile Lys Ala Ile Asn Val Leu Ala Asp Phe Ala Leu Tyr Ala
                245                 250                 255

Gly Val Gly Arg Lys Thr Thr Met Gly Met Gly Met Thr Arg Arg Ile
            260                 265                 270
```

Ala Lys Glu Lys Arg
        275

<210> SEQ ID NO 164
<211> LENGTH: 367
<212> TYPE: PRT
<213> ORGANISM: Synechocystis sp.

<400> SEQUENCE: 164

Met Val Asp Leu Lys Ser Leu Ala Gly Ala Glu Met Val Gly Leu Arg
1               5                   10                  15

Trp Gln Leu Arg Phe Asp Arg Pro Cys Arg Leu Glu Ser His Tyr Val
            20                  25                  30

Lys Gly Leu His Ala Trp Phe Leu His Gln Val Gln Ala Ile Asp Pro
        35                  40                  45

Asp Val Ser Ala Trp Leu His Asp Gly Gln Gly Glu Lys Pro Phe Thr
    50                  55                  60

Ile Ser Arg Leu Ile Gly Pro Thr Leu Trp Gln Glu Gly His Trp His
65                  70                  75                  80

Trp Gln Ile Asn Lys Thr Tyr His Trp Gln Leu Asn Leu Leu Ser Gly
                85                  90                  95

Ala Leu Ile Glu Ala Leu Gln Pro Trp Leu Ala Arg Leu Pro Asn Lys
            100                 105                 110

Ile Val Leu Ala Arg Gln Thr Leu Trp Val Glu Ala Val Asp Cys Tyr
        115                 120                 125

Leu Ala Pro His Asn Tyr Gln Gln Leu Trp Pro Gln Gly Ala Leu Pro
    130                 135                 140

Arg Arg Gln Glu Phe Thr Phe Thr Ser Pro Thr Ser Phe Arg Arg Gln
145                 150                 155                 160

Gly Asn His Tyr Pro Leu Pro Glu Pro Arg Asn Val Leu Gln Ser Tyr
                165                 170                 175

Leu Arg Arg Trp Asn Asp Phe Ser Gly Leu Ala Phe Glu Pro Glu Pro
            180                 185                 190

Phe Leu Asp Tyr Trp Val Pro Gln Asn Val Val Ile Asp Arg His Trp
        195                 200                 205

Leu Glu Ser Val Lys Thr Thr Ala Gly Lys Gln Gly Ser Val Val Gly
    210                 215                 220

Phe Val Gly Ala Val Ser Leu Val Leu Thr Pro Gln Ala Arg Asn Asp
225                 230                 235                 240

Gly Asp Asp Tyr Gly Arg Leu Phe His Ala Leu Cys Arg Tyr Gly Pro
                245                 250                 255

Tyr Cys Gly Thr Gly His Lys Thr Thr Phe Gly Leu Gly Gln Thr Met
            260                 265                 270

Ala Gly Trp Ala Thr Pro Asp Leu Lys Thr Phe Ala Cys Leu Gln Glu
        275                 280                 285

Asp Leu Gln Thr Gln Val Leu Thr Gln Arg Ile Asp Gln Cys Ala Ser
    290                 295                 300

Leu Leu Leu Ala Gln Arg Gln Arg Thr Gly Gly Gln Arg Ala Gln Glu
305                 310                 315                 320

Ile Cys His Thr Leu Ala Thr Ile Phe Val Arg Arg Glu Gln Gly Glu
                325                 330                 335

Ser Leu Gln Glu Ile Ala Leu Asp Leu Gln Leu Pro Tyr Glu Thr Ala
            340                 345                 350

Arg Thr Tyr Ser Lys Arg Ala Lys Arg Ala Leu Ala Asn Val Gln
        355                 360                 365

<210> SEQ ID NO 165
<211> LENGTH: 262
<212> TYPE: PRT
<213> ORGANISM: Synechocystis sp.

<400> SEQUENCE: 165

Met Phe Asp Asp Arg Tyr Ser Leu Tyr Ser Val Val Ile Glu Leu Gly
1               5                   10                  15

Ala Ala Lys Lys Gly Phe Pro Thr Gly Ile Leu Gly Arg Ala Leu His
            20                  25                  30

Ser Gln Val Leu Glu Trp Leu Lys Ile Gly Glu Pro Ser Leu Ala Glu
        35                  40                  45

Glu Leu His Gln Ser Gln Ile Ser Pro Phe Ser Ile Ser Pro Leu Ile
    50                  55                  60

Gly Lys Arg Arg Ser Lys Leu Thr Glu Glu Gly Asp Arg Phe Phe Phe
65                  70                  75                  80

Arg Ile Ser Leu Leu Asn Gly Ser Leu Leu Gln Pro Leu Leu Lys Gly
                85                  90                  95

Leu Glu Gln Gln Asp Lys Gln Ile Val Met Leu Asp Lys Phe Ala Phe
            100                 105                 110

Arg Leu Cys His Ile His Ile Leu Pro Gly Ser His Ser Leu Ala Arg
        115                 120                 125

Ala Ser Ser Tyr Ala Leu Thr Thr Gln Ala Pro Thr Ser Ser Lys Ile
    130                 135                 140

Thr Leu Lys Phe His Ser Ala Thr Ser Phe Lys Ile Asp Arg Asn Thr
145                 150                 155                 160

Ile Gln Pro Phe Pro Leu Gly Asp Ser Val Phe Asn Ser Leu Leu Arg
                165                 170                 175

Arg Trp Asn His Phe Ala Pro Glu Glu Leu Tyr Phe Pro Ser Val Ser
            180                 185                 190

Trp Gln Ile Pro Val Ala Ala Phe Glu Leu Lys Thr Tyr Ser Val Gln
        195                 200                 205

Leu Lys Lys Ser Glu Ile Gly Ser Glu Gly Trp Val Thr Tyr Leu Phe
    210                 215                 220

Pro Asp Gln Glu Gln Ala Lys Ile Ala Ser Val Leu Ser Gln Phe Ala
225                 230                 235                 240

Phe Phe Ala Gly Val Gly Arg Lys Thr Ser Met Gly Met Gly Gln Val
                245                 250                 255

Ser Val Asn Asn His Gly
            260

<210> SEQ ID NO 166
<211> LENGTH: 393
<212> TYPE: PRT
<213> ORGANISM: Synechococcus sp.

<400> SEQUENCE: 166

Met Leu Ile Val Ala Val Asp Trp Glu Trp Ala Val Pro Met Leu Ser
1               5                   10                  15

Phe Ser Glu Pro Ser Ala Asp Arg Glu Ala Asn Gly Lys Trp Pro Thr
            20                  25                  30

Gly Ser Glu Leu Val Gly Ile Thr Leu Glu Val Gln Ala Pro Arg Ser
        35                  40                  45

Tyr Leu Leu Asp Pro His Tyr Ala Lys Gly Leu His Ala Trp Phe Leu
    50                  55                  60

Ser Gln Val Gln Glu Thr Asp Pro Gln Leu Ser Ala Tyr Leu His Asp
65                  70                  75                  80

Gly Glu Ser Glu Lys Pro Phe Thr Leu Ser Arg Leu Met Gly Pro Phe
                85                  90                  95

Arg Glu Gln Gly Gly Arg Pro Leu Ile Pro Pro His Leu Pro Phe Arg
            100                 105                 110

Trp Trp Ile Thr Gly Leu Asn Pro Pro Val Val Glu Trp Leu Arg Gly
        115                 120                 125

Trp Cys Gln Arg Leu Pro Thr Trp Leu Glu Leu Arg Gly Ser Pro Leu
    130                 135                 140

Gln Ile Leu Gly Trp Gln Ile Ser Ile Pro Pro Arg Thr Tyr Arg Gln
145                 150                 155                 160

Leu Leu Glu Gln Pro Leu Ser Pro Arg Ser Trp Ser Leu Ser Phe Val
                165                 170                 175

Ser Pro Thr Ser Phe Arg His Arg Gly His His Leu Pro Leu Pro Ile
            180                 185                 190

Pro Arg Asn Leu Phe His Ser Tyr Leu Arg Arg Trp Asn Asp Phe Ser
        195                 200                 205

Gly Leu Pro Ile Glu Ala Glu Pro Phe Leu Asp Trp Val Asp Gly Glu
    210                 215                 220

Val Ile Ile Gln Arg His Arg Leu Glu Ser Val Lys Thr Thr Ala Gly
225                 230                 235                 240

Arg Gln Gly Ser Val Thr Gly Phe Ile Gly Cys Val Gln Leu Ala Val
                245                 250                 255

Ser Ser Arg Ala Pro Glu Leu Leu Gln Gln Leu Gln Ala Leu Ile
            260                 265                 270

His Leu Ala Pro Tyr Cys Gly Thr Gly His Lys Thr Pro Phe Gly Leu
        275                 280                 285

Gly Gln Thr Arg Leu Gly Trp Leu Ala Glu Leu Pro Ala Ser Pro
    290                 295                 300

Val Pro Ser Arg Glu Glu Gln Val Ala Gln Arg Ile Glu Glu Leu Ser
305                 310                 315                 320

Ala Leu Phe Leu Ser Gln Arg Gln Arg Gln Gly Gly Ser Arg Ala Glu
                325                 330                 335

Lys Thr Ala Gln Leu Trp Ala Thr Ile Leu Ala Arg Arg Glu Gly Gly
            340                 345                 350

Glu Ser Leu Gln Gln Ile Ala Ala Asp Leu Glu Met Pro Tyr Glu Thr
        355                 360                 365

Val Lys Thr Tyr Ala Lys Leu Ala Arg Arg Ser Leu Gln Ser Gly Ser
    370                 375                 380

Gln Asp Tyr Ser Ser Ser Ser Leu Pro
385                 390

<210> SEQ ID NO 167
<211> LENGTH: 383
<212> TYPE: PRT
<213> ORGANISM: Synechococcus sp.

<400> SEQUENCE: 167

Met Leu Thr Lys Leu Ser Phe Ser Glu Pro Pro Val Ala Gly Ala Glu
1               5                   10                  15

Asn Ser Lys Trp Pro Ala Gly Ser Glu Leu Val Gly Ile Ala Leu Glu
            20                  25                  30

Val Gln Ala Pro Gln Pro Tyr Leu Leu Asp Pro His Tyr Ala Lys Gly

```
                35                  40                  45
Leu His Ala Trp Phe Leu Ser Gln Val Gln Glu Thr Asp Pro Gln Leu
 50                  55                  60

Ser Ala Tyr Leu His Asp Gly Glu Ser Glu Lys Pro Phe Thr Leu Ser
 65                  70                  75                  80

Arg Leu Met Gly Pro Phe Arg Glu Gln Gly Arg Leu Leu Ile Pro
                 85                  90                  95

Pro Gln Ile Pro Phe Arg Trp Ser Ile Thr Ala Leu Asn Pro Gln Val
                100                 105                 110

Val Glu Trp Leu Arg Glu Trp Cys Arg Arg Leu Pro Pro Trp Leu Glu
            115                 120                 125

Leu Arg Gly Ser Pro Leu Gln Ile Leu Gly Trp Lys Val Ser Ala Pro
        130                 135                 140

Pro Arg Thr Tyr Arg Gln Leu Leu Glu Gln Pro Leu Ser Pro Arg Ser
145                 150                 155                 160

Trp Ser Leu Ser Phe Val Ser Pro Thr Ser Phe Arg His Arg Gly His
                165                 170                 175

His Leu Pro Leu Pro Ile Pro Arg Asn Leu Phe His Ser Tyr Leu Arg
            180                 185                 190

Arg Trp Asn Asp Phe Ser Gly Leu Pro Ile Glu Ala Glu Pro Phe Leu
        195                 200                 205

Asp Trp Val Asp Gly Glu Val Ile Ile Gln Arg His Arg Leu Glu Ser
210                 215                 220

Val Lys Thr Thr Ala Gly Arg Gln Gly Ser Val Thr Gly Phe Ile Gly
225                 230                 235                 240

Cys Val Gln Leu Ala Val Ser Ser Arg Ala Pro Glu Leu Leu Gln Gln
                245                 250                 255

Gln Leu Gln Ala Leu Ile His Leu Ala Pro Tyr Cys Gly Thr Gly His
            260                 265                 270

Lys Thr Pro Phe Gly Leu Gly Gln Thr Arg Leu Gly Trp Leu Ala Glu
        275                 280                 285

Glu Leu Pro Ala Thr Pro Val Leu Cys Arg Glu Gln Leu Ala Arg
290                 295                 300

Arg Ile Glu Glu Leu Ser Ala Leu Phe Leu Ser Gln Arg Gln Arg Gln
305                 310                 315                 320

Gly Gly Ser Arg Ala Glu Lys Thr Ala Gln Leu Trp Ala Thr Ile Leu
                325                 330                 335

Ala Arg Arg Glu Gly Gly Glu Ser Leu Gln Gln Ile Ala Ala Asp Leu
            340                 345                 350

Glu Met Pro Tyr Glu Thr Val Lys Thr Tyr Ala Lys Leu Ala Arg Arg
        355                 360                 365

Ser Leu Gln Ser Gly Ser Gln Asp Tyr Ser Ser Ser Leu Pro
    370                 375                 380

<210> SEQ ID NO 168
<211> LENGTH: 381
<212> TYPE: PRT
<213> ORGANISM: Nodularia spumigena

<400> SEQUENCE: 168

Met Val Arg Thr Ala Lys Pro Thr Asn Arg Gln Gln Lys Pro Lys Ser
  1               5                  10                  15

Ser Pro Thr Ala Thr Leu Pro Thr Trp Ala Asp Asn Thr Glu Leu Val
                 20                  25                  30
```

Gly Leu Glu Phe Asp Leu Glu Ala Leu Thr Thr Ser Ser Leu Tyr Ser
            35                   40                  45

Gln Tyr Thr Ile Ala Leu His Ala Trp Phe Leu Asp Gln Val Arg Gln
 50                      55                  60

Leu Asp Pro Asp Leu Ser Ala Tyr Leu His Asp Gly Glu Ser Glu Lys
 65                  70                  75                  80

Pro Phe Asn Ile Ser Ala Leu Glu Ser Gln Leu Leu Pro Thr Gly Lys
                 85                  90                  95

Gln Leu Gln Leu Glu Ala Asn Gln Ile Leu His Trp Gln Val Asn Ala
            100                 105                 110

Leu Ser Ala Lys Val Ala Glu Phe Leu Gln Leu Trp Leu Thr Gln Leu
        115                 120                 125

Pro Gln Thr Leu Asn Leu Arg Gly Ala Thr Leu Gln Ile Lys Gln Val
130                 135                 140

Arg Ile Ala His Pro Pro Thr Thr Tyr Ala Gln Leu Leu Gln Pro Pro
145                 150                 155                 160

Ala Lys Tyr Ser Gln Val Asn Leu Ser Phe Ile Ser Pro Thr Ser Phe
                165                 170                 175

Arg Arg Lys Gly His His Phe Pro Leu Pro Val Pro Val Asn Leu Phe
            180                 185                 190

His Ser Tyr Leu Arg Arg Trp Asn Asp Phe Ser Gln Ile Pro Ile Ser
        195                 200                 205

Gln Ala Asp Phe Leu Asp Trp Ile Asp Glu Asn Val Ile Ile His Gln
    210                 215                 220

His Arg Leu Glu Ser Val Lys Val Ala Ala Gly Lys Arg Gly Ser Val
225                 230                 235                 240

Thr Gly Phe Thr Gly Ala Ile Ser Cys Gly Leu Ser Lys Ala Ala Leu
                245                 250                 255

Ala Asn Thr Glu Phe Thr Gln Leu Phe Tyr Ala Leu Val Lys Leu Ala
            260                 265                 270

Pro Tyr Cys Gly Thr Gly His Lys Thr Thr Phe Gly Leu Gly Gln Thr
        275                 280                 285

Ser Leu Ser Trp Val Glu Pro Glu Ala Ser Ser Pro Thr Gln Leu Leu
    290                 295                 300

Thr Asn Leu Leu Gly Glu Arg Ile Glu Glu Leu Thr Ala Ile Phe Thr
305                 310                 315                 320

Ala Gln Arg Lys Arg Ser Gly Gly Asp Arg Thr Asp Lys Ile Ala Ala
                325                 330                 335

Thr Trp Ala Thr Ile Leu Ala Arg Arg Glu Met Gly Glu Ser Leu Lys
            340                 345                 350

Leu Ile Ala Glu Asp Leu Glu Met Pro Val Asp Thr Val Lys Thr Tyr
        355                 360                 365

Thr Lys Leu Ala Arg Arg Ser Leu Lys Asp Ala Asp Leu
370                 375                 380

<210> SEQ ID NO 169
<211> LENGTH: 290
<212> TYPE: PRT
<213> ORGANISM: Anabaena variabilis

<400> SEQUENCE: 169

Met Pro His Ser Leu Val Leu Asn Leu Leu Pro Gln Ser Pro Ile Pro
 1               5                  10                  15

Pro Gln Tyr Ile Thr Gly Arg His Leu His Ala Leu Phe Leu Thr Leu
            20                  25                  30

Val Ser Ser Val Asp Ser Thr Leu Gly Asp Arg Leu His Asp Ser Thr
            35                  40                  45

Ala Asp Lys Ala Phe Thr Leu Ser Pro Leu Gln Ile Lys Gly Glu Glu
 50                  55                  60

Arg Gly Arg Tyr Lys Ser Lys Ile Pro His Gly Gln Ser Leu Gln Tyr
 65                  70                  75                  80

Phe His Gln Gln Ala Ile Pro Ala Gly Thr Pro Cys Trp Trp Arg Ile
                 85                  90                  95

Ser Leu Leu Asp Asp Thr Leu Phe Ser Gln Leu Thr Gln Leu Trp Leu
                100                 105                 110

Asn Leu Asn Pro Ser His Pro Trp His Leu Gly Pro Ala Asn Leu Tyr
                115                 120                 125

Ile Thr Ser Ile Gln Gly Thr Pro Gln Ser Thr Gln Pro Trp Ala Asn
130                 135                 140

Ala Thr Thr Tyr Ala Gln Leu Tyr Glu Gln Ala Gly Glu Ser Asn Asp
145                 150                 155                 160

Val Arg Ser Leu Val Asn Asn Arg Thr Leu Asn Phe Thr Phe Thr Thr
                165                 170                 175

Pro Thr Ala Phe Arg Gln Gly Lys Phe Asp Thr Thr Leu Pro Thr Arg
                180                 185                 190

Glu Cys Val Phe Asn Ser Leu Leu Ser Arg Trp Asn Lys Tyr Ser Gly
                195                 200                 205

Ile Glu Phe Ser Glu Ile Ala Ile Glu Ser Ile Phe Pro Ser Phe Leu
                210                 215                 220

Asn Ile His Thr Glu Ile Leu Ala Asp Ser Ser Lys Phe Ile Gly
225                 230                 235                 240

Ile Leu Gly Glu Ile Asn Tyr Arg Ile Leu Gly Asp Ile Glu Pro Ile
                245                 250                 255

Gln Ile Lys Gln Ile Asn Ala Leu Ala Asp Phe Ala Met Tyr Ala Gly
                260                 265                 270

Ile Gly Arg Lys Thr Thr Met Gly Met Gly Met Ile Arg Arg Leu Tyr
                275                 280                 285

Ser Ala
    290

<210> SEQ ID NO 170
<211> LENGTH: 281
<212> TYPE: PRT
<213> ORGANISM: Nostoc punctiforme

<400> SEQUENCE: 170

Met Pro His Ser Leu Val Leu Asn Leu Leu Pro Gln Ser Pro Ile Pro
1               5                   10                  15

Pro Gln Tyr Leu Thr Gly Arg His Leu His Ala Leu Phe Leu Thr Leu
                20                  25                  30

Val Ser Ser Val Asp Ser Thr Leu Gly Asp Arg Leu His Asp Ser Thr
            35                  40                  45

Ala Asp Lys Ala Phe Thr Leu Ser Pro Leu Gln Ile Ser Asn Thr Asn
 50                  55                  60

Ser Pro Leu Leu Lys Gly Gly Lys Gly Ser Lys Leu Gln Tyr Ser
 65                  70                  75                  80

His Gln Gln Pro Ile Pro Ala Gly Thr Pro Cys Trp Trp Arg Ile Ser
                 85                  90                  95

Leu Leu Asp Asp Thr Leu Phe Gly Lys Leu Thr Gln Leu Trp Leu Asn

```
              100                 105                 110
Leu Asn Pro Asn Arg Pro Trp His Leu Gly Pro Ala Asp Leu Tyr Ile
            115                 120                 125

Thr Ser Ile Gln Gly Thr Pro Gln Ser Ile Gln Pro Trp Ala Asn Ala
        130                 135                 140

Asn Thr Tyr Ala Gln Leu Tyr Glu Glu Ala Ser Asp Gly Asn Ser Ser
145                 150                 155                 160

Ile Asn Leu Thr Phe Ser Thr Pro Thr Ala Phe Arg Gln Gly Gln Tyr
                165                 170                 175

Asp Thr Thr Leu Pro Thr Arg Glu Ser Val Phe Asn Ser Leu Leu Ser
            180                 185                 190

Arg Trp Asn Lys Tyr Ser Gly Ile Glu Phe Ser Gln Ile Ala Ile Glu
        195                 200                 205

Ser Ile Phe Pro Ser Phe Val Asn Ile His Thr Glu Ile Leu Ala Asp
        210                 215                 220

Ser Arg Ser Lys Phe Ile Gly Ile Gly Glu Val Thr Tyr Lys Ile
225                 230                 235                 240

Leu Gly Ala Val Glu Pro Ile Gln Ile Lys Gln Ile Asn Ala Leu Ala
                245                 250                 255

Asp Phe Ala Leu Tyr Thr Gly Val Gly Arg Lys Thr Met Gly Met
                260                 265                 270

Gly Met Thr Arg Gln Met Tyr Ser Pro
            275                 280

<210> SEQ ID NO 171
<211> LENGTH: 290
<212> TYPE: PRT
<213> ORGANISM: Anabaena sp.

<400> SEQUENCE: 171

Met Pro His Ser Leu Val Leu Asn Leu Leu Pro Gln Ser Pro Ile Pro
1               5                   10                  15

Pro Gln Tyr Leu Thr Gly Arg His Leu His Ala Leu Phe Leu Thr Leu
            20                  25                  30

Val Ser Ser Val Asp Ser Thr Leu Gly Asp Arg Leu His Asp Ser Thr
        35                  40                  45

Ala Asp Lys Ala Phe Thr Leu Ser Pro Leu Gln Ile Gln Gly Glu Glu
    50                  55                  60

Arg Gly Arg Tyr Lys Ser Lys Ile Pro Asn Ser Tyr Ser Leu Gln Tyr
65                  70                  75                  80

Leu His Gln Gln Ala Ile Pro Ala Gly Thr Pro Cys Trp Trp Arg Ile
                85                  90                  95

Ser Leu Leu Asp Asp Thr Leu Phe Ser Gln Leu Thr Gln Leu Trp Leu
            100                 105                 110

Asn Leu Asn Pro Asn His Pro Trp His Leu Gly Pro Ala Asn Leu Tyr
        115                 120                 125

Ile Thr Ser Ile Gln Gly Thr Pro Gln Ser Thr Gln Pro Trp Ala Asn
    130                 135                 140

Ala Ile Thr Tyr Thr Gln Leu Tyr Glu Gln Ala Gly Glu Asn Asn Asp
145                 150                 155                 160

Leu Arg Ser Leu Gly Asn Asn His Thr Leu Asn Phe Thr Phe Thr Thr
                165                 170                 175

Pro Thr Ala Phe Arg Gln Gly Lys Phe Asp Thr Thr Leu Pro Thr Arg
            180                 185                 190
```

```
Glu Cys Val Phe Asn Ser Leu Leu Ser Arg Trp Asn Lys Tyr Ser Gly
            195                 200                 205

Ile Glu Phe Ser Glu Ile Ala Leu Glu Ala Ile Phe Pro Ser Phe Leu
    210                 215                 220

Asn Ile His Thr Glu Ile Leu Ala Asp Ser Arg Ser Lys Phe Ile Gly
225                 230                 235                 240

Ile Leu Gly Glu Ile Asn Tyr Arg Ile Leu Gly Asp Ile Glu Pro Ile
                245                 250                 255

Gln Ile Lys Gln Ile Asn Ala Leu Ala Asp Phe Ala Met Tyr Ala Gly
            260                 265                 270

Val Gly Arg Lys Thr Thr Met Gly Met Gly Met Ile Arg Arg Leu Tyr
    275                 280                 285

Ser Ser
    290

<210> SEQ ID NO 172
<211> LENGTH: 377
<212> TYPE: PRT
<213> ORGANISM: Anabaena sp.

<400> SEQUENCE: 172

Met Pro Arg Ala Ala Thr Thr Pro Lys Arg Lys Pro Arg Ala Lys Ser
1               5                   10                  15

Ala Pro Thr Ser Leu Val Pro Thr Trp Ala Asp Glu Thr Glu Leu Val
            20                  25                  30

Gly Leu Val Phe Asp Leu Glu Ala Thr Asp Ser Gly Ser Leu Tyr Ser
        35                  40                  45

Gln Tyr Thr Ile Gly Leu His Ala Trp Phe Leu His Gln Val Gln Gln
    50                  55                  60

Val Asp Pro Asp Leu Ser Ala Tyr Leu His Asp Gly Glu Ser Glu Lys
65                  70                  75                  80

Pro Phe Asn Ile Ser Ala Leu Glu Gly Gln Leu Leu Pro Ser Gly Lys
                85                  90                  95

Gln Leu Arg Leu Glu Ala Lys Gln Thr Tyr His Trp His Ile Asn Ala
            100                 105                 110

Leu Ser Gln Lys Val Ala Leu Phe Leu Lys Glu Trp Leu Thr Asn Leu
        115                 120                 125

Pro Lys Thr Ile Glu Leu Ser Gly Thr Pro Leu Gln Ile Lys Gln Val
    130                 135                 140

Ser Ile Ala His Ala Pro Thr Thr Tyr Ala Gln Leu Leu Gln Pro Ser
145                 150                 155                 160

Thr Gln Pro Ser Leu Val Asn Leu Ser Phe Val Ser Pro Thr Ser Phe
                165                 170                 175

Arg Arg Lys Gly His His Phe Pro Leu Pro Val Pro Glu Asn Leu Phe
            180                 185                 190

His Ser Tyr Leu Arg Arg Trp Asn Asp Phe Ser Asn Met Leu Val Asn
        195                 200                 205

Gln Glu Ser Phe Leu Glu Trp Ile Asp Glu Asn Val Ile Ile His Gln
    210                 215                 220

His Arg Leu Gln Ser Glu Lys Val Ala Ala Gly Lys Arg Gly Ser Val
225                 230                 235                 240

Thr Gly Phe Thr Gly Ala Ile Ser Leu Gly Leu Ser Arg Ala Gly Leu
                245                 250                 255

Ala Asn Ala Asp Phe Thr Lys Leu Phe Tyr Ala Leu Val Gln Leu Ser
            260                 265                 270
```

```
Pro Tyr Cys Gly Thr Gly His Lys Thr Thr Phe Gly Leu Gly Gln Thr
        275                 280                 285

Arg Leu Asp Trp Leu Glu Gln Lys Pro Thr Thr Ser Ala Gln Leu Leu
        290                 295                 300

Glu Asn Ile Leu Ala Glu Arg Ile Glu Leu Thr Glu Ile Phe Thr
305                 310                 315                 320

Ala Gln Arg Lys Arg Lys Gly Gly Asp Arg Thr Asp Lys Ile Ala Ala
                325                 330                 335

Thr Trp Ala Thr Val Leu Ala Arg Arg Asp Met Gly Asp Ser Leu Gln
                340                 345                 350

Ala Ile Ala Asp Asp Leu Glu Met Pro Leu Leu Thr Val Lys Thr Tyr
                355                 360                 365

Val Lys Leu Ala Arg Lys Ala Leu Lys
        370                 375

<210> SEQ ID NO 173
<211> LENGTH: 235
<212> TYPE: PRT
<213> ORGANISM: Campylobacter hominis

<400> SEQUENCE: 173

Met Leu Ile Tyr Glu Leu Asn Val Thr Val Lys Leu Lys Lys Ala Val
1               5                   10                  15

Lys Phe Ser Gln Ile Pro Gly Phe Leu Ser Lys Asn Ile Asn Tyr Ser
                20                  25                  30

Phe Leu Leu Asp Lys Asn Leu Lys Asn Leu His Ser Lys Asn His Ile
            35                  40                  45

Lys Pro Tyr Ser Leu Ser Phe Leu Gln Ser His Glu Gly Arg Lys Asp
        50                  55                  60

Leu Phe Asp Val Asn Glu Ile Ala Phe Phe Lys Ile Arg Ser Val Phe
65                  70                  75                  80

Pro Glu Phe Ile Glu Ser Met Lys Tyr Cys Leu Glu Asn Ser Lys Gly
                85                  90                  95

Phe Asp Phe Gln Val Leu Gly Thr Leu Thr Thr Asp Phe Ala Pro Thr
                100                 105                 110

Asn Ile Gln Ser Leu Tyr Thr Met Ser Pro Ala Val Val Thr Ile Ser
            115                 120                 125

Ile Asp Asn Lys Ser Tyr Cys Trp Thr Lys Lys Asp Ser Asp Ile Leu
        130                 135                 140

Thr Leu Lys Asn Ser Leu Glu Thr Asn Leu Lys Asn Lys Phe Ser Leu
145                 150                 155                 160

Phe Val Asn Asp Ser Val Ser Phe Asn Asp Asp Ile Ile Glu Leu Ile
                165                 170                 175

Glu Ile Lys Asn Asp Lys Pro Phe Met Phe Pro Tyr Lys Gly Gly Lys
                180                 185                 190

Ile Phe Ala Tyr Arg Tyr Lys Val Tyr Phe Ala Asn Asn Ser Tyr Ala
            195                 200                 205

Arg Glu Leu Ala Lys Ile Ala Leu Ala Leu Gly Leu Gly Glu Lys Gly
        210                 215                 220

Ser Leu Thr Phe Gly Phe Cys Glu Lys Gly Arg
225                 230                 235

<210> SEQ ID NO 174
<211> LENGTH: 238
<212> TYPE: PRT
```

<213> ORGANISM: Campylobacter fetus

<400> SEQUENCE: 174

```
Met Lys Ile Tyr Gln Leu Lys Val Phe Leu Lys Leu Asn Gln Asn Val
1               5                   10                  15

Asp Phe Val Asn Ser Pro Glu Phe Leu Ser Ser Asn Leu His Lys Ser
            20                  25                  30

Met Leu Gly Asp Glu Ala Leu Arg Ser Ile His Met Gln Arg Tyr Leu
        35                  40                  45

Lys Pro Tyr Ser Ile Gly Phe Leu Tyr Gly Met Lys Gly Lys Lys Asp
    50                  55                  60

Gly Phe Thr Ser Gly Glu Asp Met Tyr Phe Tyr Val Arg Ser Ile Asp
65                  70                  75                  80

Glu Ser Phe Ile Ser Lys Leu Arg Ile Cys Leu Glu Asn Ser Lys Asn
                85                  90                  95

Leu Gly Phe Asn Val Tyr Ala Ser Lys Leu Glu Val Leu Asp Ser Lys
            100                 105                 110

Arg Ile Asp Cys Leu Tyr Thr Met Ser Pro Ala Thr Val Val Leu Lys
        115                 120                 125

Glu Gly Asp Lys Thr Ile Pro Trp Arg Arg Glu Asn Ser Asp Ile Ala
    130                 135                 140

Ala Leu Lys Asp Ala Leu Ile Leu Asn Leu Lys Asn Lys Tyr Glu Tyr
145                 150                 155                 160

Phe Leu Asp Lys Lys Ile Glu Ile Thr Asp Asp Ile Ile Glu Leu Ile
                165                 170                 175

Glu Ile Lys Thr Asn Arg Ala Phe Ala Phe Lys Tyr Lys Asn Gly Lys
            180                 185                 190

Ile Tyr Ala Tyr Arg Tyr Gln Ile His Phe Ser Gly Asn Lys Thr Ala
        195                 200                 205

Gln Glu Phe Ala Asn Ile Ala Met Ile Leu Gly Val Gly Val Lys Asn
    210                 215                 220

Thr Leu Gly Phe Gly Phe Cys Met Arg Ser Lys Asn Val Val
225                 230                 235
```

<210> SEQ ID NO 175
<211> LENGTH: 369
<212> TYPE: PRT
<213> ORGANISM: Lyngbya sp.

<400> SEQUENCE: 175

```
Met Lys Arg Ser Phe Lys Asn Thr Ser Leu Ser Trp Ser Ala Asp
1               5                   10                  15

Thr Glu Leu Val Gly Leu Val Leu Ala Leu Arg Pro Thr Gly Ala Asp
            20                  25                  30

Leu Leu Tyr Pro Gln Tyr Thr Ile Gly Leu His Ala Trp Phe Leu Asp
        35                  40                  45

Gln Val Arg Gln Thr Ser Pro Asp Leu Ser Ala Tyr Leu His Asp Gly
    50                  55                  60

Glu Ser Glu Lys Pro Phe Thr Ile Ser Gly Leu Glu Gly Ala Leu Lys
65                  70                  75                  80

Leu Ser Gly Lys His Leu Gln Leu Gln Pro Glu Gln Thr Tyr Phe Trp
                85                  90                  95

Ser Ile Thr Ala Leu Ser Lys Pro Val Val Gln Trp Leu Val Glu Trp
            100                 105                 110

Val Lys Cys Leu Pro Thr Gln Val Glu Leu Arg Asn Ala Pro Leu Thr
```

```
                115                 120                 125
Ile Gln Ser Cys Gln Met Ala Leu Ala Pro Thr Thr Tyr Arg Gln Leu
            130                 135                 140

Phe Asp Ala Pro Thr Pro Lys Pro Ala Lys Val Asn Leu Ser Phe Met
145                 150                 155                 160

Ser Pro Thr Ser Phe Arg Arg Lys Gly His His Phe Pro Leu Pro Leu
                165                 170                 175

Pro Thr Asn Leu Phe His Ser Tyr Leu Arg Arg Trp Asn Asp Phe Ser
            180                 185                 190

Asn Leu Pro Val Glu Gln Glu Ser Phe Leu Asp Trp Val Asp Glu Ser
        195                 200                 205

Val Ile Ile Gln Arg His Gln Ile Ala Ser Thr Lys Val Ala Ala Gly
        210                 215                 220

Lys Arg Gly Met Val Thr Gly Phe Thr Gly Ala Ile Glu Leu Ser Leu
225                 230                 235                 240

Ser Lys Lys Ser Ser Leu Ala Ser Thr Gln Asn Gln Leu Phe Tyr
                245                 250                 255

Ala Leu Gly Arg Phe Ala Pro Tyr Cys Gly Thr Gly His Lys Thr Thr
            260                 265                 270

Phe Gly Leu Gly Gln Thr Arg Phe Glu Trp Gln Ile Glu Glu Thr Glu
        275                 280                 285

Met Ile Pro Thr Ser Ser Gln Gln Leu Gly Glu Arg Ile Ala Glu Leu
290                 295                 300

Ala Glu Gln Phe Thr Ile Gln Arg Lys Arg Thr Gly Gly Thr Arg Thr
305                 310                 315                 320

Gln Lys Ile Ala Glu Thr Trp Ala Thr Ile Leu Ala Arg Arg Glu Asp
                325                 330                 335

Gly Glu Ser Leu Gln Ala Ile Ala Val Asp Leu Glu Met Pro Tyr Glu
            340                 345                 350

Thr Val Lys Thr Tyr Ala Lys Leu Ala Arg Arg Ala Leu Arg Gln Pro
355                 360                 365

Asp

<210> SEQ ID NO 176
<211> LENGTH: 290
<212> TYPE: PRT
<213> ORGANISM: Lyngbya sp.

<400> SEQUENCE: 176

Met Pro Tyr Ser Leu Val Leu Asn Leu Ile Pro Leu Ser Ser Ile Ser
1               5                   10                  15

Pro Thr Tyr Leu Ser Gly Arg His Leu His Ala Leu Phe Leu Thr Leu
                20                  25                  30

Val Ser Ser Val Asp Lys Gln Leu Gly Asp Tyr Leu His Glu Pro Lys
            35                  40                  45

Thr Glu Lys Ser Phe Thr Leu Ser Pro Leu Gln Thr Cys Ser Lys His
        50                  55                  60

Arg Arg Val Glu Gln Thr Leu Gln Trp Glu His Ser Gln Pro Ile Ser
65                  70                  75                  80

Val Gly Thr Pro Cys Trp Trp Arg Ile Ser Leu Leu Asp Glu Gly Leu
                85                  90                  95

Phe Ser Lys Leu Thr His Leu Trp Leu Asn Leu Asn Pro Asp Gln Pro
            100                 105                 110

Trp His Leu Gly Ser Ala Asn Leu Lys Ile Thr Ser Val Leu Ala Thr
```

```
                    115                 120                 125
Pro Gln Ser Thr Gln Pro Trp Ala Asn Thr Cys Ser Tyr Ser Gln Leu
    130                 135                 140

Tyr Gln Gln Ala Ser Asn Ser Asp Arg Ser Met Thr Leu Ile Phe Cys
145                 150                 155                 160

Thr Pro Thr Ala Phe Arg Gln Gly Lys Phe Asp Thr Ser Leu Pro Thr
                165                 170                 175

Ala Glu Ile Ile Phe Asn Ser Leu Leu Asn Arg Trp Asn Lys Tyr Ser
            180                 185                 190

Gly Ile Glu Phe Lys Gln Leu Pro Leu Asn Ser Ile Phe Pro Ser Phe
        195                 200                 205

Phe Asn Ile Lys Thr Glu Met Val Ala Asp Ser Arg Ser Lys Phe Ile
    210                 215                 220

Gly Cys Val Gly Lys Val Asn Tyr Arg Leu Leu Gly Asn Val Glu Pro
225                 230                 235                 240

Glu Ile Ile Gln Gln Val Asn Thr Leu Ala Asp Phe Ala Phe Tyr Cys
                245                 250                 255

Gly Val Gly Arg Lys Thr Pro Met Gly Met Gly Met Leu Arg Arg Leu
            260                 265                 270

Gln Lys Glu Gly Thr Gly Asp Arg Gly Gln Gly Thr Glu Ser Leu Arg
        275                 280                 285

Arg Leu
    290

<210> SEQ ID NO 177
<211> LENGTH: 278
<212> TYPE: PRT
<213> ORGANISM: Microcystis aeruginosa

<400> SEQUENCE: 177

Met Pro Tyr Ser Leu Val Leu Asn Leu Thr Pro Arg Ser Pro Ile Tyr
1               5                   10                  15

Pro Asn Phe Leu Thr Gly Arg His Leu His Ala Leu Phe Leu Thr Leu
            20                  25                  30

Val Ser Ser Val Asp Gln Glu Leu Gly Lys Ile Leu His Ala Ala Glu
        35                  40                  45

Ala Asp Lys Ala Phe Thr Leu Ser Pro Leu Gln Ile Gln Ser Arg Gly
    50                  55                  60

Lys Ile Thr Ile Asn Ser Pro Gln Trp Arg His Glu Arg Glu Ile Ala
65                  70                  75                  80

Ser Glu Thr Pro Cys Trp Trp Arg Ile Ser Leu Leu Asp Asp Arg Leu
                85                  90                  95

Phe Gly Lys Leu Thr Ser Leu Trp Leu Asn Leu Asn Pro Lys Gln Pro
            100                 105                 110

Trp His Leu Gly Ser Ala Asp Leu Val Ile Thr Ser Val Leu Ala Thr
        115                 120                 125

Pro Gln Ser Val Gln Pro Trp Ala Asn Ser Cys Thr Tyr Gln Tyr Leu
    130                 135                 140

Tyr Glu Asn Ala Ser Glu Thr Asn Arg Glu Phe Asp Phe Leu Phe Ala
145                 150                 155                 160

Thr Pro Val Thr Phe Arg Gln Gly Lys Phe Asp Ser Ala Leu Pro Thr
                165                 170                 175

Arg Glu Leu Val Phe Asn Ser Leu Leu Asn Arg Trp Asn Arg Tyr Ser
            180                 185                 190
```

```
Gly Ile Pro Phe Asp Ser Ile Ala Leu Glu Ser Ile Phe Pro Ser Phe
        195                 200                 205

Phe Asp Ile Gln Thr Lys Leu Ala Asp Glu Ala Tyr Lys Asn Gln Ser
210                 215                 220

Phe Gly Cys Val Gly Glu Ile His Tyr Arg Leu Leu Gly Glu Val Glu
225                 230                 235                 240

Pro Ala Lys Ile Lys Ala Ile Asn Val Leu Ala Asp Phe Ala Leu Tyr
                245                 250                 255

Ala Gly Val Gly Arg Lys Thr Thr Met Gly Met Gly Met Thr Arg Arg
            260                 265                 270

Ile Ala Lys Glu Lys Arg
        275

<210> SEQ ID NO 178
<211> LENGTH: 277
<212> TYPE: PRT
<213> ORGANISM: Microcystis aeruginosa

<400> SEQUENCE: 178

Met Pro Tyr Ser Leu Val Leu Asn Leu Thr Pro Arg Ser Pro Ile Tyr
1               5                   10                  15

Pro Asn Phe Leu Thr Gly Arg His Leu His Ala Leu Phe Leu Thr Leu
            20                  25                  30

Val Ser Ser Val Asp Gln Glu Leu Gly Lys Ile Leu His Thr Ala Glu
        35                  40                  45

Ala Asp Lys Ala Phe Thr Leu Ser Pro Leu Gln Met Gln Ser Gly Gly
    50                  55                  60

Lys Thr Ile Asn Ser Pro Gln Trp Arg Tyr Glu Arg Pro Ile Ala Pro
65                  70                  75                  80

Glu Thr Pro Cys Trp Trp Arg Ile Ser Leu Leu Asp Asp Arg Leu Phe
                85                  90                  95

Gly Lys Leu Thr Pro Leu Trp Leu Asn Leu Asn Pro Lys His Pro Trp
            100                 105                 110

His Leu Gly Ser Ala Asp Leu Val Ile Thr Ser Val Leu Ala Thr Pro
        115                 120                 125

Gln Ser Val Gln Pro Trp Ala Asn Ser Cys Thr Tyr Gln Tyr Leu Tyr
    130                 135                 140

Glu Asn Ala Ser Glu Thr Asn Arg Glu Phe Asp Phe Leu Phe Ala Thr
145                 150                 155                 160

Pro Val Thr Phe Arg Gln Gly Lys Phe Asp Ser Ala Leu Pro Thr Arg
                165                 170                 175

Glu Leu Val Phe Asn Ser Leu Leu Asn Arg Trp Asn Arg Tyr Ser Ala
            180                 185                 190

Ile Pro Phe Asp Ser Ile Val Leu Glu Ser Ile Phe Pro Ser Phe Phe
        195                 200                 205

Asp Ile Gln Thr Lys Leu Ala Asp Glu Ala Tyr Lys Asn Gln Ser Phe
    210                 215                 220

Gly Cys Val Gly Glu Ile His Tyr Arg Leu Leu Gly Glu Val Glu Pro
225                 230                 235                 240

Ala Lys Ile Lys Ala Ile Asn Val Leu Ala Asp Phe Ala Leu Tyr Ala
                245                 250                 255

Gly Val Gly Arg Lys Thr Thr Met Gly Met Gly Met Thr Arg Arg Ile
            260                 265                 270

Ala Lys Glu Lys Arg
        275
```

<210> SEQ ID NO 179
<211> LENGTH: 367
<212> TYPE: PRT
<213> ORGANISM: Synechocystis sp.

<400> SEQUENCE: 179

```
Met Val Asp Leu Lys Ser Leu Ala Gly Ala Glu Met Val Gly Leu Arg
1               5                   10                  15

Trp Gln Leu Arg Phe Asp Arg Pro Cys Arg Leu Glu Ser His Tyr Val
            20                  25                  30

Lys Gly Leu His Ala Trp Phe Leu His Gln Val Gln Ala Ile Asp Pro
        35                  40                  45

Asp Val Ser Ala Trp Leu His Asp Gly Gln Gly Glu Lys Pro Phe Thr
    50                  55                  60

Ile Ser Arg Leu Ile Gly Pro Thr Leu Trp Gln Gly His Trp His
65                  70                  75                  80

Trp Gln Ile Asn Lys Thr Tyr His Trp Gln Leu Asn Leu Leu Ser Gly
                85                  90                  95

Ala Leu Ile Glu Ala Leu Gln Pro Trp Leu Ala Arg Leu Pro Asn Lys
            100                 105                 110

Ile Val Leu Ala Arg Gln Thr Leu Trp Val Glu Ala Val Asp Cys Tyr
        115                 120                 125

Leu Ala Pro His Asn Tyr Gln Gln Leu Trp Pro Gln Gly Ala Leu Pro
    130                 135                 140

Arg Arg Gln Glu Phe Thr Phe Thr Ser Pro Thr Ser Phe Arg Arg Gln
145                 150                 155                 160

Gly Asn His Tyr Pro Leu Pro Glu Pro Arg Asn Val Leu Gln Ser Tyr
                165                 170                 175

Leu Arg Arg Trp Asn Asp Phe Ser Gly Leu Ala Phe Glu Pro Glu Pro
            180                 185                 190

Phe Leu Asp Tyr Trp Val Pro Gln Asn Val Val Ile Asp Arg His Trp
        195                 200                 205

Leu Glu Ser Val Lys Thr Thr Ala Gly Lys Gln Gly Ser Val Val Gly
    210                 215                 220

Phe Val Gly Ala Val Ser Leu Val Leu Thr Pro Gln Ala Arg Asn Asp
225                 230                 235                 240

Gly Asp Asp Tyr Gly Arg Leu Phe His Ala Leu Cys Arg Tyr Gly Pro
                245                 250                 255

Tyr Cys Gly Thr Gly His Lys Thr Thr Phe Gly Leu Gly Gln Thr Met
            260                 265                 270

Ala Gly Trp Ala Thr Pro Asp Leu Lys Thr Phe Ala Cys Leu Gln Glu
        275                 280                 285

Asp Leu Gln Thr Gln Val Leu Thr Gln Arg Ile Asp Gln Cys Ala Ser
    290                 295                 300

Leu Leu Leu Ala Gln Arg Gln Thr Gly Gly Gln Arg Ala Gln Glu
305                 310                 315                 320

Ile Cys His Thr Leu Ala Thr Ile Phe Val Arg Arg Glu Gln Gly Glu
                325                 330                 335

Ser Leu Gln Glu Ile Ala Leu Asp Gln Leu Pro Tyr Glu Thr Ala
            340                 345                 350

Arg Thr Tyr Ser Lys Arg Ala Lys Arg Ala Leu Ala Asn Val Gln
        355                 360                 365
```

```
<210> SEQ ID NO 180
<211> LENGTH: 262
<212> TYPE: PRT
<213> ORGANISM: Synechocystis sp.

<400> SEQUENCE: 180
```

Met Phe Asp Asp Arg Tyr Ser Leu Tyr Ser Val Val Ile Glu Leu Gly
1               5                   10                  15

Ala Ala Lys Lys Gly Phe Pro Thr Gly Ile Leu Gly Arg Ala Leu His
            20                  25                  30

Ser Gln Val Leu Glu Trp Leu Lys Ile Gly Glu Pro Ser Leu Ala Glu
        35                  40                  45

Glu Leu His Gln Ser Gln Ile Ser Pro Phe Ser Ile Ser Pro Leu Ile
    50                  55                  60

Gly Lys Arg Arg Ser Lys Leu Thr Glu Glu Gly Asp Arg Phe Phe Phe
65                  70                  75                  80

Arg Ile Ser Leu Leu Asn Gly Ser Leu Leu Gln Pro Leu Leu Lys Gly
                85                  90                  95

Leu Glu Gln Gln Asp Lys Gln Ile Val Met Leu Asp Lys Phe Ala Phe
            100                 105                 110

Arg Leu Cys His Ile His Ile Leu Pro Gly Ser His Ser Leu Ala Arg
        115                 120                 125

Ala Ser Ser Tyr Ala Leu Thr Thr Gln Ala Pro Thr Ser Ser Lys Ile
    130                 135                 140

Thr Leu Lys Phe His Ser Ala Thr Ser Phe Lys Ile Asp Arg Asn Thr
145                 150                 155                 160

Ile Gln Pro Phe Pro Leu Gly Asp Ser Val Phe Asn Ser Leu Leu Arg
                165                 170                 175

Arg Trp Asn His Phe Ala Pro Glu Glu Leu Tyr Phe Pro Ser Val Ser
            180                 185                 190

Trp Gln Ile Pro Val Ala Ala Phe Glu Leu Lys Thr Tyr Ser Val Gln
        195                 200                 205

Leu Lys Lys Ser Glu Ile Gly Ser Glu Gly Trp Val Thr Tyr Leu Phe
    210                 215                 220

Pro Asp Gln Glu Gln Ala Lys Ile Ala Ser Val Leu Ser Gln Phe Ala
225                 230                 235                 240

Phe Phe Ala Gly Val Gly Arg Lys Thr Ser Met Gly Met Gly Gln Val
                245                 250                 255

Ser Val Asn Asn His Gly
            260

```
<210> SEQ ID NO 181
<211> LENGTH: 393
<212> TYPE: PRT
<213> ORGANISM: Synechococcus sp.

<400> SEQUENCE: 181
```

Met Leu Ile Val Ala Val Asp Trp Glu Trp Ala Val Pro Met Leu Ser
1               5                   10                  15

Phe Ser Glu Pro Ser Ala Asp Arg Glu Ala Asn Gly Lys Trp Pro Thr
            20                  25                  30

Gly Ser Glu Leu Val Gly Ile Thr Leu Glu Val Gln Ala Pro Arg Ser
        35                  40                  45

Tyr Leu Leu Asp Pro His Tyr Ala Lys Gly Leu His Ala Trp Phe Leu
    50                  55                  60

Ser Gln Val Gln Glu Thr Asp Pro Gln Leu Ser Ala Tyr Leu His Asp

```
                65                  70                  75                  80
Gly Glu Ser Glu Lys Pro Phe Thr Leu Ser Arg Leu Met Gly Pro Phe
                    85                  90                  95

Arg Glu Gln Gly Gly Arg Pro Leu Ile Pro Pro His Leu Pro Phe Arg
                    100                 105                 110

Trp Trp Ile Thr Gly Leu Asn Pro Val Val Glu Trp Leu Arg Gly
            115                 120                 125

Trp Cys Gln Arg Leu Pro Thr Trp Leu Glu Leu Arg Gly Ser Pro Leu
            130                 135                 140

Gln Ile Leu Gly Trp Gln Ile Ser Ile Pro Pro Arg Thr Tyr Arg Gln
145                 150                 155                 160

Leu Leu Glu Gln Pro Leu Ser Pro Arg Ser Trp Ser Leu Ser Phe Val
                    165                 170                 175

Ser Pro Thr Ser Phe Arg His Arg Gly His His Leu Pro Leu Pro Ile
                    180                 185                 190

Pro Arg Asn Leu Phe His Ser Tyr Leu Arg Arg Trp Asn Asp Phe Ser
                    195                 200                 205

Gly Leu Pro Ile Glu Ala Glu Pro Phe Leu Asp Trp Val Asp Gly Glu
                    210                 215                 220

Val Ile Ile Gln Arg His Arg Leu Glu Ser Val Lys Thr Thr Ala Gly
225                 230                 235                 240

Arg Gln Gly Ser Val Thr Gly Phe Ile Gly Cys Val Gln Leu Ala Val
                    245                 250                 255

Ser Ser Arg Ala Pro Glu Leu Leu Gln Gln Gln Leu Gln Ala Leu Ile
                    260                 265                 270

His Leu Ala Pro Tyr Cys Gly Thr Gly His Lys Thr Pro Phe Gly Leu
                    275                 280                 285

Gly Gln Thr Arg Leu Gly Trp Leu Ala Glu Glu Leu Pro Ala Ser Pro
                    290                 295                 300

Val Pro Ser Arg Glu Glu Gln Val Ala Gln Arg Ile Glu Glu Leu Ser
305                 310                 315                 320

Ala Leu Phe Leu Ser Gln Arg Gln Gln Gly Gly Ser Arg Ala Glu
                    325                 330                 335

Lys Thr Ala Gln Leu Trp Ala Thr Ile Leu Ala Arg Arg Glu Gly Gly
                    340                 345                 350

Glu Ser Leu Gln Gln Ile Ala Ala Asp Leu Glu Met Pro Tyr Glu Thr
                    355                 360                 365

Val Lys Thr Tyr Ala Lys Leu Ala Arg Arg Ser Leu Gln Ser Gly Ser
370                 375                 380

Gln Asp Tyr Ser Ser Ser Leu Pro
385                 390

<210> SEQ ID NO 182
<211> LENGTH: 383
<212> TYPE: PRT
<213> ORGANISM: Synechococcus sp.

<400> SEQUENCE: 182

Met Leu Thr Lys Leu Ser Phe Ser Glu Pro Val Ala Gly Ala Glu
1               5                   10                  15

Asn Ser Lys Trp Pro Ala Gly Ser Glu Leu Val Gly Ile Ala Leu Glu
                20                  25                  30

Val Gln Ala Pro Gln Pro Tyr Leu Leu Asp Pro His Tyr Ala Lys Gly
            35                  40                  45
```

Leu His Ala Trp Phe Leu Ser Gln Val Gln Glu Thr Asp Pro Gln Leu
    50                  55                  60

Ser Ala Tyr Leu His Asp Gly Glu Ser Glu Lys Pro Phe Thr Leu Ser
 65                 70                  75                  80

Arg Leu Met Gly Pro Phe Arg Glu Gln Gly Arg Leu Leu Ile Pro
                85                  90                  95

Pro Gln Ile Pro Phe Arg Trp Ser Ile Thr Ala Leu Asn Pro Gln Val
            100                 105                 110

Val Glu Trp Leu Arg Glu Trp Cys Arg Arg Leu Pro Pro Trp Leu Glu
            115                 120                 125

Leu Arg Gly Ser Pro Leu Gln Ile Leu Gly Trp Lys Val Ser Ala Pro
    130                 135                 140

Pro Arg Thr Tyr Arg Gln Leu Leu Glu Gln Pro Leu Ser Pro Arg Ser
145                 150                 155                 160

Trp Ser Leu Ser Phe Val Ser Pro Thr Ser Phe Arg His Arg Gly His
                165                 170                 175

His Leu Pro Leu Pro Ile Pro Arg Asn Leu Phe His Ser Tyr Leu Arg
            180                 185                 190

Arg Trp Asn Asp Phe Ser Gly Leu Pro Ile Glu Ala Glu Pro Phe Leu
    195                 200                 205

Asp Trp Val Asp Gly Glu Val Ile Ile Gln Arg His Arg Leu Glu Ser
210                 215                 220

Val Lys Thr Thr Ala Gly Arg Gln Gly Ser Val Thr Gly Phe Ile Gly
225                 230                 235                 240

Cys Val Gln Leu Ala Val Ser Ser Arg Ala Pro Glu Leu Leu Gln Gln
                245                 250                 255

Gln Leu Gln Ala Leu Ile His Leu Ala Pro Tyr Cys Gly Thr Gly His
            260                 265                 270

Lys Thr Pro Phe Gly Leu Gly Gln Thr Arg Leu Gly Trp Leu Ala Glu
    275                 280                 285

Glu Leu Pro Ala Thr Pro Val Leu Cys Arg Glu Gln Leu Ala Arg
290                 295                 300

Arg Ile Glu Glu Leu Ser Ala Leu Phe Leu Ser Gln Arg Gln Arg Gln
305                 310                 315                 320

Gly Gly Ser Arg Ala Glu Lys Thr Ala Gln Leu Trp Ala Thr Ile Leu
                325                 330                 335

Ala Arg Arg Glu Gly Gly Ser Leu Gln Gln Ile Ala Ala Asp Leu
            340                 345                 350

Glu Met Pro Tyr Glu Thr Val Lys Thr Tyr Ala Lys Leu Ala Arg Arg
    355                 360                 365

Ser Leu Gln Ser Gly Ser Gln Asp Tyr Ser Ser Ser Leu Pro
370                 375                 380

<210> SEQ ID NO 183
<211> LENGTH: 381
<212> TYPE: PRT
<213> ORGANISM: Nodularia spumigena

<400> SEQUENCE: 183

Met Val Arg Thr Ala Lys Pro Thr Asn Arg Gln Gln Lys Pro Lys Ser
 1               5                  10                  15

Ser Pro Thr Ala Thr Leu Pro Thr Trp Ala Asp Asn Thr Glu Leu Val
             20                  25                  30

Gly Leu Glu Phe Asp Leu Glu Ala Leu Thr Thr Ser Ser Leu Tyr Ser
         35                  40                  45

Gln Tyr Thr Ile Ala Leu His Ala Trp Phe Leu Asp Gln Val Arg Gln
    50                  55                  60

Leu Asp Pro Asp Leu Ser Ala Tyr Leu His Asp Gly Glu Ser Glu Lys
65                  70                  75                  80

Pro Phe Asn Ile Ser Ala Leu Glu Ser Gln Leu Leu Pro Thr Gly Lys
                85                  90                  95

Gln Leu Gln Leu Glu Ala Asn Gln Ile Leu His Trp Gln Val Asn Ala
            100                 105                 110

Leu Ser Ala Lys Val Ala Glu Phe Leu Gln Leu Trp Leu Thr Gln Leu
        115                 120                 125

Pro Gln Thr Leu Asn Leu Arg Gly Ala Thr Leu Gln Ile Lys Gln Val
130                 135                 140

Arg Ile Ala His Pro Pro Thr Thr Tyr Ala Gln Leu Leu Gln Pro Pro
145                 150                 155                 160

Ala Lys Tyr Ser Gln Val Asn Leu Ser Phe Ile Ser Pro Thr Ser Phe
                165                 170                 175

Arg Arg Lys Gly His His Phe Pro Leu Pro Val Pro Val Asn Leu Phe
            180                 185                 190

His Ser Tyr Leu Arg Arg Trp Asn Asp Phe Ser Gln Ile Pro Ile Ser
        195                 200                 205

Gln Ala Asp Phe Leu Asp Trp Ile Asp Glu Asn Val Ile Ile His Gln
210                 215                 220

His Arg Leu Glu Ser Val Lys Val Ala Ala Gly Lys Arg Gly Ser Val
225                 230                 235                 240

Thr Gly Phe Thr Gly Ala Ile Ser Cys Gly Leu Ser Lys Ala Ala Leu
                245                 250                 255

Ala Asn Thr Glu Phe Thr Gln Leu Phe Tyr Ala Leu Val Lys Leu Ala
            260                 265                 270

Pro Tyr Cys Gly Thr Gly His Lys Thr Thr Phe Gly Leu Gly Gln Thr
        275                 280                 285

Ser Leu Ser Trp Val Glu Pro Glu Ala Ser Ser Pro Thr Gln Leu Leu
290                 295                 300

Thr Asn Leu Leu Gly Glu Arg Ile Glu Glu Leu Thr Ala Ile Phe Thr
305                 310                 315                 320

Ala Gln Arg Lys Arg Ser Gly Gly Asp Arg Thr Asp Lys Ile Ala Ala
                325                 330                 335

Thr Trp Ala Thr Ile Leu Ala Arg Arg Glu Met Gly Glu Ser Leu Lys
            340                 345                 350

Leu Ile Ala Glu Asp Leu Glu Met Pro Val Asp Thr Val Lys Thr Tyr
        355                 360                 365

Thr Lys Leu Ala Arg Arg Ser Leu Lys Asp Ala Asp Leu
370                 375                 380

<210> SEQ ID NO 184
<211> LENGTH: 290
<212> TYPE: PRT
<213> ORGANISM: Anabaena variabilis

<400> SEQUENCE: 184

Met Pro His Ser Leu Val Leu Asn Leu Leu Pro Gln Ser Pro Ile Pro
1               5                   10                  15

Pro Gln Tyr Ile Thr Gly Arg His Leu His Ala Leu Phe Leu Thr Leu
            20                  25                  30

Val Ser Ser Val Asp Ser Thr Leu Gly Asp Arg Leu His Asp Ser Thr

-continued

```
                35                  40                  45
Ala Asp Lys Ala Phe Thr Leu Ser Pro Leu Gln Ile Lys Gly Glu Glu
 50                  55                  60

Arg Gly Arg Tyr Lys Ser Lys Ile Pro His Gly Gln Ser Leu Gln Tyr
 65                  70                  75                  80

Phe His Gln Gln Ala Ile Pro Ala Gly Thr Pro Cys Trp Trp Arg Ile
                 85                  90                  95

Ser Leu Leu Asp Asp Thr Leu Phe Ser Gln Leu Thr Gln Leu Trp Leu
                100                 105                 110

Asn Leu Asn Pro Ser His Pro Trp His Leu Gly Pro Ala Asn Leu Tyr
                115                 120                 125

Ile Thr Ser Ile Gln Gly Thr Pro Gln Ser Thr Gln Pro Trp Ala Asn
130                 135                 140

Ala Thr Thr Tyr Ala Gln Leu Tyr Glu Gln Ala Gly Glu Ser Asn Asp
145                 150                 155                 160

Val Arg Ser Leu Val Asn Asn Arg Thr Leu Asn Phe Thr Phe Thr Thr
                165                 170                 175

Pro Thr Ala Phe Arg Gln Gly Lys Phe Asp Thr Thr Leu Pro Thr Arg
                180                 185                 190

Glu Cys Val Phe Asn Ser Leu Leu Ser Arg Trp Asn Lys Tyr Ser Gly
                195                 200                 205

Ile Glu Phe Ser Glu Ile Ala Ile Glu Ser Ile Phe Pro Ser Phe Leu
                210                 215                 220

Asn Ile His Thr Glu Ile Leu Ala Asp Ser Arg Ser Lys Phe Ile Gly
225                 230                 235                 240

Ile Leu Gly Glu Ile Asn Tyr Arg Ile Leu Gly Asp Ile Glu Pro Ile
                245                 250                 255

Gln Ile Lys Gln Ile Asn Ala Leu Ala Asp Phe Ala Met Tyr Ala Gly
                260                 265                 270

Ile Gly Arg Lys Thr Thr Met Gly Met Gly Met Ile Arg Arg Leu Tyr
                275                 280                 285

Ser Ala
    290

<210> SEQ ID NO 185
<211> LENGTH: 281
<212> TYPE: PRT
<213> ORGANISM: Nostoc punctiforme

<400> SEQUENCE: 185

Met Pro His Ser Leu Val Leu Asn Leu Leu Pro Gln Ser Pro Ile Pro
  1               5                  10                  15

Pro Gln Tyr Leu Thr Gly Arg His Leu His Ala Leu Phe Leu Thr Leu
                 20                  25                  30

Val Ser Ser Val Asp Ser Thr Leu Gly Asp Arg Leu His Asp Ser Thr
                 35                  40                  45

Ala Asp Lys Ala Phe Thr Leu Ser Pro Leu Gln Ile Ser Asn Thr Asn
 50                  55                  60

Ser Pro Leu Leu Lys Gly Gly Lys Gly Ser Lys Leu Gln Tyr Ser
 65                  70                  75                  80

His Gln Gln Pro Ile Pro Ala Gly Thr Pro Cys Trp Trp Arg Ile Ser
                 85                  90                  95

Leu Leu Asp Asp Thr Leu Phe Gly Lys Leu Thr Gln Leu Trp Leu Asn
                100                 105                 110
```

```
Leu Asn Pro Asn Arg Pro Trp His Leu Gly Pro Ala Asp Leu Tyr Ile
            115                 120                 125

Thr Ser Ile Gln Gly Thr Pro Gln Ser Ile Gln Pro Trp Ala Asn Ala
        130                 135                 140

Asn Thr Tyr Ala Gln Leu Tyr Glu Glu Ala Ser Asp Gly Asn Ser Ser
145                 150                 155                 160

Ile Asn Leu Thr Phe Ser Thr Pro Thr Ala Phe Arg Gln Gly Gln Tyr
                165                 170                 175

Asp Thr Thr Leu Pro Thr Arg Glu Ser Val Phe Asn Ser Leu Leu Ser
            180                 185                 190

Arg Trp Asn Lys Tyr Ser Gly Ile Glu Phe Ser Gln Ile Ala Ile Glu
        195                 200                 205

Ser Ile Phe Pro Ser Phe Val Asn Ile His Thr Glu Ile Leu Ala Asp
210                 215                 220

Ser Arg Ser Lys Phe Ile Gly Ile Ile Gly Glu Val Thr Tyr Lys Ile
225                 230                 235                 240

Leu Gly Ala Val Glu Pro Ile Gln Ile Lys Gln Ile Asn Ala Leu Ala
                245                 250                 255

Asp Phe Ala Leu Tyr Thr Gly Val Gly Arg Lys Thr Thr Met Gly Met
            260                 265                 270

Gly Met Thr Arg Gln Met Tyr Ser Pro
        275                 280

<210> SEQ ID NO 186
<211> LENGTH: 290
<212> TYPE: PRT
<213> ORGANISM: Anabaena sp.

<400> SEQUENCE: 186

Met Pro His Ser Leu Val Leu Asn Leu Leu Pro Gln Ser Pro Ile Pro
1               5                   10                  15

Pro Gln Tyr Leu Thr Gly Arg His Leu His Ala Leu Phe Leu Thr Leu
            20                  25                  30

Val Ser Ser Val Asp Ser Thr Leu Gly Asp Arg Leu His Asp Ser Thr
        35                  40                  45

Ala Asp Lys Ala Phe Thr Leu Ser Pro Leu Gln Ile Gln Gly Glu Glu
50                  55                  60

Arg Gly Arg Tyr Lys Ser Lys Ile Pro Asn Ser Tyr Ser Leu Gln Tyr
65                  70                  75                  80

Leu His Gln Gln Ala Ile Pro Ala Gly Thr Pro Cys Trp Trp Arg Ile
                85                  90                  95

Ser Leu Leu Asp Asp Thr Leu Phe Ser Gln Leu Thr Gln Leu Trp Leu
            100                 105                 110

Asn Leu Asn Pro Asn His Pro Trp His Leu Gly Pro Ala Asn Leu Tyr
        115                 120                 125

Ile Thr Ser Ile Gln Gly Thr Pro Gln Ser Thr Gln Pro Trp Ala Asn
    130                 135                 140

Ala Ile Thr Tyr Thr Gln Leu Tyr Glu Gln Ala Gly Glu Asn Asn Asp
145                 150                 155                 160

Leu Arg Ser Leu Gly Asn Asn His Thr Leu Asn Phe Thr Phe Thr Thr
                165                 170                 175

Pro Thr Ala Phe Arg Gln Gly Lys Phe Asp Thr Thr Leu Pro Thr Arg
            180                 185                 190

Glu Cys Val Phe Asn Ser Leu Leu Ser Arg Trp Asn Lys Tyr Ser Gly
        195                 200                 205
```

```
Ile Glu Phe Ser Glu Ile Ala Leu Glu Ala Ile Phe Pro Ser Phe Leu
    210                 215                 220

Asn Ile His Thr Glu Ile Leu Ala Asp Ser Arg Ser Lys Phe Ile Gly
225                 230                 235                 240

Ile Leu Gly Glu Ile Asn Tyr Arg Ile Leu Gly Asp Ile Glu Pro Ile
                245                 250                 255

Gln Ile Lys Gln Ile Asn Ala Leu Ala Asp Phe Ala Met Tyr Ala Gly
                260                 265                 270

Val Gly Arg Lys Thr Thr Met Gly Met Gly Met Ile Arg Arg Leu Tyr
            275                 280                 285

Ser Ser
    290

<210> SEQ ID NO 187
<211> LENGTH: 377
<212> TYPE: PRT
<213> ORGANISM: Anabaena sp.

<400> SEQUENCE: 187

Met Pro Arg Ala Ala Thr Thr Pro Lys Arg Lys Pro Arg Ala Lys Ser
1               5                   10                  15

Ala Pro Thr Ser Leu Val Pro Thr Trp Ala Asp Glu Thr Glu Leu Val
                20                  25                  30

Gly Leu Val Phe Asp Leu Glu Ala Thr Asp Ser Gly Ser Leu Tyr Ser
            35                  40                  45

Gln Tyr Thr Ile Gly Leu His Ala Trp Phe Leu His Gln Val Gln Gln
    50                  55                  60

Val Asp Pro Asp Leu Ser Ala Tyr Leu His Asp Gly Glu Ser Glu Lys
65                  70                  75                  80

Pro Phe Asn Ile Ser Ala Leu Glu Gly Gln Leu Leu Pro Ser Gly Lys
                85                  90                  95

Gln Leu Arg Leu Glu Ala Lys Gln Thr Tyr His Trp His Ile Asn Ala
                100                 105                 110

Leu Ser Gln Lys Val Ala Leu Phe Leu Lys Glu Trp Leu Thr Asn Leu
            115                 120                 125

Pro Lys Thr Ile Glu Leu Ser Gly Thr Pro Leu Gln Ile Lys Gln Val
    130                 135                 140

Ser Ile Ala His Ala Pro Thr Thr Tyr Ala Gln Leu Leu Gln Pro Ser
145                 150                 155                 160

Thr Gln Pro Ser Leu Val Asn Leu Ser Phe Val Ser Pro Thr Ser Phe
                165                 170                 175

Arg Arg Lys Gly His His Phe Pro Leu Pro Val Pro Glu Asn Leu Phe
            180                 185                 190

His Ser Tyr Leu Arg Arg Trp Asn Asp Phe Ser Asn Met Leu Val Asn
    195                 200                 205

Gln Glu Ser Phe Leu Glu Trp Ile Asp Glu Asn Val Ile Ile His Gln
    210                 215                 220

His Arg Leu Gln Ser Glu Lys Val Ala Ala Gly Lys Arg Gly Ser Val
225                 230                 235                 240

Thr Gly Phe Thr Gly Ala Ile Ser Leu Gly Leu Ser Arg Ala Gly Leu
                245                 250                 255

Ala Asn Ala Asp Phe Thr Lys Leu Phe Tyr Ala Leu Val Gln Leu Ser
                260                 265                 270

Pro Tyr Cys Gly Thr Gly His Lys Thr Thr Phe Gly Leu Gly Gln Thr
```

```
                 275                 280                 285

Arg Leu Asp Trp Leu Glu Gln Lys Pro Thr Thr Ser Ala Gln Leu Leu
    290                 295                 300

Glu Asn Ile Leu Ala Glu Arg Ile Glu Glu Leu Thr Glu Ile Phe Thr
305                 310                 315                 320

Ala Gln Arg Lys Arg Lys Gly Gly Asp Arg Thr Asp Lys Ile Ala Ala
                325                 330                 335

Thr Trp Ala Thr Val Leu Ala Arg Arg Asp Met Gly Asp Ser Leu Gln
            340                 345                 350

Ala Ile Ala Asp Asp Leu Glu Met Pro Leu Leu Thr Val Lys Thr Tyr
        355                 360                 365

Val Lys Leu Ala Arg Lys Ala Leu Lys
    370                 375

<210> SEQ ID NO 188
<211> LENGTH: 193
<212> TYPE: PRT
<213> ORGANISM: artificial
<220> FEATURE:
<223> OTHER INFORMATION: domain present in TIGR01877

<400> SEQUENCE: 188

Tyr Leu His Glu Val Lys Gly Pro Lys Leu Phe Thr Tyr Ser Leu Phe
1               5                   10                  15

Met Ala Glu Lys Arg Glu His Pro Lys Gly Leu Pro Tyr Phe Leu Gly
            20                  25                  30

Tyr Lys Lys Gly Phe Phe Tyr Phe Ser Thr Cys Val Pro Glu Ile Ala
        35                  40                  45

Glu Ala Leu Val Asn Gly Leu Leu Met Asn Pro Glu Val Arg Leu Trp
    50                  55                  60

Asp Glu Arg Phe Tyr Leu His Glu Ile Lys Val Leu Arg Glu Pro Lys
65                  70                  75                  80

Lys Phe Asn Gly Ser Thr Phe Val Thr Leu Ser Pro Ile Ala Val Thr
                85                  90                  95

Val Val Arg Lys Gly Lys Ser Tyr Asp Val Pro Pro Met Glu Lys Glu
            100                 105                 110

Phe Tyr Ser Ile Ile Lys Asp Asp Leu Gln Asp Lys Tyr Val Met Ala
        115                 120                 125

Tyr Gly Asp Lys Pro Pro Ser Glu Phe Glu Met Glu Val Leu Ile Ala
    130                 135                 140

Lys Pro Lys Arg Phe Arg Ile Lys Pro Gly Ile Tyr Gln Thr Ala Trp
145                 150                 155                 160

His Leu Val Phe Arg Ala Tyr Gly Asn Asp Asp Leu Leu Lys Val Gly
                165                 170                 175

Tyr Glu Val Gly Phe Gly Glu Lys Asn Ser Leu Gly Phe Gly Met Val
            180                 185                 190

Lys

<210> SEQ ID NO 189
<211> LENGTH: 144
<212> TYPE: PRT
<213> ORGANISM: artificial
<220> FEATURE:
<223> OTHER INFORMATION: domain present in PR01881

<400> SEQUENCE: 189

Val Asn Gly Leu Leu Met Asn Pro Glu Val Arg Leu Trp Asp Glu Arg
```

```
                1               5                  10                 15
              Phe Tyr Leu His Glu Ile Lys Val Leu Arg Glu Pro Lys Lys Phe Asn
                            20                  25                  30

Gly Ser Thr Phe Val Thr Leu Ser Pro Ile Ala Val Thr Val Arg
                            35                  40                  45

Lys Gly Lys Ser Tyr Asp Val Pro Pro Met Glu Lys Glu Phe Tyr Ser
               50                  55                  60

Ile Ile Lys Asp Asp Leu Gln Asp Lys Tyr Val Met Ala Tyr Gly Asp
               65                  70                  75                  80

Lys Pro Pro Ser Glu Phe Glu Met Glu Val Leu Ile Ala Lys Pro Lys
                            85                  90                  95

Arg Phe Arg Ile Lys Pro Gly Ile Tyr Gln Thr Ala Trp His Leu Val
                           100                 105                 110

Phe Arg Ala Tyr Gly Asn Asp Asp Leu Leu Lys Val Gly Tyr Glu Val
                           115                 120                 125

Gly Phe Gly Glu Lys Asn Ser Leu Gly Phe Gly Met Val Lys Val Glu
                           130                 135                 140
```

<210> SEQ ID NO 190
<211> LENGTH: 11
<212> TYPE: PRT
<213> ORGANISM: artificial
<220> FEATURE:
<223> OTHER INFORMATION: C-terminal motif
<220> FEATURE:
<221> NAME/KEY: MISC_FEATURE
<222> LOCATION: (2)..(2)
<223> OTHER INFORMATION: Xaa is any hydrophobic amino acid
<220> FEATURE:
<221> NAME/KEY: MISC_FEATURE
<222> LOCATION: (4)..(8)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any hydrophobic amino acid

<400> SEQUENCE: 190

```
Gly Xaa Gly Xaa Xaa Xaa Xaa Xaa Gly Xaa Gly
1               5                   10
```

<210> SEQ ID NO 191
<211> LENGTH: 30
<212> TYPE: DNA
<213> ORGANISM: artificial
<220> FEATURE:
<223> OTHER INFORMATION: target polynucleotide
<220> FEATURE:
<221> NAME/KEY: misc_feature
<222> LOCATION: (22)..(23)
<223> OTHER INFORMATION: cleavage site

<400> SEQUENCE: 191
gttccaataa gactaaaata gaattgaaag                                       30

<210> SEQ ID NO 192
<211> LENGTH: 28
<212> TYPE: RNA
<213> ORGANISM: artificial
<220> FEATURE:
<223> OTHER INFORMATION: target RNA
<220> FEATURE:
<221> NAME/KEY: misc_feature
<222> LOCATION: (2)..(2)
<223> OTHER INFORMATION: n is a, c, g, or u
<220> FEATURE:

```
<221> NAME/KEY: misc_feature
<222> LOCATION: (4)..(5)
<223> OTHER INFORMATION: n is a, c, g, or u
<220> FEATURE:
<221> NAME/KEY: misc_feature
<222> LOCATION: (7)..(19)
<223> OTHER INFORMATION: n is a, c, g, or u
<220> FEATURE:
<221> NAME/KEY: misc_feature
<222> LOCATION: (20)..(21)
<223> OTHER INFORMATION: cleavage site
<220> FEATURE:
<221> NAME/KEY: misc_feature
<222> LOCATION: (22)..(28)
<223> OTHER INFORMATION: n is a, c, g, or u

<400> SEQUENCE: 192
uncnnunnnn nnnnnnnnnn nnnnnnnn                                           28

<210> SEQ ID NO 193
<211> LENGTH: 29
<212> TYPE: RNA
<213> ORGANISM: artificial
<220> FEATURE:
<223> OTHER INFORMATION: target RNA
<220> FEATURE:
<221> NAME/KEY: misc_feature
<222> LOCATION: (9)..(20)
<223> OTHER INFORMATION: n is a, c, g, or u
<220> FEATURE:
<221> NAME/KEY: misc_feature
<222> LOCATION: (21)..(22)
<223> OTHER INFORMATION: cleavage site
<220> FEATURE:
<221> NAME/KEY: misc_feature
<222> LOCATION: (23)..(29)
<223> OTHER INFORMATION: n is a, c, g, or u

<400> SEQUENCE: 193
uuacaauann nnnnnnnnnn nnnnnnnnn                                          29

<210> SEQ ID NO 194
<211> LENGTH: 42
<212> TYPE: DNA
<213> ORGANISM: artificial
<220> FEATURE:
<223> OTHER INFORMATION: synthetic oligonucleotide substrate

<400> SEQUENCE: 194
taatacgact cactataggg aagaccaaaa tagaattgaa ag                           42

<210> SEQ ID NO 195
<211> LENGTH: 42
<212> TYPE: DNA
<213> ORGANISM: artificial
<220> FEATURE:
<223> OTHER INFORMATION: synthetic oligonucleotide substrate

<400> SEQUENCE: 195
ctttcaattc tattttggtc ttccctatag tgagtcgtat ta                           42

<210> SEQ ID NO 196
<211> LENGTH: 49
<212> TYPE: DNA
<213> ORGANISM: artificial
<220> FEATURE:
<223> OTHER INFORMATION: synthetic oligonucleotide substrate

<400> SEQUENCE: 196
taatacgact cactataggg ttacaataag accaaaatag ggttgaaag                    49
```

<210> SEQ ID NO 197
<211> LENGTH: 49
<212> TYPE: DNA
<213> ORGANISM: artificial
<220> FEATURE:
<223> OTHER INFORMATION: synthetic oligonucleotide substrate

<400> SEQUENCE: 197
ctttcaaccc tattttggtc ttattgtaac cctatagtga gtcgtatta            49

<210> SEQ ID NO 198
<211> LENGTH: 49
<212> TYPE: DNA
<213> ORGANISM: artificial
<220> FEATURE:
<223> OTHER INFORMATION: synthetic oligonucleotide substrate

<400> SEQUENCE: 198
taatacgact cactataggg ttacaataag accaaaatag aattgaaag             49

<210> SEQ ID NO 199
<211> LENGTH: 49
<212> TYPE: DNA
<213> ORGANISM: artificial
<220> FEATURE:
<223> OTHER INFORMATION: synthetic oligonucleotide substrate

<400> SEQUENCE: 199
ctttcaattc tattttggtc ttattgtaac cctatagtga gtcgtatta             49

<210> SEQ ID NO 200
<211> LENGTH: 49
<212> TYPE: DNA
<213> ORGANISM: artificial
<220> FEATURE:
<223> OTHER INFORMATION: synthetic oligonucleotide substrate

<400> SEQUENCE: 200
taatacgact cactataggg ttacaatttc tggtttatag aattgaaag             49

<210> SEQ ID NO 201
<211> LENGTH: 49
<212> TYPE: DNA
<213> ORGANISM: artificial
<220> FEATURE:
<223> OTHER INFORMATION: synthetic oligonucleotide substrate

<400> SEQUENCE: 201
ctttcaattc tataaaccag aaattgtaac cctatagtga gtcgtatta             49

<210> SEQ ID NO 202
<211> LENGTH: 45
<212> TYPE: DNA
<213> ORGANISM: artificial
<220> FEATURE:
<223> OTHER INFORMATION: synthetic oligonucleotide substrate

<400> SEQUENCE: 202
taatacgact cactataggg ttacaatcca aaatagaatt gaaag                 45

<210> SEQ ID NO 203
<211> LENGTH: 45
<212> TYPE: DNA
<213> ORGANISM: artificial
<220> FEATURE:

<223> OTHER INFORMATION: synthetic oligonucleotide substrate

<400> SEQUENCE: 203
ctttcaattc tattttggat tgtaaccta tagtgagtcg tatta            45

<210> SEQ ID NO 204
<211> LENGTH: 53
<212> TYPE: DNA
<213> ORGANISM: artificial
<220> FEATURE:
<223> OTHER INFORMATION: synthetic oligonucleotide substrate

<400> SEQUENCE: 204
taatacgact cactataggg ttacaatttt taagaccaaa atagaattga aag            53

<210> SEQ ID NO 205
<211> LENGTH: 53
<212> TYPE: DNA
<213> ORGANISM: artificial
<220> FEATURE:
<223> OTHER INFORMATION: synthetic oligonucleotide substrate

<400> SEQUENCE: 205
ctttcaattc tattttggtc ttaaaaattg taaccctata gtgagtcgta tta            53

<210> SEQ ID NO 206
<211> LENGTH: 40
<212> TYPE: DNA
<213> ORGANISM: artificial
<220> FEATURE:
<223> OTHER INFORMATION: synthetic oligonucleotide substrate

<400> SEQUENCE: 206
taatacgact cactataggg ttacaataag accaaaatag            40

<210> SEQ ID NO 207
<211> LENGTH: 40
<212> TYPE: DNA
<213> ORGANISM: artificial
<220> FEATURE:
<223> OTHER INFORMATION: synthetic oligonucleotide substrate

<400> SEQUENCE: 207
ctattttggt cttattgtaa ccctatagtg agtcgtatta            40

<210> SEQ ID NO 208
<211> LENGTH: 50
<212> TYPE: DNA
<213> ORGANISM: artificial
<220> FEATURE:
<223> OTHER INFORMATION: synthetic oligonucleotide substrate

<400> SEQUENCE: 208
taatacgact cactataggg caatgttaaa gaccaaaata gaattgaaag            50

<210> SEQ ID NO 209
<211> LENGTH: 50
<212> TYPE: DNA
<213> ORGANISM: artificial
<220> FEATURE:
<223> OTHER INFORMATION: synthetic oligonucleotide substrate

<400> SEQUENCE: 209
ctttcaattc tattttggtc tttaacattg ccctatagtg agtcgtatta            50

```
<210> SEQ ID NO 210
<211> LENGTH: 49
<212> TYPE: DNA
<213> ORGANISM: artificial
<220> FEATURE:
<223> OTHER INFORMATION: synthetic oligonucleotide substrate

<400> SEQUENCE: 210
taatacgact cactataggg ttacaataag accaaaatag aaaactttc                49

<210> SEQ ID NO 211
<211> LENGTH: 49
<212> TYPE: DNA
<213> ORGANISM: artificial
<220> FEATURE:
<223> OTHER INFORMATION: synthetic oligonucleotide substrate

<400> SEQUENCE: 211
gaaagttttc tattttggtc ttattgtaac cctatagtga gtcgtatta                49

<210> SEQ ID NO 212
<211> LENGTH: 117
<212> TYPE: DNA
<213> ORGANISM: artificial
<220> FEATURE:
<223> OTHER INFORMATION: synthetic oligonucleotide substrate

<400> SEQUENCE: 212
taatacgact cactataggg ttccaataag actacaaaag aattgaaagt tgtagtatgc     60
ggtccttgcg gctgagagca cttcaggttc aataagact accaaaagaa ttgaaag        117

<210> SEQ ID NO 213
<211> LENGTH: 117
<212> TYPE: DNA
<213> ORGANISM: artificial
<220> FEATURE:
<223> OTHER INFORMATION: synthetic oligonucleotide substrate

<400> SEQUENCE: 213
ctttcaattc ttttgtagtc ttattggaac ctgaagtgct ctcagccgca aggaccgcat     60
actacaactt tcaattcttt tgtagtctta ttggaacccc tatagtgagt cgtatta       117

<210> SEQ ID NO 214
<211> LENGTH: 87
<212> TYPE: DNA
<213> ORGANISM: artificial
<220> FEATURE:
<223> OTHER INFORMATION: synthetic oligonucleotide substrate

<400> SEQUENCE: 214
taatacgact cactataggg attgaaagtt gtagtatgcg gtccttgcgg ctgagagcac     60
ttcaggttac aataagacca aaataga                                        87

<210> SEQ ID NO 215
<211> LENGTH: 87
<212> TYPE: DNA
<213> ORGANISM: artificial
<220> FEATURE:
<223> OTHER INFORMATION: synthetic oligonucleotide substrate

<400> SEQUENCE: 215
tctattttgg tcttattgta acctgaagtg ctctcagccg caaggaccgc atactacaac    60
tttcaatccc tatagtgagt cgtatta                                        87
```

<210> SEQ ID NO 216
<211> LENGTH: 44
<212> TYPE: DNA
<213> ORGANISM: artificial
<220> FEATURE:
<223> OTHER INFORMATION: synthetic oligonucleotide substrate

<400> SEQUENCE: 216
taatacgact cactataggg cgtaggagga ttggggcaaa aagc                    44

<210> SEQ ID NO 217
<211> LENGTH: 30
<212> TYPE: DNA
<213> ORGANISM: artificial
<220> FEATURE:
<223> OTHER INFORMATION: synthetic oligonucleotide substrate

<400> SEQUENCE: 217
cactaatcga agacttcgta agagataacg                                    30

<210> SEQ ID NO 218
<211> LENGTH: 30
<212> TYPE: RNA
<213> ORGANISM: artificial
<220> FEATURE:
<223> OTHER INFORMATION: synthetic oligonucleotide substrate

<400> SEQUENCE: 218
guuacaauaa gaccaaaaua gaauugaaag                                    30

<210> SEQ ID NO 219
<211> LENGTH: 45
<212> TYPE: RNA
<213> ORGANISM: artificial
<220> FEATURE:
<223> OTHER INFORMATION: synthetic oligonucleotide substrate

<400> SEQUENCE: 219
auugaaaguu guaguaugcg guccuugcgg cugagagcac uucag                   45

<210> SEQ ID NO 220
<211> LENGTH: 12
<212> TYPE: RNA
<213> ORGANISM: artificial
<220> FEATURE:
<223> OTHER INFORMATION: synthetic oligonucleotide substrate

<400> SEQUENCE: 220
guuacaauaa ga                                                       12

<210> SEQ ID NO 221
<211> LENGTH: 52
<212> TYPE: DNA
<213> ORGANISM: artificial
<220> FEATURE:
<223> OTHER INFORMATION: oligonucleotide primer

<400> SEQUENCE: 221
ggaagattta atagcgttgg ctattaaacc ctggaggtag tattgatgat tg           52

<210> SEQ ID NO 222
<211> LENGTH: 52
<212> TYPE: DNA
<213> ORGANISM: artificial
<220> FEATURE:
<223> OTHER INFORMATION: oligonucleotide primer

<400> SEQUENCE: 222
caatcatcaa tactacctcc agggtttaat agccaacgct attaaatctt cc    52

<210> SEQ ID NO 223
<211> LENGTH: 52
<212> TYPE: DNA
<213> ORGANISM: artificial
<220> FEATURE:
<223> OTHER INFORMATION: oligonucleotide primer

<400> SEQUENCE: 223
ggaagattta atagcgttga atattaaacc ctggaggtag tattgatgat tg    52

<210> SEQ ID NO 224
<211> LENGTH: 52
<212> TYPE: DNA
<213> ORGANISM: artificial
<220> FEATURE:
<223> OTHER INFORMATION: oligonucleotide primer

<400> SEQUENCE: 224
caatcatcaa tactacctcc agggtttaat attcaacgct attaaatctt cc    52

<210> SEQ ID NO 225
<211> LENGTH: 42
<212> TYPE: DNA
<213> ORGANISM: artificial
<220> FEATURE:
<223> OTHER INFORMATION: oligonucleotide primer

<400> SEQUENCE: 225
gtttagggcc cttaacttca gcgagatatg ttgcaagctt cg    42

<210> SEQ ID NO 226
<211> LENGTH: 42
<212> TYPE: DNA
<213> ORGANISM: artificial
<220> FEATURE:
<223> OTHER INFORMATION: oligonucleotide primer

<400> SEQUENCE: 226
cgaagcttgc aacatatctc gctgaagtta agggccctaa ac    42

<210> SEQ ID NO 227
<211> LENGTH: 42
<212> TYPE: DNA
<213> ORGANISM: artificial
<220> FEATURE:
<223> OTHER INFORMATION: oligonucleotide primer

<400> SEQUENCE: 227
cgaagcttgc aacatatctc gctgaagtta agggccctaa ac    42

<210> SEQ ID NO 228
<211> LENGTH: 42
<212> TYPE: DNA
<213> ORGANISM: artificial
<220> FEATURE:
<223> OTHER INFORMATION: oligonucleotide primer

<400> SEQUENCE: 228
cgaagcttgc aacatatctc caggaagtta agggccctaa ac    42

<210> SEQ ID NO 229

```
<211> LENGTH: 52
<212> TYPE: DNA
<213> ORGANISM: artificial
<220> FEATURE:
<223> OTHER INFORMATION: oligonucleotide primer

<400> SEQUENCE: 229
cggccataaa aagtgaatac gtaaagagtg cagggccctt aacttcatgg ag          52

<210> SEQ ID NO 230
<211> LENGTH: 52
<212> TYPE: DNA
<213> ORGANISM: artificial
<220> FEATURE:
<223> OTHER INFORMATION: oligonucleotide primer

<400> SEQUENCE: 230
ctccatgaag ttaagggccc tgcactcttt acgtattcac tttttatggc cg          52

<210> SEQ ID NO 231
<211> LENGTH: 57
<212> TYPE: DNA
<213> ORGANISM: artificial
<220> FEATURE:
<223> OTHER INFORMATION: oligonucleotide primer

<400> SEQUENCE: 231
cggccataaa aagtgaatac gtaaagagtt cagggccctt aacttcatgg agatatg     57

<210> SEQ ID NO 232
<211> LENGTH: 57
<212> TYPE: DNA
<213> ORGANISM: artificial
<220> FEATURE:
<223> OTHER INFORMATION: oligonucleotide primer

<400> SEQUENCE: 232
catatctcca tgaagttaag ggccctgaac tctttacgta ttcactttt atggccg      57

<210> SEQ ID NO 233
<211> LENGTH: 49
<212> TYPE: DNA
<213> ORGANISM: artificial
<220> FEATURE:
<223> OTHER INFORMATION: oligonucleotide primer

<400> SEQUENCE: 233
taatacgact cactataggg ttacaataag accaaaatag aattgaaag              49

<210> SEQ ID NO 234
<211> LENGTH: 49
<212> TYPE: DNA
<213> ORGANISM: artificial
<220> FEATURE:
<223> OTHER INFORMATION: oligonucleotide primer

<400> SEQUENCE: 234
ctttcaattc tattttggtc ttattgtaac cctatagtga gtcgtatta              49

<210> SEQ ID NO 235
<211> LENGTH: 25
<212> TYPE: DNA
<213> ORGANISM: artificial
<220> FEATURE:
<223> OTHER INFORMATION: oligonucleotide primer

<400> SEQUENCE: 235
```

-continued

```
gtatgcggtc cttgcggctg agagc                                              25

<210> SEQ ID NO 236
<211> LENGTH: 30
<212> TYPE: RNA
<213> ORGANISM: artificial
<220> FEATURE:
<223> OTHER INFORMATION: oligonucleotide primer

<400> SEQUENCE: 236
guuacaauaa gaccaaaaua gaauugaaag                                         30

<210> SEQ ID NO 237
<211> LENGTH: 12
<212> TYPE: DNA
<213> ORGANISM: artificial
<220> FEATURE:
<223> OTHER INFORMATION: target polynucleotide

<400> SEQUENCE: 237
gttacaataa ga                                                            12

<210> SEQ ID NO 238
<211> LENGTH: 30
<212> TYPE: RNA
<213> ORGANISM: artificial
<220> FEATURE:
<223> OTHER INFORMATION: RNA repeat
<220> FEATURE:
<221> NAME/KEY: misc_feature
<222> LOCATION: (22)..(23)
<223> OTHER INFORMATION: cleavage site

<400> SEQUENCE: 238
guuacaauaa gacuaaaaua gaauugaaag                                         30

<210> SEQ ID NO 239
<211> LENGTH: 274
<212> TYPE: PRT
<213> ORGANISM: Victivallis vadensis

<400> SEQUENCE: 239
```

Met Gln Ile Glu Leu Gln Leu Ser Pro Val Gly Asp Gly Leu Leu Ala
1               5                  10                  15

Arg Asp Cys His His Glu Leu Ala Ser Ala Leu Tyr Gln Ala Leu Ser
            20                  25                  30

Arg Ser Gln Pro Lys Leu Ala Glu Glu Leu His Asp Gly Asn His Arg
        35                  40                  45

Ser Arg Leu Lys Leu Phe Val Phe Ser Leu Phe Asn Ser Asp Pro Lys
    50                  55                  60

Pro Val Ala Ala Glu Leu Pro Asp Gly Thr Arg Ala Leu Lys Phe Gly
65                  70                  75                  80

Ser Arg Ile Trp Met Arg Phe Ala Ser Ile Trp Pro Glu Leu Val Tyr
                85                  90                  95

Gly Met Ala Glu Ala Leu Gln Lys Gln Lys Glu Leu Asn Val Arg Gly
            100                 105                 110

Leu Arg Phe Arg Leu Glu Glu Ile Arg Met Val Pro Thr Pro Asp Phe
        115                 120                 125

Arg Pro Thr Met Thr Tyr Arg Pro Phe Gly Gln Ala Asp Phe Ile Val
    130                 135                 140

Cys Arg Tyr Gln Lys Asp Gly Lys Asn Tyr Phe Arg Met Pro Asp Asp

```
            145                 150                 155                 160
    Ser Glu Pro Gly Ile Pro Ser Cys Ala Asp Leu Ile Ala Gly Asn Leu
                    165                 170                 175

Arg His Lys Leu Leu Arg Leu Arg Glu Ile Arg Leu Asp Ile Phe Glu
                    180                 185                 190

Asn Leu Met Ser Ile Gly Gly Leu Asp Ala Ser Ala Val Ala Ala Leu
                    195                 200                 205

Pro Ile Gln Val Glu Phe Leu Pro Leu Met Glu Gly Arg Ala Tyr Arg
        210                 215                 220

Thr Arg Leu Thr Arg Ile Arg Gly Ile Asn Val Arg Ala Phe Arg Ala
    225                 230                 235                 240

Pro Leu Arg Ile Thr Ala Pro Glu Ala Val His Arg Leu Val Trp Glu
                    245                 250                 255

Thr Gly Val Gly Ser Met Asn Ser Met Gly Phe Gly Leu Val Cys Gly
                    260                 265                 270

Gly Arg

<210> SEQ ID NO 240
<211> LENGTH: 254
<212> TYPE: PRT
<213> ORGANISM: Clostridium difficile

<400> SEQUENCE: 240

Met His Leu Val Arg His Leu Ile Leu Thr Val Asp Asn Glu Val
1               5                   10                  15

Val Leu Asp Tyr Asn Tyr Gln Tyr Glu Leu Met Lys Arg Ile Tyr Glu
                20                  25                  30

Ala Ile Glu Ile Asn Asp Lys Arg Lys Ala Leu Ser Leu His Asn Glu
                35                  40                  45

Gly Tyr Lys Val Asp Lys Lys Val Phe Lys Leu Phe Asn Tyr Thr Ile
        50                  55                  60

Met Phe Glu Asn Ala Lys Tyr Leu Lys Glu Gly Ile His Leu Asn Pro
65                  70                  75                  80

Gln Thr Lys Ile Lys Leu Ile Leu Ser Gly Tyr Asp Asp Ile Leu Asn
                85                  90                  95

Asn Ile Ile Lys Gly Phe Ile Lys Cys Lys Val Phe Lys Leu Asn Asn
                100                 105                 110

Ile Glu Phe Lys Val Ser Asp Ile Glu Glu Asp Ser Lys Lys Asn Phe
            115                 120                 125

Asn Asn Ile Thr Leu Tyr Lys Val Arg Ser Pro Ile Val Ala Ser Leu
        130                 135                 140

Tyr Asp Leu Lys Ser Arg Lys Gln Val Tyr Leu Asn Pro Met Gln Glu
145                 150                 155                 160

Glu Phe Tyr Lys Ala Leu His Asp Asn Leu Gly Asn Lys Tyr Lys Leu
                165                 170                 175

Ile His Asn Lys Glu Tyr Thr Gly Glu Leu Tyr Phe Asp Ile Glu Asp
                180                 185                 190

Val Leu Ala Val Lys Lys Lys Tyr Ile Thr Asn Ile Lys Gly Lys Gly
            195                 200                 205

Phe Ile Ile Gly Tyr Thr Asp Phe Glu Ile Phe Val Gln Ala Asn Lys
        210                 215                 220

Asp Met Gln Glu Val Ile Tyr Tyr Cys Gly Leu Gly Glu Lys Asn Ser
225                 230                 235                 240

Ile Gly Met Gly Leu Leu Thr Tyr Ile Thr Ser Arg Arg Ala
```

```
<210> SEQ ID NO 241
<211> LENGTH: 86
<212> TYPE: PRT
<213> ORGANISM: artificial
<220> FEATURE:
<223> OTHER INFORMATION: consensus sequence

<400> SEQUENCE: 241

Met Arg Ile Leu Leu Pro Asn Tyr Asn Tyr Leu Gln Ile Tyr Leu Asn
1               5                   10                  15

Ala Phe Leu His Glu Gly Phe Phe Lys Leu Thr Phe Ser Leu Ile Ser
            20                  25                  30

Ser Pro Glu Glu Leu Gly Leu Leu Glu Val Ile Gly Asn Ile Leu Ser
        35                  40                  45

Pro Ile Asn Gly Tyr Pro Glu Phe Glu Leu Lys Tyr Glu Lys Ile Lys
    50                  55                  60

Asn Ile Gly Phe Gly Asp Glu Leu Leu Ala Tyr Asp Gly Gly Lys Asn
65                  70                  75                  80

Ser Gly Phe Gly Met Val
                85

<210> SEQ ID NO 242
<211> LENGTH: 23
<212> TYPE: RNA
<213> ORGANISM: artificial
<220> FEATURE:
<223> OTHER INFORMATION: CAS6 recognition domain
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (15)..(23)
<223> OTHER INFORMATION: n is a, c, g, or u

<400> SEQUENCE: 242
nuuacaauaa gaccnnnnnn nnn                                    23
```

METHOD FOR CLEAVING A TARGET RNA USING A CAS6 POLYPEPTIDE

CONTINUING APPLICATION DATA

This application is the §371 U.S. National Stage of International Application No. PCT/US2009/063432, filed 5 Nov. 2009, which claims the benefit of U.S. Provisional Application Ser. No. 61/112,040, filed Nov. 6, 2008, each of which are incorporated by reference herein.

GOVERNMENT FUNDING

The present invention was made with government support under Grant No. R01 GM54682, awarded by the NIH. The Government has certain rights in this invention.

SEQUENCE LISTING

This application contains a Sequence Listing electronically submitted via EFS-Web to the United States Patent and Trademark Office as an ASCII text file entitled "235.01260101_ST25.txt" having a size of 442 kilobytes and created on Dec. 28, 2015. The information contained in the Sequence Listing is incorporated by reference herein.

BACKGROUND

All genomes are potential targets of invasion by molecular parasites such as viruses and transposable elements, and organisms have evolved RNA-directed defense mechanisms to cope with the constant threat of genome invaders (Farazi et al., 2008. Development 135: 1201-1214; Girard and Hannon, 2008. Trends Cell Biol. 18:136-148). The well-known subpathway of RNA silencing referred to as RNAi functions in defense against viruses in eukaryotes (Ding and Voinnet, 2007. Cell 130: 413-426). The RNAi defense response is mediated by short (~22-nucleotide [nt]) RNAs termed siRNAs. The siRNAs are generated from invading viral RNAs by dsRNA-specific, RNase III-like endonucleases called Dicers (Jaskiewicz and Filipowicz, 2008. Curr. Top. Microbiol. Immunol. 320: 77-97). The mature siRNAs are assembled with host effector proteins and target them to corresponding viral target RNAs to effect viral gene silencing via RNA destruction or other mechanisms (Farazi et al., 2008. Development 135: 1201-1214; Girard and Hannon, 2008. Trends Cell Biol. 18:136-148).

Compelling evidence has recently emerged for the existence of an RNA-mediated genome defense pathway in archaea and numerous bacteria that has been hypothesized to parallel the eukaryotic RNAi pathway (for reviews, see Godde and Bickerton, 2006. J. Mol. Evol. 62: 718-729; Lillestol et al., 2006. Archaea 2: 59-72; Makarova et al., 2006. Biol. Direct 1: 7.; Sorek et al., 2008. Nat. Rev. Microbiol. 6: 181-186). Known as the CRISPR-Cas system or prokaryotic RNAi (pRNAi), the pathway is proposed to arise from two evolutionarily and often physically linked gene loci: the CRISPR (clustered regularly interspaced short palindromic repeats) locus, which encodes RNA components of the system, and the cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60). The individual Cas proteins do not share significant sequence similarity with protein components of the eukaryotic RNAi machinery, but have analogous predicted functions (e.g., RNA binding, nuclease, helicase, etc.) (Makarova et al., 2006. Biol. Direct 1: 7).

Unlike the siRNAs of the eukaryotic RNAi system, the effector RNAs of pRNAi are encoded in the host genome. CRISPR loci encode short (typically ~30- to 35-nt) invader-derived sequences interspersed between short (typically ~30- to 35-nt) direct repeat sequences (Bolotin et al., 2005. Microbiology 151: 2551-2561; Mojica et al., 2005. J. Mol. Evol. 60: 174-182; Pourcel et al., 2005. Microbiology 151: 653-663; Godde and Bickerton, 2006. J. Mol. Evol. 62: 718-729; Lillestol et al., 2006. Archaea 2: 59-72; Makarova et al., 2006. Biol. Direct 1:7; Horvath et al., 2008. J. Bacteriol. 190: 1401-1412; Sorek et al., 2008. Nat. Rev. Microbiol. 6: 181-186). Recent studies have provided clear experimental evidence that correlates the presence of virus-specific CRISPR sequences with viral immunity (Barrangou et al., 2007. Science 315: 1709-1712; Brouns et al., 2008. Science 321: 960-964; Deveau et al., 2008. J. Bacteriol. 190: 1390-1400). Furthermore, viral infection has been shown to result in the appearance of new corresponding CRISPR elements in surviving strains (Barrangou et al., 2007. Science 315: 1709-1712; Deveau et al., 2008. J. Bacteriol. 190: 1390-1400). This rapidly adapting CRISPR-based immunity acts within natural microbial populations to promote host cell fitness and to influence microbial ecology (Andersson and Banfield, 2008. Science 320: 1047-1050; Tyson and Banfield, 2008. Microbiol. 10: 200-207).

The primary products of the CRISPR loci appear to be short RNAs that contain the invader targeting sequences, and are termed guide RNAs or prokaryotic silencing RNAs (psiRNAs) based on their hypothesized role in the pathway (Makarova et al., 2006. Biol. Direct 1: 7; Hale et al., 2008. RNA, 14: 2572-2579). RNA analysis indicates that CRISPR locus transcripts are cleaved within the repeat sequences to release ~60- to 70-nt RNA intermediates that contain individual invader targeting sequences and flanking repeat fragments (FIG. 1A; Tang et al., 2002. Proc. Natl. Acad. Sci. 99: 7536-7541; Tang et al., 2005. Mol. Microbiol. 55: 469-481; Lillestol et al., 2006. Archaea 2: 59-72; Brouns et al., 2008. Science 321: 960-964; Hale et al., 2008. RNA, 14: 2572-2579). In the archaeon *Pyrococcus furiosus*, these intermediate RNAs are further processed to abundant, stable ~35- to 45-nt mature psiRNAs (Hale et al., 2008. RNA, 14: 2572-2579).

SUMMARY OF THE INVENTION

Provided herein are polynucleotides. The polynucleotides may include a nucleotide sequence encoding a polypeptide having Cas6 endoribonuclease activity, wherein the amino acid sequence of the polypeptide and the amino acid sequence of SEQ ID NO:2 have at least 80% identity, or the complement thereof. The polynucleotides may include a nucleotide sequence encoding a polypeptide having Cas6 endoribonuclease activity, wherein the nucleotide sequence of the isolated polynucleotide and the nucleotide sequence of SEQ ID NO:1 have at least 80% identity, or the complement thereof. The polynucleotides may be enriched, isolated, or purified. The polynucleotides may include a heterologous polynucleotide, such as a regulatory sequence, or a vector.

In another aspect, a polynucleotide, referred to herein as a target RNA polynucleotide, may include a Cas6 recognition domain, wherein the Cas6 recognition domain includes 5'-GTTACAATAAGA (SEQ ID NO:237), or the complement thereof. For instance, the polynucleotide may include UNCNNUNNNNNNNNNNNNNNNNNNNNNN (SEQ ID NO:192), UUACAAUANNNNNNNN- NNNNNNNNNNNN (SEQ ID NO:193), GTTCCAATAA-GACTAAAATAGAATTGAAAG (SEQ ID NO:191), or the complements thereof. The polynucleotide may include an operably linked regulatory sequence or a vector, and the polynucleotide may be RNA.

Also provided herein are polypeptides. A polypeptide has Cas6 endoribonuclease activity, and the polypeptide includes an amino acid sequence, wherein the amino acid sequence and the amino acid sequence of SEQ ID NO:2 have at least 80% identity. The polypeptides may further include a heterologous polypeptide. A polypeptide may be enriched, isolated, or purified.

Further provided herein are genetically modified microbes. A genetically modified microbe may include a polynucleotide described herein or a polypeptide described herein. The microbe may be, for instance, a bacteria, such as a gram positive or a gram negative microbe, for example, *E. coli*, or an archeae, such as *Haloferax volcanii*. Also provided herein are compositions that include the polynucleotides, the polypeptides, and/or the genetically modified microbes described herein. For instance, a composition may include a polypeptide having Cas6 activity, a target RNA polynucleotide, or the combination.

Provided herein are methods for using the polynucleotides, polypeptides, and genetically modified microbes described herein. In one aspect, the methods may be used to cleave a nucleotide sequence. The method may include incubating a target RNA polynucleotide with a polypeptide under conditions suitable for cleavage of the target RNA polynucleotide, wherein the target RNA polynucleotide includes a Cas6 recognition domain. The polypeptide may be a Cas6 polypeptide from a microbe genome, for instance, the polypeptide includes an amino acid sequence having at least 80% with the amino acid sequence of SEQ ID NO:2, an amino acid sequence depicted in FIG. 1, an amino acid sequence depicted in FIG. 2, or an amino acid sequence depicted in FIG. 3, and has Cas6 endoribonuclease activity. The polypeptide cleaves the target RNA polynucleotide at a cleavage site. The cleavage site may be located 5 to 20 nucleotides downstream of the Cas6 recognition domain. The target RNA polynucleotide may include a Cas6 recognition domain. The Cas6 recognition domain may be one that is present in a microbe genome, such as 5'-GTTACAATAAGA (SEQ ID NO:237). The target RNA polynucleotide may include UNCN-NUNNNNNNNNNNNNNNNNNNNNNN (SEQ ID NO:192), or UUA-CAAUANNNNNNNNNNNNNNNNNNNNN (SEQ ID NO:193), or GTTCCAATAAGACTAAAATAGAAT-TGAAAG (SEQ ID NO:191). The methods may be in vivo or in vitro.

As used herein, an "enriched" polynucleotide means that a polynucleotide constitutes a significantly higher fraction of the total DNA or RNA present in a mixture of interest than in cells from which the sequence was taken. A person skilled in the art could enrich a polynucleotide by preferentially reducing the amount of other polynucleotides present, or preferentially increasing the amount of the specific polynucleotide, or both. However, polynucleotide enrichment does not imply that there is no other DNA or RNA present, the term only indicates that the relative amount of the sequence of interest has been significantly increased. The term "significantly" qualifies "increased" to indicate that the level of increase is useful to the person using the polynucleotide, and generally means an increase relative to other nucleic acids of at least 2 fold, or more preferably at least 5 to 10 fold or more. The term also does not imply that there is no polynucleotide from other sources. Other polynucleotides may, for example, include DNA from a bacterial genome, or a cloning vector.

As used herein, an "enriched" polypeptide defines a specific amino acid sequence constituting a significantly higher fraction of the total of amino acids present in a mixture of interest than in cells from which the polypeptide was separated. A person skilled in the art can preferentially reduce the amount of other amino acid sequences present, or preferentially increase the amount of specific amino acid sequences of interest, or both. However, the term "enriched" does not imply that there are no other amino acid sequences present. Enriched simply means the relative amount of the sequence of interest has been significantly increased. The term "significant" indicates that the level of increase is useful to the person making such an increase. The term also means an increase relative to other amino acids of at least 2 fold, or more preferably at least 5 to 10 fold, or even more. The term also does not imply that there are no amino acid sequences from other sources. Other amino acid sequences may, for example, include amino acid sequences from a host organism.

As used herein, an "isolated" substance is one that has been removed from its natural environment, produced using recombinant techniques, or chemically or enzymatically synthesized. For instance, a polypeptide or a polynucleotide can be isolated. A substance may be purified, i.e., is at least 60% free, preferably at least 75% free, and most preferably at least 90% free from other components with which it is naturally associated.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, enzyme, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring. As used herein, "heterologous amino acids" or "heterologous polypeptides" refer to amino acids that are not normally associated with a polypeptide in a wild-type cell. Examples of heterologous polypeptides include, but are not limited to a tag useful for purification or a carrier polypeptide useful to increase immunogenicity of a polypeptide. A polypeptide that includes heterologous polypeptides may be referred to as a fusion polypeptide.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region" and "coding sequence" are used interchangeably and refer to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

A polynucleotide that includes a coding region may include heterologous nucleotides that flank one or both sides of the coding region. As used herein, "heterologous nucleotides" refer to nucleotides that are not normally present flanking a coding region that is present in a wild-type cell. For instance, a coding region present in a wild-type microbe and encoding a Cas6 polypeptide is flanked by homologous sequences, and any other nucleotide sequence flanking the coding region is considered to be heterologous. Examples of heterologous nucleotides include, but are not limited to regulatory sequences. Typically, heterologous nucleotides are present in a polynucleotide disclosed herein through the use of standard genetic and/or recombinant methodologies well known to one skilled in the art. A polynucleotide disclosed herein may be included in a suitable vector.

As used herein, an "exogenous polynucleotide" refers to a polynucleotide that is not normally or naturally found in a microbe. As used herein, the term "endogenous polynucleotide" refers to a polynucleotide that is normally or naturally found in a cell microbe. An "endogenous polynucleotide" is also referred to as a "native polynucleotide."

As used herein, "identity" refers to sequence similarity between two polypeptides or two polynucleotides. The sequence similarity between two polypeptides is determined by aligning the residues of the two polypeptides (e.g., a candidate amino acid sequence and a reference amino acid sequence, such as SEQ ID NO:2) to optimize the number of identical amino acids along the lengths of their sequences; gaps in either or both sequences are permitted in making the alignment in order to optimize the number of shared amino acids, although the amino acids in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence analysis techniques such as the BESTFIT or GAP algorithm in the GCG package (Madison Wis.), or the Blastp program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, sequence similarity between two amino acid sequences is determined using the Blastp program of the BLAST 2 search algorithm. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, sequence similarity is referred to as "identities."

The sequence similarity between two polynucleotides is determined by aligning the residues of the two polynucleotides (e.g., a candidate nucleotide sequence and a reference nucleotide sequence, such as SEQ ID NO:1) to optimize the number of identical nucleotides along the lengths of their sequences; gaps in either or both sequences are permitted in making the alignment in order to optimize the number of shared nucleotides, although the nucleotides in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as GCG FastA (Genetics Computer Group, Madison, Wis.), MacVector 4.5 (Kodak/IBI software package) or other suitable sequence analysis programs or methods known in the art. Preferably, sequence similarity between two nucleotide sequences is determined using the Blastn program of the BLAST 2 search algorithm, as described by Tatusova, et al. (1999, *FEMS Microbiol Lett.*, 174:247-250), and available through the World Wide Web, for instance at the internet site maintained by the National Center for Biotechnology Information, National Institutes of Health. Preferably, the default values for all BLAST 2 search parameters are used, including reward for match=1, penalty for mismatch=−2, open gap penalty=5, extension gap penalty=2, gapx dropoff=50, expect=10, wordsize=11, and optionally, filter on. In the comparison of two nucleotide sequences using the BLAST search algorithm, sequence similarity is referred to as "identities."

As used herein "prokaryotic microbe" and "microbe" are used interchangeably and refer to members of the domains Bacteria and Archaea.

As used herein, "genetically modified microbe" refers to a microbe which has been altered "by the hand of man." A genetically modified microbe includes a microbe into which has been introduced an exogenous polynucleotide. Genetically modified microbe also refers to a microbe that has been genetically manipulated such that endogenous nucleotides have been altered to include a mutation, such as a deletion, an insertion, a transition, a transversion, or a combination thereof. For instance, an endogenous coding region could be deleted. Such mutations may result in a polypeptide having a different amino acid sequence than was encoded by the endogenous polynucleotide. Another example of a genetically modified microbe is one having an altered regulatory sequence, such as a promoter, to result in increased or decreased expression of an operably linked endogenous coding region.

Conditions that are "suitable" for an event to occur, such as cleavage of a polynucleotide, or "suitable" conditions are conditions that do not prevent such events from occurring. Thus, these conditions permit, enhance, facilitate, and/or are conducive to the event.

As used herein, "in vitro" refers to an artificial environment and to processes or reactions that occur within an artificial environment. In vitro environments can consist of, but are not limited to, test tubes. The term "in vivo" refers to the natural environment (e.g., a cell, including a genetically modified microbe) and to processes or reaction that occur within a natural environment.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 15. Amino acid sequences of Cas6 polypeptides from Archeae. The alphanumeric code above each sequence is the UniProtKB/TrEMBL accession number.

FIG. 16. Amino acid sequences of Cas6 polypeptides from Bacteria. The alphanumeric code above each sequence is the UniProtKB/TrEMBL accession number.

FIG. 17. Amino acid sequences of Cas6 polypeptides from Cyanobacteria. The alphanumeric code above each sequence is the UniProtKB/TrEMBL accession number.

FIG. 18. Amino acid sequences of a Cas6 polypeptide (SEQ ID NO:2) and a nucleotide sequence (SEQ ID NO:1) encoding the polypeptide.

FIG. 19. Alignments between Cas6 polypeptide regions and domains of hidden Markov models present in the TIGR-FAM database of protein families. Amino acids 44 to 236 or 95 to 238 of SEQ ID NO:2), domain present in TIGR01877 (SEQ ID NO:188), domain present in PR01881 (SEQ ID NO:189).

DETAILED DESCRIPTION OF ILLUSTRATIVE EMBODIMENTS

Polypeptides

Figure 1:
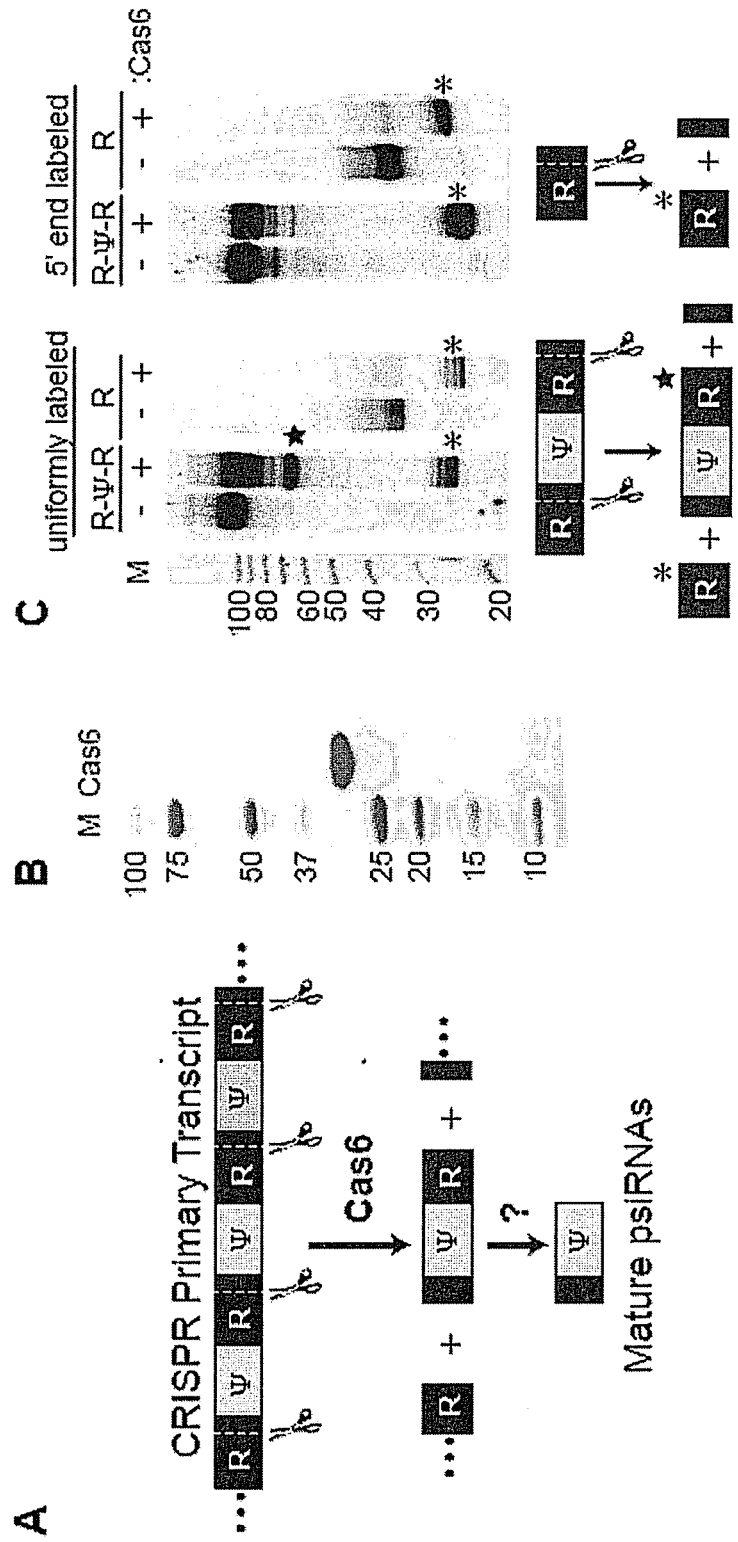
FIG. 1. Cas6 is an endoribonuclease that cleaves CRISPR RNAs within repeat sequences. (A) psiRNA biogenesis pathway model. The primary CRISPR transcript contains unique invader targeting or guide sequences (shaded blocks) flanked by direct repeat sequences (R). Cas6 catalyzes site-specific cleavage within each repeat, releasing individual invader targeting units. The Cas6 cleavage products undergo further processing to generate smaller mature psiRNA species. (B) Purified recombinant PfCas6 expressed in E. coli. The sizes (in kilodaltons) of protein markers (M) are indicated. (C) Radiolabeled RNAs (repeat-guide-repeat [R-g-R] or repeat alone [R], as diagrammed) were either uniformly or 5'-end-labeled and incubated in the absence (−) or presence (+) of PfCas6 protein (500 nM). Products were resolved by denaturing gel electrophoresis and visualized using a phosphorimager. The main cleavage products are indicated by a star or asterisk on the gel and in the diagram.

Provided herein are polypeptides having endoribonuclease activity. A polypeptide having endoribonuclease activity as described below is referred to herein as a Cas6 polypeptide, and the endoribonuclease activity is referred to herein as Cas6 endoribonuclease activity. Examples of Cas6 polypeptides are depicted at Genbank Accession No. AAL81255 (SEQ ID NO:2), FIG. 15, FIG. 16, and FIG. 17. Other examples of Cas6 polypeptides provided herein include those having sequence similarity with the amino acid sequence of SEQ ID NO:2, an amino acid sequence depicted in FIG. 15, an amino acid sequence depicted in FIG. 16, or an amino acid sequence depicted at FIG. 17. A Cas6 polypeptide having sequence similarity with the amino acid sequence depicted at SEQ ID NO:2, FIG. 15, FIG. 16, or FIG. 17 has Cas6 endoribonuclease activity. A Cas6 polypeptide may be enriched, isolated, or purified from a microbe having a CRISPR locus and the cas (CRISPR-associated) locus, such as, but not limited to, *Pyrococcus furiosus*, or may be produced using recombinant techniques, or chemically or enzymatically synthesized using routine methods. In some aspects, a Cas6 polypeptide may be enriched, isolated, or purified from a microbe that does not have CRISPR loci.

The amino acid sequence of a Cas6 polypeptide having sequence similarity to an amino acid sequence disclosed herein, such as SEQ ID NO:2, an amino acid sequence depicted in FIG. 15, an amino acid sequence depicted in FIG. 16, or an amino acid sequence depicted in FIG. 17, may include conservative substitutions of amino acids present in an amino acid sequence. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) may generally be substituted for another amino acid without substantially altering the secondary and/or tertiary structure of a polypeptide. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group containing side chains); Class VI: H is, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids.

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a polypeptide sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

Figure 8A:
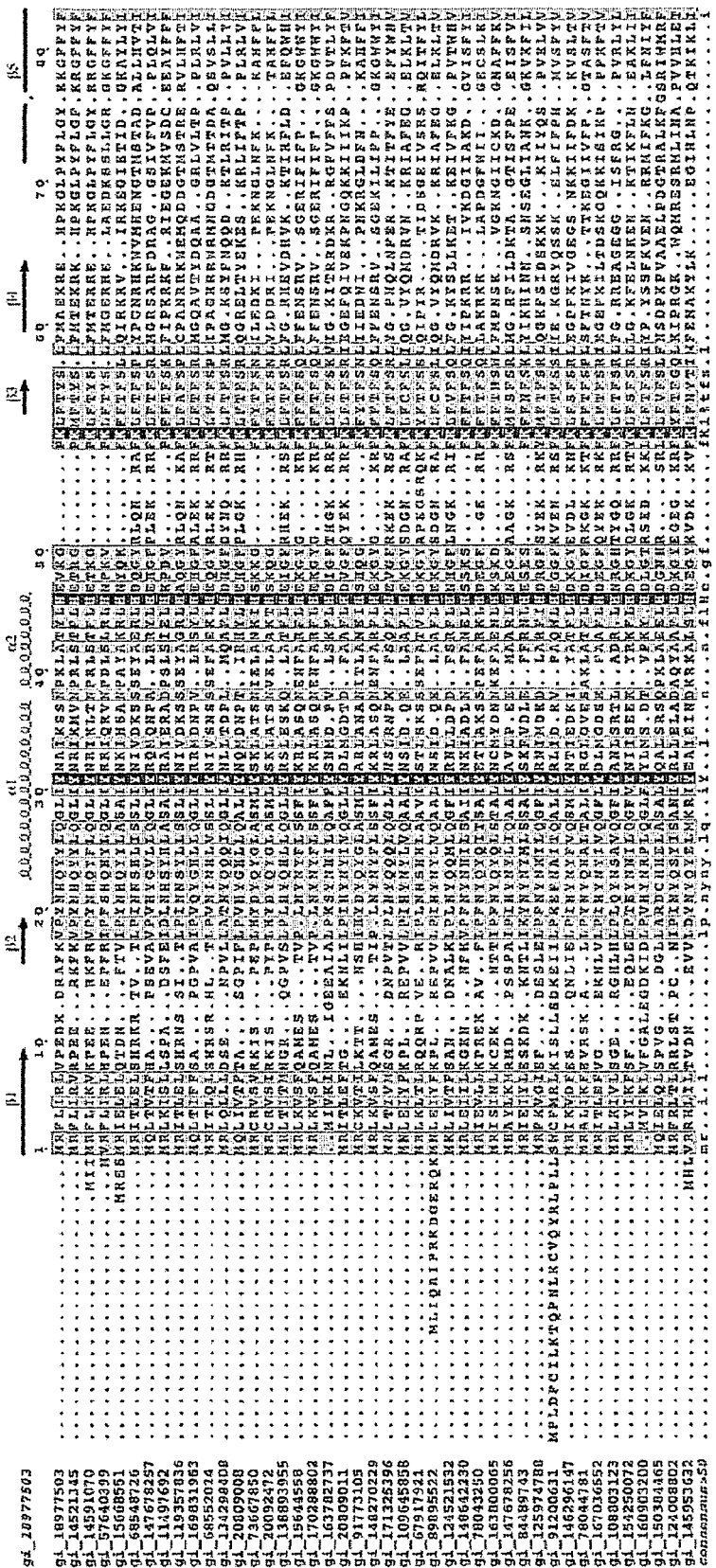
FIG. 8. Amino acid sequence alignment of Cas6 proteins. PSI-BLAST of PF1131 amino acid sequence against the non-redundant protein database (nr) at NCBI yielded 151 protein sequences that have E-values of less than $10^{-4}$. It was immediately clear that many organisms contain more than one Cas6-related sequence. These fell into two distinctive classes: one that includes the conserved triad residues (like PfCas6) and one that does not. We aligned 42 Cas6 homologs that appear to belong to the first class and have E-values of less than $10^{-23}$. In this alignment, the strictly conserved residues are the putative catalytic triad residues and the four glycine residues in the G-rich loop. β1, β2, etc., α1, α2, etc., and TT refer to predicted secondary structure elements, β-strand, α helix, β-turn, respectively. Organisms and genes listed include: *Pyrococcus furiosus* DSM 3638 (gi_18977503; SEQ ID NO:2), *Pyrococcus abyssi* GE5 (gi_14521345; SEQ ID NO:39), *Pyrococcus horikoshii* OT3 (gi_14591070; SEQ ID NO:42), *Thermococcus kodakaraensis* KOD1 (gi_57640399; SEQ ID NO:36), *Methanocaldococcus jannaschii* DSM 2661 (gi_15668551; SEQ ID NO:26), *Pelodictyon phaeoclathratiforme* BU-1 (gi_68548726; SEQ ID NO:65), *Archaeoglobus fulgidus* DSM 4304 (gi_11497692; SEQ ID NO:46), *Chlorobium phaeobacteroides* DSM 266 (gi_119357836; SEQ ID NO:63), *Candidatus Desulforudis audaxviator* MP104C (gi_169831963; SEQ ID NO:157), *Prosthecochloris aestuarii* DSM 271 (gi_68552024; SEQ ID NO:59), *Desulfotomaculum reducens* MI-1 (gi_134298408; SEQ ID NO:151), *Thermoanaerobacter tengcongensis* MB4 (gi_20809008; SEQ ID NO:122), *Methanosarcina barkeri* str. Fusaro (gi_73667850; SEQ ID NO:48), *Methanosarcina acetivorans* C2A (gi_20092472; SEQ ID NO:47), *Geobacillus thermodenitrificans* NG80-2 (gi_138893955; SEQ ID NO:105), *Thermotoga maritima* MSB8 (gi_15644558; SEQ ID NO:84), *Thermotoga* sp. RQ2 (gi_170288802; SEQ ID NO:85), *Hydrogenivirga* sp. 128-5-R1-1 (gi_163782737; SEQ ID NO:73), *Thermoanaerobacter tengcongensis* MB4 (gi_20809011; SEQ ID NO:121), *Methanococcoides burtonii* DSM 6242 (gi_91773105; SEQ ID NO:49), *Thermotoga petrophila* RKU-1 (gi_148270229; SEQ ID NO:83), *Geobacillus* sp. WCH70 (gi_171325396; SEQ ID NO:107), *Desulfitobacterium hafniense* DCB-2 (gi_109645858; SEQ ID NO:153), *Chlorobium limicola* DSM 245 (gi_67917921; SEQ ID NO:64), *Desulfitobacterium hafniense* Y51 gi_89895522; SEQ ID NO:154), *Methanobrevibacter smithii* ATCC 35061 (gi_148642230; SEQ ID NO:22), *Carboxydothermus hydrogenoformans* Z-2901 (gi_78043250; SEQ ID NO:120), *Methanococcus voltae* A3 (gi_163800065; SEQ ID NO:28), *Pelotomaculum thermopropionicum* SI (gi_147678256; SEQ ID NO:155), *Methanosphaera stadtmanae* DSM 3091 (gi_84489743; SEQ ID NO:23), *Clostridium thermocellum* ATCC 27405 (gi_125974788; SEQ ID NO:145), *Candidatus Kuenenia stuttgartiensis* (gi_91200631; SEQ ID NO:103), *Caldicellulosiruptor saccharolyticus* DSM 8903 (gi_146296147; SEQ ID NO:125), *Carboxydothermus hydrogenoformans* Z-2901 (gi_78044781; SEQ ID NO:119), *Thermoanaerobacter pseudethanolicus* ATCC 33223 (gi_167036552; SEQ ID NO:124), *Rubrobacter xylanophilus* DSM 9941 (gi_108803123; SEQ ID NO:92), *Fervidobacterium nodosum* Rt17-B1 (gi_154250072; SEQ ID NO:89), *Petrotoga mobilis* SJ95 (gi_160903200; SEQ ID NO:91), *Victivallis vadensis* ATCC BAA-548 (gi_150384465; SEQ ID NO:239), *Microscilla marina* ATCC 23134 (gi_124008802; SEQ ID NO:53), *Clostridium difficile* QCD-32g58 (gi_145953632; SEQ ID NO:240). The consensus sequence is SEQ ID NO:241.
Figure 8B:
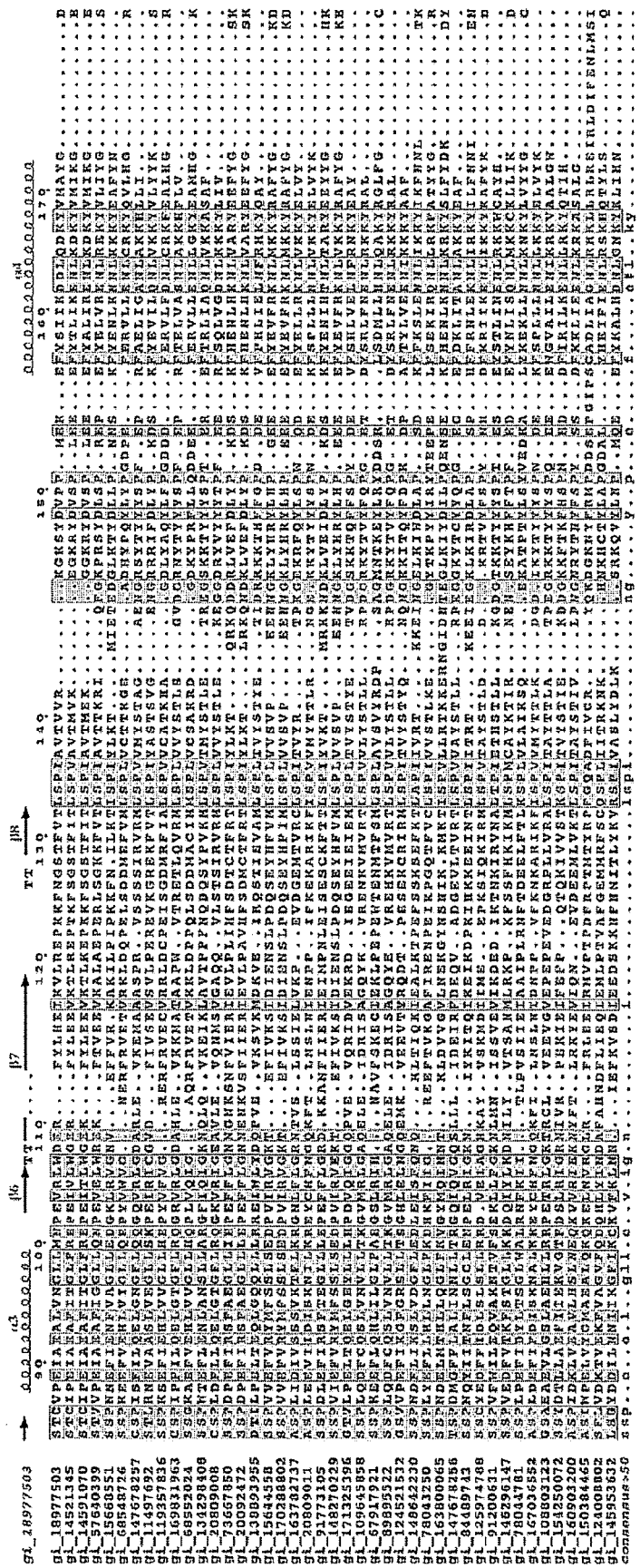

A Cas6 polypeptide may include a GhGxxxxxGhG (SEQ ID NO:190) motif (where "h" indicates a hydrophobic amino acid) near the C-terminus. An Arg or Lys may be, and often is, found within the central stretch of 5 amino acids (i.e. xxxxx). A Cas6 polypeptide contains at least one residue—the His46 shown in FIG. 8—that may play a role in catalysis, or conservative substitution thereof. A Cas6 polypeptide may contain other residues—the Tyr31 and Lys52 shown in FIG. 8—which may also play a role in catalysis, or conservative substitution thereof. The residue(s) expected to play a role in catalysis may be located near the G-rich loop that contains the Cas6 signature motif in the 3D structure of the protein as described in Example 1 herein. Other areas that are conserved, as well as areas that are not conserved, are shown in FIG. 8. Cas6 polypeptides may include domains present in the TIGRFAM database at accession numbers TIGR01877 and PF01881, as shown in FIG. 19. The TIGRFAM database includes families of polypeptides for which function is conserved (Haft et al., Nucl. Acids Res., 2003, 31:371-373, Bateman and Haft, 2002, Briefings Bioinformatics, 3:236-245, and Haft et al., 2005, PLoS Computational Biol., 1(6):e60).

Other examples of Cas6 polypeptides provided herein include those present in prokaryotic microbes having a CRISPR locus and a cas locus. Examples include those depicted in FIG. 15, FIG. 16, and FIG. 17. Cas6 polypeptides can be easily identified in any microbe that includes a CRISPR locus. A coding region encoding a Cas6 polypeptide is typically in a cas locus located in close proximity to a CRISPR locus. Haft et al. (2005, PLoS Computational Biol., 1(6):e60) review the Cas protein family, and created rules for the identification of specific subtypes of the CRISPR/Cas system. Haft et al describe the coding region encoding Cas6 polypeptides as being found in association with at least four separate CRISPR/Cas subtypes (Tneap, Hmari, Apern, and Mtube), and as typically being the cas coding region located most distal to the CRISPR locus. Cas6 polypeptides may be identified using the resources available at the JCVI Comprehensive Microbial Resource ("cmr.jcvi.org"). For instance, running a genome property search against all available genomes for the genome property CRISPR Regions {Guild} results in a list of microbes that are predicted to include a Cas6 polypeptide. Thus, Cas6 polypeptides that are useful in the methods described herein can be identified by the skilled person using routine methods.

Examples of prokaryotic microbes with known whole genomic sequences containing coding regions expected to encode a Cas6 polypeptide include *Thermotoga maritima* MSB8, *Campylobacter fetus* subsp. *fetus* 82-40, *Fusobacterium nucleatum* ATCC 25586, *Streptococcus thermophilus* LMG 18311, *Thermoanaerobacter tengcongensis* MB4(T), *Moorella thermoacetica* ATCC 39073, *Desulfitobacterium hafniense* Y51, *Clostridium tetani* E88, *Clostridium perfringens* SM101, *Clostridium difficile* QCD-32g58, *Clostridium botulinum* Hall A Sanger, *Clostridium botulinum* F Langeland, *Clostridium botulinum* B1 strain Okra, *Clostridium botulinum* A3 strain Loch Maree, *Clostridium botulinum* A Hall, *Clostridium botulinum* A ATCC 19397, *Carboxydothermus hydrogenoformans* Z-2901, *Staphylococcus epidermidis* RP62A, *Thermus thermophilus* HB8, *Thermus thermophilus* HB27, *Nostoc* sp. PCC 7120, *Anabaena variabilis* ATCC 29413, *Synechococccus* sp. OS Type B prime, *Synechococccus* sp. OS Type A, *Porphyromonas gingivalis* W83, *Bacteroides fragilis* YCH46, *Bacteroides fragilis* NCTC9343, *Aquifex aeolicus* VF5, *Rubrobacter xylanophilus* DSM 9941, *Mycobacterium tuberculosis* H37Rv (lab strain), *Mycobacterium tuberculosis* CDC1551, *Mycobacterium bovis* subsp. bovis AF2122/97, *Frankia alni* ACN14a, *Thermoplasma volcanium* GSS1, *Picrophilus torridus* DSM 9790, *Thermococcus kodakarensis* KOD1, *Pyrococcus hori-koshii shinkaj* OT3, *Pyrococcus furiosus* DSM 3638, *Pyrococcus abyssi* GE5, *Methanosarcina barkeri fusaro*, *Methanosarcina acetivorans* C2A, *Methanococcoides burtonii* DSM 6242, *Methanococcus jannaschii* DSM2661, *Methanobacterium thermoautotrophicum* delta H, *Haloarcula marismortui* ATCC 43049, *Archaeoglobus fulgidus* DSM4304, *Pyrobaculum aerophilum* 1M2, *Sulfolobus tokodaii* strain 7, *Sulfolobus solfataricus* P2, *Sulfolobus acidocaldarius* DSM 639, *Aeropyrum pernix* K1. Other examples of Cas6 polypeptides are known to the skilled person, see, for instance, members of the COG1583 group of polypeptides (available at the Clusters of Orthologous Groups of proteins (COGs) web page through the National Center for Biotechnology Information internet site, see also Tatusov et al., 1997, Science, 278:631-637, and Tatusov et al. 2003, BMC Bioinformatics, 4(1):41), members of the InterPro family having accession number IPRO10156, Makarova et al., (2002, Nuc. Acids Res., 30:482-496) and Haft et al. (2005, PLoS Comput. Biol., 1(6): e60, 474-483).

A Cas6 polypeptide having Cas6 endoribonuclease activity is able to cleave a target RNA polynucleotide. Whether a polypeptide has Cas6 endoribonuclease activity can be determined by in vitro assays. An in vitro assay may be carried out by combining a suitable target RNA polynucleotide with a polypeptide expected to have Cas6 endoribonulease activity. The characteristics of the target RNA polynucleotide may depend upon the amino acid sequence of the Cas6 polypeptide. Target RNA polynucleotides are described below. The target RNA polynucleotide may be between 0.01 μmol to 0.1 μmol, such as 0.05 μmol, and the Cas6 polypeptide may be between 50 nM and 1 μM, such as 200 nM or 500 nM. The polypeptide to be tested may be enriched, isolated, or purified. For instance, the polypeptide may be from a whole cell extract, such as an S100 extract, or from an immunoprecipitation reaction. The suitable target RNA polynucleotide and polypeptide may be incubated in a buffer such as HEPES-KOH at 15 mM to 25 mM, preferably 20 mM, and pH between 6.5. and 7.5, preferably 7.0. The mixture may also include KCl at 240 mM to 260 mM, preferably 250 mM, DTT at 0.7 mM to 0.8 mM, preferably 0.75 mM, $MgCl_2$ at 1.0 mM to 2.0 mM, preferably 1.5 mM, glycerol at 5% to 15%, preferably 10%, and additional RNA, such as *E. coli* tRNA at 5 μg per 20-μL reaction volume. This may be incubated at a suitable temperature such as at least 30° C., at least 40° C., at least 50° C., at least 60° C., at least 70° C., at least 80° C., and at least 90° C., for at least 30 minutes. A portion of the mixture may be removed and resolved on a native polyacrylamide gel to measure binding of the polypeptide to the target RNA polynucleotide. To measure cleavage, the polypeptide may be removed by extraction and the mixture resolved on a denaturing (7 M urea), 12%-15% polyacrylamide gel. The presence of a band that runs at a molecular weight that is less than the original target RNA polynucleotide indicates the polypeptide is a Cas6 polypeptide.

Polynucleotides

Also provided herein are enriched, optionally isolated polynucleotides, encoding a Cas6 polypeptide. A polynucleotide encoding a Cas6 polypeptide having Cas6 endoribonuclease activity is referred to herein as a Cas6 polynucleotide. Cas6 polynucleotides may have a nucleotide sequence encoding a polypeptide having the amino acid sequence shown in SEQ ID NO:2. An example of the class of nucleotide sequences encoding such a polypeptide is the nucleotide sequence depicted at Genbank Accession No. AE010223 (SEQ ID NO:1). It should be understood that a polynucleotide encoding a Cas6 polypeptide represented by SEQ ID NO:2 is not limited to the nucleotide sequence disclosed at SEQ ID NO:1, but also includes the class of polynucleotides encoding such polypeptides as a result of the degeneracy of the genetic code. For example, the naturally occurring nucleotide sequence SEQ ID NO:1 is but one member of the class of nucleotide sequences encoding a polypeptide having the amino acid sequence SEQ ID NO:2. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid. Examples of other Cas6 polynucleotides include those having a nucleotide sequence encoding a polypeptide having the amino acid sequence shown in FIG. 15, 16, or 17.

A Cas6 polynucleotide may have sequence similarity with the nucleotide sequence of SEQ ID NO:1. Cas6 polynucleotides having sequence similarity with the nucleotide sequence of SEQ ID NO:1 encode a Cas6 polypeptide. A Cas6 polynucleotide may be isolated from a microbe having CRISPR loci, such as, but not limited to, *Pyrococcus furiosus*, or may be produced using recombinant techniques, or chemically or enzymatically synthesized using routine methods. A Cas6 polynucleotide may further include heterologous nucleotides flanking the open reading frame encoding the Cas6 polynucleotide. Typically, heterologous nucleotides may be at the 5' end of the coding region, at the 3' end of the coding region, or the combination thereof. The number of heterologous nucleotides may be, for instance, at least 10, at least 100, or at least 1000.

The present invention also includes fragments of the polypeptides described herein, and the polynucleotides encoding such fragments. For instance, the present invention includes fragments of SEQ ID NO:2, as well as fragments having structural similarity to SEQ ID NO:2. A polypeptide fragment may include a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 amino acid residues.

A polypeptide disclosed herein or a fragment thereof may be expressed as a fusion polypeptide that includes a polypeptide disclosed herein or a fragment thereof and an additional heterologous amino acid sequence. For instance, the additional amino acid sequence may be useful for purification of the fusion polypeptide by affinity chromatography. Various methods are available for the addition of such affinity purification moieties to proteins. Representative examples may be found in Hopp et al. (U.S. Pat. No. 4,703,004), Hopp et al. (U.S. Pat. No. 4,782,137), Sgarlato (U.S. Pat. No. 5,935,824), and Sharma (U.S. Pat. No. 5,594,115). In another example, the additional amino acid sequence may be a carrier polypeptide. The carrier polypeptide may be used to increase the immunogenicity of the fusion polypeptide to increase production of antibodies that specifically bind to a polypeptide of the invention. The invention is not limited by the types of carrier polypeptides that may be used to create fusion polypeptides. Examples of carrier polypeptides include, but are not limited to, keyhole limpet hemacyanin, bovine serum albumin, ovalbumin, mouse serum albumin, rabbit serum albumin, and the like.

A polynucleotide disclosed herein, such as a polynucleotide encoding a Cas6 polypeptide or a polynucleotide encoding a target RNA polynucleotide, may be present in a vector. Target RNA polynucleotides are described below. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, Molecular Cloning: A Laboratory Manual., Cold Spring Harbor Laboratory Press (1989). A vector may provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and artificial chromosome vectors. Examples of viral vectors include, for instance, adenoviral vectors, adeno-associated viral vectors, lentiviral vectors, retroviral vectors, and herpes virus vectors. Typically, a vector is capable of replication in a microbial host, for instance, a fungus, such as *S. cerevisiae*, or a prokaryotic bacterium, such as *E. coli*. Preferably the vector is a plasmid.

Selection of a vector depends upon a variety of desired characteristics in the resulting construct, such as a selection marker, vector replication rate, and the like. In some aspects, suitable host cells for cloning or expressing the vectors herein include eukaryotic cells. Suitable eukaryotic cells include fungi, such as *S. cerevisiae* and *P. pastoris*. In other aspects, suitable host cells for cloning or expressing the vectors herein include prokaryotic cells. Suitable prokaryotic cells include bacteria, such as gram-negative microbes, for example, *E. coli*. Other suitable prokaryotic cells include archeae, such as *Haloferax vokanii*. Vectors may be introduced into a host cell using methods that are known and used routinely by the skilled person. For example, calcium phosphate precipitation, electroporation, heat shock, lipofection, microinjection, and viral-mediated nucleic acid transfer are common methods for introducing nucleic acids into host cells.

Polynucleotides of the present invention may be obtained from microbes, for instance, members of the genus *Pyrococcus*, such as *P. furiosus*, or produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known. Likewise, polypeptides of the present invention may be obtained from microbes, or produced in vitro or in vivo.

An expression vector may optionally include a promoter that results in expression of an operably linked coding region. Promoters act as regulatory signals that bind RNA polymerase in a cell to initiate transcription of a downstream (3' direction) coding region. Promoters present in prokaryotic microbes typically include two short sequences at −10 (often referred to as the Pribnow box, or the −10 element) and −35 positions (often referred to as the −35 element), or a short sequence at −30 (often referred to as a TATA box) located 5' from the transcription start site, for bacterial and archael organisms, respectively. The promoter used may be a constitutive or an inducible promoter. It may be, but need not be, heterologous with respect to a host cell. Target RNA polynucleotides of the present invention do not encode a polypeptide, and expression of a target RNA polynucleotide present in a vector results in a non-coding RNA. Thus, a vector including a target RNA polynucleotide may also include a transcription start signal and/or a transcription terminator operably linked to the target RNA polynucleotide, but a translation start signal and/or translation stop signal typically are not operably linked to a target RNA polynucleotide. Promoters have been identified in many microbes and are known to the skilled person. Many computer algorithms have been developed to detect promoters in genomic sequences, and promoter prediction is a common element of many gene prediction methods. Thus, the skilled person can easily identify nucleotide sequences present in microbes that will function as promoters.

An expression vector may optionally include a ribosome binding site and a start site (e.g., the codon ATG) to initiate translation of the transcribed message to produce the polypeptide. It may also include a termination sequence to end translation. A termination sequence is typically a codon for which there exists no corresponding aminoacetyl-tRNA, thus ending polypeptide synthesis. The polynucleotide used to transform the host cell may optionally further include a transcription termination sequence.

A vector introduced into a host cell optionally includes one or more marker sequences, which typically encode a molecule that inactivates or otherwise detects or is detected by a compound in the growth medium. For example, the inclusion of a marker sequence may render the transformed cell resistant to a selective agent, such as an antibiotic, or it may confer compound-specific metabolism on the transformed cell. Examples of a marker sequence include, but are not limited to, sequences that confer resistance to kanamycin, ampicillin, chloramphenicol, tetracycline, streptomycin, and neomycin. Another example of a marker that renders a cell resistant to a selective agent is 3-hydroxy-3-methylglutaryl coenzyme A reductase (HMG-CoA), an enzyme used for archaeal membrane lipid biosynthesis (Matsumi et al., J. Bacteriol., 2007, 189:2683-2691). Certain statins, such as mevinolin and its analog simvastatin, inhibit HMG-CoA reductase activity, and overexpression of HMG-CoA reductase can confer resistance to mevinolin and/or simvastatin. Yet another example of a marker is a nutritional marker. A nutritional marker is typically a coding region that, when mutated in a cell, confers on that cell a requirement for a particular compound. Cells containing such a mutation will not grow on defined medium that does not include the appropriate compound, and cells receiving a coding region that complements the mutation can grow on the defined medium in the absence of the compound. Examples of nutritional markers include, but are not limited to, coding regions encoding polypeptides in biosynthetic pathways, such as nucleic acid biosynthesis (e.g., biosynthesis of uracil), amino acid biosynthesis (e.g., biosynthesis of histidine and tryptophan), vitamin biosynthesis (e.g., biosynthesis of thiamine), and the like.

Polypeptides useful in the methods described herein, such as the polypeptides described herein and other Cas6 polypeptides, may be obtained from a microbe that has a CRISPR locus. Examples of such microbes are listed above. Polypeptides and fragments thereof useful in the present invention may be produced using recombinant DNA techniques, such as an expression vector present in a cell. Such methods are routine and known in the art. The polypeptides and fragments thereof may also be synthesized in vitro, e.g., by solid phase peptide synthetic methods. The solid phase peptide synthetic methods are routine and known in the art. A polypeptide obtained from a microbe having a CRISPR locus, produced using recombinant techniques, or by solid phase peptide synthetic methods may be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity. Typically, obtaining polypeptides includes conditions that minimize RNAse and proteinase activity, such as by including RNAse inhibitors and protease inhibitors.

Genetically Modified Microbes

The present invention also includes genetically modified microbes that have a polynucleotide encoding target RNA polynucleotide, a Cas6 polypeptide, or the combination. Compared to a control microbe that is not genetically modified according to the present invention, a genetically modified microbe may exhibit production of an exogenous polynucleotide or an exogenous polypeptide disclosed herein, or increased production of an endogenous Cas6 polypeptide. A polynucleotide encoding a target RNA polynucleotide or a Cas6 polypeptide disclosed herein may be present in the microbe as a vector or integrated into a chromosome. Examples of microbes that can be genetically modified include, but are not limited to, eukaryotic cells, such as *S. cerevisiae* and *P. pastoris*, bacteria, such as gram-negative microbes, for example, *E. coli*, and archeae, such as *Haloferax volcanii*.

Methods of Use

Also provided herein are methods for cleaving a polynucleotide. The methods include incubating a target RNA polynucleotide with a Cas6 polypeptide under conditions suitable for cleavage of the polynucleotide by the Cas6 polypeptide. Restriction endonucleases recognize a specific nucleotide sequence (a recognition domain) of a target polynucleotide and cleave the target at a specific location which can be within the recognition domain or outside of the recognition domain. A Cas6 polypeptide cleaves a target outside of the recognition domain, but unlike a restriction endonuclease, the nucleotide sequence to which different Cas6 polypeptides bind can vary. Target polynucleotides described herein are not limited to those possessing a recognition domain with a specific nucleotide sequence. Moreover, unlike restriction endonucleases known in the art, the target polynucleotide may be RNA.

A target RNA polynucleotide has a Cas6 recognition domain, i.e., the site to which a Cas6 polypeptide binds, and a cleavage site, i.e., the site enzymatically cleaved by a Cas6 polypeptide. While the term target RNA polynucleotide suggests the nucleotides are ribonucleotides, polynucleotides described herein also include the corresponding deoxyribonucleotide sequence, and the RNA and DNA complements thereof. It should be understood that the sequences disclosed herein as DNA sequences can be converted from a DNA sequence to an RNA sequence by replacing each thymidine nucleotide with a uridine nucleotide. In one aspect, a target RNA polynucleotide may be based on a nucleotide sequence from a CRISPR locus. A CRISPR locus of a prokaryotic microbe includes, from 5' to 3', a repeat followed immediately by a spacer (referred to herein as a "repeat-spacer unit"). Typically, a CRISPR locus includes multiple repeat-spacer units. In a CRISPR locus, each repeat is nearly identical (Barrangou et al., U.S. Published Patent Application 2008/0124725), and is typically 30 to 35 nucleotides in length. In contrast to the repeats, each spacer of a CRISPR locus is typically a different nucleotide sequence. The Cas6 endoribonuclease activity of a Cas6 polypeptide disclosed herein cleaves a repeat region derived from a CRISPR locus. The location of the cleavage site is on the 5' side of the nucleotide located 10, 9, 8, 7, 6, or 5 nucleotides from the 3' end of the repeat. In some aspects, the cleavage site is on the 5' side of the nucleotide located 8 nucleotides from the 3' end of the repeat.

The nucleotide sequence of a repeat present in a CRISPR locus can easily be identified in any microbe that includes a CRISPR locus. For instance, the genomic sequences of many microbes are known, and the location of CRISPR loci in these microbes is often known, or can easily be located using routine bioinformatic methods known in the art. For instance, Edgar (BMC Bioinformatics, 2007, 8:18) describes a computer program specifically designed for the identification and analysis of CRISPR repeats, and includes a list of predicted repeats based on 346 prokaryotic genomes (see Edgar, Supplementary Table 1). Grissa et al. (BMC Bioinformatics, 2007, 8:172, and Nucl. Acids Res., 2007, 35(Web Server issue):W52-W57) describe a computer program which identifies CRISPRs from genomic sequences, extracts the repeat and spacer sequences, and constructs a database which is automatically updated monthly using newly released genome sequences. Thus, the nucleotide sequence of a repeat in a CRISPR locus can be determined by the skilled person using routine methods. For example, a repeat present in *Pyrococcus furiosus* is GTTCCAATAAGACTAAAATAGA↓ATTGAAAG (SEQ ID NO:191), and the location of the site cleaved by a Cas6 polypeptide, such as SEQ ID NO:2, is shown by the arrow, i.e., 8 nucleotides from the 3' end of the repeat.

In another aspect, a target RNA polynucleotide may include other nucleotide sequences downstream of the cleavage site, i.e., the nucleotides that correspond to the 3' end of a repeat present in a microbe and downstream of a cleavage site may be different relative to the nucleotides present in a repeat present in a microbe. It is expected that the nucleotides downstream of a cleavage site may include at least 1, at least 2, at least 3, at least 4, at least 5, or at least 6 substitutions when compared to the nucleotides present in a repeat present in a microbe. A target RNA polynucleotide based on a repeat present in a microbe may include fewer than 8 nucleotides downstream of the cleavage site. For instance, a target RNA polynucleotide based on a repeat present in a microbe may include at least 1, at least 2, at least 3, at least 4, at least 5, or at least 6 nucleotides downstream of the cleavage site. Optionally and preferably, one or both of the nucleotides flanking the cleavage site are the same as found in the wild-type microbe.

In some aspects, a target RNA polynucleotide based on a repeat obtained from a particular microbe may include other variations in nucleotide sequence relative to the repeat present in the microbe. Typically, such variations occur outside of the Cas6 recognition domain. A Cas6 recognition domain is located near the 5' end of a repeat. In one aspect, a Cas6 recognition domain includes the nucleotide beginning at position 1 (i.e., the nucleotide at the 5' end of the repeat) and extends to nucleotide 6, nucleotide 7, nucleotide 8, nucleotide 9, nucleotide 10, nucleotide 11, nucleotide 12, or nucleotide 13. A Cas6 recognition domain may be located within the first 5 to 15 nucleotides of a CRISPR repeat. The Cas6 recognition domain of a target RNA polynucleotide may be defined relative to its distance from the cleavage site. For instance, a Cas6 recognition domain includes nucleotides located 5, 6, 7, 8, 9, 10, 11, 12, 13, 14, 15, 16, 17, 18, 19, 20, and/or 21 or more nucleotides upstream of the cleavage site. The size of a Cas6 recognition domain may span at least 5 nucleotides, at least 6 nucleotides, at least 7 nucleotides, or at least 8 nucleotides to no greater than 9, no greater than 10, no greater than 12 nucleotides, or no greater than 13 nucleotides. For instance, when the Cas6 polypeptide is SEQ ID NO:2 or has sequence similarity with SEQ ID NO:2, a Cas6 recognition domain may include the nucleotides located 15, 18, and 20 nucleotides upstream of the cleavage site, and can be represented as UNCNNUNNNNNNNNNNNNN↓NNNNNNNN (SEQ ID NO:192), where the arrow refers to the cleavage site, and one or both of the nucleotides flanking the cleavage site is A. Preferably, when the Cas6 polypeptide is SEQ ID NO:2 or has sequence similarity with SEQ ID NO:2, a Cas6 recognition domain includes the nucleotides located 14 to 21 nucleotides upstream of the cleavage site, and can be represented as UUACAAUANNNNNNNNNNNNN↓NNNNNNNN (SEQ ID NO:193), where the arrow refers to the cleavage site, and one or both of the nucleotides flanking the cleavage site is A. Thus, for a target RNA polynucleotide that is based on a repeat present in a CRISPR locus, the nucleotides sequence between the Cas6 recognition domain and the cleavage site may vary from the sequence present in a wild-type repeat. In one embodiment, when the Cas6 polypeptide is SEQ ID NO:2 or has sequence similarity with SEQ ID NO:2, a Cas6 recognition domain may include $N_1$UUACAAUAAGACCN$_2$N↓N, where the arrow refers to the cleavage site and one or both of the nucleotides flanking the cleavage site is A, where $N_1$ may be G, and $N_2$ is 7 nucleotides.

Typically, when a target RNA polynucleotide is based on a repeat obtained from a particular microbe, the Cas6 polypeptide used to cleave the target RNA polynucleotide is a Cas6 polypeptide present in that microbe (or a microbe with a similar CRISPR repeat sequence), or has sequence similarity to such a Cas6 polypeptide. Thus, when a target RNA polynucleotide is based on a repeat identical or similar to that present in *Pyrococcus furiosus*, the Cas6 polypeptide is SEQ ID NO:2 or has sequence similarity to SEQ ID NO:2. When a target RNA polynucleotide is based on a repeat identical or similar to that present in *Korarchaeum cryptofilum*, the Cas6 polypeptide is SEQ ID NO:3 or has sequence similarity to SEQ ID NO:3. Likewise, when a target RNA polynucleotide is based on a repeat identical or similar to that present in a microbe listed in FIG. 15, FIG. 16, or FIG. 17, the Cas6 polypeptide is, or has sequence similarity to, a Cas6 polypeptide present in that microbe. The Cas6 polypeptide may also be one present in a microbe with an identical or similar CRISPR repeat sequence as that in the target RNA polynucleotide. Identifying nucleotide sequences encoding Cas6 polypeptides is described above. In view of the present disclosure, the skilled person now knows which target RNA polynucleotide and Cas6 polypeptide can be used to result in cleavage of a target RNA polynucleotide.

A target RNA polynucleotide may include an additional polynucleotide at the 3' end, at the 5' end, or at both ends. If the target RNA polynucleotide is identical to a CRISPR repeat, the additional polynucleotide may be referred to as a heterologous polynucleotide. This additional polynucleotide at the 3' end can be chosen by a skilled person and cleaved using the methods described herein. Thus, the skilled person can design a target RNA polynucleotide that will result in the production of an RNA with a predictable and known 5' end. It is expected that there is no upper limit on the number of nucleotides that may added to the 3' end of a repeat. For instance, a target RNA polynucleotide may include at least 10, at least 50, or at least 100 additional nucleotides at the 3' end.

The methods may be in vitro or in vivo. Practicing the method in vivo may include introducing a polynucleotide into a microbe. The introduced polynucleotide may include the target RNA polynucleotide, or the introduced polynucleotide may encode the target RNA polynucleotide. The microbe may be; but is not limited to, a genetically modified microbe. An example of a genetically modified microbe for use in the methods includes one with an exogenous polynucleotide encoding a Cas6 polypeptide. The method may be practiced at a suitable temperature such as at least 30° C., at least 40° C., at least 50° C., at least 60° C., at least 70° C., at least 80° C., or at least 90° C.

Also provided herein are target RNA polynucleotides that include a Cas6 recognition domain as described above. The polynucleotide may be RNA, or may be DNA. If it is DNA it may be operably linked to a regulatory sequence, such as a promoter, and may be present in a vector. Optionally, the polynucleotide may include nucleotides downstream of the cleavage site to facilitate the ligation of a different polynucleotide downstream of the cleavage site. For instance, nucleotides downstream of the cleavage site may include a restriction endonuclease site or a multiple cloning site.

The present invention also provides kits. A kit may include one or more of the polynucleotides or polypeptides described herein. For instance, a kit may include a target RNA polynucleotide or a DNA polynucleotide encoding a target RNA polynucleotide, a polynucleotide encoding a Cas6 polypeptide, a Cas6 polypeptide, or a combination thereof. Kits may be used, for instance, for modifying a microbe to express a Cas6 polypeptide and/or a target RNA polynucleotide. Kits may be used for in vitro cleavage of a target RNA polynucleotide. The kit components are present in a suitable packaging material in an amount sufficient for at least one assay. Optionally, other reagents such as buffers and solutions needed to practice the invention are also included. Instructions for use of the packaged polypeptide and/or polynucleotide are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the components can be used for methods as described herein. In addition, the packaging material contains instructions indicating how the materials within the kit are employed. As used herein, the term "package" refers to a solid matrix or material such as glass, plastic, paper, foil, and the like, capable of holding within fixed limits a kit component. Thus, for example, a package can be a glass vial used to contain milligram quantities of a polypeptide or polynucleotide. "Instructions for use" typically include a tangible expression describing the reagent concentration or at least one assay method parameter.

The present invention is illustrated by the following examples. It is to be understood that the particular examples, materials, amounts, and procedures are to be interpreted broadly in accordance with the scope and spirit of the invention as set forth herein.

EXAMPLE 1

An RNA-based gene silencing pathway that protects bacteria and archaea from viruses and other genome invaders is hypothesized to arise from guide RNAs encoded by CRISPR loci and proteins encoded by the cas genes. CRISPR loci contain multiple short invader-derived sequences separated by short repeats. The presence of virus-specific sequences within CRISPR loci of prokaryotic genomes confers resistance against corresponding viruses. The CRISPR loci are transcribed as long RNAs that must be processed to smaller guide RNAs. Here a *Pyrococcus furiosus* Cas6 was identified as a novel endoribonuclease that cleaves CRISPR RNAs within the repeat sequences to release individual invader targeting RNAs. Cas6 interacts with a specific sequence motif in the 5' region of the CRISPR repeat element and cleaves at a defined site within the 3' region of the repeat. The 1.8 angstrom crystal structure of the enzyme reveals two ferredoxin-like folds that are also found in other RNA-binding proteins. The predicted active site of the enzyme is similar to that of tRNA splicing endonucleases, and concordantly, Cas6 activity is metal-independent. cas6 is one of the most widely distributed CRISPR-associated genes. Our findings indicate that Cas6 functions in the generation of CRISPR-derived guide RNAs in numerous bacteria and archaea.

Materials and Methods

Purification of PF1131 Protein for Cleavage and RNA-Binding Assays.

N-terminal, 6×-histidine-tagged PF1131 protein (PfCas6 from *P. furiosus* DSM 3638 strain) was expressed in *Escherichia coli* BL21 codon+(DE3, Invitrogen) cells harboring a pET24d plasmid containing the appropriate gene insert (obtained from Michael Adams, University of Georgia, Athens, Ga.). Protein expression was induced by growing the cells to an ($OD_{600}$ of 0.6 and adding isopropylthio-β-D-galactoside (IPTG) to a final concentration of 1 mM. The cells were disrupted by sonication (Misonix Sonicator 3000) in buffer A (20 mM sodium phosphate [pH 7.0], 500 mM NaCl and 0.1 mM phenylmethylsulfonyl fluoride). The lysate was then cleared by centrifugation and the supernatant was incubated for 20 minutes at 70° C. This sample was centrifuged and the supernatant was applied to a Ni-NTA agarose column (Qiagen) that had been equilibrated with Buffer A. The protein was eluted from the column with Buffer A containing 350 mM imidazole. The purity of the protein was evaluated by SDS-PAGE and staining with coomassie blue. Buffer exchange into 40 mM HEPES-KOH (pH 7.0), 500 mM KCL was carried out using Microcon PL-10 filter columns (Millipore). The protein concentration was determined by the BCA assay (Pierce).

Generation of RNA Substrates.

Synthetic RNAs (listed in Table 1) and the RNA size standards (Decade Markers) were purchased from Integrated DNA Technologies (IDT) and Ambion, respectively. These RNAs were 5'-end-labeled with T4 Polynucleotide kinase (Ambion) in a 20-4 reaction containing 20 μmol of RNA, 500 μCi of [$\gamma^{32}P$] ATP (3000 Ci/mmol; MP Biomedicals), and 20 U of T4 kinase. The RNAs were separated by electrophoresis on denaturing (7 M urea) 15% polyacrylamide gels, and the appropriate RNA species were excised from the gel with a sterile razor blade guided by a brief autoradiographic exposure. The RNAs were eluted from the gel slices by end-over-end rotation in 400 μL of RNA elution buffer (500 mM NH4OAc, 0.1% SDS, 0.5 mM EDTA) for 12-14 h at 4° C. The RNA was then extracted with phenol/chloroform/isoamyl alcohol (PCI, 25:24:1 at pH 5.2), and precipitated with 2.5 volumes of 100% ethanol in the presence of 0.3 M sodium acetate and 20 μg of glycogen after incubation for 1 hour at −20° C.

TABLE 1

Oligonucleotides used in this study

| # (SEQ ID NO:) | DNA oligonucleotides (5'-3') |
|---|---|
| 1 (194) | TAATACGACTCACTATAGGGAAGACCAAAATAGAATTGAAAG |
| 2 (195) | CTTTCAATTCTATTTTGGTCTTCCCTATAGTGAGTCGTATTA |

TABLE 1-continued

Oligonucleotides used in this study

| # (SEQ ID NO:) | |
|---|---|
| 3 (196) | TAATACGACTCACTATAGGGTTACAATAAGACCAAAATAGGGTTGAAAG |
| 4 (197) | CTTTCAACCCTATTTTGGTCTTATTGTAACCCTATAGTGAGTCGTATTA |
| 5 (198) | TAATACGACTCACTATAGGGTTACAATAAGACCAAAATAGAATTGAAAG |
| 6 (199) | CTTTCAATTCTATTTTGGTCTTATTGTAACCCTATAGTGAGTCGTATTA |
| 7 (200) | TAATACGACTCACTATAGGGTTACAATTTCTGGTTTATAGAATTGAAAG |
| 8 (201) | CTTTCAATTCTATAAACCAGAAATTGTAACCCTATAGTGAGTCGTATTA |
| 9 (202) | TAATACGACTCACTATAGGGTTACAATCCAAAATAGAATTGAAAG |
| 10 (203) | CTTTCAATTCTATTTTGGATTGTAACCCTATAGTGAGTCGTATTA |
| 11 (204) | TAATACGACTCACTATAGGGTTACAATTTTTAAGACCAAAATAGAATTGAAAG |
| 12 (205) | CTTTCAATTCTATTTTGGTCTTAAAAATTGTAACCCTATAGTGAGTCGTATTA |
| 13 (206) | TAATACGACTCACTATAGGGTTACAATAAGACCAAAATAG |
| 14 (207) | CTATTTTGGTCTTATTGTAACCCTATAGTGAGTCGTATTA |
| 15 (208) | TAATACGACTCACTATAGGGCAATGTTAAAGACCAAAATAGAATTGAAAG |
| 16 (209) | CTTTCAATTCTATTTTGGTCTTTAACATTGCCCTATAGTGAGTCGTATTA |
| 17 (210) | TAATACGACTCACTATAGGGTTACAATAAGACCAAAATAGAAAACTTTC |
| 18 (211) | GAAAGTTTTCTATTTTGGTCTTATTGTAACCCTATAGTGAGTCGTATTA |
| 19 (212) | TAATACGACTCACTATAGGGTTCCAATAAGACTACAAAAGAATTGAAAG<br>TTGTAGTATGCGGTCCTTGCGGCTGAGAGCACTTCAGGTTCCAATAAGA<br>CTACCAAAAGAATTGAAAG |
| 20 (213) | CTTTCAATTCTTTTGTAGTCTTATTGGAACCTGAAGTGCTCTCAGCCG<br>CAAGGACCGCATACTACAACTTTCAATTCTTTTGTAGTCTTATTGGAA<br>CCCCTATAGTGAGTCGTATTA |
| 21 (214) | TAATACGACTCACTATAGGGATTGAAAGTTGTAGTATGCGGTCCTTGC<br>GGCTGAGAGCACTTCAGGTTACAATAAGACCAAAATAGA |
| 22 (215) | TCTATTTTGGTCTTATTGTAACCTGAAGTGCTCTCAGCCGCAAGGAC<br>CGCATACTACAACTTTCAATCCCTATAGTGAGTCGTATTA |
| 23 (216) | TAATACGACTCACTATAGGGCGTAGGAGGATTGGGGCAAAAAGC |
| 24 (217) | CACTAATCGAAGACTTCGTAAGAGATAACG |

Figure 3:
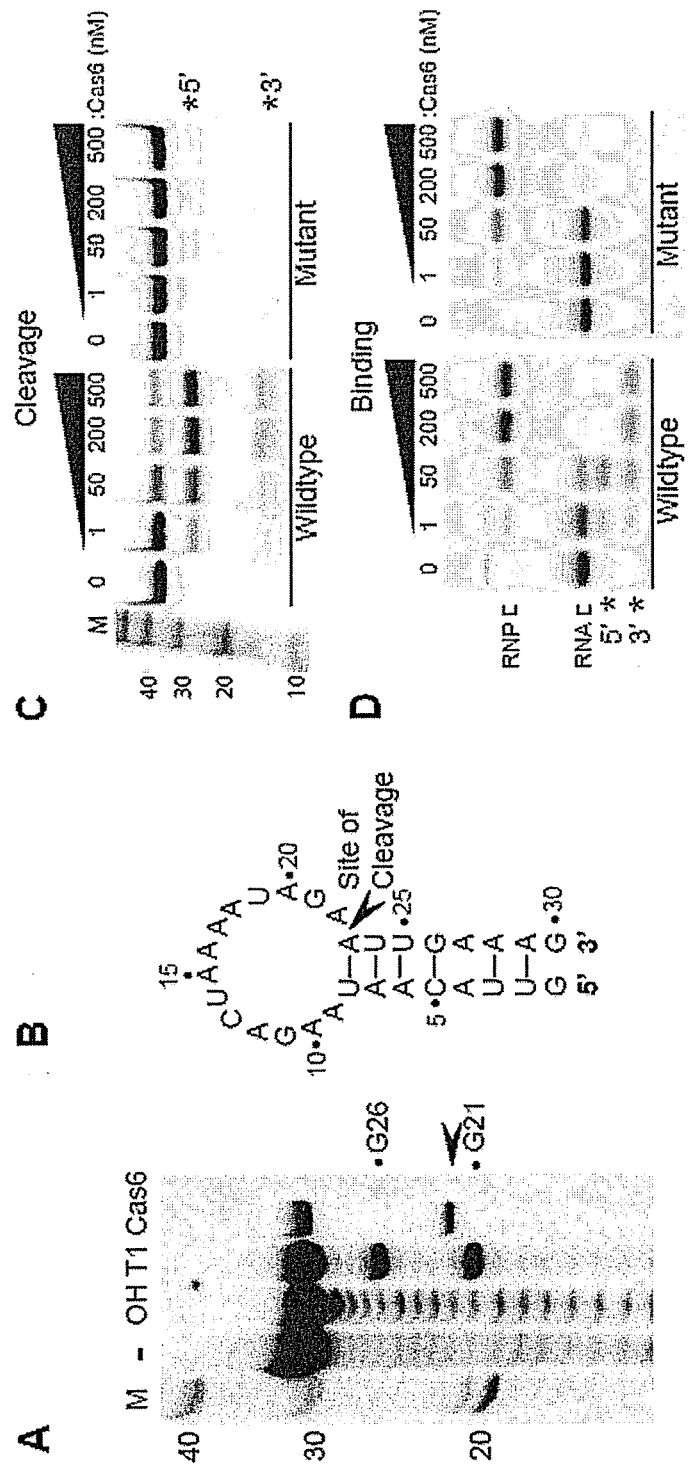
FIG. 3. Identification of the site of PfCas6 cleavage within the CRISPR repeat RNA. (A) The site of PfCas6 cleavage within the CRISPR repeat RNA was mapped by incubating 5' end labeled repeat RNA with PfCas6 nuclease and comparing the size of the 5' RNA cleavage product (arrow) with RNAse T1 (T1) and alkaline hydrolysis (OH) sequence ladders. (B) Potential secondary structure of P. furiosus repeat RNA (SEQ ID No: 238) with cleavage site indicated. (C) Analysis of cleavage of wild-type and cleavage site mutant (AA to GG) repeat RNAs with increasing concentrations (0, 1, 50, 200, and 500 nM) of PfCas6. (D) Native gel mobility shift analysis of wild-type and mutant repeat RNAs with increasing concentrations of PfCas6. The positions of the free (RNA) and protein-bound (RNP) RNAs are indicated. 5' and 3' cleavage products are indicated in both C and D. The sizes of RNA markers (M) are indicated in A and C.

| # (SEQ ID NO:) | RNA Oligonuleotides (5'-3') |
|---|---|
| 25 (218) | GUUACAAUAAGACCAAAAUAGAAUUGAAAG (Repeat) |
| 26 (219) | AUUGAAAGUUGUAGUAUGCGGUCCUUGCGGCUGAGAGCACUUCAG (FIG. 3b) |
| 27 (220) | GUUACAAUAAGA (FIG. 3h) |

All other RNAs were generated by in vitro transcription using T7 RNA polymerase (Ambion) and uniformly labeled with [α-$^{32}$P] UTP (700 Ci/mmol; MP Biomedicals) as described (Baker et al., 2005. Genes & Dev. 19: 1238-1248). The templates used were either annealed DNA oligonucleotides or PCR products (see Tables 1, 2), both containing the T7 promoter sequence. A typical reaction contained 200 ng of PCR product or annealed deoxyoligonucleotides, 1 mM DTT, 10 U SUPERase-IN RNase inhibitor (Ambion), 500 μM ATP, CTP, and GTP, 50 μM UTP, 30 μCi [α-$^{32}$P] UTP, 1 transcription buffer (Ambion), and 40 U T7 RNA polymerase in a total volume of 20 μL.

TABLE 2

Combinations of deoxyoligonucleotides used to generate RNAs in this study

| RNA | 5' and 3' oligos | PCR or IVT |
|---|---|---|
| Repeat | 5 + 6 | IVT |
| R-guide-R | 19 + 20 | IVT |
| AA to GG mutant | 3 + 4 | IVT |
| FIG. 2c | 21 + 22 | IVT |
| sub. 1-8 | 15 + 16 | IVT |

TABLE 2-continued

Combinations of deoxyoligonucleotides used to generate RNAs in this study

| RNA | 5' and 3' oligos | PCR or IVT |
|---|---|---|
| del. 1-8 | 1 + 2 | IVT |
| sub. 23-30 | 17 + 18 | IVT |
| del. 23-30 | 13 + 14 | IVT |
| del. 9-12 | 9 + 10 | IVT |
| ins 8-9 UUUU | 11 + 12 | IVT |
| sub. 9-14 | 7 + 8 | IVT |
| LR-guide-R guide | 23 + 24 | PCR |

The oligos were either annealed directly (IVT) or were used as PCR primers to generate template DNA (PCR) for in vitro transcription reactions. Oligo sequences are listed in Table 1.

RNA-Binding and Cleavage Reactions

Typically, identical reaction conditions were used to assay the ability of PfCas6 protein to bind to and to cleave substrate RNAs. These reactions were initiated by incubating 0.05 μmol of $^{32}$P-radiolabeled RNAs (either uniformly or 5'-end-labeled) with up to 1 (as indicated in the figure legends) of PfCas6 protein in 20 mM HEPES-KOH (pH 7.0), 250 mM KCl, 0.75 mM DTT, 1.5 mM MgCl$_2$, 5 μg of E. coli tRNA, and 10% glycerol in a 20-μL reaction volume for 30 minutes at 70° C. Half of the reactions were directly run on native 8% polyacrylamide gels to assay RNA binding by gel mobility shift essentially as described (Baker et al., 2005. Genes & Dev. 19: 1238-1248). RNA cleavage was assayed using the remaining half of the reaction by deproteinizing (PCI extraction and ethanol precipitation) the RNAs and separating them by electrophoresis on denaturing (7 M urea), 12%-15% polyacrylamide gels. Gels were dried and the radiolabeled RNAs visualized by phosphorimaging.

Cleavage Site Mapping.

In order to map the site of RNA cleavage by Cas6, a standard cleavage reaction was set up using 5' end labeled repeat RNA as described above. Alkaline hydrolysis and RNase T1 (0.1 U) ladders were generated as described previously (Youssef et al., 2007. Nucleic Acids Res. 35: 6196-6206). Following the reactions, the RNAs were extracted with PCI, ethanol precipitated, and separated by electrophoresis on large, denaturing (7 M urea), 15% polyacrylamide (19:1 acrylamide:bis) gels. The gels were dried and the RNAs visualized by phosphorimaging.

Purification of PfCas6 for Structure Determination.

N-terminal polyhistidine-tagged wild-type and selenomethionine-labeled PF1131 protein was expressed in E. coli and purified from cell extract by heat-denaturation and two chromatography steps. The cells were disrupted by sonication in a buffer containing 25 mM sodium phosphate (pH 7.5), 5% (v/v) glycerol, 1 M NaCl, 5 mM β-mercaptoethanol (@ME), and 0.2 mM phenylmethylsulfonyl fluoride. The cell lysate was heated for 15 minutes to 70° C. before being pelleted. The supernatant was then directly loaded at room temperature onto a Ni-NTA (Qiagen) column equilibrated with 25 mM sodium phosphate (pH 7.5), 5% (v/v) glycerol, 1 M NaCl, and 5 mM imidazole. The column was washed with the loading buffer containing 25 mM imidazole and then the bound protein was eluted using the loading buffer containing 350 mM imidazole. Fractions containing PF1131 were pooled and loaded onto a Superdex 200 (Hiload 26/60, Pharmacia) size-exclusion column equilibrated with 20 mM Tris-HCl (pH 7.4), 500 mM KCl, 5% glycerol, 0.5 mM ethylenediamine-tetraacetic acid (EDTA), and 5 mM PME. The fractions corresponding to PF1131 were pooled and concentrated to 100 mg/mL for crystallization.

Crystallization of PF1131 and Selenomethionine-Labeled PF1131.

Both the wild-type and selenomethionine-labeled PF1131 protein were crystallized using vapor diffusion in a hanging drop at 30° C. The droplets of PF1131 at 40 mg/mL were combined in equal volume with a well solution that contained 50 mM MES (pH 6.0), 30 mM MgCl$_2$, and 15% (v/v) isopropanol. The crystals formed in 1-5 days with a cubic shape and to a size of ~0.4 mm×0.4 mm×0.4 mm.

Data Collection and Structure Determination.

Crystals were soaked briefly in a cryo-protecting solution containing the mother liquor plus 20% (w/v) polyethylene glycol 4000 before being flash frozen in a nitrogen stream at 100 Kelvin. The crystals of the native and selenomethionine-labeled PF1131 diffracted to $d_{min}$=1.8-2.2 Å at the Southeast Regional Collaborative Access Team (SER-CAT) beamline 22ID. The space group of the crystals was determined to be P3$_2$21 and the cell dimensions are listed in Table 3. A single wavelength data set was collected at the anomalous peak of selenine from a selenomethionine-labeled crystal. The solvent content was calculated to be 54.9% if the crystal was assumed to contain one PF1131 in one asymmetric unit. The structure of PF1131 was solved by a SAD phasing method using the automated crystallographic structure solution program SOLVE (Terwilliger and Berendzen, 1999. Acta Crystallogr. D Biol. Crystallogr. 55: 849-861). The initial model traced by SOLVE was further improved by the program COOT (Emsley and Cowtan, 2004. Acta Crystallogr. D Biol. Crystallogr. 60: 2126-2132), followed by refinement using CNS (Brunger et al., 1998. Acta Crystallogr. D Biol. Crystallogr. 54: 905-921) and REFMAC5 (Murshudov et al., 1997. Acta Crystallogr. D Biol. Crystallogr. 53: 240-255) to $R_{work}$/$R_{free}$ of 23.6/27.3. The quality of the structure model was checked by PROCHECK (Laskowski et al., 1993. J. Appl. Crystallogr. 26: 283-291) and was found to be of satisfactory stereochemical properties.

TABLE 3

Data collection and refinement statistics (values in parentheses refer to those of the highest resolution shell)

| Crystal information | |
|---|---|
| space group | P3$_2$21 |
| unit cell parameters (Å/°): a/c/g | 84.745/81.679/120 |
| SAD data | |
| wavelength (Å) | 0.97925 |
| resolution range (Å) | 50.0-2.25 (2.33-2.25) |
| number of unique reflections | 16705 |
| redundancy | 20.8 (17.7) |
| completeness (%) | 99.7 (99.7) |
| I/σ (I) | 93.6 (8.1) |
| $R_{sym}$ (%) | 6.9 (42.0) |
| Refinement data and statistics | |
| resolution range (Å) | 50.0-1.8 (1.86-1.80) |
| number of unique reflections | 30102 (1923) |
| redundancy | 16.0 (5.1) |
| completeness (%) | 94.5 (61.0) |
| I/σ (I) | 78.9 (2.4) |
| $R_{sym}$ (%) | 5.9 (43.9) |
| $R_{work}$ (%) | 23.6 (35.8) |
| $R_{free}$ (%) | 27.3 (40.1) |

TABLE 3-continued

Data collection and refinement statistics
(values in parentheses refer to those of the highest resolution shell)

| Model information | |
|---|---|
| number of amino-acid | 232 |
| number of protein atoms | 1951 |
| number of waters | 35 |
| R.M.S.D of the model | |
| bond length (Å) | 0.007 |
| bond angle (°) | 1.041 |
| Ramachandran plot | |
| residues in most favored region | 183 [92.9%] |
| residues in additionally allowed region | 13 [6.6%] |
| residues in generously allowed region | 1 [0.5%] |
| residues in disallowed region | 0 [0%] |

Results

Figure 2:
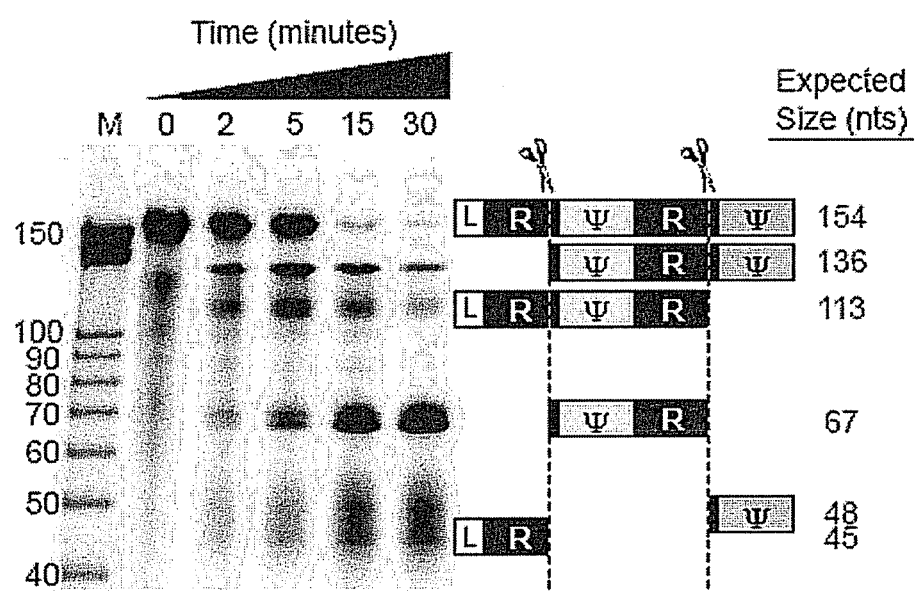
FIG. 2. PfCas6 cleavage of a CRISPR RNA containing two repeat-guide RNA units. A uniformly radiolabeled substrate RNA containing two guide (invader targeting) sequences (w), two repeats (R) and a short (natural) 5' leader (L) sequence was incubated with 1 μM PfCas6 protein and samples were analyzed by denaturing gel electrophoresis at the indicated times. The expected sizes and compositions of the RNA products (based on site-specific cleavage within each repeat) are indicated, as are the sizes of the marker RNAs (M).

The psiRNAs, which are thought to be primary agents in prokaryotic genome defense, are derived from CRISPR RNA transcripts that consist of a series of individual invader targeting sequences separated by a common repeat sequence (FIG. 1A). To identify the enzyme required for dicing CRISPR RNA transcripts and releasing the individual embedded psiRNAs, a number of recombinant *P. furiosus* Cas proteins were screened for the ability to cleave CRISPR repeat sequences. A single protein was identified, Cas6 (PF1131), that cleaves specifically within the repeat sequence of radiolabeled substrate RNAs consisting of either a guide (invader targeting or "spacer") sequence flanked by two repeat sequences or the repeat sequence alone (FIG. 1B,C). Examination of the cleavage products generated from uniformly labeled and 5'-end-labeled RNA substrates indicates that cleavage occurs ~20-25 nt from the 5' end of the repeat. Cleavage also occurs within each repeat of an extended substrate RNA containing two guide sequences and flanking repeats (FIG. 2).

More than 40 CRISPR-associated genes have been identified; however, only a subset of the cas genes is found in any given genome, and no cas gene appears to be present in all organisms that possess the CRISPR-Cas system (Haft et al., 2005. PLoS Comput. Biol. 1:e60; Makarova et al., 2006. Biol. Direct 1:7). Cas6 is among the most widely distributed Cas proteins and is found in both bacteria and archaea (Haft et al., 2005. PLoS Comput. Biol. 1:e60). A distinct protein with similar activity was very recently reported in *Escherichia coli* (Brouns et al., 2008. Science 321: 960-964). This protein, Cse3 (CRISPR-Cas system subtype *E. coli*, also referred to as CasE), is found in some bacteria that lack Cas6 (Haft et al., 2005. PLoS Comput. Biol. 1:e60). Both Cas6 and Cse3 are members of the RAMP (repeat-associated mysterious protein) superfamily, as are a large number of the Cas proteins (Makarova et al., 2002. Nucleic Acids Res. 30: 482-496; Makarova et al., 2006. Biol. Direct 1: 7). RAMP proteins contain G-rich loops and are predicted to be RNA-binding proteins (Makarova et al., 2002. Nucleic Acids Res. 30: 482-496; Makarova et al., 2006. Biol. Direct 1: 7). Cas6 is distinguished from the many other RAMP family members by a conserved sequence motif within the predicted C-terminal G-rich loop (consensus GhGxxxxxGhG (SEQ ID NO:190), where h is hydrophobic and xxxxx has at least one lysine or arginine) (Makarova et al., 2002. Nucleic Acids Res. 30: 482-496; Haft et al., 2005. PLoS Comput. Biol. 1: e60). Nuclease activity was not predicted for Cas6 based on sequence analysis.

To determine the precise PfCas6 cleavage site within the CRISPR repeat sequence, 5'-end-labeled repeat RNA was incubated with the purified enzyme and the 5' cleavage product was mapped relative to RNase T1 (cuts after guanosines) and alkaline hydrolysis (cuts after each nucleotide) cleavage products (FIG. 3A). A 22-nt 5' cleavage product was identified indicating that cleavage occurs between adenosine 22 and adenosine 23 of the 30-nt repeat sequence (FIG. 3A,B). The resulting 5' end generated by PfCas6 is the same as that observed in mature psiRNA species isolated from *P. furiosus* cells. Mutation of the two nucleotides spanning the cleavage site (AA to GG) drastically reduced the cleavage activity of PfCas6 (FIG. 3C) without preventing binding of the enzyme to the RNA (assayed by RNA gel mobility shift; FIG. 3D). The site of cleavage is at a junction within a potential stem-loop structure that may form by base-pairing between weakly palindromic sequences commonly found at the 5' and 3' termini of CRISPR repeat sequences (FIG. 3B; Godde and Bickerton, 2006. J. Mol. Evol. 62: 718-729; Kunin et al., 2007. Genome Biol. 8: R61).

Figure 4:
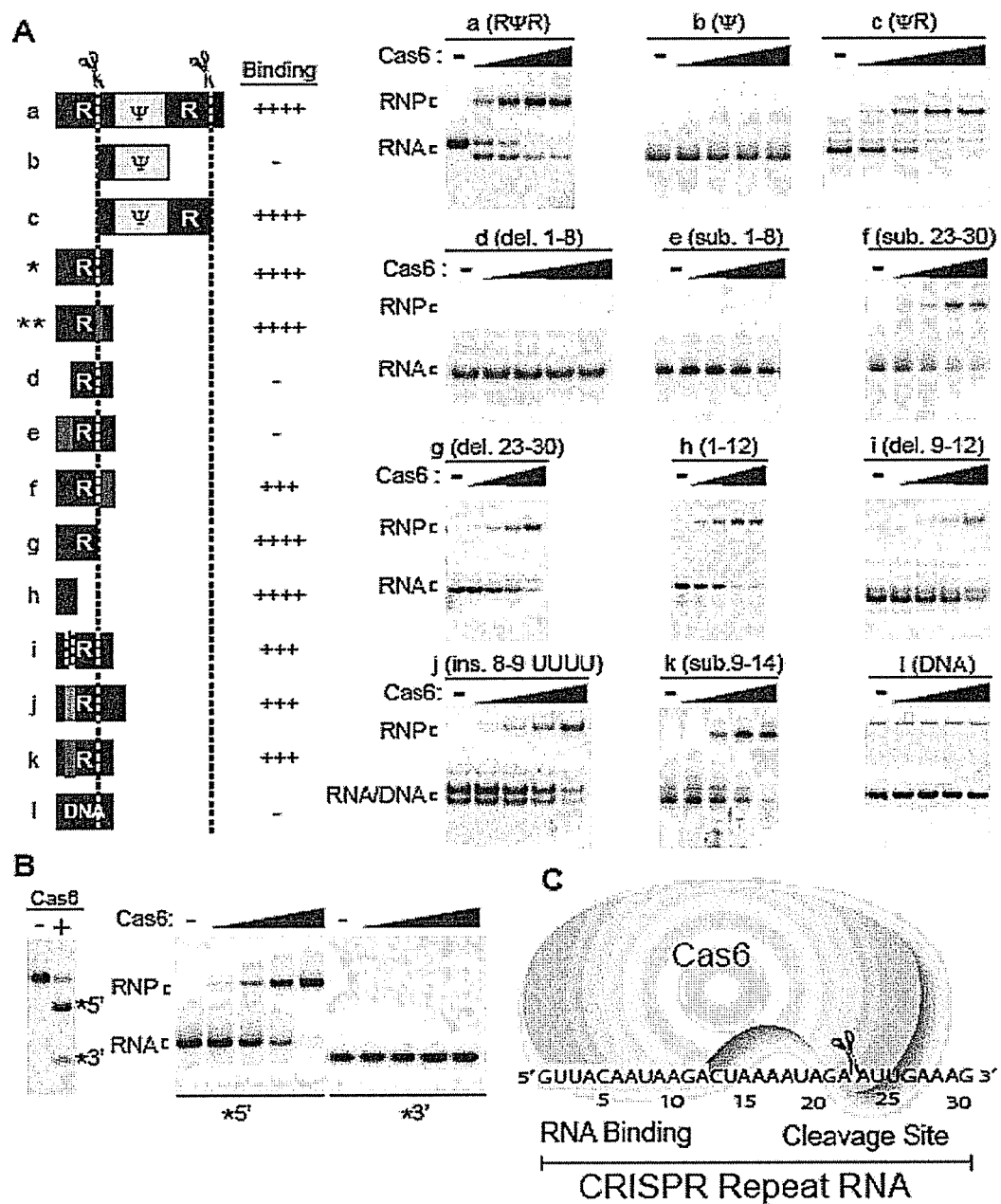
FIG. 4. CRISPR repeat sequence requirements for PfCas6 binding. (A) Detailed analysis of binding with a series of CRISPR-derived RNAs and mutants. The left panel illustrates the RNAs tested, with repeat (R) and invader targeting (ψ) sequences, and PfCas6 cleavage site (dashed lines) indicated. The shaded portion of j denotes an insertion, dashed block denotes an internal deletion, and The shaded portions of **, e, f, and k denote substitutions (with complementary sequence). DNA indicates a DNA repeat sequence substrate. PfCas6 binding is summarized relative to binding to the 5' cleavage product (++++). Corresponding RNA diagrams and data panels are designated with lowercase letters. The right panels show gel mobility shift analysis of the indicated RNAs with increasing concentrations (0, 1, 50, 200, and 500 nM) of PfCas6. Substrates are uniformly radiolabeled except for those shown in panels a, b, c, and 1, which are 5'-end-labeled. Data for the intact repeat (*) and cleavage site mutant (**) are shown in FIG. 3D. (B) PfCas6 interacts with the gel-purified 5' cleavage product. The left panel shows the products of incubation of uniformly radiolabeled repeat RNA with (+) or without (−) PfCas6 (1 μM). The positions of the 5' and 3' cleavage products are indicated. The right panel shows native gel mobility shift analysis of the gel-purified 5' and 3' PfCas6 cleavage products (from the left panel) with increasing concentrations (0, 1, 50, 200, and 500 nM) of PfCas6. The positions of free (RNA) and protein-bound RNA (RNP) are indicated. (C) Model summarizing the minimal PfCas6-binding site within the CRISPR repeat RNA (SEQ ID No: 238) relative to the cleavage site.
Figure 5:
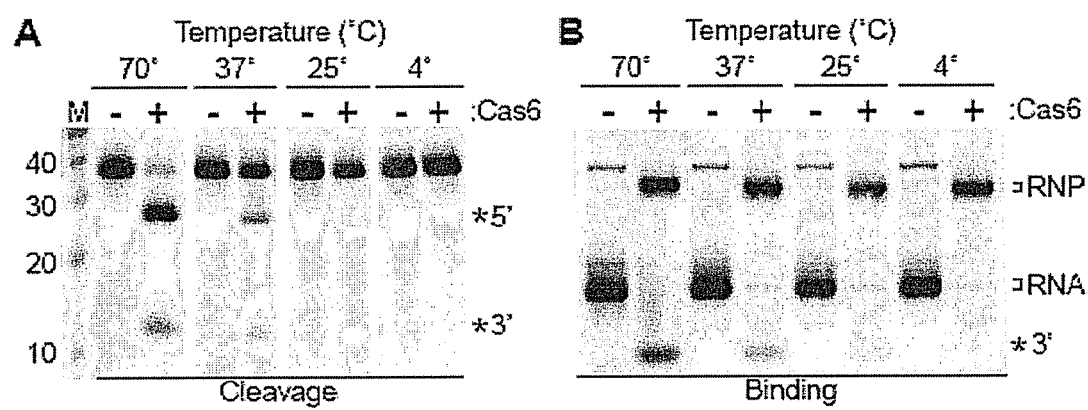
FIG. 5. Influence of temperature on the ability of PfCas6 to bind and cleave CRISPR repeat RNA. Repeat RNA (uniformly radiolabeled) was incubated with (+) or without (−) 1 μM PfCas6 protein at the indicated temperatures and the products were resolved by electrophoresis on denaturing (A) or native (B) polyacrylamide gels to assess RNA binding or cleavage, respectively. The positions of the 5' and 3' cleavage products are indicated. The positions of the free (RNA) and protein-bound (RNP) RNAs are indicated in panel B. Based on the data shown in panel A, the RNPs in panel B include primarily the 5' cleavage product at higher temperatures and the intact repeat at lower temperatures.

We next investigated the RNA sequence requirements of Cas6 binding and endonucleolytic cleavage. To identify the RNA-binding determinants, we performed gel mobility shift assays with a series of RNAs (FIG. 4A). The results indicate that sequences in the 5' region of the CRISPR repeat are important for PfCas6 binding. Under normal assay conditions, rapid cleavage prevents unambiguous observation of PfCas6 binding to the intact repeat (FIG. 3C,D), although binding can be observed with the cleavage site mutant (FIG. 3D) and at reduced temperatures where PfCas6 cleavage activity is inhibited (FIG. 5). However, incubation of PfCas6 with the repeat RNA (FIG. 3D) or with a guide sequence flanked by two repeat sequences (FIG. 4A, panel a) under conditions compatible with cleavage reveals interaction of the protein with the 5' cleavage product generated during incubation. PfCas6 also interacts with the gel-purified 5' cleavage product, but not with the 3' cleavage product (FIG. 4B). Furthermore, we found that PfCas6 binds each tested RNA that contains the repeat sequences found upstream of the cleavage site (i.e., the first 22 nt of the repeat) (FIG. 4A, panels c,f,g), but not an RNA that contains only the downstream region (last 8 nt) of the repeat (FIG. 4A, panel b).

Further analysis indicates that the first 12 nucleotides of the 5' region of the CRISPR repeat play a critical role in Cas6 binding. PfCas6 binds to an RNA comprised of the first 12 nucleotides of the repeat with similar affinity as the 5' cleavage product (FIG. 4A, panel h). Furthermore, protein binding is abolished by substitution or deletion of the first eight nucleotides of the repeat (FIG. 4A, panels d,e). In addition, substitution, insertion or deletion in the region of nucleotides 9-12 appears to have slightly reduced interaction (FIG. 4A, panels i,j,k). No binding was observed with a DNA repeat sequence (FIG. 4A, panel 1). Taken together, the results indicate that PfCas6 requires sequence and/or structure information present within the first 12 nucleotides of the CRISPR repeat RNA for stable interaction (FIG. 4C).

Figure 6:
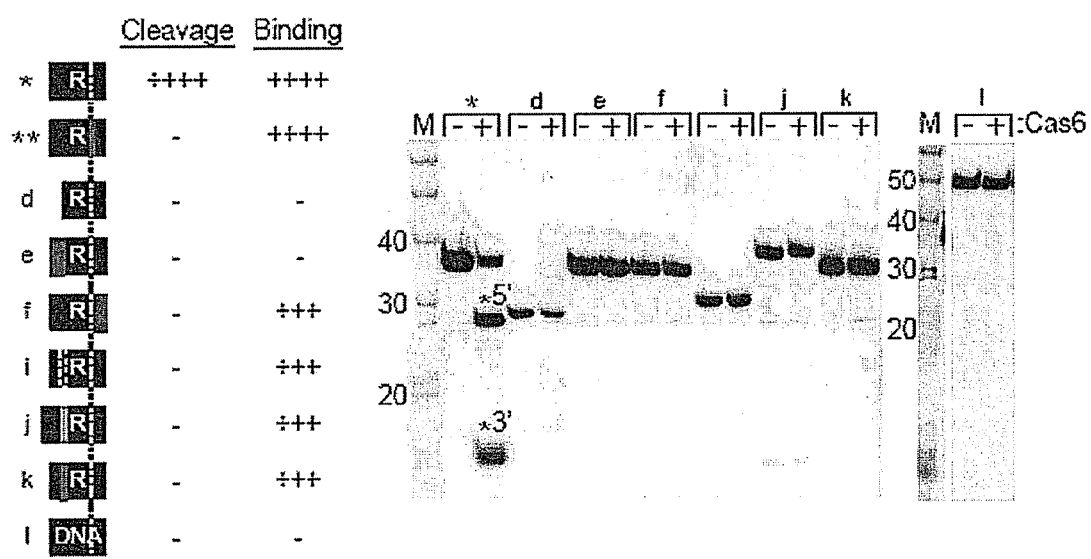
FIG. 6. CRISPR repeat sequence requirements for PfCas6 cleavage. Detailed analysis of cleavage with a series of CRISPR-derived RNAs and mutants. The left panel illustrates the RNAs tested as in FIG. 4. PfCas6 cleavage is summarized relative to cleavage of the intact repeat RNA (++++). PfCas6 binding is summarized from FIG. 4. Corresponding RNA diagrams and data panels are designated with lowercase letters. The right panels show cleavage assays using uniformly radiolabeled repeat RNA with (+) or without (−) PfCas6 (500 nM). Data for the intact repeat (*) is shown on right and data for the cleavage site mutant (**) is shown in FIG. 3C.

While nucleotides at the 5' end of the CRISPR repeat are sufficient for robust PfCas6 binding, cleavage appears to involve additional elements. As expected, mutations that disrupt protein binding also eliminate cleavage activity (FIG. 6, panels d,e). However, other mutations dramatically reduced cleavage efficiency without disrupting PfCas6 binding. As indicated above, substitution of the two adenosines at the cleavage site disrupts cleavage but not binding (FIG. 3C,D). In addition, substitution of the last 8 nucleotides of the repeat specifically disrupted cleavage (FIG. 6, panel f). PfCas6 cleavage activity was also significantly reduced by small (4-nt) insertions or deletions between the PfCas6-binding site and cleavage site (FIG. 6, panels i,j). Substitution of 6 nt between the binding and cleavage sites also disrupted cleavage (FIG. 6, panel k). No cleavage activity was observed with a DNA repeat sequence (FIG. 6, panel 1). These results suggest that cleavage depends upon sequence elements along the length of the repeat and perhaps upon the distance between the binding and cleavage sites, and are consistent with a requirement for a specific RNA fold such as the predicted hairpin structure (FIG. 3B; Godde and Bickerton, 2006. J. Mol. Evol. 62: 718-729; Kunin et al., 2007. Genome Biol. 8: R61).

P. furiosus has seven CRISPR loci with five slightly varied repeat sequences, and the elements that we identified as most important for Cas6 recognition and cleavage map to the regions of greatest sequence conservation. Variation is observed at only one position within each the first 12 and last 11 nucleotides of the P. furiosus repeat sequences, consistent with the importance of these two regions in Cas6 binding and cleavage. On the other hand, variation occurs at three positions between the binding and cleavage sites (positions 14, 16, and 19), suggesting that nucleotide identities are less important in this region.

Figure 7:
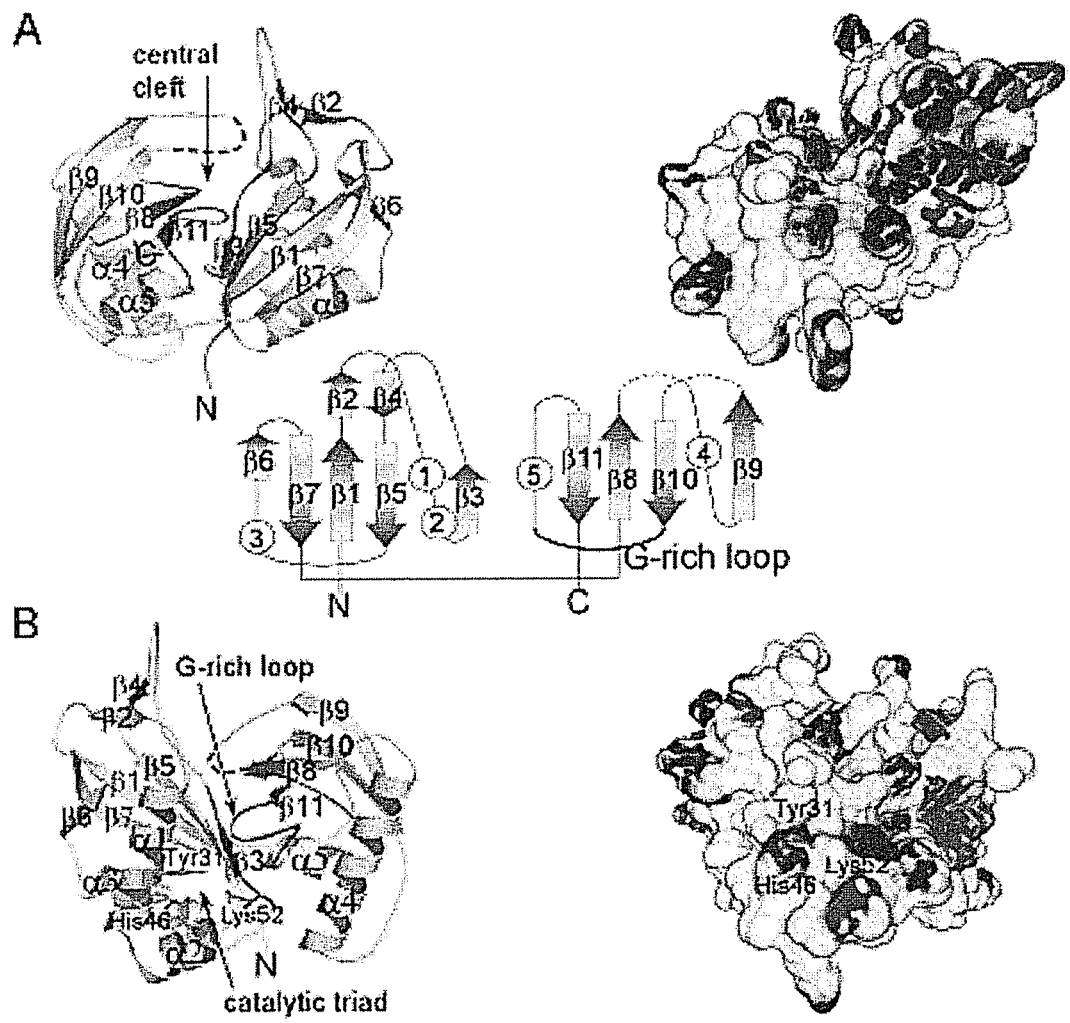
FIG. 7. Structural features of PfCas6. Front (A) and back (B) views of the structure of PfCas6 represented in ribbon diagrams (left) and shaded electrostatic surface potential (right). In the center, the fold topology is illustrated with arrows (β-strands) and circles (α-helices). In the ribbon diagrams, the G-rich loop characteristic of RAMP proteins is designated "β11" in A and "G-rich loop" in B and the predicted catalytic triad residues are labeled Tyr31, His46, and Lys52 in B. The electrostatic potential was computed using the GRASP2 program (Petrey and Honig 2003. Methods Enzymol. 374: 492-509) and is shaded dark and light, for negative and positive potentials, respectively.

To gain a more detailed understanding of PfCas6, we obtained a crystal structure of the protein at 1.8 Å resolution (FIG. 6; see Table 3 for structure determination details). PfCas6 contains a duplicated ferredoxin-like fold linked by an extended peptide (residues 118-123). The close arrangement of the β-sheets of the two ferredoxin-like folds creates a well-formed central cleft (FIG. 7A). The ferredoxin fold is a common protein fold also found in the structures of other RNA-binding proteins including the well-characterized RNA recognition motif (RRM), which primarily functions in ssRNA binding (Maris et al., 2005. FEBS J. 272: 2118-2131). However, PfCas6 appears to exploit a distinct mechanism of base-specific ssRNA recognition. Most notably, PfCas6 lacks the prevalent aromatic and positive residues that characterize the β-sheets of RRMs (Maris et al., 2005. FEBS J. 272: 2118-2131). The central regions of both the front and back surfaces of PfCas6 display positive potential that coincides with regions of conserved amino acids (FIG. 7) suggesting that the composite surfaces formed by the tandem ferredoxin-like folds correspond to RNA-binding sites.

Figure 9:
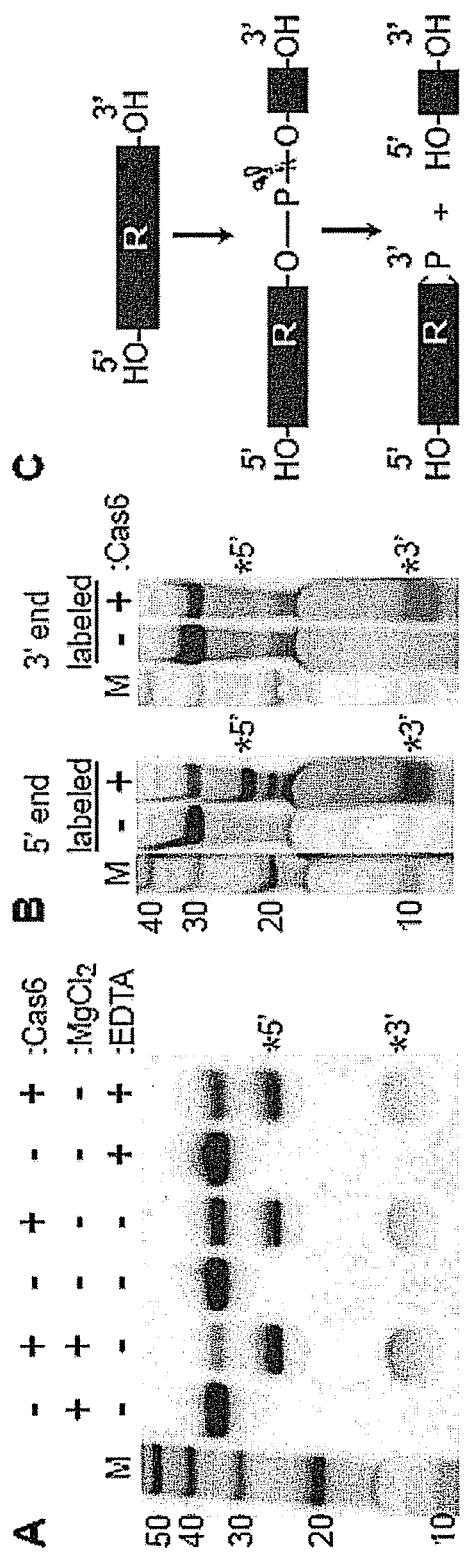
FIG. 9. Catalytic features of PfCas6 cleavage activity. (A) Cleavage activity is not dependent on divalent metal ions. Uniformly radiolabeled repeat RNA was incubated with 1 μM PfCas6 in the absence (−) or presence (+) of 1.5 mM $MgCl_2$ or 20 mM metal chelator EDTA as indicated. (B) Analysis of the termini of PfCas6 cleavage products. The products of cleavage reactions performed with unlabeled repeat RNA substrates (initially containing hydroxyl groups at both the 5' and 3' termini) were radiolabeled at either their 5' ends (using $^{32}$P-ATP and polynucleotide kinase) or 3' ends (using 32 pCp and RNA ligase). The positions of the 5' and 3' cleavage products are indicated in A and B. (C) The pattern of radio-labeling of the RNA cleavage products (B) indicates that PfCas6 cleaves on the 5' side of the phosphodiester bond, as is the case for other metal-independent ribonucleases. Cleavage likely generates 5' hydroxyl (OH) and 2', 3' cyclic phosphate (>P) RNA termini.

The structure of PfCas6 allows us to predict the site of catalysis and catalytic mechanism of the enzyme. Several candidate catalytic residues are evident as strictly conserved residues in aligned Cas6 sequences (FIG. 8). These include Tyr31, His46, and Lys52, which cluster within 6 Å of each other and are found in close proximity to the G-rich loop that contains the Cas6 signature motif (FIG. 7B). These three residues may form a catalytic triad for RNA cleavage similar to that of the tRNA intron splicing endonuclease (Calvin and Li., 2008. Cell. Mol. Life. Sci. 65: 1176-1185). The G-rich loop is located immediately above the putative catalytic triad and may facilitate the placement of CRISPR repeat RNA substrates. Consistent with the corresponding predicted general acid-base catalytic mechanism (proposed for the splicing endonuclease) (Calvin and Li., 2008. Cell. Mol. Life. Sci. 65: 1176-1185), PfCas6 does not require divalent metals and like other metal-independent nucleases cleaves on the 5' side of the phosphodiester bond, likely generating 5' hydroxyl (OH) and 2', 3' cyclic phosphate RNA end groups (FIG. 9). Finally, while binding of the enzyme occurs over a wide temperature range, PfCas6 cleavage activity is sharply temperature-dependent with significantly more activity at 70° C. than 37° C. (FIG. 5).

Discussion

The results presented here indicate that Cas6 plays a central role in the production of the psiRNAs in the emerging prokaryotic RNAi pathway. Cas6 is a novel riboendonuclease. Through direct binding and cleavage of CRISPR repeat sequences, Cas6 dices long, single-stranded CRISPR primary transcripts into units that consist of an individual guide sequence flanked by a short (8-nt) repeat sequence at the 5' end and by the remaining repeat sequence at the 3' end of the RNA (FIG. 1A). Mature psiRNAs retain the short repeat-derived sequence established by Cas6 at their 5' ends in P. furiosus, which we speculate functions as a psiRNA identity tag that allows recognition of the guide RNAs by components of the pRNAi machinery. A repeat sequence of the same length was observed on the 5' ends of RNAs associated with E. coli Cse3, indicating that this may indeed be a generally conserved feature (Brouns et al., 2008. Science 321: 960-964). The 3' ends of Cas6 cleavage products appear to be further processed since mature psiRNAs lack repeat sequences at their 3' termini in P. furiosus. Because Cas6 remains bound to the CRISPR repeat sequences at the 3' end of the cleavage product (FIGS. 3, 4B), Cas6 could influence the subsequent 3' end processing of the RNA. Additional studies may reveal if Cas6 is also an important component of pRNAi effector complexes (serving to couple biogenesis and function), as is the case for eukaryotic Dicer enzymes (Jaskiewicz and Filipowicz, 2008. Curr. Top. Microbiol. Immunol. 320: 77-97).

Cas6 is evolutionarily, structurally, and catalytically distinct from the Dicer proteins that function in the release of individual RNAs that mediate gene silencing in eukaryotes (Hammond, 2005. FEBS Lett. 579: 5822-5829; Jaskiewicz and Filipowicz, 2008. Curr. Top. Microbiol. Immunol. 320: 77-97). However, Cas6 is one of three different ferredoxin fold Cas proteins recently found to possess nuclease activity. Cas2, another protein found in many of the prokaryotes that possess the CRISPR-Cas system, cleaves U-rich ssRNA (Beloglazova et al., 2008. J. Biol. Chem. 283: 20361-20371). The mechanism of action of Cas6 seems to be distinct from that of Cas2, which appears to be a metal-dependent, hydrolytic enzyme (Beloglazova et al., 2008. J. Biol. Chem. 283: 20361-20371). The role of Cas2 in the pRNAi pathway is currently unknown. The E. coli Cse3 protein functions like Cas6 as a CRISPR repeat cleaving enzyme (Brouns et al., 2008. Science 321: 960-964). Cse3 also cleaves RNA in a divalent metal-independent manner (Brouns et al., 2008. Science 321: 960-964). The substrate RNA recognition requirements and the precise cleavage site have not yet been defined for Cse3. Interestingly, despite the lack of significant sequence homology, the Cas6 and Cse3 proteins appear to adopt similar structures to perform a common function in psiRNA biogenesis. Moreover, some bacteria with the CRISPR-Cas system do not appear to contain either a cas6 or a cse3 gene, suggesting that there is another Cas6 functional homolog among the Cas proteins, and illustrating the diversity of the CRISPR-Cas systems present in prokaryotes.

EXAMPLE 2

Cas6 substrate recognition was probed at single nucleotide resolution using RNA footprinting. The results of this analysis confirm that sequence elements in the 5' region of the repeat are the primary determinants for recognition by Cas6 and that nucleotides 2-8 likely have direct contact with Cas6. Also, through mutational analysis, a critical role of the predicted catalytic triad was established and an acid/base catalytic mechanism involving these three amino acids is proposed. Finally, native Cas6 was isolated from P. furiosus extract, was shown to cleave CRISPR repeat RNA, and was found to co-purify with several crRNA (CRISPR RNA) processing intermediates.

Materials and Methods

Expression and purification of PfCas6 and mutants. Primers to generate site-specific mutants were designed and ordered from Eurofins MWG Operon (listed in Table 4). Mutant cas6 genes were generated from a pET24d plasmid containing the PF1131 (Cas6 from *P. furiosus*) insert using QuikChange™ site-directed mutatagenesis (Stratagene). The DNA sequences were confirmed by sequencing. N-terminal, 6× histidine-tagged proteins were expressed in *E. coli* BL21 codon+(DE3, Invitrogen) and purified to homogeneity as described in Example 1.

3350, and ~12 μmol [$\alpha^{32}$P] pCp. The uniformly labeled CRISPR repeat RNA substrate was generated by in vitro transcription by T7 polymerase using annealed DNA oligos containing the T7 promoter sequence as a template (see Tables 4 and 5 for sequence information) in the presence of [$\alpha^{32}$P] UTP (MP Biomedicals) and purified as described in example 1. All radiolabeled RNAs were extracted with phenol/chloroform/isoamyl alcohol (PCI), precipitated with ethanol, and gel purified as described in example 1.

TABLE 4

Oligonucleotides used in this study.

| # (SEQ ID NO:) | DNA oligonucleotides (5'-3') |
|---|---|
| 1 (221) | GGAAGATTTAATAGCGTTGGCTATTAAACCCTGGAGGTAGTATTGATGATTG |
| 2 (222) | CAATCATCAATACTACCTCCAGGGTTTAATAGCCAACGCTATTAAATCTTCC |
| 3 (223) | GGAAGATTTAATAGCGTTGAATATTAAACCCTGGAGGTAGTATTGATGATTG |
| 4 (224) | CAATCATCAATACTACCTCCAGGGTTTAATATTCAACGCTATTAAATCTTCC |
| 5 (225) | GTTTAGGGCCCTTAACTTCAGCGAGATATGTTGCAAGCTTCG |
| 6 (226) | CGAAGCTTGCAACATATCTCGCTGAAGTTAAGGGCCCTAAAC |
| 7 (227) | CGAAGCTTGCAACATATCTCGCTGAAGTTAAGGGCCCTAAAC |
| 8 (228) | CGAAGCTTGCAACATATCTCCAGGAAGTTAAGGGCCCTAAAC |
| 9 (229) | CGGCCATAAAAAGTGAATACGTAAAGAGTGCAGGGCCCTTAACTTCATGGAG |
| 10 (230) | CTCCATGAAGTTAAGGGCCCTGCACTCTTTACGTATTCACTTTTTATGGCCG |
| 11 (231) | CGGCCATAAAAAGTGAATACGTAAAGAGTTCAGGGCCCTTAACTTCATGGAGATATG |
| 12 (232) | CATATCTCCATGAAGTTAAGGGCCCTGAACTCTTTACGTATTCACTTTTTATGGCCG |
| 13 (233) | TAATACGACTCACTATAGGGTTACAATAAGACCAAAATAGAATTGAAAG |
| 14 (234) | CTTTCAATTCTATTTTGGTCTTATTGTAACCCTATAGTGAGTCGTATTA |
| 15 (235) | GTATGCGGTCCTTGCGGCTGAGAGC |

| # | RNA oligonucleotides (5'-3') |
|---|---|
| 16 (236) | GUUACAAUAAGACCAAAAUAGAAUUGAAAG |

Generation of radiolabeled RNAs. The synthetic RNA (see Table 4 for sequence) and RNA size standards (Decade™ markers) used in this study were purchased from Integrated DNA technologies (IDT) and Applied Biosystems, respectively. The northern probe used in this study (see Table 4, #15 for sequence) was purchased from Eurofins MWG Operon. RNAs were 5' end labeled with T4 polynucleotide kinase (Applied Biosystems) and [$\gamma^{32}$P] ATP (7000 Ci/mmol; MP Biomedicals) as described in example 1. End-labeling at the 3' end was performed with T4 RNA ligase (Promega) and [$\alpha^{32}$P] pCp (2500 Ci/mmol; MP Biomedicals). A typical reaction contained 10 μmol of RNA, 20 U T4 RNA ligase, 10 U SUPERase-IN™ RNase inhibitor (Applied Biosystems), 1×T4 RNA ligase buffer (Promega), 20% polyethylene glycol

TABLE 5

Combinations of deoxynucleotides used in this study. The oligos were either used to generate site-directed mutant PfCas6 constructs (PCR) or annealed directly and used as templates for in vitro transcription (IVT).

| Product | 5' and 3' oligos | PCR or IVT |
|---|---|---|
| Y31A | 1 + 2 | PCR |
| Y31F | 3 + 4 | PCR |
| H46A | 5 + 6 | PCR |
| H46Q | 7 + 8 | PCR |
| K52A | 9 + 10 | PCR |
| K52E | 11 + 12 | PCR |
| Repeat RNA | 13 + 14 | IVT |

RNA footprinting. Lead (II) induced and RNase A cleavage were carried out essentially as described previously (Youssef et al., 2007. Nucleic Acids Res; 35:6196-206). Briefly, 0.1 μmol of $^{32}$P end-labeled RNA (either 5' or 3') were incubated in the absence (free RNA) or presence of increasing concentrations of Cas6 at 65-70° C. for 30 minutes in buffer A (20 mM HEPES-KOH pH [7.0], 500 mM KCl). Lead (II) induced cleavage was initiated by the addition of 15 mM Pb(II) acetate (lead (II) acetate) prepared fresh in sterile water. Reactions were carried out at room temperature for 10 minutes and were stopped by the addition of EDTA to a final concentration of 20 mM followed by PCI extraction and ethanol precipitation. RNase A cleavage was initiated by the addition of 0.01 ng of RNase A (Applied Biosystems) and incubated at 37° C. for 15 minutes. Reactions were stopped by PCI extraction followed by ethanol precipitation. Alkaline hydrolysis ladders (cleavage after each nucleotide) were generated as described previously (Youssef et al., 2007. Nucleic Acids Res; 35:6196-206). In each case, precipitated RNAs were resuspended in RNA loading dye (10 M urea, 2 mM EDTA, 0.5% SDS, and 0.02% [w/v] each bromophenol blue and xylene cyanol) and separated on 38×30 cm 15% polyacrylamide (acrylamide:bis ratio 19:1) 7 M urea containing gels. The gels were dried and RNAs visualized by phosphor imaging.

RNA-binding and cleavage reactions. RNA binding and cleavage reactions were carried out as described in example 1. Briefly, 0.05 μmol of uniformly $^{32}$P-labeled RNA was incubated in the absence (free RNA) or presence of increasing concentrations of Cas6 (as indicated in figure legends) in buffer A for 30 minutes at 65-70° C. Half of each reaction was run on 8% native polyacrylamide gels to assess RNA binding by gel mobility shift analysis. RNA cleavage was assessed by separation of the RNAs on denaturing, 7 M urea containing, 15% polyacrylamide gels following PCI extraction and ethanol precipitation. For analysis of native Cas6 cleavage activity, either ~40 μg of whole cell extract (WCE) or supernatant from an immunoprecipitation reaction (see below) was incubated with 0.05 μmol of uniformly $^{32}$P labeled RNA for 30 minutes at 70° C. Alternatively, 10 μL of resin from an immunoprecipitation reaction (see below) was added. In this case, samples were mixed every five minutes by pipetting up and down during the 30 minute incubation at 70° C. The gels were dried and RNAs visualized by phosphor imaging. Quantitation of cleavage was performed using ImageQuant™ TL software (GE Life Sciences).

Preparation of P. furiosus cell extract. Four grams of P. furiosus cells were lysed in 10 mL 50 mM Tris (pH 8.0) in the presence of 100 U RQ1 DNase (Promega) and 0.1 mM phenylmethanesulfonylfluoride (PMSF). The extract was then subjected to ultracentrifugation at 100,000 g for 90 minutes. The resulting S100 was then stored at −80° C. until use.

Preparation of polyclonal antibodies against PfCas6 in Gallus gallus. Specific antibodies against PfCas6 were raised in egg laying hens (Gallus gallus). For immunization, three injections of 200 μg of 6× histidine-tagged PfCas6 in buffer B (20 mM sodium phosphate [pH 7.0], 500 mM NaCl) were done. Each injection was separated by two weeks. For the initial injection, 500 μL antigen (0.4 mg/mL) was emulsified in 200 μL of Freund's complete adjuvant prior to injection in the breast muscle. For the two booster injections, 500 μL of antigen (0.4 mg/mL) was emulsified in 200 μL of Freund's incomplete adjuvant prior to injection. One week following the final injection, immune eggs were collected daily for three months.

IgY was purified from the egg yolks by polyethylene glycol (PEG) precipitation as described previously (Polson et al., 1980. Immunol Commun; 9:475-93). Briefly, egg yolks were separated from the whites and washed with dH$_2$O. In a typical purification, three egg yolks were punctured, combined, and then resuspended in approximately 250 mL of lysis buffer (10 mM Tris [pH 7.5], 100 mM NaCl). Polyethylene glycol (PEG) 8000 (Fisher Scientific) was then added to 3.5% w/v. The sample was then mixed by shaking and centrifuged at 10,000 g for ten minutes. The supernatant was then filtered through 100% cotton cheesecloth and then PEG 8000 was added 9% w/v. The sample was mixed by shaking and then centrifuged at 10,000 g for ten minutes. The supernatant was removed and discarded. The pellet was resuspended in approximately 35 mL of Lysis buffer by incubation at 4° C. overnight. The PEG precipitation was then repeated and the pellet from the 9% w/v PEG step was resuspended in approximately 7 mL Lysis buffer and stored at either 4° C. or −80° C. until use. The protein concentration was determined by the BCA assay (Pierce).

Immunoprecipitation of Cas6 from P. furiosus extract. Immunoprecipitations (IP) were performed using anti-Cas6 IgY antibodies conjugated to CarboLink™ coupling gel (Pierce). Coupling was performed according to the manufacturer's protocol and was verified by A$^{260}$ absorbance readings.

A P. furiosus S100 cell extract was pre-cleared in a reaction containing ~8 mg of total protein, ~550 μg of non-immune IgY coupled CarboLink™ resin, 1× Complete™ Mini protease inhibitor (Roche), 50 U SUPERase-IN™ RNase inhibitor, and brought up to a total volume of 1 mL with IPP-300 (10 mM Tris [pH 8.0], 300 mM NaCl, 0.05% Igepal). The pre-clearing reaction was incubated at room temperature for two hours with end-over-end rotation. The sample was then centrifuged at 3000 g for 2 minutes and the supernatant was split between preimmune and immune LP reactions. A typical IP reaction contained 500 μL of pre-cleared cell extract (~4 mg total protein), 1× Complete™ Mini protease inhibitor, 50 U SUPERasin™ RNase inhibitor, 270-550 μg antibody (either preimmune or immune) coupled resin, and brought up to a total volume of 1 mL with IPP-300. The reactions were incubated at room temperature for 2 hours with end-over-end rotation and then washed four times with IPP-300. The pellets were resuspended in an equal volume of buffer A and stored at 4° C. for later analysis.

Northern analysis. For northern blot analysis, RNAs were extracted from immunoprecipitation sample (both immune and preimmune) and WCE using TRIzol™ LS Reagent (Invitrogen) according to manufacturer's recommendations. Northern blots were performed essentially as described previously (Hale et al., 2008. RNA; 14:2572-9). Briefly, RNAs were separated on a 15% polyacrylamide, 7 M urea containing gel (Criterion™, Bio-Rad) then transferred onto Zeta-Probe™ nylon membranes (Bio-Rad) using a Trans-Blot SD Semi-Dry Cell™ (Bio-Rad). The membranes were then baked at 80° C. for one hour before prehybridization in a ProBlot hybridization oven (LabNet) at 42° C. for one hour. Prehybridization and hybridization were performed in Oligo-UltraHyb™ (Applied Biosystems). Hybridization was initiated by adding 5' end-labeled probe to the prehybridization buffer, and hybridization was carried out at 42° C. overnight. Following hybridization, the membrane was washed twice with 2×SSC (30 mM sodium citrate [pH 7.0], 300 mM NaCl) with 0.5% SDS for 30 minutes at 42° C. RNAs were then visualized by phosphor imaging.

Results

Mapping the Cas6/CRISPR repeat RNA interaction. As discussed in Example 1, the 5' region of CRISPR repeat RNA plays a role in recognition by Cas6. Substitution or deletion of these nucleotides prevented detectable binding. Additionally, an RNA consisting of nucleotides 1-12 of the repeat displayed an binding affinity comparable to that of the full length repeat RNA. Sequence elements in the middle and 3' regions of the repeat did not appear to be important for binding given that Cas binding was insensitive to deletions or substitutions in these regions of the repeat RNA. In order to gain a more detailed understanding of Cas6 recognition of CRISPR repeat RNA, RNA footprinting was performed with radioactively labeled (either 3' or 5' end-labeled) CRISPR repeat RNA and recombinant PfCas6 protein. Lead (II) acetate (cleaves single-stranded and tertiary interactions) and RNase A (cleaves after unpaired Cs and Us) were chosen as probing reagents.

Figure 10:
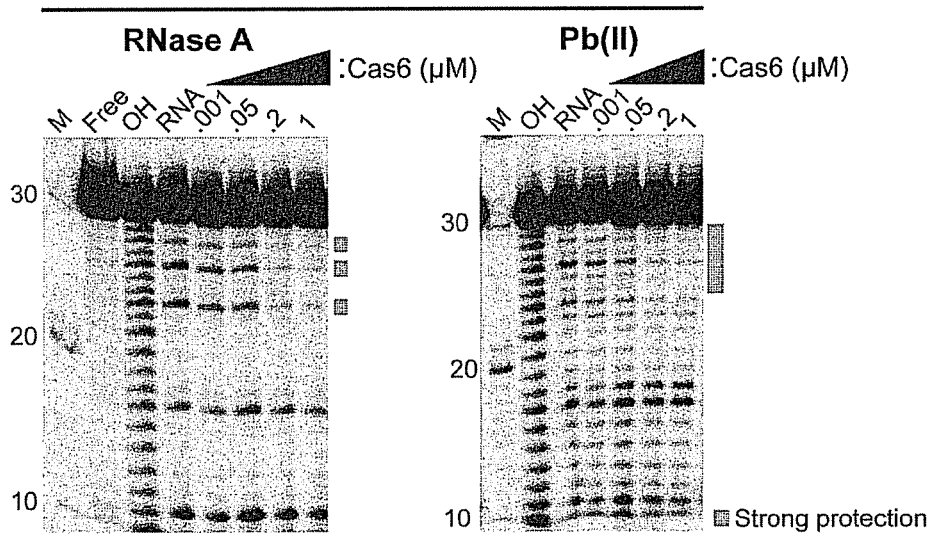
FIG. 10. Lead-induced and RNase A cleavage footprinting with CRISPR repeat RNA and PfCas6. (A) 3' end labeled CRISPR repeat RNA was incubated in the absence (RNA) or presence of increasing concentrations of PfCas6 (indicated in μM) and then subjected to RNase A cleavage (left panel) or lead-induced cleavage (right panel). RNAs were separated by 15% denaturing (7 M urea) polyacrylamide gels. Size markers include 5' end-labeled RNA markers (M) and alkaline hydrolysis ladders (OH). Bars along right side of each gel indicate strong protections. (B) 5' end-labeled CRISPR repeat RNA was used for lead-induced and RNase A cleavage as was done in (A). A summary of cleavage protections is displayed to the right of each gel. (C) A summary of cleavage protection is shown. The Cas6 cleavage site is indicated by an asterisk (*), and the nucleotides protected from cleavage are shown by the bars above and below the sequence FIG. 10. Lead-induced and RNase A cleavage footprinting with CRISPR repeat RNA and PfCas6. (A) 3' end labeled CRISPR repeat RNA was incubated in the absence (RNA) or presence of increasing concentrations of PfCas6 (indicated in μM) and then subjected to RNase A cleavage (left panel) or lead-induced cleavage (right panel). RNAs were separated by 15% denaturing (7 M urea) polyacrylamide gels. Size markers include 5' end-labeled RNA markers (M) and alkaline hydrolysis ladders (OH). Bars along right side of each gel indicate strong protections. (B) 5' end-labeled CRISPR repeat RNA was used for lead-induced and RNase A cleavage as was done in (A). A summary of cleavage protections is displayed to the right of each gel. (C) A summary of cleavage protection is shown. The Cas6 cleavage site is indicated by an asterisk (*), and the nucleotides protected from cleavage are shown by the bars above and below the sequence (SEQ ID NO: 238).
Figure 10:
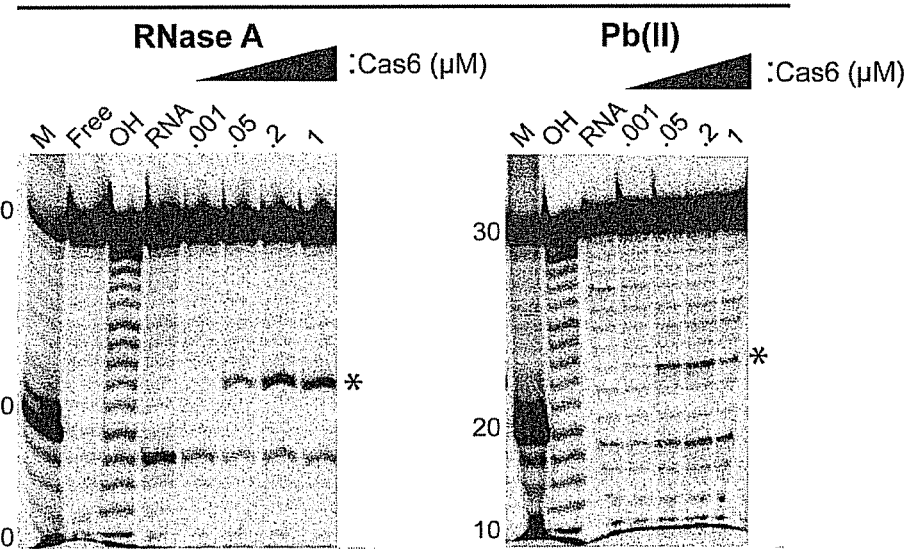

A strong protection was observed in the 5' region of the repeat with both lead (II) acetate and RNase A using 3' end-labeled repeat RNA (FIGS. 10A and 10C). Specifically, nucleotides 2-8 were protected from lead induced cleavage in a Cas6 concentration dependent manner. A similar protection profile was observed with RNase A, with cleavage products at nucleotides 3, 5, and 8 becoming less susceptible to degradation in the presence of Cas6. No protection was observed with either lead (II) acetate or RNase A within the 3' region of the repeat using 5' end labeled repeat (FIGS. 10B and 10C). Similar results were obtained when RNase T1 was used as a cleavage reagent for RNA footprinting.

These findings are in good agreement with previous results in which RNA mutagenesis revealed that sequence elements in the 5' region of the repeat are the primary determinants for recognition by Cas6. Despite weak potential for the 5' and 3' regions of repeat RNA to base-pair, consistent with predictions made by in silico analysis (Kunin et al., 2007. Genome Biol; 8:R61), repeats from *P. furiosus* appear to be mostly unstructured in solution (RNA alone in FIGS. 10A and 10B).

Mutational analysis of a putative catalytic amino acid triad. As described in Example 1, cleavage of CRISPR RNA repeats by Cas6 has been predicted to involve a conserved Tyr, His, Lys triad. This prediction was based both on the high degree of conservation of these amino acids and the observation that in the crystal structure these amino acids clustered in close proximity to one another in a similar configuration to that observed in the archaeal tRNA splicing endonuclease (Haft et al., 2005. PLoS Comput Biol; 1:e60; Calvin and Li, 2008. Cell Mol Life Sci; 65:1176-85). In order to determine whether these amino acids are required for catalysis, Cas6 proteins containing single amino acid substitutions (Y31A, Y31F, H46A, H46Q, K52A, and K52E) were expressed and purified in *Esherichia coli* (FIG. 11B) and assessed for their ability to cleave radiolabeled CRISPR repeat RNA.

Figure 11:
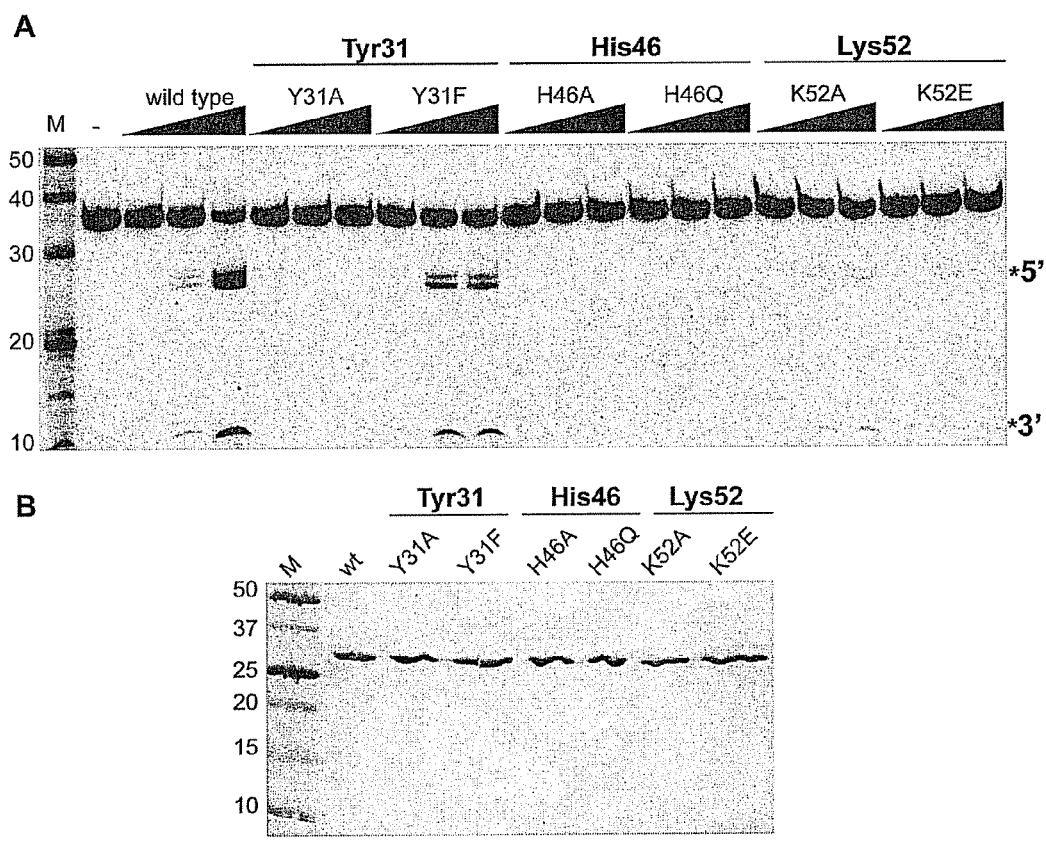
FIG. 11. Cleavage activity of Cas6 mutants. (A) Uniformly $^{32}$P labeled CRISPR repeat RNA was incubated in the absence (−) or presence of increasing concentrations of wild type or mutant Cas6 (0.001, 0.05, and 0.5 μM) followed by separation on a 15% denaturing (7 M urea) polyacrylamide gel. The 5' and 3' cleavage products are indicated. (B) Purified wild type (wt) and mutant Cas6 proteins (as indicated above) were separated by SDS-PAGE. Molecular weight markers are indicated in kDa.

Mutation of any of the three triad amino acids led to a significant decrease or complete loss of cleavage activity relative to wild type Cas6 (FIG. 11A). Cleavage of the repeat was abolished in the Y31A, H46A, and H46Q mutants indicating that Tyr31 and His46 likely play a critical role in catalysis. In the K52A and K52E mutants, cleavage was reduced >40 and >150 fold at the highest concentration tested (500 nM), respectively, suggesting a key role for this residue in catalysis. Significant cleavage activity was retained in the Y31F mutant, with only ~2-fold reduction in cleavage compared to the wild type. Similar results were obtained when residues of the catalytic triad of the tRNA splicing endonuclease from *Archaeaglobus fulgidus* and *Thermoplasma acidophilum* were mutated (Calvin et al., 2008. Biochemistry; 47:13659-65; Kim et al., 2007. J Bacteriol; 189:8339-46).

Figure 12:
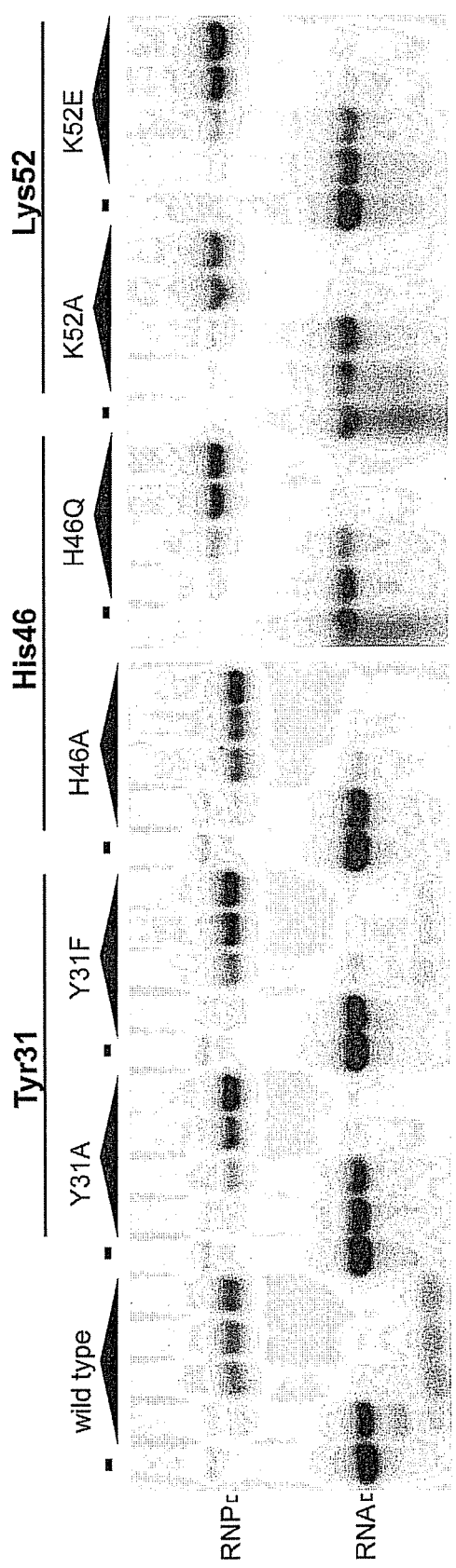
FIG. 12. Substrate recognition by Cas6 mutants. Uniformly $^{32}$P-labeled CRISPR repeat RNA was incubated in the absence (−) or presence of increasing concentrations of wild type or mutant Cas6 (0.001, 0.05, 0.2, and 0.5 µM) and then assessed for their ability to form a stable complex with the substrate RNA by employing native gel mobility shift analysis. The positions of the free (RNA) and bound (RNP) substrate RNA are indicated.

Next, we tested whether the loss or reduction of cleavage observed in each of the Cas6 mutants was due to an inability of the mutants to bind to the substrate RNA. To this end, native gel mobility shift assays were performed with each Cas6 mutant and radiolabeled CRISPR repeat RNA (FIG. 12). The ability of Cas6 to bind CRISPR repeat RNA was largely unaffected by mutations in the proposed catalytic triad. Each of the six Cas6 mutants was able to form a stable complex with CRISPR repeat RNA with a similar binding affinity as wild type Cas6 (FIG. 12). Thus Tyr31, His46, and Lys52, are required for efficient cleavage of the repeat and likely play direct roles in catalysis.

Figure 13:
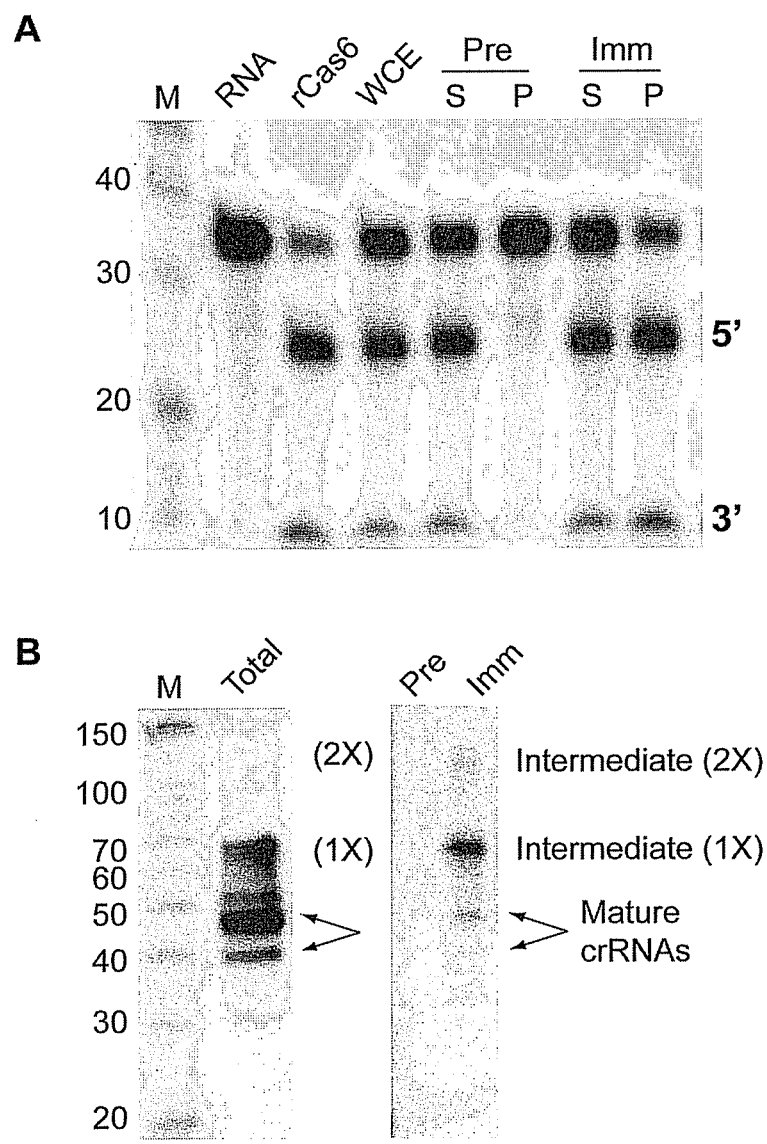
FIG. 13. Native Cas6 cleaves CRISPR repeat RNA and associates with crRNAs. (A) Uniformly $^{32}$P-labeled CRISPR repeat RNA was incubated in the absence (RNA) or presence of recombinant Cas6 (rCas6), whole cell extract (WCE), or samples from immunoprecipitation reactions using anti-Cas6 antibodies (Pre, preimmune; Imm, immune; S, supernatant; P, pellet). The RNAs were separated on a 15% denaturing, 7 M urea, containing polyacrylamide gel along with 5' end-labeled RNA markers (M). (B) Northern blot analysis of Cas6 immunoprecipitation. RNAs extracted from WCE, preimmune (Pre) and immune (Imm) supernatants (Sup, left panel), and pellets (Pel, right panel) from an immunoprecipitation using anti-Cas6 antibodies were separated on 15% denaturing, 7 M urea containing, polyacrylamide gel along with 5' end-labeled RNA markers (M). A 5' end-labeled DNA oligonucleotide that was antisense to crRNA spacer 6.01 from *P. furiosus* was used as a probe. The positions of the 2× intermediate, 1× intermediate, and mature crRNAs are indicated.

Native Cas6 cleaves CRISPR repeat RNA and associates with crRNA intermediates. In order to determine whether native Cas6 behaves similarly to the recombinant protein, polyclonal antibodies were raised against recombinant Cas6 and used to immunoprecipitate the native protein from a *P. furiosus* extract. The immunoprecipitation samples, along with whole cell extract (WCE) were then tested for Cas6 cleavage activity by incubation with uniformly labeled repeat RNA (FIG. 13A). Remarkably, in the WCE, the CRISPR repeat RNA was cleaved into the same products generated by recombinant Cas6 with no other cleavage products evident. Additionally, Cas6 cleavage activity was present in the immune, but not preimmune pellet following immunoprecipitation, indicating that the cleavage activity observed in WCE was carried out by native Cas6. The cleavage activity observed in *P. furiosus* extract was found to be divalent metal ion independent, as was shown to be the case for recombinant Cas6.

It has been shown that a similar CRISPR repeat RNA-cleaving endoribonuclease, Cse3 from *E. coli*, is found as part of a large ribonucleoprotein complex (RNP) that contains both Cas proteins and crRNAs (Browns et al., 2008. Science; 321:960-964). In order to determine whether Cas6 was also part of an RNP, RNAs were extracted from immunoprecipitation samples and probed by northern blot analysis for a crRNA spacer. Cas6 co-purifies with several crRNA species including the 2× and 1× intermediates intermediates (Hale et al., 2008. RNA; 14:2572-9), which correspond to cleavage products generated by Cas6 cleavage of the CRISPR primary transcript (FIG. 13B). Cas6 also weakly co-purified with mature crRNAs (FIG. 14B).

Discussion

The biogenesis of mature crRNAs is critical to CRISPR-Cas mediated resistance to genome invaders. The initial processing step, endonucleolytic cleavage of the primary transcript within the repeat region is performed by Cas6 in *P. furiosus*. This cleavage results in a crRNA intermediate that retains eight nucleotides of the repeat at the 5' end and ~22 nucleotides of the next repeat at the 3' end. In *P. furiosus*, it appears that this crRNA intermediate is then processed at the 3' end to yield two mature crRNA species that retain the eight nucleotide, repeat derived "tag" that we propose serves as a recognition sequence for other Cas proteins (Hale et al., 2008. RNA; 14:2572-9).

In an *E. coli* K12 strain, a ribonuclease that performs a similar function as Cas6, Cse3, was shown to be required for crRNA biogenesis (Brouns et al., 2008. Science; 321:960-964). Cse3 is a divalent metal ion independent endoribonuclease that cleaves CRISPR repeat RNAs within the 3' region of the repeat. Although the sequences of the repeat RNAs differ, the position of cleavage on *E. coli* derived CRISPR repeat RNAs and Cas6 cleavage of *P. furiosus* repeat RNAs, occurs eight nucleotides upstream of the 3' end of the repeat. This cleavage generates an eight nucleotide tag which is retained on the mature crRNAs in both *E. coli* and *P. furiosus* (Brouns et al., 2008. Science; 321:960-964; Hale et al., 2008. RNA; 14:2572-9). The presence of these eight nucleotides may be a universal feature of crRNAs, serving as a recognition sequence for effector Cas proteins that rely on the spacer sequence to guide the complex to invading mobile genetic elements.

Cse3 from *E. coli* was found to be a component of a large RNP containing a number of other Cas proteins as well as mature crRNAs (Brouns et al., 2008. Science; 321:960-964). In the present study we have shown that Cas6 appears to associate with several crRNA species, including its predicted cleavage products, the 1×crRNA intermediate (FIG. 13B). Because it remains bound to its cleavage product, Cas6 may influence the 3' end processing of the 1×crRNA intermediate. Cas6 is not likely to be a structural component of the invader-targeting effector complex because the protein only weakly associates with mature crRNAs (FIG. 13B).

The structure of Cse3 from *Thermus thermophilus* revealed a very similar overall architecture as that shown in the structure of Cas6 from *P. furiosus* (Ebihara et al., 2006. Protein Sci; 15:1494-1499). That is, Cse3 is composed of duplicated ferrodoxin folds separated by a central cleft which contains a conserved Gly-rich loop (Ebihara et al., 2006. Protein Sci; 15:1494-1499). Located adjacent to this loop is an invariant H is residue that was shown to be required for Cse3 cleavage activity (Brouns et al., 2008. Science; 321:960-964; Ebihara et al., 2006. Protein Sci; 15:1494-1499). In our study, Cas6 mediated cleavage of CRISPR repeat RNA was shown to require the highly conserved His46 residue, which is also located adjacent to the conserved Gly-rich loop characteristic of Cas6 proteins. Cse3, however, lacks conserved Tyr and Lys residues that were shown in the current study to be important for Cas6 cleavage activity. Therefore it seems that despite the aforementioned similarities between the two, Cas6 and Cse3 likely employ distinct catalytic mechanisms.

Figure 14:
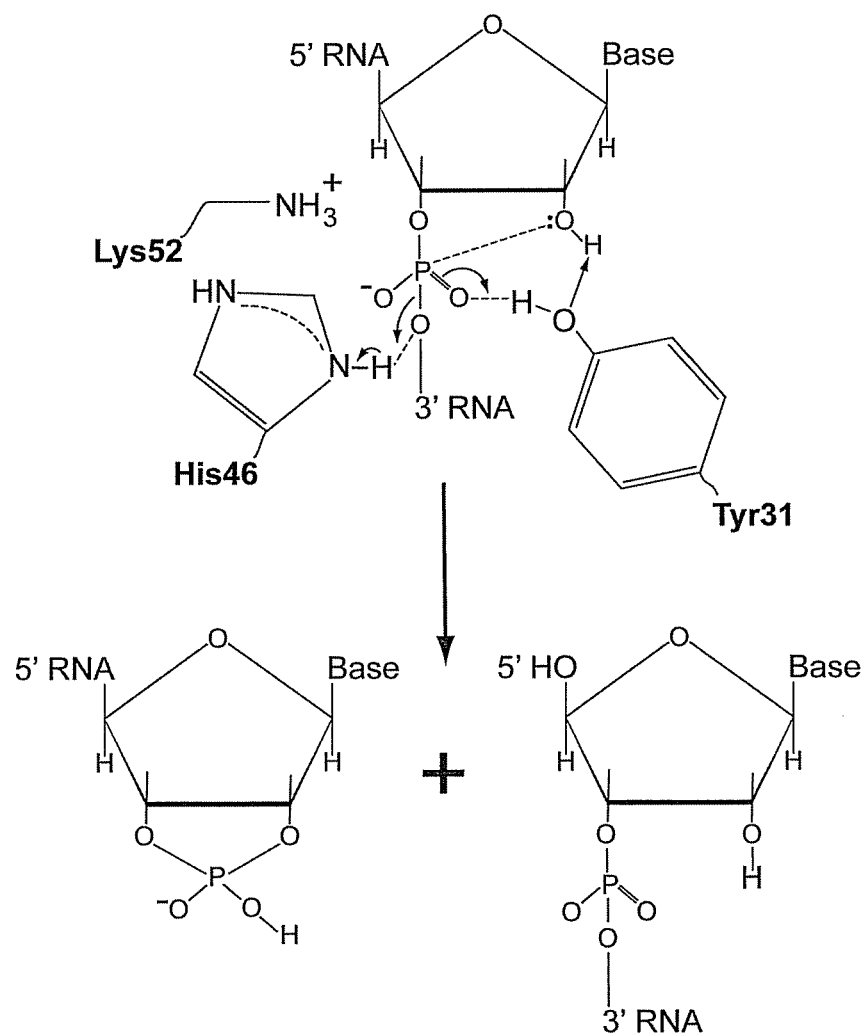
FIG. 14. The proposed catalytic mechanism of Cas6. Tyr31 acts as a general base and His46 as a general acid, while Lys52 stabilizes a predicted pentavalent intermediate. The cleavage products generated contain a 5' OH and likely 2'-3' cyclic phosphate.

Proposed Cas6 cleavage mechanism. We propose a general acid/base catalytic mechanism for Cas6 based on similar active site architecture and reaction characteristics to the archaeal tRNA splicing endonuclease. In this proposed mechanism, a proton is abstracted from the 2' hydroxyl of the ribose ring by the hydroxyl group of Tyr31 (FIG. 14). The ability of Y31F mutant to support significant cleavage activity is consistent with previous studies involving archaeal tRNA splicing endonuclease (Calvin et al., 2008. Biochemistry; 47:13659-65; Kim et al., 2007. J Bacteriol; 189:8339-46). It has been proposed that the stereochemistry of the catalytic Tyr, rather than its hydroxyl group, may account for its role in cleavage. In addition to its function as a general base, Tyr31 may also be required for proper substrate positioning in the active site. Removal of a proton from the 2' hydroxyl of the ribose ring leads to nucleophilic attack by the 2' oxygen of the ribose on the phosphate backbone, resulting in a pentavalent transition state whose negative charge is stabilized by the positive charge of the amine group of Lys52. Cleavage of the scissile phosphate bond is facilitated by proton donation from the imidazole ring of His46. This would result in cleavage products with a 5' hydroxyl and a 2'-3' cyclic phosphate, consistent with previous findings (example 1 and Calvin and Li, 2008. Cell Mol Life Sci; 65:1176-85).

Cas6 employs a distinct method of substrate recognition and cleavage. Initially, Cas6 binds to sequence elements in the 5' region of CRISPR repeat RNA and then cleavage occurs site specifically at a location outside the binding site. One model for how this might occur is that Cas6 binding to the repeat RNA induces a conformational change in the RNA, possibly involving base pairing between the 5' and 3' palindromic regions of the repeat, resulting in the proper positioning of the scissile phosphate bond in the active site. Alternatively, following substrate recognition by Cas6, the RNA may wrap itself around Cas6 through a series of weak contacts to position the cleavage site in the active site. In this were the case, the weak interactions that occur outside the primary binding site could not be detected by the techniques used in this study. Further studies are required to determine the molecular mechanisms and dynamics that allow substrate recognition and catalysis to occur in distinct regions of both the protein and substrate.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for cleaving a target RNA polynucleotide sequence comprising:

incubating an isolated target RNA polynucleotide with an isolated wild-type Cas6 (CRISPR-associated 6) polypeptide under conditions suitable for cleavage of the target RNA polynucleotide to thereby cleave the target RNA polynucleotide, wherein the target RNA polynucleotide comprises a wild-type CRISPR (Clustered regularly interspaced short palindromic repeats) locus repeat present in a wild-type prokaryotic genome, and wherein the repeat comprises a recognition domain and a cleavage site for the wild-type Cas6 polypeptide;

wherein the wild-type Cas6 polypeptide is encoded by said wild-type prokaryotic genome and has Cas6 endoribonuclease activity, wherein the wild-type Cas6 polypeptide comprises a catalytic triad of tyrosine, histidine, and lysine, at residues corresponding to Tyr31, His46, and Lys52, respectively, of SEQ ID NO: 2, and comprises a GhGxxxxxGhG (SEQ ID NO: 190) motif wherein h is a hydrophobic amino acid, and wherein x is any amino acid; and wherein the wild-type Cas6 polypeptide cleaves the target RNA polynucleotide at the cleavage site of the CRISPR locus repeat, and wherein the cleavage site is located 5 to 20 nucleotides downstream of the recognition domain for the wild-type Cas6 polypeptide.

2. The method of claim 1 wherein the incubating is at a temperature of 37° C. or 70° C.

3. The method of claim 1 wherein the target RNA polynucleotide comprises the nucleotide sequence of GUUACAAUAAGACUAAAAUAGA↓AUUGAAAG (SEQ ID NO: 238), wherein the arrow refers to the cleavage site for the wild-type Cash polypeptide.

4. A method for cleaving a target RNA polynucleotide comprising:

incubating an isolated target RNA polynucleotide with an isolated Cas6 polypeptide under conditions suitable for cleavage of the target RNA polynucleotide to thereby cleave the target RNA polynucleotide, wherein the target RNA polynucleotide comprises the nucleotide sequence of 5'-NUUACAAUAAGACCN$_1$N↓N-3' (SEQ ID NO: 242), wherein N$_1$ is 7 nucleotides, wherein the arrow refers to a cleavage site for said isolated Cas6 polypeptide, wherein N is any nucleotide, wherein one or both of the nucleotides flanking the cleavage site is A, wherein the target RNA polynucleotide comprises a recognition domain for said isolated Cas6 polypeptide, and wherein the target RNA polynucleotide is cleaved by a Cas6 polypeptide comprising the amino acid sequence of SEQ ID NO:2; and wherein the isolated Cas6 polypeptide comprises an amino acid sequence having at least 85% sequence identity with the amino acid sequence of SEQ ID NO: 2, has Cas6 endoribonuclease activity, and cleaves a target RNA polynucleotide comprising the nucleotide sequence of SEQ ID NO: 238, wherein the isolated Cas6 polypeptide comprises a catalytic triad of tyrosine, histidine, and lysine, at residues corresponding to Tyr31, His46, and Lys52, respectively, of the amino acid sequence of SEQ ID NO:2, and comprises a GhGxxxxxGhG (SEQ ID NO: 190) motif wherein h is a hydrophobic amino acid, and wherein x is any amino acid.

5. The method of claim 4 wherein the recognition domain for said isolated Cas6 polypeptide comprises the nucleotide sequence of 5'-GTTACAATAAGA-3' (SEQ ID NO: 237), wherein each thymidine of the recognition domain, or the complement thereof, is replaced with a uridine.

6. The method of claim 4 wherein the incubating is at a temperature of 37° C. or 70° C.

7. A method for cleaving a target RNA polynucleotide sequence comprising:

incubating a genetically modified microbe comprising a target RNA polynucleotide and a wild-type Cas6 polypeptide under conditions suitable for cleavage of the target RNA polynucleotide to thereby cleave the target RNA polynucleotide, wherein the genetically modified microbe comprises an exogenous polynucleotide encoding the target RNA polynucleotide or a polynucleotide encoding the wild-type Cas6 polypeptide, wherein the target RNA polynucleotide comprises a wild-type CRISPR locus repeat present in a wild-type prokaryotic genome, and wherein the repeat comprises a recognition domain and a cleavage site for the wild-type Cas6 polypeptide;

wherein the wild-type Cas6 polypeptide is encoded by said wild-type prokaryotic genome and has Cas6 endoribonuclease activity, wherein the wild-type Cas6 polypeptide comprises a catalytic triad of tyrosine, histidine, and lysine, at residues corresponding to Tyr31, His46, and Lys52, respectively, of SEQ ID NO: 2, and comprises a GhGxxxxxGhG (SEQ ID NO: 190) motif wherein h is a hydrophobic amino acid, and wherein x is any amino acid; and wherein the wild-type Cas6 polypeptide cleaves the target RNA polynucleotide at the cleavage site of the CRISPR locus repeat, and wherein the cleavage site is located 5 to 20 nucleotides downstream of the recognition domain for the wild-type Cas6 polypeptide.

8. The method of claim 1 wherein the amino acids xxxxx of the GhGxxxxxGhG (SEQ ID NO: 190) motif comprise at least one lysine or arginine.

9. The method of claim 4 wherein the amino acids xxxxx of the GhGxxxxxGhG (SEQ ID NO: 190) motif comprise at least one lysine or arginine.

10. The method of claim 7 wherein the amino acids xxxxx of the GhGxxxxxGhG (SEQ ID NO: 190) motif comprise at least one lysine or arginine.

11. The method of claim 1 wherein the recognition domain for the wild-type Cas6 polypeptide is located within the first 5 to 15 nucleotides of the CRISPR locus repeat.

* * * * *